United States Patent
Dai et al.

(10) Patent No.: US 8,536,168 B2
(45) Date of Patent: Sep. 17, 2013

(54) BENZYL AND PYRIDINYL DERIVATIVES AS MODULATORS OF THE HEDGEHOG SIGNALING PATHWAY

(75) Inventors: Miao Dai, Shanghai (CN); Feng He, Shanghai (CN); Rishi Kumar Jain, Cambridge, MA (US); Rajesh Karki, Cambridge, MA (US); Joseph Kelleher, III, Cambridge, MA (US); John Lei, Cambridge, MA (US); Luis Llamas, Cambridge, MA (US); Michael A. Mcewan, Cambridge, MA (US); Karen Miller-Moslin, Cambridge, MA (US); Lawrence Bias Perez, Cambridge, MA (US); Stefan Peukert, Cambridge, MA (US); Naeem Yusuff, Cambridge, MA (US)

(73) Assignee: Novartis AG, Basel (CH)

( * ) Notice: Subject to any disclaimer, the term of this patent is extended or adjusted under 35 U.S.C. 154(b) by 759 days.

(21) Appl. No.: 12/531,341

(22) PCT Filed: Mar. 13, 2008

(86) PCT No.: PCT/EP2008/053040
§ 371 (c)(1),
(2), (4) Date: Sep. 15, 2009

(87) PCT Pub. No.: WO2008/110611
PCT Pub. Date: Sep. 18, 2008

(65) Prior Publication Data
US 2010/0069368 A1  Mar. 18, 2010

Related U.S. Application Data

(60) Provisional application No. 60/894,991, filed on Mar. 15, 2007.

(51) Int. Cl.
| C07D 237/32 | (2006.01) |
| C07D 243/08 | (2006.01) |
| C07D 265/38 | (2006.01) |
| A61K 31/502 | (2006.01) |
| A61K 31/5377 | (2006.01) |
| A61K 31/5365 | (2006.01) |
| A61P 37/00 | (2006.01) |
| A61P 29/00 | (2006.01) |

(52) U.S. Cl.
USPC ............ 514/229.5; 514/248; 514/234.5; 540/575

(58) Field of Classification Search
USPC ............ 514/252.02, 218, 299.5, 248, 234.5, 514/229.5; 540/575, 234.5; 544/237, 121, 544/99, 235
See application file for complete search history.

(56) References Cited

U.S. PATENT DOCUMENTS

| 3,668,207 A | 6/1972 | Carney et al. |
| 4,569,934 A | 2/1986 | Moran et al. |
| 4,734,418 A | 3/1988 | Yokoyama et al. |
| 4,760,064 A | 7/1988 | Tominaga et al. |
| 5,935,958 A | 8/1999 | Kozlowski et al. |
| 6,066,636 A | 5/2000 | Kozlowski et al. |
| 8,101,610 B2 | 1/2012 | Goldsmith et al. |
| 2002/0192216 A1 | 12/2002 | Lamb et al. |
| 2003/0083347 A1* | 5/2003 | Baroni et al. ............ 514/333 |
| 2004/0126359 A1 | 7/2004 | Lamb et al. |
| 2006/0281712 A1 | 12/2006 | Yen et al. |
| 2007/0010248 A1 | 1/2007 | Dravida et al. |
| 2008/0318933 A1* | 12/2008 | Ahmed et al. ............ 514/217.08 |
| 2009/0325973 A1 | 12/2009 | Watterson et al. |
| 2010/0029655 A1* | 2/2010 | Leivers et al. ............ 514/248 |
| 2010/0069368 A1 | 3/2010 | Dai et al. |
| 2011/0071191 A1* | 3/2011 | Cassayre et al. ............ 514/318 |
| 2011/0112107 A1* | 5/2011 | Bartolom -Nebreda et al. ............ 514/252.02 |
| 2011/0190304 A1* | 8/2011 | Bastian et al. ............ 514/248 |
| 2011/0237792 A1* | 9/2011 | Ahmed et al. ............ 540/575 |
| 2011/0301162 A1* | 12/2011 | Deak et al. ............ 514/234.5 |
| 2012/0010208 A1 | 1/2012 | Pacaud et al. |

FOREIGN PATENT DOCUMENTS

| DE | 2021195 | 11/1970 |
| DE | 2643753 | 4/1978 |
| EP | 1570374 | 7/1980 |
| EP | 0055583 B1 | 7/1982 |
| EP | 0722936 A1 | 7/1996 |
| EP | 1277754 A1 | 1/2003 |
| EP | 01570374 A2 | 10/2005 |
| JP | 01061468 | 3/1989 |

(Continued)

OTHER PUBLICATIONS

Wikipedia, Acyl, last modified Mar. 23, 2010.*
IUPAC, (1997) http://www.iupac.org/goldbook/A00123.pdf, downloaded Oct. 29, 2010.*
Hawley's Condensed Chem. Dict., 14th Ed., 2002.*
Hackh's Chem. Dict., 3rd Ed., 1944, Title page.*
Hutchin, et al., Genes Dev. 2005 19: 214-223.*
Sheng, et al., Molecular Cancer 2004, 3:29, 13 pages.*
Eiden et al., "2-Aminochinoline und Pyrrolo[2,3-b]chinoline", Arch. Pharm., 1986 vol. 319 No. 4 pp. 338-347.

(Continued)

*Primary Examiner* — James O Wilson
*Assistant Examiner* — Cecilia M Jaisle
(74) *Attorney, Agent, or Firm* — Scott W. Reid

(57) ABSTRACT

The present disclosure relates to compounds relating to the diagnosis and treatment of pathologies relating to the Hedgehog pathway, including but not limited to tumor formation, cancer, neoplasia, and non-malignant hyperproliferative disorders; specifically relating to compounds of formula I:

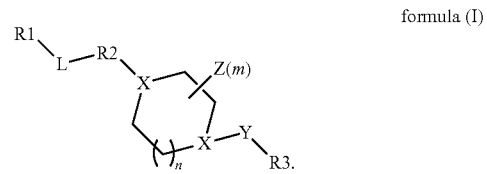

formula (I)

5 Claims, No Drawings

(56) References Cited

FOREIGN PATENT DOCUMENTS

| | | |
|---|---|---|
| JP | 02193992 | 7/1990 |
| JP | 2000281660 | 10/2000 |
| JP | 2003 073578 | 3/2003 |
| WO | 97/36889 A1 | 10/1997 |
| WO | 98/05292 A2 | 2/1998 |
| WO | WO 99/54305 A1 | 10/1999 |
| WO | 00/00488 A1 | 1/2000 |
| WO | 00/044376 A1 | 8/2000 |
| WO | 00/66558 A1 | 9/2000 |
| WO | WO 00/59509 A1 | 10/2000 |
| WO | 00/075130 A1 | 12/2000 |
| WO | 02/20491 A1 | 3/2002 |
| WO | WO 02/053160 A1 | 7/2002 |
| WO | 02/080954 A1 | 10/2002 |
| WO | WO 03/032984 A1 | 4/2003 |
| WO | WO 2004/076413 A2 | 9/2004 |
| WO | 2005/011653 A2 | 2/2005 |
| WO | 2005/019208 A1 | 3/2005 |
| WO | 2005/020897 A2 | 3/2005 |
| WO | 2005/033288 A2 | 4/2005 |
| WO | 2005/117909 A2 | 12/2005 |
| WO | WO 2006/028958 A2 | 3/2006 |
| WO | 2006/094187 A2 | 9/2006 |
| WO | WO 2006/122773 A1 | 11/2006 |
| WO | 2007/064797 A2 | 6/2007 |
| WO | 2007/090617 A2 | 8/2007 |
| WO | 2007/104783 A2 | 9/2007 |
| WO | 2007/109238 A1 | 9/2007 |
| WO | 2007/127475 A2 | 11/2007 |
| WO | 2007/128460 A1 | 11/2007 |
| WO | WO 2007/127375 A2 | 11/2007 |
| WO | WO 2007/127448 A2 | 11/2007 |
| WO | 2008/008453 A1 | 1/2008 |
| WO | 2008/061781 A1 | 5/2008 |
| WO | 2008071405 A1 | 6/2008 |
| WO | 2008/079279 A1 | 7/2008 |
| WO | 2008/107479 A1 | 9/2008 |
| WO | 2008/107480 A1 | 9/2008 |
| WO | 2008/110488 A1 | 9/2008 |
| WO | 2008/110611 A1 | 9/2008 |
| WO | 2008107481 A1 | 9/2008 |
| WO | 2008115381 A1 | 9/2008 |
| WO | 2009/035568 A1 | 3/2009 |

OTHER PUBLICATIONS

Gelain et al., "3-Heptylamino-5-Phenylpyridazine Derivatives as Analogues of Acyl-CoA: Cholesterol Acyltransferase Inhibitors Containing the N-Heptyl-N9-Arylureidic Moiety", Arch. Pharm. Chem Life Sci., 2006 vol. 339 pp. 645-651.

Hu et al., "Development of a novel therapeutic suppressor of brain proinflammatory cytokine up-regulation that attenuates synaptic dysfunction and behavioral deficits", Bioorganic & Medicinal Chemistry Letters, 2007 vol. 17 pp. 414-418.

Holava et al., "1-substituted 4-aryl-(or 4-arakyl-) phthalazines", Journal of Medicinal Chemistry, 1969 vol. 12 pp. 555-556.

Ojea et al., "Synthesis of Pyrazino[1,2-a:4,5-a]di[1,9]Naphthyridine and Pyrazino[1,2-a][1,8] Naphthyridines", Heterocycles, 1993 vol. 36 No. 6 pp. 1337-1349.

Schairer, Annelie et al., 53rd ASH Annual Meeting & Exposition, Dec. 10-13, 2011.

"The Effects of Smoothened(Smo) siRNA on Expression of Smo Gene and Proliferation, Apoptosis of Lovo Cells" http://www.tumor-res.com/tumor-marker/29544.htm, downloaded Apr. 4, 2012.

Tauchi, Tetsuzo Arthritis Research & Therapy 2012, vol. 14, Suppl 1, 17.

Ruiz-Heiland, G. et al., "Blockade of the hedgehog pathway inhibits osteophyte formation in arthritis" Ann Rheum Dis. Mar. 2012; 71(3):400-7. Epub Jan. 10, 2012.

Miller-Moslin, Karen et al., "1-Amino-4-benzylphthalazines as Orally Bioavailable Smoothened Antagonists with Antitumor Activity", Journal of Medicinal Chemistry, 2009 vol. 52, pp. 3954-3968.

Byth, Kate F. et al., "Imidazo[1,2-b]pyridazines: a potent and selective class of cyclin-dependent kinase inhibitors" Bioorganic & Medicinal Chemistry Letters, Oxford, GB, vol. 14, 2004, pp. 2249-2252, XP002415769 ISSN: 0960-894X abstract; compound 4B.

Ng, Jessica M. Y. et al., "The Hedgehog's tale: developing strategies for targeting cancer"Nature Reviews: Cancer, 11, Jul. 2011, pp. 493-501.

Rudin, Charles M. et al., "Treatment of Medulloblastoma with Hedgehog Pathway Inhibitor GDC-0449" New England J. of Medicine, 361: 12, Sep. 17, 2009, pp. 1173-1178.

Lee, Y. et al., "Loss of suppressor-of-fused function promotes tumorigenesis" Oncogene, 2007, 26, pp. 6442-6447.

Martin, S. T. et al., "Aberrant Methylation of the Human Hedgehog Interacting Protein (HHIP) Gene in Pancreatic Neoplasms" Cancer Biology & Therapy 4:7, pp. 728-733, Jul. 2005.

Kimura, Hiromichi et al., "Transient Inhibition of the Hedgehog Pathway in Young Mice Causes Permanent Defects in Bone Structure" Cancer Cell, 13, pp. 249-260, 2008.

Chemical Book, CUR61414 Basic Information, 2008, http://www.chemicalbook.com/ProductChemicalPropertiesCB31565488_EN.htm, downloaded Sep. 20, 2012.

Wikipedia, Cyclopamine, last modified Jun. 5, 2012, http://en.wikipedia.org/wiki/Cyclopamine, downloaded Sep. 20, 2012.

Berman, David M. et al., "Medulloblastoma Growth Inhibition by Hedgehog Pathway Blockade", Science, vol. 297, pp. 1559-1561, (2002).

Berman, David M. et al., "Widespread requirement for Hedgehog ligand stimulation in growth of digestive tract tumours", Nature, vol. 425, pp. 846-851, (2003).

Frank-Kamenetsky, Maria et al., "Small-molecule modulators of Hedgehog signaling: identification and characterization of Smoothened agonists and antagonists", Journal of Biology, vol. 1, Issue 2, Article 10, pp. 10.1-10.19, (2002).

Karhadkar, Sunil S. et al., "Hedgehog signalling in prostate regeneration, neoplasia and metastasis", Nature, vol. 431, pp. 707-712 (2004).

Kubo, Makoto et al., "Hedgehog Signaling Pathway is a New Therapeutic Target for Patients with Breast Cancer", Cancer Research, vol. 64, pp. 6071-6074 (2004).

Sanchez, Pilar et al., "Inhibition of prostate cancer proliferation by interference with Sonic Hedgehog-GLI1 signaling", vol. 101, No. 35, pp. 12561-12566 (2004).

Thayer, Sarah P. et al., "Hedgehog is an early and late mediator of pancreatic cancer tumorigenesis", Nature, vol. 425, pp. 851-856 (2003).

Tostar, Ulrica et al., "Deregulation of the hedgehog signalling pathway: a possible role for the PTCH and SUFU genes in human rhabdomyoma and rhabdomyosarcoma development", J Pathol, 208, pp. 17-25 (2005).

Watkins, D. Neil et al., "Hedgehog signalling within airway epithelial progenitors and in small-cell lung cancer", Nature, vol. 422, pp. 313-317 (2003).

Williams, Juliet A. et al., "Identification of a small molecule inhibitor of the hedgehog signaling pathway: Effects on basal cell carcinoma-like lesions", PNAS, vol. 100, No. 8, pp. 4616-4621 (2003).

Xie, Jingwu et al., "Activating Smoothened mutations in sporadic basal-cell carcinoma", Nature, vol. 391, pp. 90-92 (1998).

* cited by examiner

BENZYL AND PYRIDINYL DERIVATIVES AS MODULATORS OF THE HEDGEHOG SIGNALING PATHWAY

This application is a U.S. National Phase filing of International Application Serial No. PCT/EP2008/053040 filed 13 Mar. 2008 and claims priority to U.S. Provisional Application Ser. No. 60/894,991 filed 15 Mar. 2007, the contents of which are incorporated herein by reference in their entirety.

BACKGROUND OF THE INVENTION

Hedgehog (Hh) signaling was first identified in Drosophila as an important regulatory mechanism for embryonic pattern formation, or the process by which embryonic cells form ordered spatial arrangements of differentiated tissues (Nusslein-Volhard et al. (1980) Nature 287, 795-801). In mammalian cells, three Hedgehog genes, Sonic Hedgehog (Shh), Indian Hedgehog (Ihh) and Desert Hedgehog (Dhh), have been identified. Hedgehog genes encode secreted proteins, which undergo post-translational modifications, including autocatalytic cleavage and lipid modification (palmitoylation) at the N-terminus and cholesterol modification of the C-terminus.

The lipid-modified N-terminal Hedgehog protein triggers the signaling activity of the protein pathway, and cell to cell communication is engendered by the dispatch of soluble Hedgehog protein from a signaling cell and receipt by a responding cell. In responding cells, the 12-pass transmembrane receptor Patched (Ptch) acts as negative regulator of Hh signaling and the 7-pass transmembrane protein Smoothened (Smo) acts as a positive regulator of Hh signaling. At resting state, free Ptch (i.e., unbound by Hh) substoichiometrically suppresses pathway activity induced by Smo (Taipale et al. (2002) Nature 418: 892); upon binding ligand Hh protein, however, repression of Smo is relieved, and the resulting signaling cascade leads to the activation and nuclear translocation of Gli transcription factors (Gli1, Gli2 and Gli3).

Downstream target genes of Hh signaling transcription include Wnts, TGFβ, and Ptc and Gli1, which are elements of the positive and negative regulatory feedback loop. Several cell-cycle and proliferation regulatory genes, such as c-myc, cyclin D and E are also among the target genes of Hh signaling.

Hh signaling is known to regulate a diverse range of biological processes, such as cellular proliferation, differentiation, and organ formation in a tissue specific and dose dependent manner. In the development of neural tubes, Shh is expressed in the floorplate and directs the differentiation of specific subtypes of neurons, including motor and dopaminergic neurons. Hh is also known to regulate the proliferation of neuronal progenitor cells, such as cerebella granule cells and neural stem cells. In the developing intestinal tract, a low-level of Hh signaling is required for pancreatic development, while a high-level of Hh signaling blocks pancreatic organogenesis. Hh is also known to play important roles in stem cell proliferation and organogenesis in skin, prostate, testis and bone marrow.

Normally, Hh signaling is strictly controlled during cellular proliferation, differentiation and embryonic pattern formation. However, aberrant activity of the Hedgehog signaling pathway, due to mutations that constitutively activate the pathway, for instance, may have pathological consequences. By way of example, loss-of-function mutations of Patched are found in Gorlin's syndrome (a hereditary syndrome with high risk of skin and brain cancers, also known as Basal Cell Nevus Syndrome (BCNS)); and gain-of-function mutations of Smo and Gli are linked to basal cell carcinoma and glioblastoma. Basal cell carcinoma (BCC) is the most common form of skin cancer, affecting more than 90,000 Americans each year. Constitutive activation of Hh has been found to promote tumorigenesis in BCC, medulloblastoma (the most common childhood brain tumor), rhabdomyosarcoma, pancreatic cancer, small cell lung cancer, prostate cancer and breast cancer. Besides the roles in tumorigenesis, Hh signaling is also implicated in the metastasis of prostate cancer. Hh signaling may be involved in many additional types of tumors and such links are expected to continue to be discovered; this is an area of active research in many cancer centers around the world.

Proliferation of these cancer cells requires Hh pathway activation, and blocking Hh signaling pathways often inhibits cancer cell proliferation. Indeed, Hh antagonist cyclopamine and Gli1 siRNA can effectively block the proliferation of these cancer cells, and can reduce tumor size in Xenograft models, suggesting that novel Hh antagonists could provide new chemotherapeutic agents for the treatment of these cancers. Hh antagonist cyclopamine has been shown to suppress the metastasis of prostate cancer in animal models.

In addition to being involved in cancer, Hh signaling plays important roles in normal tissue homeostasis and regeneration. Hh pathway is activated after the injury of retina, bile duct, lung, bone and prostate in mouse models. Hh pathway is also constantly active in hair follicles, bone marrow, and certain regions of the central nervous system (CNS), and benign prostate hyperplasia and blood vessel formation in wet macular degeneration require Hedgehog pathway activity. Cellular regeneration processes can be blocked by anti-Shh antibody and cyclopamine. Therefore, small molecule antagonists of Hh signaling pathway might be useful in the treatment of neuronal proliferative diseases, benign prostate hyperplasia, wet macular degeneration, psoriasis, bone marrow proliferative diseases and leukemias, osteopetrosis and hair removal.

Evidence that constitutive activation of Smo results in cancers (e.g., BCC), and that Smo may be oncogenic upon its release from inhibition by Ptch, suggests utility of Smo antagonists as therapeutic agents in the treatment of such disorders. (Stone et al. (1996) Nature 384: 129). Accordingly, molecules that modulate the activity of the Hedgehog signaling pathway, e.g., which modulate Smo activity, are therapeutically useful.

SUMMARY OF THE INVENTION

The present invention relates generally to novel compounds relating to the diagnosis and treatment of pathologies relating to the Hedgehog pathway, including but not limited to tumor formation, cancer, neoplasia, and non-malignant hyperproliferative disorders. The present invention includes novel compounds, novel compositions, methods of their use and methods of their manufacture, where such compounds are generally pharmacologically useful as agents in therapies whose mechanism of action involve methods of inhibiting tumorigenesis, tumor growth and tumor survival using agents that inhibit the Hedgehog and Smo signaling pathway. The compounds and methods of the present invention (e.g., a compound of Formula I) relate to inhibiting activation of the Hedgehog signaling pathway, e.g., by inhibiting aberrant growth states resulting from phenotypes such as Ptc loss-of-function, Hedgehog gain-of-function, Smoothened gain-of-function or Gli gain-of-function, and comprise contacting the cell with a compound of the invention (e.g., a compound of Formula I) in a sufficient amount to agonize a normal Ptc activity, antagonize a normal Hedgehog activity, or antagonize Smoothened activity (e.g., to reverse or control the aberrant growth state).

The present invention relates to compounds of the formula (I):

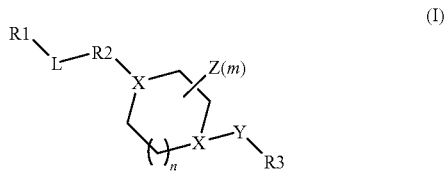

and pharmaceutically acceptable salts thereof, wherein $R_1$ is aryl or het which may be unsubstituted or substituted;

$R_2$ is het with at least one heteroring atom being N, and which may be unsubstituted or substituted;

L is lower alkyl, $(CH_2)_{1-2}$-A, -A-$(CH_2)_{1-2}$, or $CH_2$-A-$CH_2$, and A is O, S, NH, or N-alkyl, wherein lower alkyl may be unsubstituted or substituted with lower alkyl, or one or more fluorines;

X is N or CH, and at least one X is N;

Y is a bond, $CH_2$, C(O), or $SO_2$;

$R_3$ is aryl or het, which may be unsubstituted or substituted;

Z is H, lower alkyl, lower alkoxy, oxo, $C(O)OR_6$, or —CN; in which lower alkyl and lower alkoxy may be unsubstituted or substituted with one or more halo, —OH, —CN, —$NH_2$, or oxo, and two Z connected to the same atom can form a cycloalkyl ring, and m is 0 to 3;

substitutions of phenyl, aryl or het of $R_1$, $R_2$, or $R_3$ may be one or more of alkyl, cycloalkyl, alkoxy, cycloalkoxy, halo, —CN, oxo, aryl, carbalkoxy, $OCF_3$, $CF_3$, OH, —C(O)N$(R_6)_2$, C(O)$R_6$, —C(O)O$R_6$, —N$(R_6)_2$, —NHC(O)$R_6$, —$SO_2(R_6)$, —$SO_2N(R_6)_2$; $CH_2OC(O)N(R_6)_2$, —$CH_2N(R_6)_2$, —NHC(O)O$R_6$, NHC(O)N$(R_6)_2$, —$CH_2NHC(O)R_6$, $CH_2NHC(O)N(R_6)_2$, $CH_2NHSO_2(R_6)$, $CH_2NHC(O)OR_6$—OC(O)$R_6$, NHC(O)$R_6$, O-aryl, het, or O-het, in which alkyl, het, cycloalkyl, cycloalkoxy, N$(R_6)_2$, aryl, carbalkoxy, and alkoxy can be unsubstituted or substituted with one or more halo, —$OCH_3$, —$OCF_3$, —OH, —$NH_2$, alkyl, O$R_6$, oxo, —N(H)$_{0-2}$—$R_6$, —CN, —C(O)N$(R_6)_2$, C(O)$R_6$, C(O)O$R_6$, —N$(R_6)_2$, NHC(O)$R_6$, —$SO_2(R_6)$, —$SO_2N(R_6)_2$, OS$O_2R_6$, —$CH_2N(R_6)_2$, —$CH_2NHC(O)R_6$, —OC(O)$R_6$, aryl, NHC(O)$(R_6)$, O-aryl, het, O-het, or cycloalkyl;

$R_6$ is H, alkyl, alkenyl, aryl, het, or two $R_6$ on one atom may form cycloalkyl, aryl, or het; and alkyl, alkenyl, aryl, het, cycloalkyl, or het may be unsubstituted or substituted by OH, oxo, alkoxy, N$R_6$, Nalkyl, acyl, aryl or het group;

het is a 5-7 membered monocyclic heterocyclic ring which may be aromatic or non-aromatic, containing 1-4 heteroring atoms selected from N, O, and S; or an 8-12 membered fused ring system that includes at least one 5-7 membered heterocyclic ring which may be aromatic or non-aromatic, containing 1, 2, or 3 heteroring atoms selected from N, O and S, which het is unsubstituted or substituted;

aryl is an aromatic radical having 6 to 14 ring carbon atoms, and no ring heteroatoms, in which said aryl group may be monocyclic or fused bicyclic or tricyclic, which may be unsubstituted or substituted by one or more substituents; and n is 0, 1, 2, or 3.

In an embodiment of the present invention, $R_1$ is phenyl which may be unsubstituted or substituted, and $R_3$ is aryl or het which is substituted.

The present invention also relates to pharmaceutical compositions comprising therapeutically effective amounts of compounds of Formula I, as defined hereinabove, or a pharmaceutically acceptable salt thereof, and a pharmaceutical carrier therefor.

The compounds of the invention, as further described below, include small molecule inhibitors or antagonists of Smo synthesis, expression, production, stabilization, phosphorylation, relocation within the cell, and/or activity. The compounds of the invention include but are not limited to compounds of Formula I.

One aspect of the present invention makes available methods employing compounds for inhibiting Smo-dependent pathway activation. Another aspect of the present invention makes available methods employing compounds for inhibiting Hedgehog (ligand)-independent pathway activation. In certain embodiments, the present methods can be used to counteract the phenotypic effects of unwanted activation of a Hedgehog pathway, such as resulting from Hedgehog gain-of-function, Ptc loss-of-function or smoothened gain-of-function mutations. For instance, the subject method can involve contacting a cell (in vitro or in vivo) with a Smo antagonist, such as a compound of the invention (e.g., a compound of Formula I) or other small molecule in an amount sufficient to antagonize a smoothened-dependent and/or Hedgehog independent activation pathway.

The compounds and methods of the present invention may be used to regulate proliferation and/or differentiation of cells in vitro and/or in vivo, e.g., in the formation of tissue from stem cells, or to prevent the growth of hyperproliferative cells. In another particular embodiment, contacting the cell with—or introducing into the cell—a compound of the invention (e.g., a compound of Formula I) results in inhibition of cellular proliferation, inhibition of tumor cell growth and/or survival, and/or inhibition of tumorigenesis. Thus, another particular embodiment provides methods for inhibiting and/or antagonizing the Hh pathway by employing compounds of the invention (e.g., a compound of Formula I) in a tumor cell.

The methods of the present invention may employ compounds of the invention (e.g., a compound of Formula I) as formulated as pharmaceutical preparations comprising a pharmaceutically acceptable excipient or carrier, and said preparations may be administered to a patient to treat conditions involving unwanted cell proliferation such as cancers and/or tumors (such as medulloblastoma, basal cell carcinoma, etc.), and non-malignant hyperproliferative disorders.

One embodiment of the present invention provides a compound and method for inhibiting the synthesis, expression, production, stabilization, phosphorylation, relocation within the cell, and/or activity of a Smo protein in a cell in vitro or in vivo comprising, contacting said cell with, or introducing into said cell, a compound of the invention (e.g., a compound of Formula I).

Another aspect of the invention provides a compound and method of diagnosing, preventing and/or treating cellular debilitations, derangements, and/or dysfunctions; hyperplastic, hyperproliferative and/or cancerous disease states; and/or metastasis of tumor cells, in a mammal characterized by the presence and/or expression of a Smo gene or gene product (e.g., a Smo protein), comprising compounds of formula (I) and their administration to a mammal in a therapeutically effective amount.

DETAILED DESCRIPTION OF THE INVENTION

In an embodiment, the compound of formula (I) further comprises a compound where R2 is selected from:

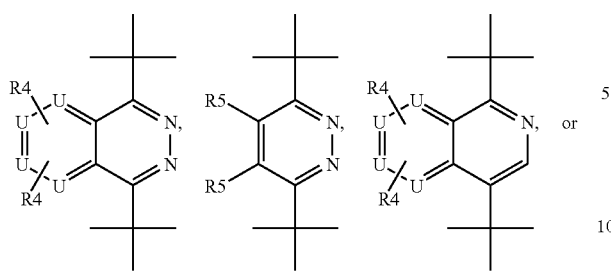

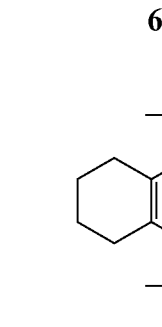

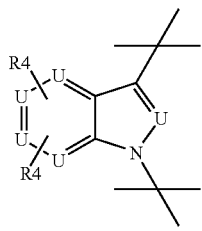

(where N is connected to L), where U is $C(H)_{0-1}$ or N, and not more than two U are N;

$R_4$ is independently H, $-N(R_6)_2$, $-OH$, halo, $-CN$, $-C(O)OR_6$, $-C(O)N(R_6)_2$, $-NH_2$, lower alkyl, or lower alkoxy, in which lower alkyl and lower alkoxy may be unsubstituted or substituted with one or more halo, $-OH$, $-CN$, $-NH_2$, $-NO_2$, $-C(O)NH_2$, $-C(O)NH(C_1-C_6\text{-alkyl})$, $-C(O)N(C_1-C_6\text{-alkyl})_2$, $-C(O)(C_1-C_6\text{-alkyl})$, $-NHC(O)(C_1-C_6\text{-alkyl})$, $NH(C_1-C_6\text{-alkyl})$, $-N(C_1-C_6\text{-alkyl})_2$, $-SO_2(C_1-C_6\text{-alkyl})$, $-SO_2NH_2$, $-SO_2NH(C_1-C_6\text{-alkyl})$; $R_5$ is H, aryl, het, lower alkyl, lower alkoxy, or cycloalkyl, which can be unsubstituted or substituted with one or more halo, cycloalkyl, aryl, het, and wherein at least one $R_5$ is not H; and L is lower alkyl.

In a further embodiment, $R_2$ can be selected from:

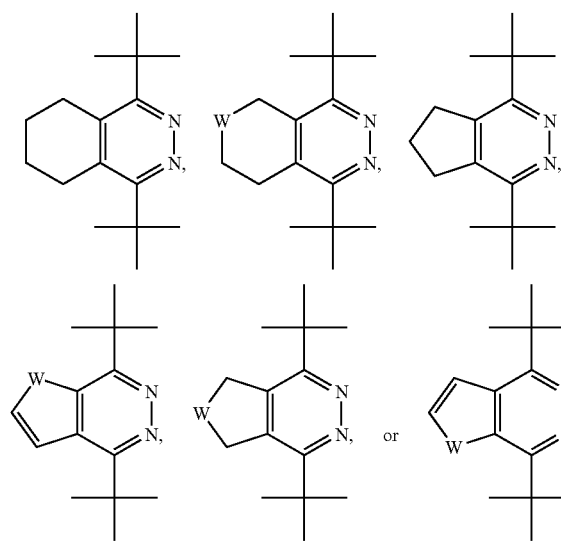

wherein W is O, $NR_7$ or $SO_2$, and $R_7$ is a bond, H, lower alkyl or lower acyl.

In another embodiment, the compound of formula I includes a compound where $R_2$ is:

and $R_3$ is het.

In a further embodiment, the compound of formula (I) includes a compound where: $R_1$ is aryl or het which may be unsubstituted or substituted; and when $R_1$ is het, at least one heteroring atom is N; $R_3$ is aryl or het which may be unsubstituted or substituted; and when $R_3$ is het, at least one heteroring atom is N; U is $C(H)_{0-1}$; $R_4$ is H, $CH_3$, halo, or CN; L is $CH_2$; X is N; Y is a bond; and Z is H or $CH_3$.

In yet a further embodiment, the present invention includes a compound of formula (I), wherein: $R_1$ is phenyl, pyridine, or naphthyl which may be unsubstituted or substituted; $R_2$ is

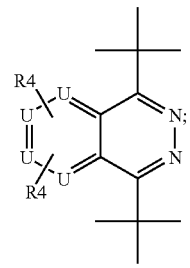

$R_4$ is H, and U is $C(H)_{0-1}$, $R_3$ is phenyl, pyridine, pyrazine, pyridazine, or pyrimidine, which may be unsubstituted or substituted; Z is H or $CH_3$; and n is 1.

In yet another embodiment, the present invention includes a compound according to formula (I) wherein: $R_1$ is phenyl which may be unsubstituted or substituted; and $R_2$ is selected from:

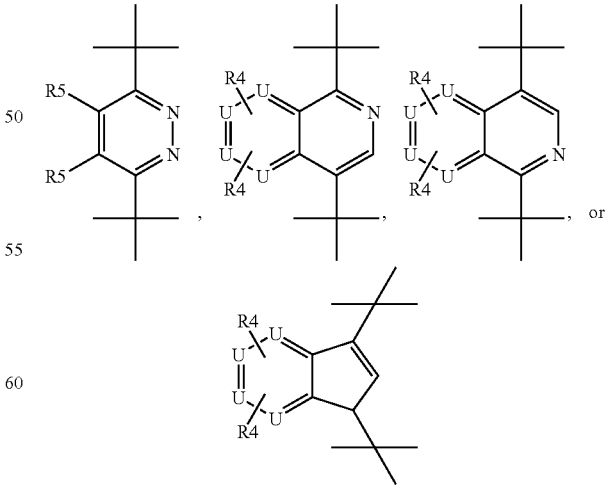

(where N is connected to L); and
at least one $R_5$ is $CH_3$.

In another embodiment, the present invention includes a pharmaceutical composition comprising a therapeutically effective amount of a compound according to formula I. In another embodiment, the present invention includes a method of treating a mammal suffering from a pathology relating to the Hedgehog pathway which comprises administering to said mammal in need of treatment a therapeutically effective amount of a compound according to formula I.

In the present description, the term "treatment" includes both prophylactic or preventive treatment as well as curative or disease suppressive treatment, including treatment of patients at risk for a disorder of the invention (e.g., a Hedgehog-related disorder (e.g., cancer)) as well as ill patients. This term further includes the treatment for the delay of progression of the disease.

By "suppress and/or reverse," e.g., a Hedgehog-related disorder (e.g., cancer), Applicants mean to abrogate said Hedgehog-related disorder (e.g., diabetes), or to render said condition less severe than before or without the treatment.

"Cure" as used herein means to lead to the remission of the Hedgehog-related disorder (e.g., cancer) in a patient, or of ongoing episodes thereof, through treatment.

The terms "prophylaxis" or "prevention" means impeding the onset or recurrence of metabolic disorders, e.g., diabetes.

"Treatment" or "treating" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted.

"Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

"Subject" or "patient" refers to a mammal, preferably a human, in need of treatment for a condition, disorder or disease.

"A compound(s) of the invention" as used herein includes but is not limited to compounds of Formula I (e.g., a compound of Formulae (I), including all variants thereof). A compound of the invention includes the specifically listed compounds listed herein, including those listed in the Examples of the present application.

"Delay of progression" as used herein means that the administration of a compound of the invention (e.g., a compound of Formula I) to patients in a pre-stage or in an early phase of a Hedgehog-related disorder (e.g., cancer) prevents the disease from evolving further, or slows down the evolution of the disease in comparison to the evolution of the disease without administration of the active compound.

"Hedgehog gain-of-function" refers to an aberrant modification or mutation of a Ptc gene, Hedgehog gene, or smoothened gene, or a change (e.g., decrease) in the level of expression of such a gene, which results in a phenotype which resembles contacting a cell with a Hedgehog protein, e.g., aberrant activation of a Hedgehog pathway. The gain-of-function may include a loss of the ability of the Ptc gene product to regulate the level of expression of Gli genes, e.g., Gli1, Gli2, and Gli3, or loss of the ability to regulate the processing, stability, localization or activity of the Gli proteins, e.g., Gli1, Gli2, and Gli3. The term "Hedgehog gain-of-function" is also used herein to refer to any similar cellular phenotype (e.g., exhibiting excess proliferation) which occurs due to an alteration anywhere in the Hedgehog signal transduction pathway, including, but not limited to, a modification or mutation of Hedgehog itself. For example, a tumor cell with an abnormally high proliferation rate due to activation of the Hedgehog signaling pathway would have a "Hedgehog gain-of-function" phenotype, even if Hedgehog is not mutated in that cell.

"Patched loss-of-function" refers to an aberrant modification or mutation of a Ptc gene, or a decreased level of expression of the gene, which results in a phenotype which resembles contacting a cell with a Hedgehog protein, e.g., aberrant activation of a Hedgehog pathway. The loss-of-function may include a loss of the ability of the Ptc gene product to regulate the level of expression, processing, stability, localization, regulation or activity of Gli genes and proteins, e.g., Gli1, Gli2 and Gli3.

"Gli gain-of-function" refers to an aberrant modification or mutation of a Gli gene, or an increased level of expression of the gene, which results in a phenotype which resembles contacting a cell with a Hedgehog protein, e.g., aberrant activation of a Hedgehog pathway.

"Smoothened gain-of-function" refers to an aberrant modification or mutation of a Smo gene, or an increased level of expression of the gene, which results in a phenotype which resembles contacting a cell with a Hedgehog protein, e.g., aberrant activation of a Hedgehog pathway.

As used herein a "small organic molecule" is an organic compound (or organic compound complexed with an inorganic compound (e.g., metal)) that has a molecular weight of less than 3 kilodaltons, and preferably less than 1.5 kilodaltons.

As used herein a "reporter" gene is used interchangeably with the term "marker gene" and is a nucleic acid that is readily detectable and/or encodes a gene product that is readily detectable such as luciferase.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

"Agent" refers to all materials that may be used to prepare pharmaceutical and diagnostic compositions, or that may be compounds, nucleic acids, polypeptides, fragments, isoforms, variants, or other materials that may be used independently for such purposes, all in accordance with the present invention.

"Analog" as used herein, refers to a small organic compound, a nucleotide, a protein, or a polypeptide that possesses similar or identical activity or function(s) as the compound, nucleotide, protein or polypeptide or compound having the desired activity and therapeutic effect of the present invention. (e.g., inhibition of tumor growth), but need not necessarily comprise a sequence or structure that is similar or identical to the sequence or structure of the preferred embodiment "Derivative" refers to either a compound, a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide.

"Inhibitors," or "antagonists" refer to inhibitory molecules identified using in vitro and in vivo assays for Hh pathway function, e.g., Smo antagonists. In particular, inhibitors and antagonists refer to compounds or agents that decrease signaling that occurs via the Hh pathway. Inhibitors may be compounds that decrease, block, or prevent, signaling via this pathway.

"Hedgehog-related disorder(s)" as used herein includes disorders associated with disruption or aberrance of the Hedgehog pathway, as well as disorders associated with normal but undesired growth states relating to activation of the Hedgehog pathway. "Hedgehog-related disorder(s)" include but are not limited to tumor formation, cancer, neoplasia, malignant hyperproliferative disorders, and non-malignant hyperproliferative disorders. "Hedgehog-related disorder(s)" also include benign prostate hyperplasia, psoriasis, wet macular degeneration, osteopetrosis and unwanted hair growth.

As used herein, the term "cancer" includes solid mammalian tumors as well as hematological malignancies. "Solid mammalian tumors" include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin, central nervous system including brain; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. In addition, a cancer at any stage of progression can be treated, such as primary, metastatic, and recurrent cancers. Information regarding numerous types of cancer can be found, e.g., from the American Cancer Society, or from, e.g., Wilson et al. (1991) Harrison's Principles of Internal Medicine, 12th Edition, McGraw-Hill, Inc. Both human and veterinary uses are contemplated.

Cancers which are particularly amenable to treatment by the compounds and methods of the invention include but are not limited to gliomas, medulloblastomas, primitive neuroectodermal tumors (PNETS), basal cell carcinoma (BCC), small cell lung cancers, large cell lung cancers, tumors of the gastrointestinal tract, rhabdomyosarcomas, soft tissue sarcomas, pancreatic tumors, bladder tumors and prostate tumors.

As used herein, the term "malignant hyperproliferative disorder(s)" includes but is not limited to cancers, neuronal proliferative disorders, bone marrow proliferative diseases and leukemias.

As used herein, the term "non-malignant hyperproliferative disorder(s)" includes but is not limited to non-malignant and non-neoplastic proliferative disorders, such as smooth muscle hyperplasia in blood vessels, cutaneous scarring, and pulmonary fibrosis.

As used herein, the term "aryl" is defined as an aromatic radical having 6 to 14 ring carbon atoms, and no ring heteroatoms. The aryl group may be monocyclic or fused bicyclic or tricyclic. It may be unsubstituted or substituted by one or more, preferably one or two, substituents, wherein the substituents are as described herein. As defined herein, the aryl moiety may be completely aromatic regardless of whether it is monocyclic or bicyclic. However, if it contains more than one ring, as defined herein, the term aryl includes moieties wherein at least one ring is completely aromatic while the other ring(s) may be partially unsaturated or saturated or completely aromatic.

"Het" as used herein, refers to heteroaryl and heterocyclic compounds containing at least one S, O or N ring heteroatom. More specifically, "Het" is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S. Examples of het, as used herein, include but are not limited to unsubstituted and substituted pyrrolidyl, tetrahydrofuryl, tetrahydrothiofuryl, piperidyl, piperazyl, purinyl, tetrahydropyranyl, morpholino, 1,3-diazapanyl, 1,4-diazapanyl, 1,4-oxazepanyl, 1,4-oxathiapanyl, furyl, thienyl, pyrryl, pyrrolyl, pyrazolyl, triazolyl, tetrazolyl, indazolyl, oxadiazolyl, imidazolyl, pyrrolidyl, pyrrolidinyl, thiazolyl, oxazolyl, pyridyl, pyrazolyl, pyrazinyl, pyrimidinyl, isoxazolyl, pyrazinyl, quinolyl, isoquinolyl, pyridopyrazinyl, pyrrolopyridyl, furopyridyl, indolyl, benzofuryl, benzothiofuryl, benzoindolyl, benzothienyl, pyrazolyl, piperidyl, piperazinyl, indolinyl, morpholinyl, benzoxazolyl, pyrroloquinolyl, pyrrolo[2,3-b]pyridinyl, benzotriazolyl, oxobenzo-oxazolyl, benco[1,3]dioxolyl, benxzoimidazolyl, quinolinyl, indanyl and the like. Heteroaryls are within the scope of the definition of het. Examples of heteroaryls are pyridyl, pyrimidinyl, quinolyl, thiazolyl and benzothiazolyl.

The most preferred het are pyridyl, pyrimidinyl and thiazolyl. The het may be unsubstituted or substituted as described herein. It is unsubstituted or if substituted it is substituted on a carbon atom by halogen, especially fluorine or chlorine, hydroxy, $C_1$-$C_4$ alkyl, such as methyl and ethyl, $C_1$-$C_4$ alkoxy, especially methoxy and ethoxy, nitro, —O—C(O)—$C_1$-$C_4$alkyl or C(O)—O—$C_1$-$C_4$alkyl, SCN or nitro or on a nitrogen atom by $C_1$-$C_4$ alkyl, especially methyl or ethyl, —O—C(O)—$C_1$-$C_4$alkyl or C(O)—O—$C_1$-$C_4$alkyl, such as carbomethoxy or carboethoxy.

When two substituents together with a commonly bound nitrogen are het, it is understood that the resulting heterocyclic ring is a nitrogen-containing ring, such as aziridine, azetidine, azole, piperidine, piperazine, morphiline, pyrrole, pyrazole, thiazole, oxazole, pyridine, pyrimidine, isoxazole, and the like, wherein such het may be unsubstituted or substituted as defined hereinabove.

As used herein, "halo" means halogen, and includes fluorine, chlorine, bromine or iodine, especially fluorine and chlorine.

Unless otherwise specified "alkyl", either above or in combination, includes straight or branched chain alkyl, such as methyl, ethyl, n-propyl, isopropyl, n-butyl, sec-butyl, tert-butyl, n-pentyl and branched pentyl, n-hexyl and branched hexyl, and the like.

A "cycloalkyl" group means $C_3$ to $C_{10}$ cycloalkyl having 3 to 10 ring carbon atoms and may be, for example, cyclopropyl, cyclobutyl, cyclopentyl, cyclohexyl, cycloheptyl or cyclooctyl, cyclononyl and the like. The cycloalkyl group may be monocyclic or fused bicyclic. Moreover, the preferred cycloalkyl group is cyclopentyl or cyclohexyl. Most preferably, cycloalkyl is cyclohexyl. The cycloalkyl group may be fully saturated or partially unsaturated, although it is preferred that it is fully saturated. As defined herein, it excludes aryl groups. The cycloalkyl groups may be unsubstituted or substituted with any of the substituents defined below, preferably halo, hydroxy or $C_1$-$C_6$ alkyl such as methyl.

Unsubstituted is intended to mean that hydrogen is the only substituent.

Except as described herein, any of the above defined aryl, het, alkyl, alkenyl, alkynyl, or cycloalkyl, may be unsubstituted or independently substituted by up to four, preferably one, two or three substituents, selected from the group consisting of: halo (such as Cl or Br); hydroxy; lower alkyl (such as $C_1$-$C_3$ alkyl); lower alkyl which may be substituted with any of the substituents defined herein; lower alkenyl; lower alkynyl; lower alkanoyl; lower alkoxy (such as methoxy); aryl (such as phenyl or naphthyl); substituted aryl (such as fluoro phenyl or methoxy phenyl); aryl lower alkyl such as benzyl, amino, mono or di-lower alkyl (such as dimethylamino); lower alkanoyl amino acetylamino; amino lower alkoxy (such as ethoxyamine); nitro; cyano; cyano lower alkyl; carboxy; lower carbalkoxy (such as methoxy carbonyl; n-propoxy carbonyl or iso-propoxy carbonyl), lower aryloyl, such as benzoyl; carbamoyl; N-mono- or N,N di-lower alkyl carbamoyl; lower alkyl carbamic acid ester; amidino; guanidine; ureido; mercapto; sulfo; lower alkylthio; sulfoamino; sulfonamide; benzosulfonamide; sulfonate; sulfanyl lower alkyl (such as methyl sulfanyl); sulfoamino; aryl sulfonamide; halogen substituted or unsubstituted aryl sulfonate (such as chloro-phenyl sulfonate); lower alkylsulfinyl; aryl-sulfinyl; aryl-lower alkylsulfinyl; lower alkylarylsulfinyl; lower alkanesulfonyl; arylsulfonyl; aryl-lower alkylsulfonyl; lower aryl alkyl; lower alkylarylsulfonyl; halogen-lower alkylmercapto; halogen-lower alkylsulfonyl; such as trifluoromethane sulfonyl; phosphono (—P(=O)(OH)$_2$); hydroxy-lower alkoxy phosphoryl or di-lower alkoxy-phosphoryl; urea and substituted urea; alkyl carbamic acid ester or carbamates (such as ethyl-N-phenyl-carbamate); or lower alkyl (e.g. methyl, ethyl or propyl).

In an embodiment, the above mentioned alkyl, cycloalkyl, and aryl groups are independently unsubstituted or are substituted by lower alkyl, aryl, aryl lower alkyl, carboxy, lower carbalkoxy and especially halogen, —OH, —SH, —OCH$_3$, —SCH$_3$, —CN, —SCN or nitro.

As defined herein the term "lower alkyl", when used alone or in combination refers to alkyl containing 1-6 carbon atoms. The alkyl group may be branched or straight-chained, and is as defined hereinabove.

The term "lower alkenyl" refers to a alkenyl group which contains 2-6 carbon atoms. An alkenyl group is a hydrocarbyl group containing at least one carbon-carbon double bond. As defined herein, it may be unsubstituted or substituted with the substituents described herein. The carbon-carbon double bonds may be between any two carbon atoms of the alkenyl group. It is preferred that it contains 1 or 2 carbon-carbon double bonds and more preferably one carbon-carbon double bond. The alkenyl group may be straight chained or branched. Examples include but are not limited to ethenyl, 1-propenyl, 2-propenyl, 1-butenyl, 2-butenyl, 2-methyl-1-propenyl, 1,3-butadienyl, and the like.

The term "lower alkynyl", as used herein, refers to an alkynyl group containing 2-6 carbon atoms. An alkynyl group is a hydrocarbyl group containing at least one carbon-carbon triple bond. The carbon-carbon triple bond may be between any two carbon atom of the alkynyl group. In an embodiment, the alkynyl group contains 1 or 2 carbon-carbon triple bonds and more preferably one carbon-carbon triple bond. The alkynyl group may be straight chained or branched. Examples include but are not limited to ethynyl, 1-propynyl, 2-propynyl, 1-butynyl, 2-butynyl and the like.

As used herein, the term "aryl alkyl" refers to a aryl group connected to the main chain by a bridging alkylene group. Examples include but are not limited to benzyl, phenethyl, naphthylmethyl, and the like. Similarly, cyano alkyl group refers to a cyano group connected to the main chain by a bridging alkylene group.

The term "alkyl aryl" on the other hand, refers to an alkyl group bridged to the main chain through a phenylene group. Examples include but are not limited to methylphenyl, ethylphenyl, and the like.

As used herein, the term lower alkanoyl refers to a lower alkyl chain in which one of the carbon atoms is replaced by a C=O group. The C=O group may be present at one of the ends of the substituent or in the middle of the moiety. Examples include but are not limited to formyl, acetyl, 2-propanoyl, 1-propanoyl and the like.

The term "alkoxy" refers to an alkyl group as defined herein, connected to the main chain by an oxygen atom. Examples include but are not limited to methoxy, ethoxy, and the like.

The term "carbalkoxy" refers to an alkoxycarbonyl group, where the attachment to the main chain is through the carbonyl group (C(O)). Examples include but are not limited to methoxy carbonyl, ethoxy carbonyl, and the like.

As used herein, "oxo" refers to a double-bonded oxygen (i.e., =O). It is also to be understood that the terminology C(O) refers to a C=O group, whether it be ketone, aldehyde or acid or acid derivative. Similarly, S(O) refers to a S=O group.

Pharmaceutically acceptable salts of any acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly acid addition salts, such as of mineral acids, organic carboxylic, and organic sulfonic acids e.g., hydrochloric acid, methanesulfonic acid, maleic acid, are possible provided a basic group, such as amino or pyridyl, constitutes part of the structure.

The present invention relates to the discovery that signal transduction pathways regulated by Hh and/or Smo can be modulated by the compounds of the invention.

In one embodiment, the compounds and methods of the present invention comprise compounds of formula (I) for inhibiting Smo-dependent pathway activation. Another aspect of the present invention includes compounds and methods for inhibiting Hedgehog (ligand)-independent pathway activation. In certain embodiments, the present compounds and methods can be used to counteract the phenotypic effects of unwanted activation of a Hedgehog pathway, such as resulting from Hedgehog gain-of-function, Ptc loss-of-function or smoothened gain-of-function mutations. For instance, the subject compounds and method can involve contacting a cell (in vitro or in vivo) with a Smo antagonist, such as a compound of Formula (I) in an amount sufficient to antagonize a smoothened-dependent and/or Hedgehog independent activation pathway.

In one embodiment, the compounds of the invention (e.g., compounds of Formula I) inhibit Hh signaling by locking the three dimensional structure of the Smo protein in an inactive conformation or preventing Smo from adopting an active conformation. In another embodiment, the compounds of the invention (e.g., compounds of Formula I) inhibit Hh signaling by preventing endogenous activating ligands for Smo from binding to or activating Smo (i.e., acting via negative cooperativity with endogenous agonists). In another embodiment, the compounds of the invention (e.g., compounds of Formula I) inhibit Hh signaling by increasing binding of endogenous inactivating ligands for Smo from binding to or inactivating Smo (i.e., acting via positive cooperativity with endogeous antagonist).

In another embodiment, the compounds of the invention (e.g., compounds of Formula I) inhibit Hh signaling by preventing Smo from localizing to the plasma membrane. In another embodiment, the compounds of the invention (e.g., compounds of Formula I) inhibit Hh signaling by preventing signaling from Ptch to Smo, in the presence or absence of Hh ligand. In another embodiment, the compounds of the invention (e.g., compounds of Formula I) inhibit Hh signaling by preventing the stabilization of Smo. In another embodiment, the compounds of the invention (e.g., compounds of Formula I) inhibit Hh signaling by preventing the phosphorylation of Smo on activating sites. In another embodiment, the compounds of the invention (e.g., compounds of Formula I) inhibit Hh signaling by increasing the phosphorylation of Smo on inhibitory sites.

In still another embodiment, the compounds of the invention (e.g., compounds of Formula I) inhibit Hh signaling by preventing Smo from activating downstream targets, such as transcription factor Gli. In another embodiment, the compounds of the invention (e.g., compounds of Formula I) inhibit Hh signaling by effecting the inactivation, sequestration, and/or degradation of Smo.

In another embodiment, the methods of the present invention may be used to regulate proliferation and/or differentiation of cells in vitro and/or in vivo, e.g., in the formation of tissue from stem cells, or to prevent the growth of hyperproliferative cells. In another particular embodiment, contacting the cell with—or introducing into the cell—a compound of the invention (e.g., a compound of Formula I) results in inhibition of cellular proliferation, inhibition of cancer/tumor cell growth and/or survival, and/or inhibition of tumorigenesis. Thus, another particular embodiment provides methods for inhibition and/or antagonism of the Hh pathway by employing compounds of the invention (e.g., a compound of Formula I) in a tumor cell.

In yet another embodiment, the methods of the present invention employ compounds of the invention (e.g., a compound of Formula I) as formulated as a pharmaceutical preparation comprising a pharmaceutically acceptable excipient or carrier, and said preparations may be administered to a patient to treat conditions involving unwanted cell proliferation such as cancers and/or tumors (such as medulloblastoma, basal cell carcinoma, etc.), and non-malignant hyperproliferative disorders.

One embodiment of the present invention provides a method for inhibiting the synthesis, expression, production, and/or activity of a Smo protein in a cell in vitro or in vivo comprising, contacting said cell with, or introducing into said cell, a compound of the invention (e.g., a compound of Formula I).

Another embodiment of the invention provides a method of diagnosing, preventing and/or treating cellular debilitations, derangements, and/or dysfunctions; hyperplastic, hyperproliferative and/or cancerous disease states; and/or metastasis of tumor cells, in a mammal characterized by the presence and/or expression of a Smo gene or gene product (e.g., a Smo protein), comprising administering to a mammal a therapeutically effective amount of an agent that inhibits or antagonizes the synthesis and/or expression and/or activity of a compound of the invention (e.g., a compound of Formula I).

It is, therefore, specifically contemplated that compounds of Formula I which interfere with aspects of Hh, Ptc, or smoothened signal transduction activity will likewise be capable of inhibiting proliferation (or other biological consequences) in normal cells and/or cells having a patched loss-of-function phenotype, a Hedgehog gain-of-function phenotype, a smoothened gain-of-function phenotype or a Gli gain-of-function phenotype. Thus, it is contemplated that in certain embodiments, these compounds may be useful for inhibiting Hedgehog activity in normal cells, e.g., which do not have a genetic mutation that activates the Hedgehog pathway. In preferred embodiments, the compounds are capable of inhibiting at least some of the biological activities of Hedgehog proteins, preferably specifically in target cells.

Thus, the methods of the present invention include the use of compounds of Formula I which agonize Ptc inhibition of Hedgehog signaling, such as by inhibiting activation of smoothened or downstream components of the signal pathway, in the regulation of repair and/or functional performance of a wide range of cells, tissues and organs, including normal cells, tissues, and organs, as well as those having the phenotype of Ptc loss-of-function, Hedgehog gain-of-function, smoothened gain-of-function or Gli gain-of-function. For instance, the subject method has therapeutic and cosmetic applications ranging from regulation of neural tissues, bone and cartilage formation and repair, regulation of spermatogenesis, regulation of benign prostate hyperplasia, regulation of blood vessel formation in wet macular degeneration, psoriasis, regulation of smooth muscle, regulation of lung, liver and other organs arising from the primitive gut, regulation of hematopoietic function, regulation of skin and hair growth, etc. Moreover, the subject methods can be performed on cells which are provided in culture (in vitro), or on cells in a whole animal (in vivo).

In certain embodiments, a compound of Formula I can inhibit activation of a Hedgehog pathway by binding to smoothened or its downstream proteins.

In another embodiment, the present invention provides the use of pharmaceutical preparations comprising, as an active ingredient, a Hedgehog signaling modulator such as a compound of Formula I, a smoothened antagonist such as described herein, formulated in an amount sufficient to inhibit, in vivo, proliferation or other biological consequences of Ptc loss-of-function, Hedgehog gain-of-function, smoothened gain-of-function or Gli gain-of-function.

The treatment of subjects by administering compounds of the invention (e.g., compounds of Formula I) can be effective for both human and animal subjects. Animal subjects to which the invention is applicable extend to both domestic animals and livestock, raised either as pets or for commercial purposes. Examples are dogs, cats, cattle, horses, sheep, hogs, goats, and llamas.

The present invention also makes available methods and compounds for inhibiting activation of the Hedgehog signaling pathway, e.g., to inhibit normal but undesired growth states, for example benign prostate hyperplasia or blood vessel formation in wet macular degeneration, resulting from physiological activation of the Hedgehog signaling pathway, comprising contacting the cell with a compound of Formula I, in a sufficient amount to antagonize smoothened activity, or antagonize Gli activity, e.g., to reverse or control the normal growth state.

The present invention makes available methods and compounds for inhibiting activation of the Hedgehog signaling pathway, e.g., to inhibit aberrant growth states resulting from phenotypes such as Ptc loss-of-function, Hedgehog gain-of-function, smoothened gain-of-function or Gli gain-of-function, comprising contacting the cell with a compound of Formula I, in a sufficient amount to antagonize smoothened activity, or antagonize Gli activity e.g., to reverse or control the aberrant growth state.

Members of the Hedgehog family of signaling molecules mediate many important short- and long-range patterning processes during vertebrate development. Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation. The effects of developmental cell interactions are varied: responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation.

The vertebrate family of Hedgehog genes includes three members that exist in mammals, known as Desert (Dhh), Sonic (Shh) and Indian (Ihh) Hedgehogs, all of which encode secreted proteins. These various Hedgehog proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule which becomes covalently bound to the C-terminal end of the N-peptide, tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities.

Smoothened (Smo) encodes a 1024 amino acid transmembrane protein that acts as a transducer of the Hedgehog (Hh) signal. Smo protein has 7 hydrophobic membrane-spanning domains, an extracellular amino-terminal region, and an intracellular carboxy-terminal region. Smo bears some similarity to G protein-coupled receptors and is most homologous to the Frizzled (Fz) family of serpentine proteins. (Alcedo et al. (1996) Cell 86: 221)

An inactive Hedgehog signaling pathway is where the transmembrane protein receptor Patched (Ptc) inhibits the stabilization, phosphorylation, and activity of Smoothened (Smo). The transcription factor Gli, a downstream component of Hh signaling, is prevented from entering the nucleus through interactions with cytoplasmic proteins, including Fused (Fu) and Suppressor of fused (Sufu). As a consequence, transcriptional activation of Hedgehog target genes is repressed. Activation of the pathway is initiated through binding of any of the three mammalian ligands (Dhh, Shh or Ihh) to Ptc.

Ligand binding by Hh alters the interaction of Smo and Ptc, reversing the repression of Smo, whereupon Smo moves from internal structures within the cell to the plasma membrane. The localization of Smo to the plasma membrane triggers activation of Hh pathway target genes in an Hh-independent manner. (Zhu et al. (2003) Genes Dev. 17(10):1240) The cascade activated by Smo leads to the translocation of the active form of the transcription factor Gli to the nucleus. The activation of Smo, through translocated nuclear Gli, activates Hh pathway target gene expression, including of Wnts, TGFβ, and Ptc and Gli themselves.

Increased levels of Hedgehog signaling are sufficient to initiate cancer formation and are required for tumor survival. These cancers include, but are not limited to, prostate cancer (Karhadkar et al. (2004) Nature 431:707; Sanchez et al. (2004) PNAS 101(34):12561), breast cancer (Kubo et al. (2004) Cancer Res. 64(17):6071), medulloblastoma (Berman et al. (2002) Science 297(5586):1559), basal cell carcinoma (BCC) (Williams et al. (2003) PNAS 100(8):4616); Xie et al. (1998) Nature 391(6662):90), pancreatic cancer (Thayer et al. (2003) Nature 425(6960):851; Berman et al. (2003) Nature 425(6960):846), small-cell lung cancer (Watkins et al. (2003) Nature 422(6929):313), glioma (Kinzler et al. (1988) Nature 332:371), cancers of the digestive tract (Berman et al. (2003) Nature 425(6960):846) and esophageal cancers (Ma et al. (2006) Int J Cancer 118(1):139.

In accordance with the foregoing, the present invention further provides a method for preventing or treating any of the diseases or disorders described above in a subject in need of such treatment, which method comprises administering to said subject a therapeutically effective amount of a compound of the invention (e.g., a compound of Formula I) or a pharmaceutically acceptable salt thereof. For any of the above uses, the required dosage will vary depending on the mode of administration, the particular condition to be treated and the effect desired.

Human patients with Gorlin's syndrome, a hereditary syndrome with high risk of skin and brain cancers, also known as Basal Cell Nevus Syndrome (BCNS) develop basal cell carcinoma (BCC) with high frequency, and other solid tumors (e.g., meduloblastomas) at lower frequency, due to germline loss of function mutations in Ptch. These patients, as well as other, non-Gorlin's patients with BCC who have somatic loss of function mutations in Ptch, are would not be expected to respond to treatments associated with Hedgehog ligands. They would, however, respond to inhibitors of Hh signaling downstream from the Hh ligands, such as the compounds of the invention (e.g., a compound of Formula I), which can act as Smo inhibitors. Similarly, other solid tumors due to patched or Smo mutations will not respond to Hh ligand-related inhibition but will respond to Smo blockade (e.g., by administration of the compounds of the invention).

Administration and Pharmaceutical Compositions

The invention relates to the use of pharmaceutical compositions comprising compounds of Formula (I) in the therapeutic (and, in a broader aspect of the invention, prophylactic) treatment of a Hedgehog-related disorder(s).

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions.

The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with immunomodulatory or anti-inflammatory substances or other anti-tumor therapeutic agents. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

Representative examples of synthesis of the compounds of the invention, e.g., compounds of Formula (I), can be found in the Examples section of the present application.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

EXAMPLES

The present invention is further exemplified, but not limited, by the following representative examples, which are intended to illustrate the invention and are not to be construed as being limitations thereon. The structure of final products described herein can be confirmed by standard analytical methods, e.g., spectrometric and spectroscopic methods (e.g. MS, NMR). Abbreviations used are those conventional in the art. Compounds are purified by standard methods, e.g. crystallization, flash chromatography or reversed phase HPLC.

The following abbreviations will be used throughout the examples:

LIST OF ABBREVIATIONS

BINAP (±)-(1,1'-binaphthalene-2-2'diyl)bis(diphenylphosphine)
DCM Dichloromethane
DIEA Diethylamine
DIPEA Diisoproylethylamine
DMF Dimethylformamide
HPLC High pressure liquid chromatography
HR MS High resolution mass spectrometry
HBTU O-Benzotriazol-1-yl-N,N,N',N'-tetramethyluronium hexafluorophosphate
HOBt 1-Hydroxy-1H-benzotriazol
LC/MS Liquid chromatography/mass spectrometry
NMM N-methylmorpholine
NMP N-methylpyrrolidine
RT room temperature
THF Tetrahydrofuran
Compound Synthesis
Phthalazines As illustrated in Scheme 1, compounds of Formula Ia,b,c can be prepared either via Route A, i.e., chloride displacement from an intermediate of Type II with a substituted amine, or via an intermediate of Type III utilizing either Route B (direct nucleophilic displacement) or Route C (Buchwald amination conditions).

SCHEME 1.

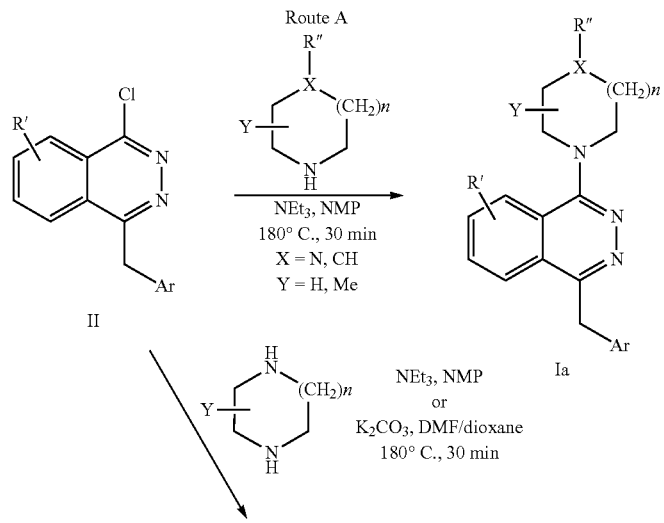

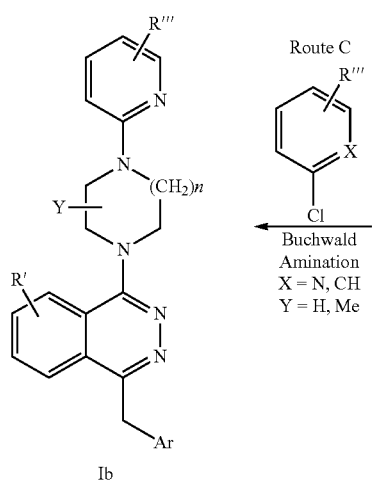

Ib

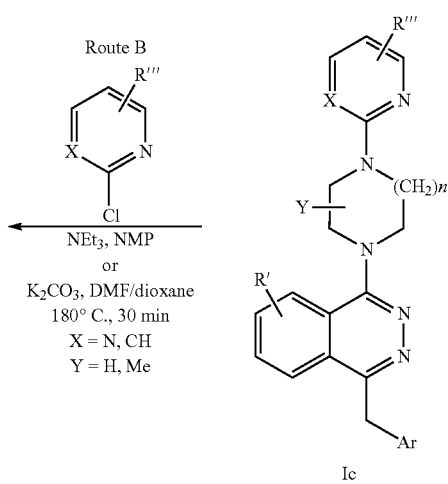

Ic

Synthesis of Intermediates

1-Chloro-4-(3,5-dichloro-benzyl)-phthalazine (Compound 1)

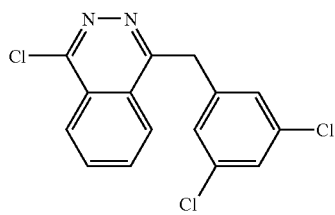 [SMILES: Clc1cc(Cl)cc(Cc2nnc(Cl)c3ccccc23)c1]

In a 50 mL round-bottom flask 4-(3,5-dichlorobenzyl)-4-phthalazin-1-one (200 mg, 0.655 mmol, 1 eq) is dissolved in dichloroethane (5 ml), and DIEA is added (101 ul, 0.721, 1.1 eq), followed by the slow addition of $POCl_3$ (67.9 ul, 0.721 mmol, 1.1 equiv). The reaction is stirred and refluxed for 12 h at 60° C. upon which the solution is cooled on ice and treated with a saturated solution of sodium bicarbonate (5 mL) Dichloromethane (2×10 mL) is added and is washed with water (10 mL). The combined organic fractions are dried over magnesium sulfate and concentrated under reduced pressure. The residue is triturated with ethyl acetate and is dried under high vacuum to afford the product as a white powder (222 mg, 44% yield).

1-(5-(Dimethylphosphoryl)pyridin-2-yl)piperazine (Compound 2)

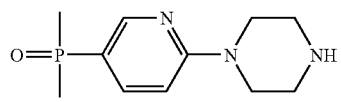

To a solution of tert-butyl 4-(5-bromopyridin-2-yl)piperazine-1-carboxylate (250 mg, 0.730 mmol) in 2.5 mL anhydrous THF was added 2.5 M n-butyllithium (320 µL, 0.80 mmol) at −78° C. under nitrogen atmosphere. After stirring for 45 mins, the reaction mixture was charged with dimethyl phosphinic chloride (164.4 mg, 1.46 mmol) in 1 mL anhydrous THF. The reaction mixture was warmed to −30° C. over 3 h. The mixture was quenched with saturated ammonium chloride aqueous solution and the mixture was partitioned between DCM and brine. The organic layer was dried over $Na_2SO_4$ and concentrated to afford the crude material. The resulting solid was purified by flash chromatography on silica gel, eluting with 20-100% EtOAc:heptane. Fractions containing the desired product were combined and concentrated to afford an off white solid (100 mg, 40.3% yield). The Boc protected title compound was dissolved in 2-PrOH (1 mL) and charged with 4 N HCl. The reaction mixture was heated at 70° C. for 30 min, and concentrated to afford the titled product as a HCl salt.

MS (m/z, MH+): meas. 240.2 calc. 240.3

2,2,2-Trifluoro-1-(6-(piperazin-1-yl)pyridin-3-yl)ethanol (Compound 3)

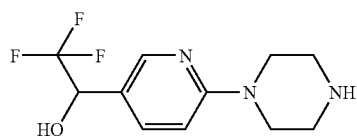 [SMILES: OC(c1ccc(N2CCNCC2)nc1)C(F)(F)F]

Trifluorooacetaldehyde hydrate (1.7 g, 14.6 mmol) was added dropwise into a stirred mixture consisting of phosphorus pentoxide (1 g, 7.3 mmol) and 4 mL of concentrated sulfuric acid at 95° C. The freshly produced gaseous trifluoroacetaldehyde was trapped with a dry ice-filled cold finger and dripped into a THF solution of tert-butyl 4-(5-bromopyridin-2-yl)piperazine-1-carboxylate (1 g, 2.92 mmol) with 2.5 M n-butyllithium in hexanes (1.3 mL, 3.2 mmol) at −78° C. under nitrogen atmosphere. After addition, the reaction mixture was warmed to room temperature and stirred for 2 h. The mixture was quenched with saturated ammonium chloride aqueous solution at −78° C. and the mixture was partitioned between DCM and brine. The organic layer was dried over $Na_2SO_4$ and concentrated to afford a brown solid. The crude material was purified by flash chromatography on silica gel, eluting with 10-80% EtOAc:heptane. Fractions containing the desired product were combined and concentrated to afford yellow sticky solid (450 mg, 42.6% yield). The Boc protected titled compound (380 mg, 1.1 mmol) was stirred in 20% TFA in DCM (5 mL) for 10 min. The reaction mixture was concentrated to afford the titled product as a TFA salt (260 mg, yield 95%).

MS (m/z, MH+): meas. 262.2 calc. 262.25

1,1,1,3,3,3-Hexafluoro-2-(6-(piperazin-1-yl)pyridin-3-yl)propan-2-ol (Compound 4)

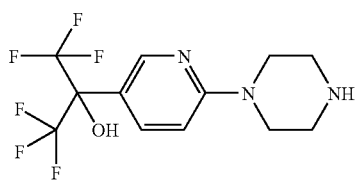 [SMILES: OC(c1ccc(N2CCNCC2)nc1)(C(F)(F)F)C(F)(F)F]

The gaseous trifluoroacetaldehyde was trapped with the dry ice-filled cold finger and dripped into a THF solution of 4-(5-bromo-pyridin-2-yl)-piperazine-1-carboxylic acid tent-butyl ester (1 g, 2.92 mmol) with 2.5 M n-butyllithium in hexanes (1.29 mL, 3.2 mmol) at −78° C. under nitrogen atmosphere. After addition, the reaction mixture was warmed to room temperature and stirred for 1 h. The mixture was quenched with saturated ammonium chloride aqueous solution at −78° C. and the mixture was partitioned between DCM and brine. The organic layer was dried over $Na_2SO_4$ and concentrated to afford a light yellow solid. The crude material was purified by flash chromatography on silica gel, eluting with 10-80% EtOAc:heptane. Fractions containing the desired product were combined and concentrated to afford a colorless sticky solid (450 mg, 35.9% yield). The Boc protected titled compound (200 mg, 0.466 mmol) was stirred in 50% TFA in DCM (5 mL) for 10 min. The reaction mixture was concentrated to afford the titled product as a TFA salt (150 mg, yield 98%).

MS (m/z, MH+): meas. 330.0 calc. 329.25

3-(6-(piperazin-1-yl)pyridin-3-yl)oxetan-3-ol (Compound 5)

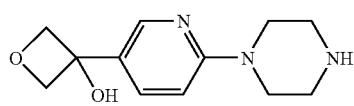

To a solution of 4-(5-bromo-pyridin-2-yl)-piperazine-1-carboxylic acid tert-butyl ester (250 mg, 0.73 mmol) in 3.5 mL anhydrous THF was added 1.6 M n-butyllithium (500 μL, 0.80 mmol) at −78° C. under nitrogen atmosphere. After stirring for 45 min, the reaction mixture was charged with oxetan-3-one (131 mg, 1.82 mmol) in 200 μL DCM. The reaction mixture was stirred at −78° C. for 2 h and at room temperature for 16 h. The mixture was quenched with saturated ammonium chloride aqueous solution and the mixture was partitioned between DCM and brine. The organic layer was dried over $Na_2SO_4$ and concentrated to afford the crude material. The resulting solid was purified by flash chromatography on silica gel, eluting with 20-100% EtOAc:heptane. Fractions containing the desired product were combined and concentrated to afford a off white solid (80 mg, 32.7% yield). The Boc protected title compound (140 mg, 0.417 mmol) was dissolved in DCM and charged with lutidine (194 μL, 1.67 mmol). The reaction mixture was cooled at 0° C., charged with trimethylsilyl trifluoromethanesulfonate (1.25 mmol, 228 uL) and stirred at 0° C. for 2 h. The reaction mixture was poured into ice and the mixture was partitioned between DCM and water. The organic layer was dried over $Na_2SO_4$ and concentrated to afford a brown greasy solid (70 mg, yield 71%).

MS (m/z, MH+): meas. 236.4 calc. 236.3

6-((S)-3-Methyl-piperazin-1-yl)-nicotinonitrile (Compound 6)

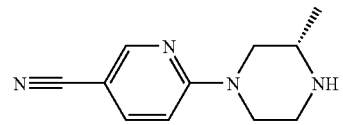

Triethylamine (4.13 g, 3 mL, 40.8 mmol, 4 eq) is added to a solution of 6-chloro-nicotinonitrile (1.38 g, 10 mmol, 1 eq), (S)-2-methyl-piperazine (1.00 g, 10 mmol, 1 eq) in DMF (15 mL), and the resulting solution is stirred at rt for 14 h. A white precipitate of triethylamine hydrochloride forms in the course of the reaction. Water (15 mL) and EtOAc (100 mL) are added, the organic layer is separated, dried over sodium sulfate and concentrated under reduced pressure to a white residue. The solid is further dried under high vacuum to yield the desired product as a white solid (1.4 g, 69%).

$^1$H NMR (400 MHz, CHLOROFORM-d) δ ppm 8.38 (s, 1H), 7.58 (d, J=9.60 Hz, 1H), 6.59 (d, J=9.09 Hz, 1H), 4.19-4.31 (m, 2H), 3.08-3.15 (m, 1H), 2.92-3.04 (m, 1H), 2.81-2.91 (m, 2H), 2.57-2.65 (m, 1H), 1.15 (d, J=6.32 Hz, 3H).

6-((R)-3-Methyl-piperazin-1-yl)-nicotinonitrile (Compound 7)

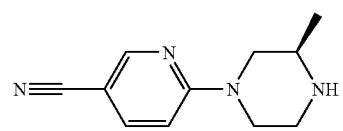

Triethylamine (5.51 g, 4 mL, 54.6 mmol, 2.7 eq) is added to a solution of 6-chloro-nicotinonitrile (2.76 g, 20 mmol, 1 eq), (R)-2-methyl-piperazine (2.00 g, 20 mmol, 1 eq) in DMF (15 mL), and the resulting solution is stirred at rt for 36 h. A white precipitate of triethylamine hydrochloride forms in the course of the reaction. Water (15 mL) and EtOAc (100 mL) are added, the organic layer is separated, dried over sodium sulfate and concentrated under reduced pressure to a white residue. The solid is further dried under high vacuum to yield the desired product as a white solid (2.3 g, 59%).

1H NMR (400 MHz, CHLOROFORM-d) δ ppm 8.32 (d, J=2.40 Hz, 1H), 7.52 (dd, J=9.09, 2.27 Hz, 1H), 6.52 (d, J=8.97 Hz, 1H), 4.14-4.24 (m, 2H), 3.01-3.07 (m, 1H), 2.72-2.94 (m, 3H), 2.52 (dd, J=12.76, 10.36 Hz, 1H), 1.07 (d, J=6.32 Hz, 3H).

6-((2R,5S)-2,5-Dimethyl-piperazin-1-yl)-nicotinonitrile (Compound 8)

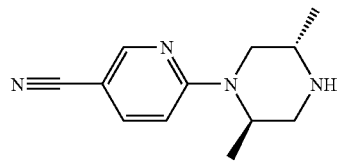 [SMILES: C[C@@H]1CN[C@@H](C)CN1c1ccc(C#N)cn1]

Combine (2S,5R)-2,5-dimethyl-piperazine (200 mg, 1.75 mmol), 6-chloro-nicotinonitrile (1.75 mmol) and triethylamine (5.25 mmol) in a 0.875 M solution of 1-methyl-2-pyrrolidinone. Microwave reaction mixture for 30 min at 150° C. Partition between ethyl acetate and water, collecting organic phase. Wash aqueous layer again with ethyl acetate and combine organics. Dry with sodium sulfate, filter and concentrate. Purify on preparative HPLC to give the title compound. (9% yield)
1H NMR (400 MHz, CHLOROFORM-d) δ ppm 8.32 (d, J=2.15 Hz, 1H), 7.51 (dd, J=9.09, 2.40 Hz, 1H), 6.46 (d, J=9.09 Hz, 1H), 4.24-4.37 (m, 1H), 3.87 (d, J=10.99 Hz, 1H), 3.19-3.36 (m, 3H), 2.61 (dd, J=13.07, 3.09 Hz, 1H), 1.48 (br. s., 1H), 1.20 (d, J=6.69 Hz, 3H), 1.12 (d, J=6.82 Hz, 3H).

1-Benzyl-4-piperazin-1-yl-phthalazine (Compound 9)

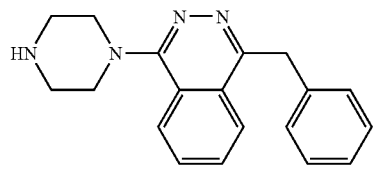 [SMILES: c1ccc(Cc2nnc(N3CCNCC3)c3ccccc23)cc1]

1-Benzyl-4-chlorophthalazine (1.06 g, 4.18 mmol) and piperazine (1.82 g, 20.9 mmol) are added into a microwave vial, followed by NMP (5 ml) and triethylamine (6.62 ml, 12.5 mmol). The vial is sealed and irradiated in the microwave at 180° C. (high absorption setting) for 30 minutes. Dichloromethane (10 mL) is added to form a precipitate, which is washed with additional dichloromethane and dried under reduced pressure to afford the product as a white powder (745 mg, 58% yield).

1-Benzyl-4-[1,4]diazepam-1-yl-phthalazine (Compound 10)

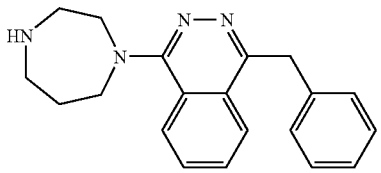 [SMILES: c1ccc(Cc2nnc(N3CCCNCC3)c3ccccc23)cc1]

1-Benzyl-4-chlorophthalazine (1.11 g, 4.35 mmol) and homopiperazine (2.20 g, 21.7 mmol) are added into a microwave vial, followed by NMP (5 ml) and triethylamine (1.84 mL, 13.1 mmol). The vial is sealed and irradiated in the microwave at 180° C. (high absorption setting) for 30 min. Dichloromethane is added and is washed with water. The combined organic fractions are dried over magnesium sulfate, and are evaporated under reduced pressure to afford the title compound as a yellow oil (640 mg, 41.5% yield).

1-Benzyl-4-((R)-3-methyl-piperazin-1-yl)-phthalazine (Compound 11)

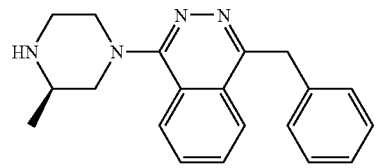 [SMILES: C[C@@H]1CN(c2nnc(Cc3ccccc3)c3ccccc23)CCN1]

Solid Na₂CO₃ (200 mg, 1.9 mmol, 1.9 eq) is added to a solution of 1-benzyl-4-chlorophthalazine (250 mg, 0.98 mmol, 1 eq) and (R)-2-methyl-piperazine (400 mg, 4.0 mmol, 4.0 eq) in dioxane (5 mL) in a microwave vial. The vial is sealed and irradiated in the microwave at 150° C. (high absorption setting) for 30 minutes. The reaction mixture is filtered and concentrated, then diluted with EtOAc (50 mL) and water (15 mL). The organic fraction washed with water and then brine, then is dried over sodium sulfate. The solvent is evaporated under reduced pressure to afford the title compound as a white solid (180 mg, 58% yield).
1H NMR (400 MHz, CHLOROFORM-d) δ ppm 8.08 (d, J=7.07 Hz, 1H) 8.00 (d, J=7.71 Hz, 1H) 7.69-7.79 (m, 2H) 7.34-7.39 (m, 2H) 7.25-7.32 (m, 2H) 7.20 (d, J=7.20 Hz, 1H) 4.61-4.65 (m, 2H) 3.76-3.82 (m, 2H) 3.13-3.30 (m, 4H) 2.85 (dd, J=12.63, 10.23 Hz, 1H) 1.17 (d, J=6.32 Hz, 3H)
MS (m/z, MH+): meas. 319.1

1-Benzyl-4-((S)-3-methyl-piperazin-1-yl)-phthalazine (Compound 12)

Solid Na₂CO₃ (400 mg, 3.8 mmol, 3.8 eq) is added to a solution of 1-benzyl-4-chlorophthalazine (250 mg, 0.98 mmol, 1 eq) and (S)-2-methyl-piperazine (400 mg, 4.0 mmol, 4.0 eq) in dioxane (5 mL). The resulting suspension is heated at 100° C. for 48 h. The reaction mixture is concentrated, EtOAc (50 mL) and water (15 mL) are added. The organic fraction washed with water and then brine, then is dried over sodium sulfate. The solvent is evaporated under reduced pressure to afford the title compound as a white solid (200 mg, 64% yield).
1H NMR (400 MHz, CHLOROFORM-d) δ ppm 7.97 (d, J=7.07 Hz, 1H) 7.89 (d, J=8.21 Hz, 1H) 7.58-7.68 (m, 2H) 7.24-7.28 (m, 2H) 7.14-7.22 (m, 2H) 7.06-7.11 (m, 1H) 3.69 (d, J=12.38 Hz, 2H) 3.61 (s, 2H) 3.03-3.20 (m, 4H) 2.74 (dd, J=12.63, 10.23 Hz, 1H) 1.07 (d, J=6.32 Hz, 3H)
MS (m/z, MH+): meas. 319.1

2-Chloro-pyrimidine-5-carbonitrile (Compound 13)

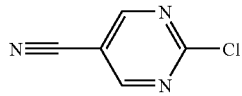

(Prepared according to: Organic Synthesis, Vol 4, p. 182.) In a 3-necked, round-bottom flask is placed 5.4 mL of concentrated HCl (65 mmol). The solution is cooled to 0° C. and 2-amino-5-cyanopyrimidine (515 mg, 4.28 mmol) is added portion wise with stirring until a homogeneous solution is obtained. The solution is then cooled to −15° C. A 100 mL addition funnel is fitted to the flask and a cold solution of NaNO$_2$ (592 mg, 8.6 mmol) in 5 ml of water is then added dropwise with stirring over period of 20 min. (The temperature is kept at −15 to −10° C.) The solution is stirred an additional hour and the temperature is allowed to rise to −5. At this point, the mixture is carefully neutralized to about pH 7 with a 30% solution of NaOH, taking care that the temperature does not rise above 0° C. The solution is extracted with EtOAc (3×20 ml), dried over MgSO$_4$, filtered and evaporated to give a yellow solid (159 mg, 21.3% yield).

1-(6-Chloropyridin-3-yl)pyrrolidin-2-one (Compound 14)

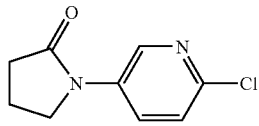 [SMILES: O=C1CCCN1c1ccc(Cl)nc1]

To a solution of 2-chloro-5-iodopyridine (200 mg, 0.84 mmol) in 4 mL anhydrous dioxane was added 2-pyrrolidinone (60.8 μL, 0.79 mmol), K$_2$CO$_3$ (415.6 mg, 3 mmol), CuI (15.9 mg, 0.084 mmol), and N,N'-dimethyl-1,2-ethanediamine (11.8 μL, 0.083 mmol) in a 2 dram screw-top vial. The vial is evacuated and flushed with nitrogen. The reaction mixture was heated to reflux for 18 h. The reaction mixture was filtered through celite and filtrate was concentrated to afford the crude material. The mixture was purified by flash chromatography on silica gel, eluting with 50-100% EtOAc: heptane. Fractions containing the desired products were combined and concentrated to afford the desired product as a white solid (160 mg, yield: 97.4%).

MS (m/z, MH+): meas. 197.1 calc. 197.64

1-(6-Chloropyridin-3-yl)cyclopropanol (Compound 15)

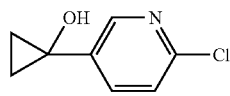

To a suspension of methyl 6-chloropyridine-3-carboxylate (1 g, 5.83 mmol) in 17 mL anhydrous ether was charged with 3 M ethyl magnesium bromide (8.5 mL, 26 mmol) in ether and stirred for 1 h before the addition of titanium isopropoxide (1.73 mL, 5.84 mmol) to the reaction mixture. The mixture was stirred for 16 h under nitrogen atmosphere. The mixture was quenched with saturated ammonium chloride aqueous solution and aqueous phase was adjusted to pH 3 with 1 N HCl. The mixture was partitioned between DCM and brine. The organic layer was dried over Na$_2$SO$_4$ and concentrated to afford the crude material. The resulting solid was purified by flash chromatography on silica gel, eluting with 10-80% EtOAc:heptane. Fractions containing the desired product were combined and concentrated to afford a brown greasy solid (180 mg, yield: 18.2%).

MS (m/z, MH+): meas. 170.1 calc. 170.61

2-(4-tert-Butoxycarbonyl-piperazin-1-yl)-pyrimidine-5-carboxylic acid (Compound 16)

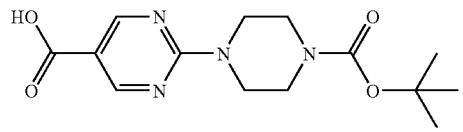

5-Bromo-2-(4-Boc-piperazin-1-yl)-pyrimidine (1.00 g, 2.91 mmol) is added to a dry 250-mL 3-necked round-bottom flask under N2 followed by THF (20.0 mL). A low temperature thermometer is inserted. Flask is kept in a dry ice bath for 15 min to reach the internal temperature −74° C. and n-BuLi (2.92 mL, 7.29 mmol) is added dropwise. The reaction is stirred for 1.5 h, and then CO$_2$ is bubbled into the reaction mixture for 45 min while keeping the internal temperature at −70° C. Reaction mixture is then taken out of the bath and allowed to come to 0° C., at which point it is quenched with water. The organics are extracted with dichloromethane. The combined organic layers are washed with brine and dried over Na$_2$SO$_4$, filtered and concentrated under reduced pressure. The crude compound is triturated with dichloromethane and methanol to afford some pure product. The impure material is purified via flash chromatography on silica gel (0-20% methanol in CH$_2$Cl$_2$) to afford the title compound (235 mg, 27% yield).

2-(4-tert-Butoxycarbonyl-piperazin-1-yl)-pyrimidine-5-carboxylic acid methyl ester (Compound 17)

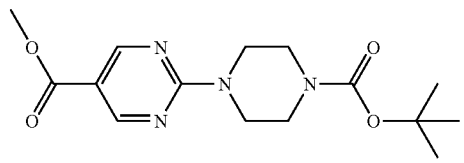

To 2-(4-tert-Butoxycarbonyl-piperazin-1-yl)-pyrimidine-5-carboxylic acid (150 mg, 0.486 mmol) in an oven dried round-bottom flask is added methanol (1.0 mL) and benzene (3.7 mL) under nitrogen, and the reaction stirred for 10 min. Trimethylsilyldiazomethane (0.34 ml, 0.678 mmol) is added and the reaction stirred for 1 h. Glacial acetic acid (0.05 ml) is then added until the yellow color has disappeared. The reaction mixture is concentrated under reduced pressure and co-evaporated with benzene. It is dried under high vacuum to yield the title compound as a white solid (155 mg, 99% yield).

2-piperazin-1-yl-pyrimidine-5-carboxylic acid methyl ester (Compound 18)

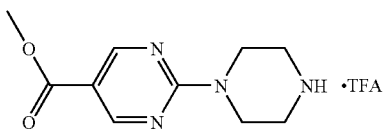 [SMILES: COC(=O)c1cnc(N2CCNCC2)nc1]

2-(4-tert-Butoxycarbonyl-piperazin-1-yl)-pyrimidine-5-carboxylic acid methyl ester (140 mg, 0.434 mmol) is dissolved in dichloromethane (3.0 mL) under N2. Trifluoroacetic acid (0.83 ml, 10.85 mmol) is added and the reaction mixture is stirred for 2 h. The reaction mixture is concentrated under reduced pressure and co-evaporated several times with dichloromethane. It is dried under high vacuum to afford the title compound as a TFA salt (130 mg, 90% yield).

6-Hydroxymethyl-nicotinic acid methyl ester (Compound 19)

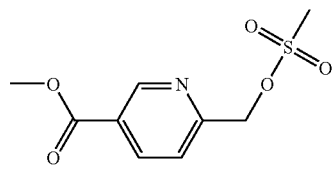 [SMILES: COC(=O)c1ccc(COS(C)(=O)=O)nc1]

Methyl-6-(hydroxymethyl)nicotinate (500 mg, 2.99 mmol) is added to an oven dried round-bottom flask under N2 followed by dichloromethane (20.0 mL). Triethylamine (2.85 mL, 20.93 mmol) is added and then the flask is kept in an ice bath for 50 min. Methanesulfonylchloride (0.81 mL, 10.47 mmol) is added drop-wise. The reaction is stirred for 45 min at low temperature and then stirred at room temperature overnight. The reaction mixture is then poured into ice water. The organics are extracted with dichloromethane. The combined organic layers are washed with brine and dried over $Na_2SO_4$, filtered and concentrated under reduced pressure. It is further dried on high vacuum to give to afford the title compound (365 mg, 50% yield).

Synthesis of Examples 1-38 Via Route A

General Protocol for the Addition of Amines to 1-chlorophthalazines

The desired 1-chlorophthalazine (2 mmol, 1 eq) and amine (2.6 mmol, 1.3 eq) are added to a microwave vial equipped with a stir bar. NMP (3 ml) is added followed by triethylamine (3.2 mL, 6 mmol, 3 eq). The vial is sealed and irradiated in the microwave at 180° C. (high absorption setting) for 30 minutes. Water (50 mL) is then added to the reaction mixture to form a precipitate which is isolated by filtration, washed with additional cold water, and then dried in vacuo. The products are further purified by either flash chromatography on silica gel or reverse phase HPLC.

Example 1

6-[4-(4-Benzyl-phthalazin-1-yl)-piperazin-1-yl]-nicotinonitrile

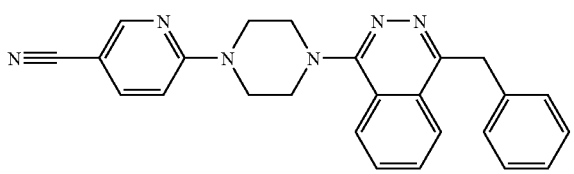

Following the general protocol, 1-benzyl-4-chlorophthalazine (515 mg, 2.02 mmol, 1 eq) and 6-piperazino-nicotinitrile (495 mg, 2.63 mmol, 1.3 eq) afford 430 mg of desired product as a white solid (51% yield).

$^1$H NMR (400 MHz, CDCl$_3$): δ=3.65 (m, 4H), 3.96 (m, 4H), 4.64 (s, 2H), 6.71 (d, J=9 Hz, 1H), 7.19 (t, J=7 Hz, 1H), 7.27 (t, J=7 Hz, 2H), 7.33-7.36 (m, 2H), 7.67 (dd, J=9, 2 Hz, 1H), 7.73-7.82 (m, 2H), 8.02-8.12 (m, 2H), 8.45 (d, J=2.53 Hz, 1H).

HR-MS (m/z, MH+): meas. 407.1987

Examples 2-38, 106-119

The following table (Table 1) lists examples of compounds prepared by Route A in a similar fashion to that described above.

TABLE 1

| Example | Structure | MS [m/z; M + 1] |
|---|---|---|
| 2 | 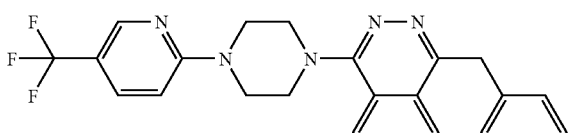 | 450 |
| 3 | 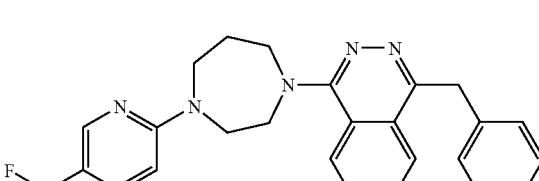 | 464 |

TABLE 1-continued
| Example | Structure | MS [m/z; M + 1] |
|---|---|---|
| 4 | 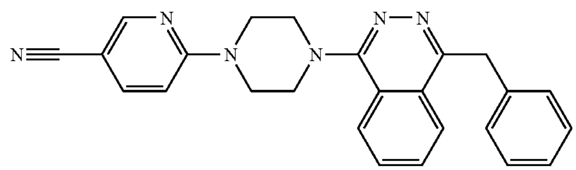 [SMILES: N#Cc1ccc(N2CCN(c3nnc(Cc4ccccc4)c4ccccc34)CC2)nc1] | 408 |
| 5 | 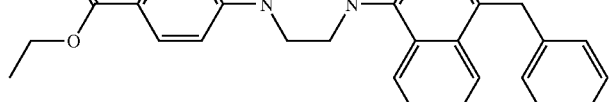 | 453 |
| 6 | 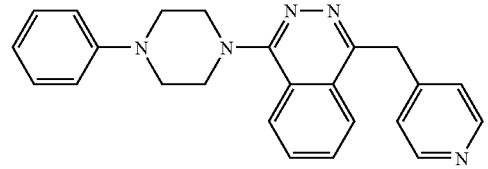 | 382 |
| 7 | 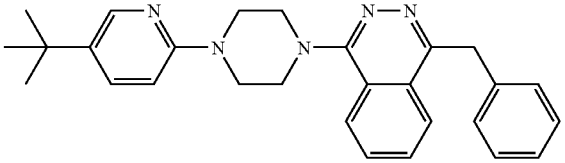 | 437 |
| 8 | 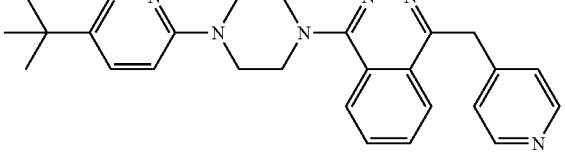 | 438 |
| 9 | 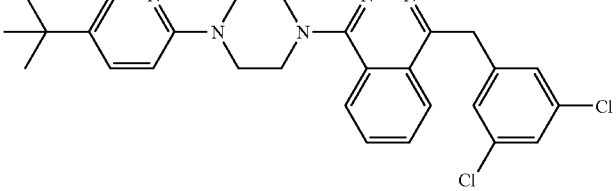 | 506 |
| 10 | 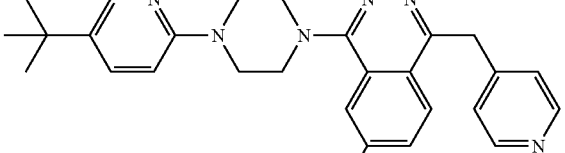 | 452 |
| 11 | 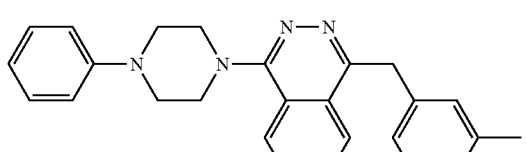 | 396 |

TABLE 1-continued

| Example | Structure | MS [m/z; M + 1] |
|---------|-----------|-----------------|
| 12 | 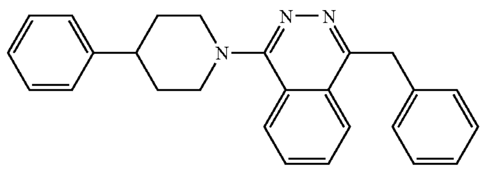 | 380 |
| 13 | 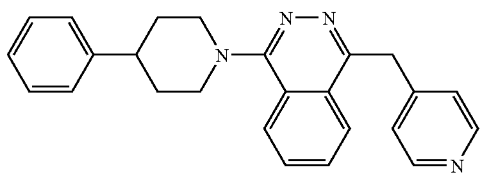 | 381 |
| 14 | 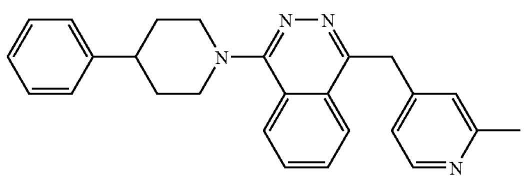 [SMILES: Cc1cc(Cc2nnc(N3CCN(c4ccccc4)CC3)c3ccccc23)ccn1] | 395 |
| 15 | 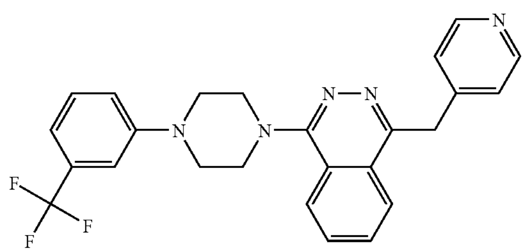 [SMILES: FC(F)(F)c1cccc(N2CCN(c3nnc(Cc4ccncc4)c4ccccc34)CC2)c1] | 450 |
| 16 | 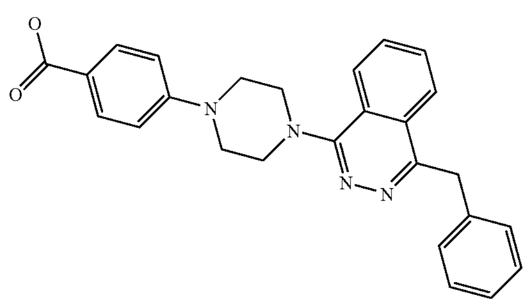 [SMILES: O=C(O)c1ccc(N2CCN(c3nnc(Cc4ccccc4)c4ccccc34)CC2)cc1] | 425 |
| 17 | 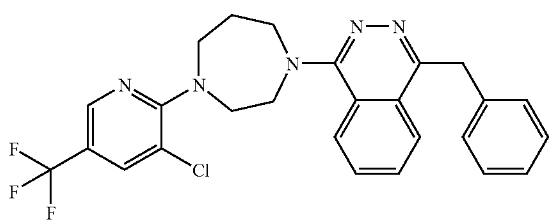 [SMILES: FC(F)(F)c1cnc(N2CCCN(c3nnc(Cc4ccccc4)c4ccccc34)CC2)c(Cl)c1] | 498 |
| 18 | 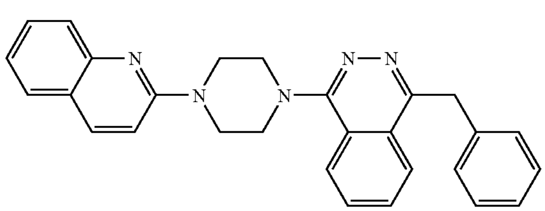 [SMILES: c1ccc(Cc2nnc(N3CCN(c4ccc5ccccc5n4)CC3)c3ccccc23)cc1] | 432 |

TABLE 1-continued

| Example | Structure | MS [m/z; M + 1] |
|---|---|---|
| 19 | 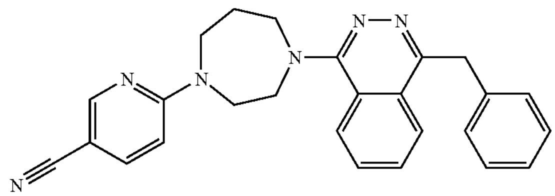 [SMILES: N#Cc1ccc(N2CCCN(c3nnc(Cc4ccccc4)c4ccccc34)CC2)nc1] | 421 |
| 20 | 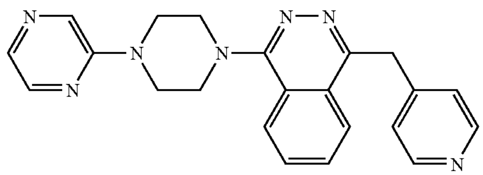 | 384 |
| 21 | 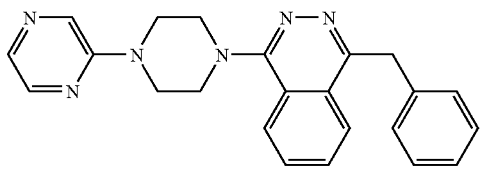 [SMILES: c1ccc(Cc2nnc(N3CCN(c4cnccn4)CC3)c3ccccc23)cc1] | 383 |
| 22 | 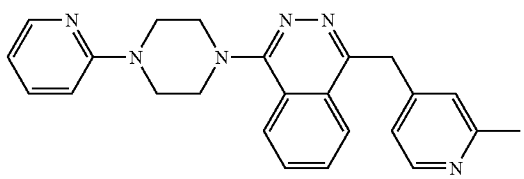 | 397 |
| 23 | 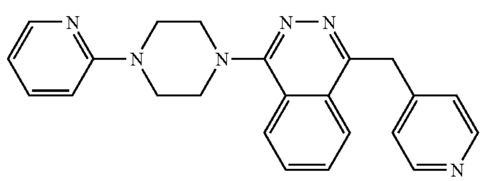 [SMILES: c1ccc(N2CCN(c3nnc(Cc4ccncc4)c4ccccc34)CC2)nc1] | 383 |
| 24 | 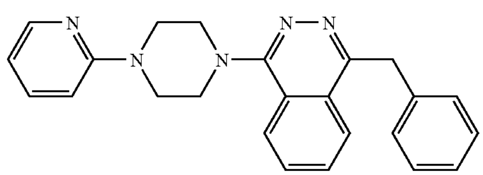 [SMILES: c1ccc(Cc2nnc(N3CCN(c4ccccn4)CC3)c3ccccc23)cc1] | 382 |
| 25 | 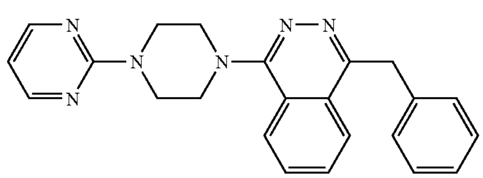 [SMILES: c1ccc(Cc2nnc(N3CCN(c4ncccn4)CC3)c3ccccc23)cc1] | 383 |
| 26 | 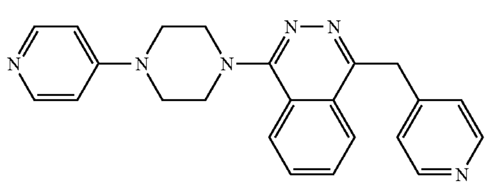 [SMILES: c1ccc2c(N3CCN(c4ccncc4)CC3)nnc(Cc3ccncc3)c2c1] | 383 |

TABLE 1-continued

| Example | Structure | MS [m/z; M + 1] |
|---|---|---|
| 27 | 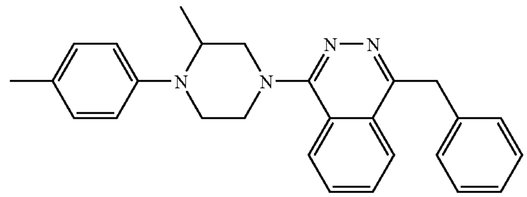 [SMILES: Cc1ccc(N2CCN(c3nnc(Cc4ccccc4)c4ccccc34)CC2C)cc1] | 409 |
| 28 | 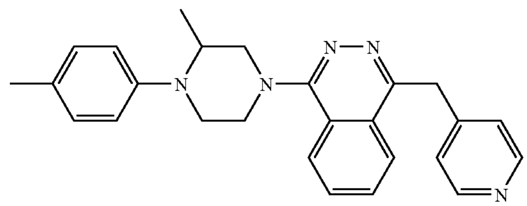 [SMILES: Cc1ccc(N2CCN(c3nnc(Cc4ccncc4)c4ccccc34)CC2C)cc1] | 410 |
| 29 | 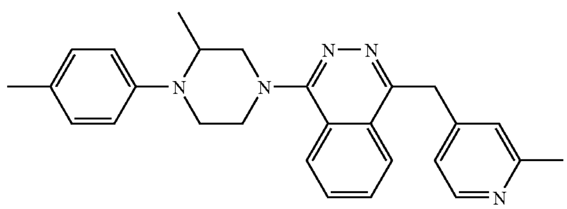 | 424 |
| 30 | 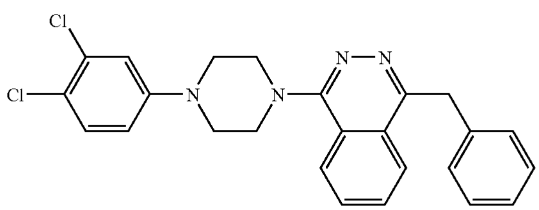 [SMILES: Clc1ccc(N2CCN(c3nnc(Cc4ccccc4)c4ccccc34)CC2)cc1Cl] | 450 |
| 31 | 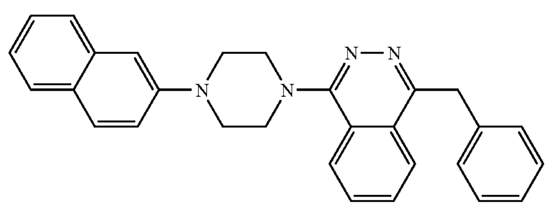 [SMILES: c1ccc(Cc2nnc(N3CCN(c4ccc5ccccc5c4)CC3)c3ccccc23)cc1] | 431 |
| 32 | 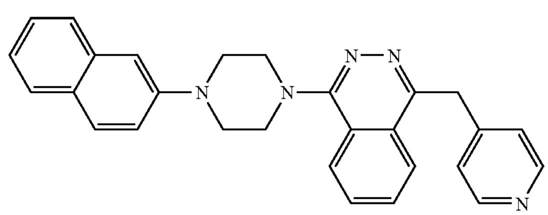 [SMILES: c1ccc2cc(N3CCN(c4nnc(Cc5ccncc5)c5ccccc45)CC3)ccc2c1] | 432 |
| 33 | 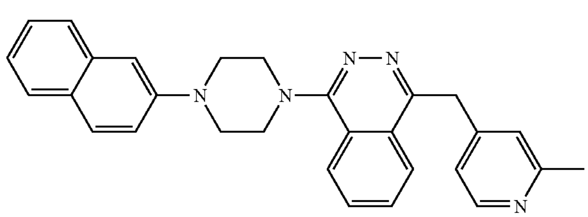 [SMILES: Cc1cc(Cc2nnc(N3CCN(c4ccc5ccccc5c4)CC3)c3ccccc23)ccn1] | 446 |

TABLE 1-continued

| Example | Structure | MS [m/z; M + 1] |
|---|---|---|
| 34 | 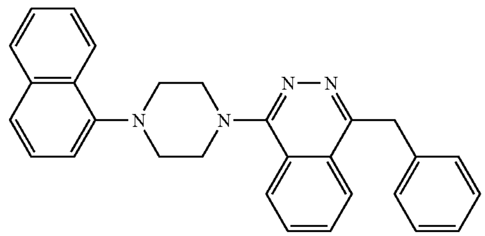 [SMILES: c1ccc(Cc2nnc(N3CCN(c4cccc5ccccc45)CC3)c3ccccc23)cc1] | 431 |
| 35 | 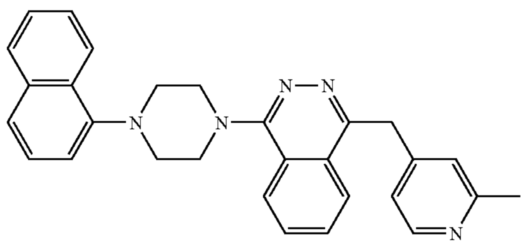 [SMILES: Cc1cc(Cc2nnc(N3CCN(c4cccc5ccccc45)CC3)c3ccccc23)ccn1] | 446 |
| 36 | 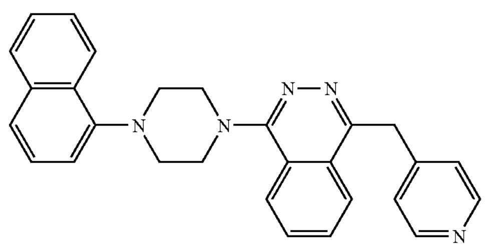 [SMILES: c1ccc2c(N3CCN(c4nnc(Cc5ccncc5)c5ccccc45)CC3)cccc2c1] | 432 |
| 37 | 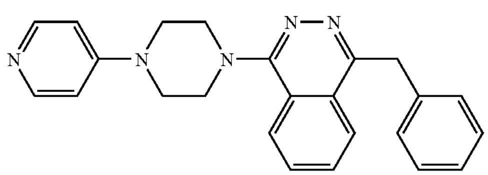 [SMILES: c1ccc(Cc2nnc(N3CCN(c4ccncc4)CC3)c3ccccc23)cc1] | 382 |
| 38 | 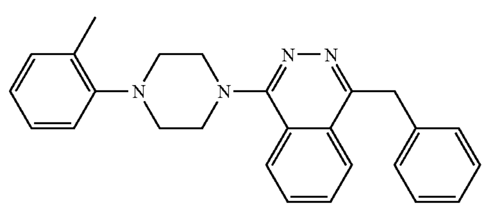 [SMILES: Cc1ccccc1N1CCN(c2nnc(Cc3ccccc3)c3ccccc23)CC1] | 395 |
| 106 | 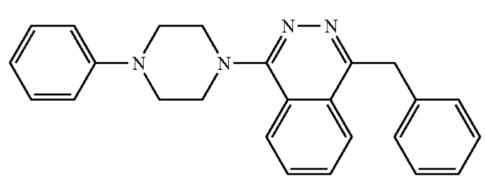 | 381 |
| 107 | 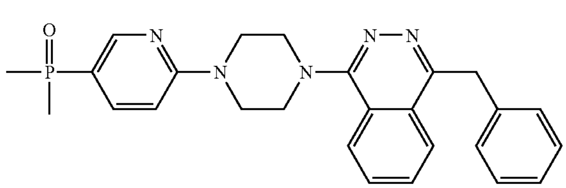 [SMILES: CP(C)(=O)c1ccc(N2CCN(c3nnc(Cc4ccccc4)c4ccccc34)CC2)nc1] | 458 |

TABLE 1-continued
| Example | Structure | MS [m/z; M + 1] |
|---|---|---|
| 108 | 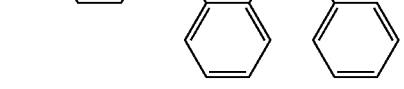 | 395 |
| 109 | 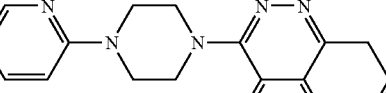 | 480 |
| 110 | 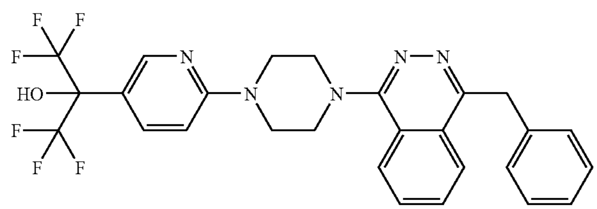 [SMILES: OC(c1ccc(N2CCN(c3nnc(Cc4ccccc4)c4ccccc34)CC2)nc1)(C(F)(F)F)C(F)(F)F] | 548 |
| 111 | 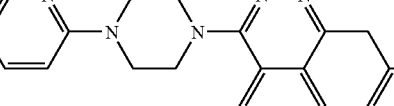 | 454 |
| 112 | 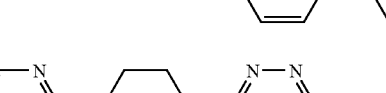 | 438 |
| 113 | 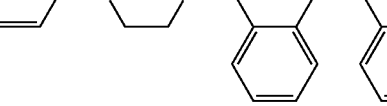 | 419 |
| 114 | 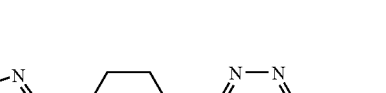 | 420 |
| 115 | 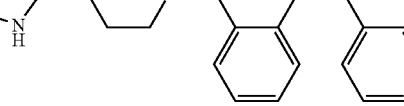 | 438 |

TABLE 1-continued

| Example | Structure | MS [m/z; M + 1] |
|---|---|---|
| 116 | 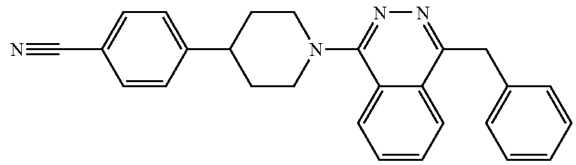 [SMILES: N#Cc1ccc(C2CCN(c3nnc(Cc4ccccc4)c4ccccc34)CC2)cc1] | 405 |
| 117 | 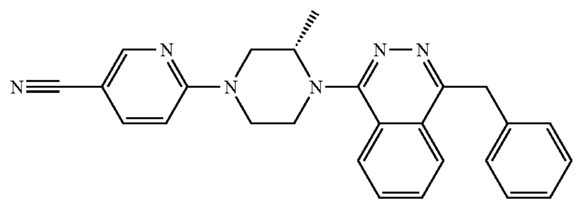 [SMILES: C[C@H]1CN(c2ccc(C#N)cn2)CCN1c1nnc(Cc2ccccc2)c2ccccc12] | 421 |
| 118 | 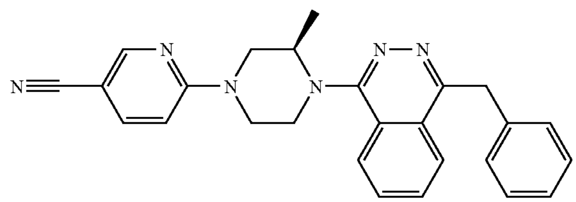 [SMILES: C[C@@H]1CN(c2ccc(C#N)cn2)CCN1c1nnc(Cc2ccccc2)c2ccccc12] | 421 |
| 119 | 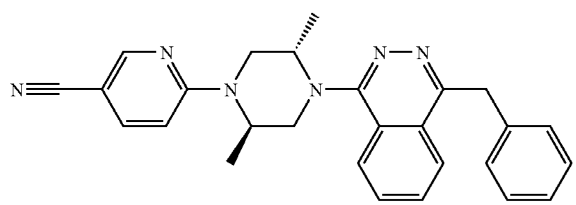 [SMILES: C[C@@H]1CN(c2nnc(Cc3ccccc3)c3ccccc23)[C@@H](C)CN1c1ccc(C#N)cn1] | 435 |

Interconversion of Example 1 into Further Examples by Grignard Addition

Example 120

2-(6-(4-(4-Benzylphthalazin-1-yl)piperazin-1-yl)pyridin-3-yl)propan-2-amine

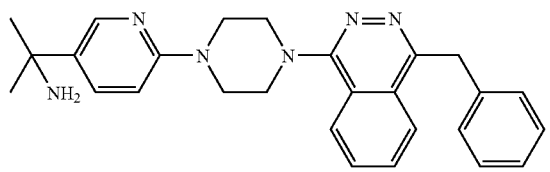 [SMILES: CC(C)(N)c1ccc(N2CCN(c3nnc(Cc4ccccc4)c4ccccc34)CC2)nc1]

Cerium(III) chloride hydrate (454.8 mg, 1.84 mmol) was added into a 40 mL vial and heated to 150 C under high vacuum for 2 h. The hot vial was filled with nitrogen and cooled to room temperature before charging with 2 mL THF. The mixture was stirred for 2 h and charged with 3 M methyl magnesium bromide in THF (0.62 mL, 1.9 mmol) at −78° C. The reaction mixture was stirred for 30 min under nitrogen atmosphere. A THF (1 mL) solution of 1 (250 mg, 0.62 mmol) was added to MeCeCl$_2$ mixture. The reaction was gently warmed to room temperature and continued stirring overnight. The mixture was filtered through celite and evaporated to afford a crude material. The crude material was purified by running through semi-prep HPLC, eluting with 10-100% acetonitrile:water (both mobile phases modified by 3% n-PrOH). Fractions containing the desired product were combined and freeze-dried to afford a white solid (100 mg, yield: 37.2%).

HR-MS (m/z, MH+): meas. 439.2618 calc. 439.2610

Interconversion of Example 120 into Further Examples by Amidation

Example 121

N-(2-(6-(4-(4-Benzylphthalazin-1-yl)piperazin-1-yl)pyridin-3-yl)propan-2-yl)-2-methoxyacetamide

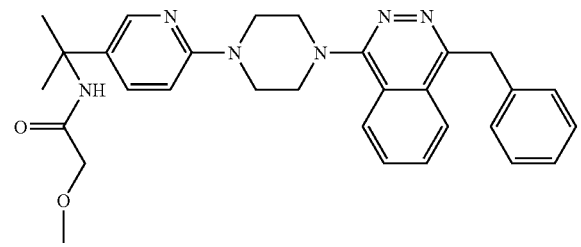 [SMILES: COCC(=O)NC(C)(C)c1ccc(N2CCN(c3nnc(Cc4ccccc4)c4ccccc34)CC2)nc1]

To a solution of 120 (70 mg, 0.16 mmol) in 2 mL anhydrous DCM was added EDC HCl (31 mg, 0.16 mmol), catalytic amount of DMAP and TEA (44 μL, 0.32 mmol). The reaction mixture was stirred at room temperature for 16 h. The mixture was concentrated and the crude material was purified by running through semi-prep HPLC, eluting with 10-100% acetonitrile in water (both mobile phases modified by 3% n-PrOH). Fractions containing the desired product were combined and freeze-dried to afford a white solid (60 mg, yield: 74.1%).

HR-MS (m/z, MH+): meas. 511.2810 calc. 511.2821

Examples 122-123

The following table (Table 1a) lists examples of compounds prepared by amidation in a similar fashion to that described above.

Additional water was added and the organic solvent was extracted with EtOAc. The combined organic layers were washed with aq. NaHCO$_3$ and concentrated. HPLC purification of the crude product with acetonitrile in water (from 10% to 100% with 3% 1-propanol) at 220 nm wavelength detection provided the desired product as a yellow colored powder (54 mg, 54%).

$^1$H NMR (400 MHz, DMSO-d$_6$): δ=8.16 (m, 2H), 7.89 (m, 2H), 7.16-7.44 (m, 9H), 4.59 (s, 2H), 3.89 (d, J=12.6 Hz, 2H), 3.11 (t, J=11.7 Hz, 2H), 2.78 (m, 1H), 2.01 (m, 4H), 1.42 (s, 6H).

HR-MS (m/z, MH+): meas. 438.2546 calc. 438.2545

TABLE 1a

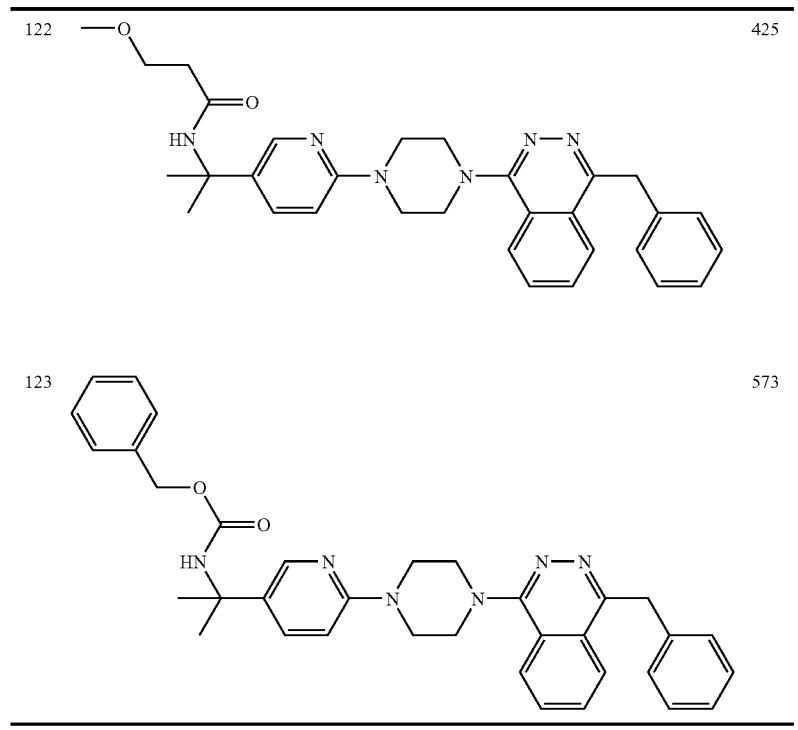

Interconversion of Example 115 into Further Examples by Grignard Addition

Example 124

2-{4-[1-4-Benzyl-phthalazine-1-yl]-piperidine-4-yl}-phenyl}-propan-2-ol

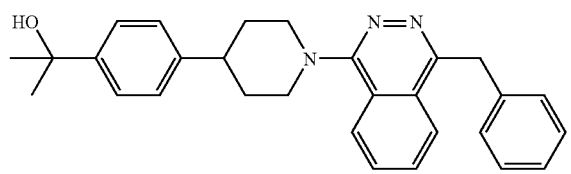 [SMILES: CC(C)(O)c1ccc(C2CCN(c3nnc(Cc4ccccc4)c4ccccc34)CC2)cc1]

To a solution of 115 (100 mg, 0.127 mmol) in THF (5 mL) at −78° C. was added dropwise MeMgBr (85 μL, 3.0 M solution in Et$_2$O, 0.5 mmol). The reaction mixture was stirred at RT for 4 h and quenched with sat. NH$_4$Cl (aq, 3 mL).

Interconversion of Example 116 into Further Examples by Reduction/Acetylation

Example 125

4-[1-(4-Benzyl-phthalazine-1-yl)-piperidine-4-yl]-benzylamine

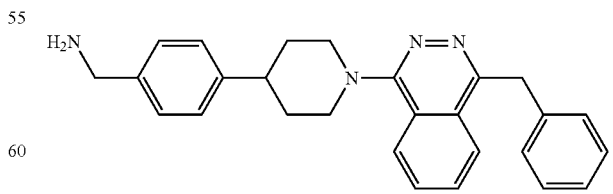

To the solution of 116 (2.5 g, 6.19 mmol) in MeOH was added NiCl$_2$ (962 mg, 7.42 mmol) and NaBH$_4$ (1.17 g, 30.9 mmol) at 0° C. The reaction mixture was warmed up to room temperature for another 10 h, afterwards it was filtered and washed with DCM. The organic layer was removed to afford the crude product. HPLC purification of the crude product with acetonitrile in water (from 10% to 100% with 3% 1-propanol) at 220 nm wavelength detection provided the title compound as a white solid (1.5 g, 59%).

$^1$H NMR (400 MHz, DMSO-$d_6$): δ=8.09 (m, 2H), 7.83 (m, 2H), 7.16-7.44 (m, 9H), 4.51 (s, 2H), 3.83 (d, J=12.6 Hz, 2H), 3.63 (s, 2H), 3.03 (t, J=10.6 Hz, 2H), 2.72 (m, 1H), 1.93 (m, 4H).

MS (m/z, MH+): meas. 408.55

Example 126

N-{4-[1-(4-Benzyl-phthalazine-1-yl)-piperidine-4-yl)-benzyl}-acetamide

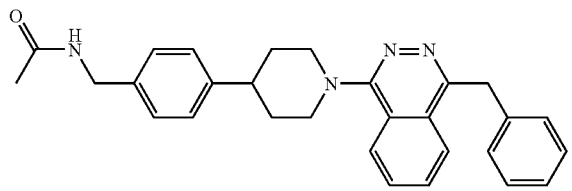 [SMILES: CC(=O)NCc1ccc(C2CCN(c3nnc(Cc4ccccc4)c4ccccc34)CC2)cc1]

To the solution of 125 (60 mg, 0.147 mmol) in MeOH (4 mL) was added acetic anhydride in excess and the reaction mixture was stirred at room temperature for 4 h. The solution was concentrated and washed with DCM, then quenched with aq. NaHCO$_3$. The organic layer was removed to afford crude product. HPLC purification of the crude product with acetonitril in water (from 10% to 100% with 3% 1-propanol) at 220 nm wavelength detection provided the title compound (40 mg, 60%).

$^1$H NMR (400 MHz, DMSO-$d_6$): δ=8.22 (s, 1H), 8.12 (m, 2H), 7.83 (m, 2H), 7.14-7.27 (m, 9H), 4.51 (s, 2H), 4.16 (d, J=5.5 Hz, 2H), 4.82 (d, J=12.1 Hz, 2H), 3.03 (t, J=11.6 Hz, 2H), 2.43 (m, 1H), 1.89 (m, 4H), 1.80 (s, 3H).

HR-MS (m/z, MH+): meas. 451.2479 calc. 451.2498

Example 127

1-Benzyl-4-[4-(4-nitro-phenyl)-piperidine-1-yl]-phthalazine

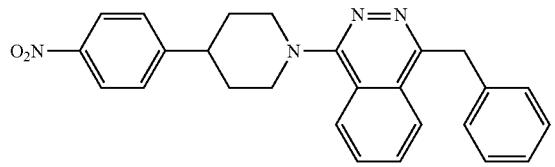

To a solution of 1-benzyl-4-chloro-phthalazine (1.08 g, 4.04 mmol) in 8 mL NMP is added 4-(4-nitro-phenyl)piperidine (1 g, 4.85 mmol), TEA (1.68 mL, 12.12 mmol). The reaction mixture was heated to 150° C. for 45 min in a microwave reactor. Water was added to the reaction mixture to form a precipitate and the solid is collected by filtration and dried under vacuum. The resulting solid is purified by HPLC with acetonitril in water (from 20% to 100% with 3% 1-propanol) at 220 nm wavelength detection to provide the title compound (1.4 g, 78%).

$^1$H NMR (400 MHz, DMSO-$d_6$): δ=8.21 (m, 4H), 7.91 (m, 2H), 7.67 (d, J=8.6 Hz, 2H), 7.16-7.34 (m, 5H), 4.59 (s, 2H), 3.97 (d, J=12.6 Hz, 2H), 3.13 (t, J=10.1 Hz, 2H), 3.02 (m, 1H), 2.05 (m, 4H).

MS (m/z, MH+): meas. 424.50

Example 128

4-[1-(4-benzyl-phthalazine-1-yl)-piperidine-4-yl]-phenylamine

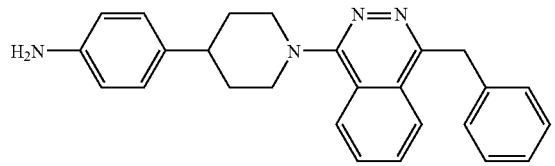 [SMILES: O=[N+]([O-])c1ccc(C2CCN(c3nnc(Cc4ccccc4)c4ccccc34)CC2)cc1]

To the solution of compound 20 (120 mg, 0.269 mmol) in MeOH (8 mL) was added Pd/C (57 mg) and the reaction mixture was stirred under a hydrogen atmosphere at room temperature for 12 h. The reaction mixture was filtered to remove Pd/C and the organic solvent was removed in vacuo to afford crude product. The crude product was purified by HPLC at 220 nm wavelength detection with acetonitrile in water (from 30% to 100% with 3% 1-propanol) to provide the title compound (100 mg, 94%).

$^1$H NMR (400 MHz, DMSO-$d_6$): δ=8.15 (m, 2H), 7.87 (m, 2H), 7.17-7.34 (m, 5H), 7.09 (d, J=8.6 Hz, 2H), 6.54 (d, J=11.6 Hz, 2H), 4.85 (s, 2H), 3.86 (d, J=12.7 Hz, 2H), 3.07 (t, J=5.6 Hz, 2H), 2.65 (m, 1H), 1.90 (m, 4H).

MS (m/z, MH+): meas. 394.52

Example 129

N-{4-[1-(1-(4-Benzyl-phthalazin-1-yl)-piperidin-4-yl)-phenyl]-acetamide

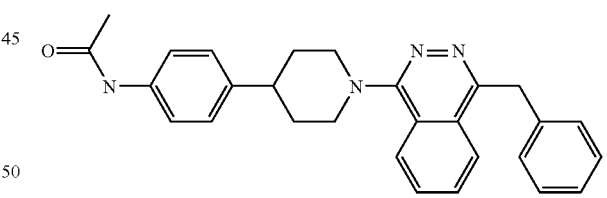

4-[1-(4-Benzyl-phthalazine-1-yl)-piperidine-4-yl]-phenylamine (100 mg, 0.241 mmol), acetyl chloride (23.9 μL, 0.336 mmol) and TEA (62.4 μL, 0.448 mmol) were mixed in DMF (5 mL) and stirred at room temperature for 12 h. The mixture is then filtered over Celite and washed with MeOH. The organic solvent was removed to afford the crude product. HPLC purification of the crude product with acetonitril in water (from 30% to 100% with 3% 1-propanol) at 220 nm wavelength detection provided the title compound (12 mg, 11%).

$^1$H NMR (400 MHz, DMSO-$d_6$): δ=9.86 (s, 1H), 8.13 (m, 2H), 7.91 (m, 2H), 7.18-7.54 (m, 9H), 4.59 (s, 2H), 3.89 (d, J=12.7 Hz, 2H), 3.10 (t, J=10.1 Hz, 2H), 2.77 (m, 1H), 2.01 (s, 3H), 1.99 (m, 4H).

HR-MS (m/z, MH+): meas. 437.2322 calc. 437.2341

Synthesis of Compounds 39-54, 130-147 Via Route B

General Protocol for the Addition of Amines to Heteroaryl Chlorides

The desired amino-phthalazine III (0.33 mmol, 1 eq) and heteroaryl chloride (0.46 mmol, 1.4 eq) are combined in a 2 mL microwave vial. Triethylamine (68 μL, 0.49 mmol, 1.5 eq) and NMP (1 mL) are added. The vial is sealed and irradiated in the microwave (high absorption setting) at 180° C. for 15 min. Water (15 mL) is then added to the reaction mixture to form a precipitate which is isolated by filtration, washed with additional cold water, and then dried in vacuo. The products are further purified by either flash chromatography on silica gel or reverse phase HPLC.

Example 39

2-[4-(4-Benzyl-phthalazin-1-yl)-piperazin-1-yl]-pyrimidine-5-carbonitrile

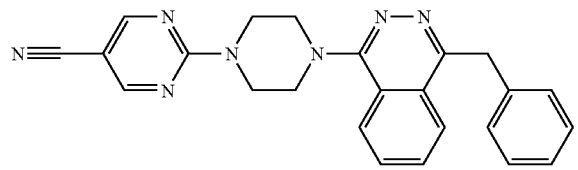

Using the general protocol, 1-benzyl-4-piperazin-1-yl-phthalazine (56 mg, 0.184 mmol) and 2-chloro-5-cyanopyrimidine (44.5 mg, 0.239 mmol) are added into a microwave vial, equipped with a stir bar, and MeCN (0.5 ml) and NMP (0.5 ml) are dispensed. The vial is sealed and the reaction was irradiated at high level absorption in the microwave at 180° C. for 15 min. The product is observed as the main peak (m/z; M+1=408). The compound is purified by preparative HPLC using a C8-254 nm method.

$^1$H NMR (400 MHz, CD$_3$OD): δ=8.70 (s, 2H), 8.51 (t, J=16 Hz, 8 Hz, 2H), 8.19 (m, 2H), 7.36 (m, 4H), 7.36 (m, 1H), 4.78 (s, 2H), 4.29 (t, J=10 Hz, 6 Hz, 4H), 3.92 (t, J=10 Hz, 6 Hz, 4H).

Examples 40-54, 130-141

The following table (Table 2) lists examples of compounds prepared by Route B in a similar fashion to that described above.

TABLE 2

| Example | Structure | MS [m/z; M + 1] |
|---|---|---|
| 40 | 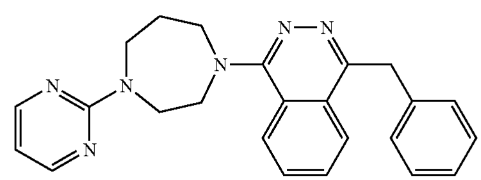 [SMILES: c1ccc(Cc2nnc(N3CCCN(c4ncccn4)CC3)c3ccccc23)cc1] | 397 |
| 41 | 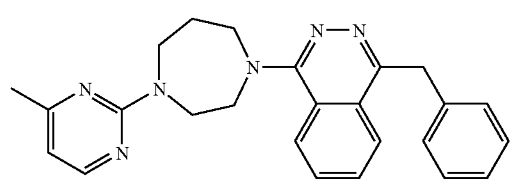 [SMILES: Cc1ccnc(N2CCCN(c3nnc(Cc4ccccc4)c4ccccc34)CC2)n1] | 411 |
| 42 | 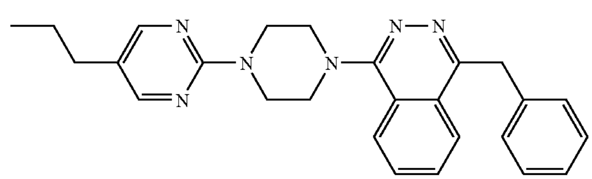 [SMILES: CCCc1cnc(N2CCN(c3nnc(Cc4ccccc4)c4ccccc34)CC2)nc1] | 425 |
| 43 | 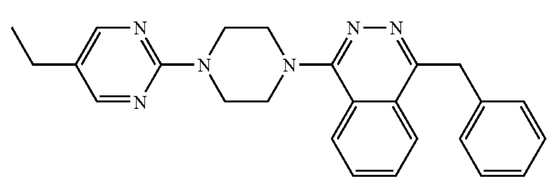 [SMILES: CCc1cnc(N2CCN(c3nnc(Cc4ccccc4)c4ccccc34)CC2)nc1] | 411 |

TABLE 2-continued

| Example | Structure | MS [m/z; M + 1] |
|---|---|---|
| 44 | 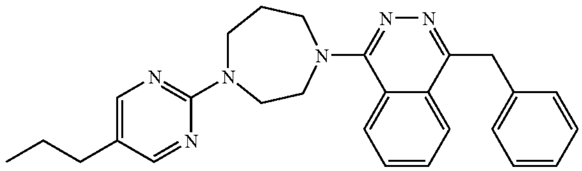 [SMILES: CCCc1cnc(N2CCCN(c3nnc(Cc4ccccc4)c4ccccc34)CC2)nc1] | 439 |
| 45 | 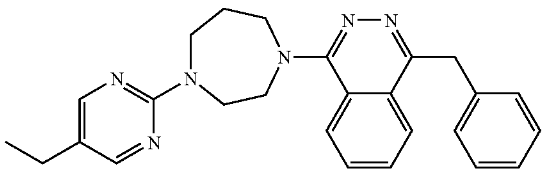 [SMILES: CCc1cnc(N2CCCN(c3nnc(Cc4ccccc4)c4ccccc34)CC2)nc1] | 425 |
| 46 | 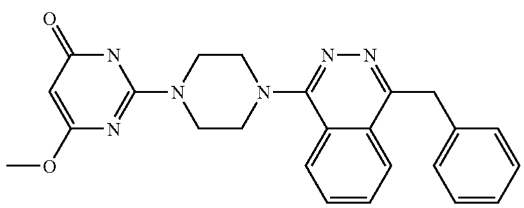 [SMILES: COc1cc(=O)[nH]c(N2CCN(c3nnc(Cc4ccccc4)c4ccccc34)CC2)n1] | 429 |
| 47 | 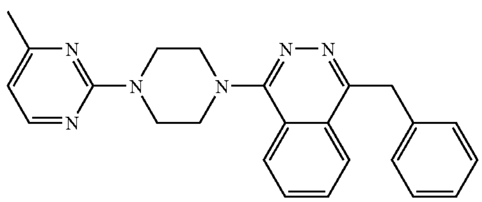 [SMILES: Cc1ccnc(N2CCN(c3nnc(Cc4ccccc4)c4ccccc34)CC2)n1] | 397 |
| 48 | 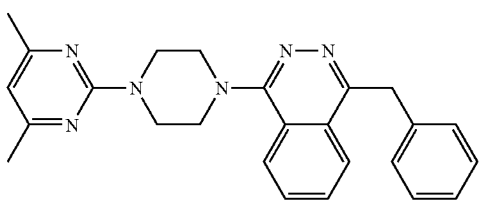 [SMILES: Cc1cc(C)nc(N2CCN(c3nnc(Cc4ccccc4)c4ccccc34)CC2)n1] | 411 |
| 49 | 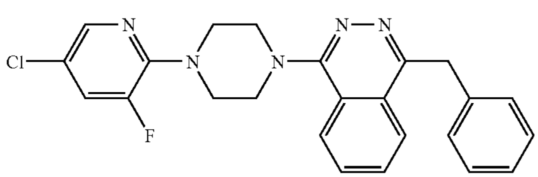 [SMILES: Fc1cc(Cl)cnc1N1CCN(c2nnc(Cc3ccccc3)c3ccccc23)CC1] | 434 |
| 50 | 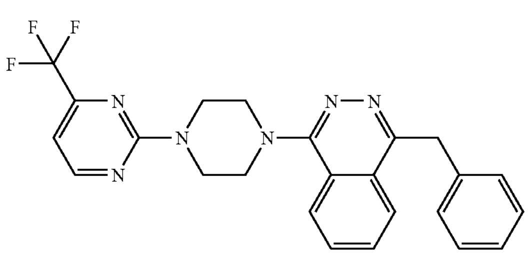 [SMILES: FC(F)(F)c1ccnc(N2CCN(c3nnc(Cc4ccccc4)c4ccccc34)CC2)n1] | 451 |

TABLE 2-continued

| Example | Structure | MS [m/z; M + 1] |
|---|---|---|
| 51 | 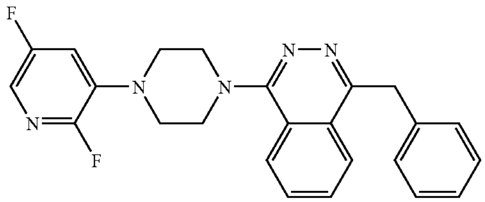 [SMILES: Fc1cnc(F)c(N2CCN(c3nnc(Cc4ccccc4)c4ccccc34)CC2)c1] | 418 |
| 52 | 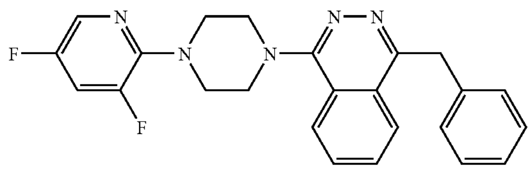 [SMILES: Fc1cnc(N2CCN(c3nnc(Cc4ccccc4)c4ccccc34)CC2)c(F)c1] | 418 |
| 53 | 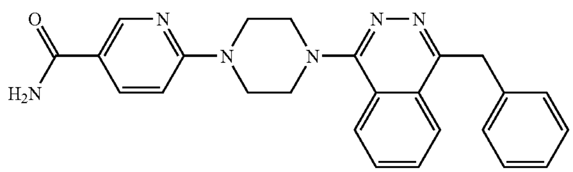 [SMILES: NC(=O)c1ccc(N2CCN(c3nnc(Cc4ccccc4)c4ccccc34)CC2)nc1] | 425 |
| 54 | 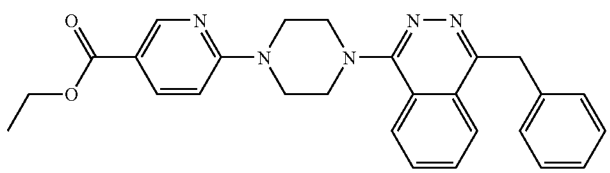 | 454 |
| 130 | 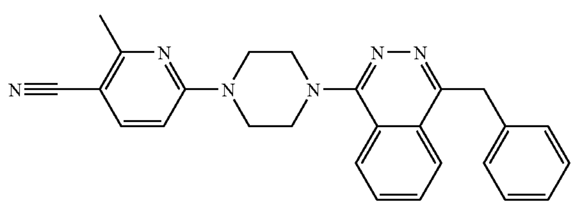 [SMILES: Cc1nc(N2CCN(c3nnc(Cc4ccccc4)c4ccccc34)CC2)ccc1C#N] | 422 |
| 131 | 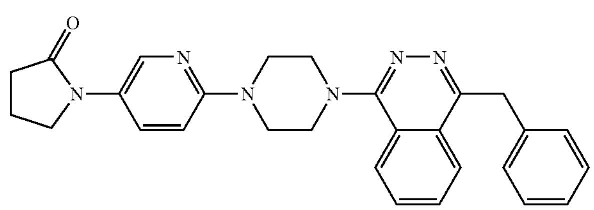 [SMILES: O=C1CCCN1c1ccc(N2CCN(c3nnc(Cc4ccccc4)c4ccccc34)CC2)nc1] | 466 |
| 132 | 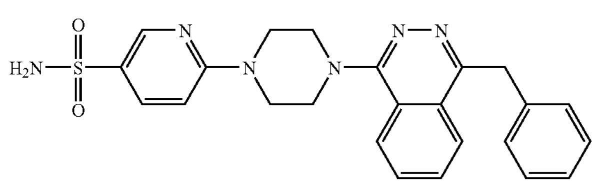 [SMILES: NS(=O)(=O)c1ccc(N2CCN(c3nnc(Cc4ccccc4)c4ccccc34)CC2)nc1] | 462 |
| 133 | 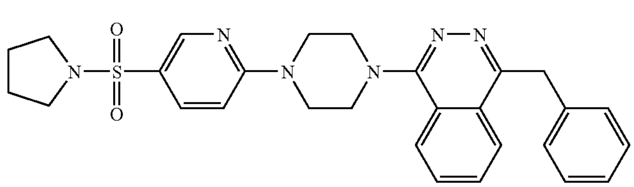 [SMILES: O=S(=O)(c1ccc(N2CCN(c3nnc(Cc4ccccc4)c4ccccc34)CC2)nc1)N1CCCC1] | 516 |

TABLE 2-continued

| Example | Structure | MS [m/z; M + 1] |
|---|---|---|
| 134 | 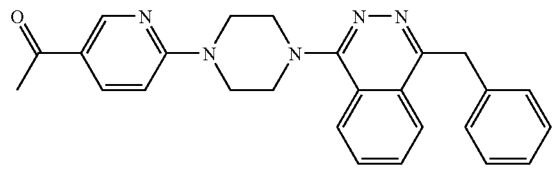 [SMILES: CC(=O)c1ccc(N2CCN(c3nnc(Cc4ccccc4)c4ccccc34)CC2)nc1] | 425 |
| 135 | 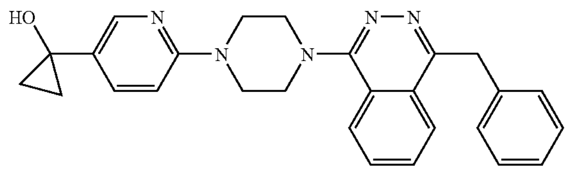 [SMILES: OC1(c2ccc(N3CCN(c4nnc(Cc5ccccc5)c5ccccc45)CC3)nc2)CC1] | 439 |
| 136 | 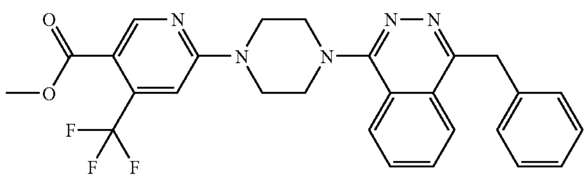 [SMILES: COC(=O)c1cnc(N2CCN(c3nnc(Cc4ccccc4)c4ccccc34)CC2)cc1C(F)(F)F] | 509 |
| 137 | 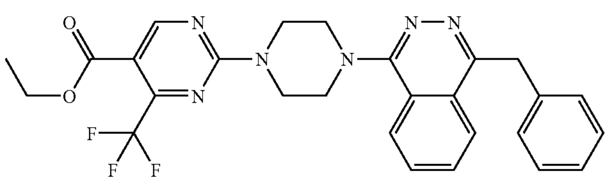 [SMILES: CCOC(=O)c1cnc(N2CCN(c3nnc(Cc4ccccc4)c4ccccc34)CC2)nc1C(F)(F)F] | 524 |
| 138 | 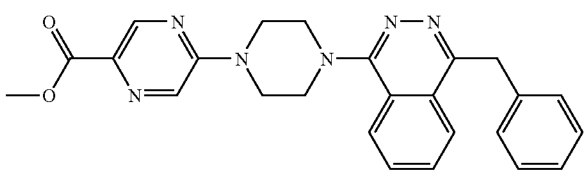 | 442 |
| 139 | 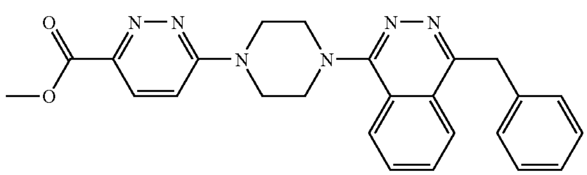 [SMILES: COC(=O)c1ccc(N2CCN(c3nnc(Cc4ccccc4)c4ccccc34)CC2)nn1] | 442 |
| 140 | 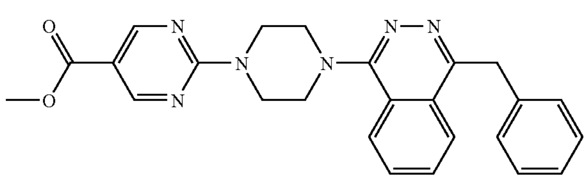 | 442 |
| 141 | 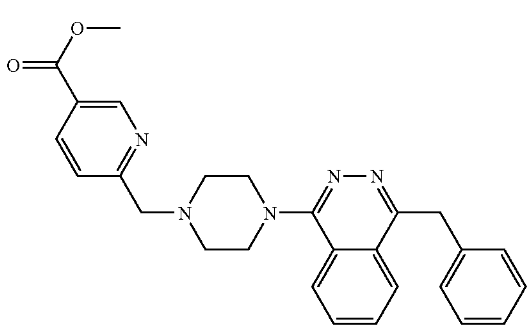 [SMILES: COC(=O)c1ccc(CN2CCN(c3nnc(Cc4ccccc4)c4ccccc34)CC2)nc1] | 455 |

Example 142

6-[(R)-4-(4-Benzyl-phthalazin-1-yl)-2-methyl-piperazin-1-yl]-nicotinonitrile

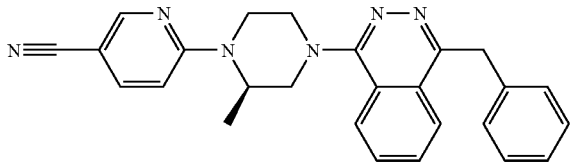 [SMILES: C[C@@H]1CN(c2nnc(Cc3ccccc3)c3ccccc23)CCN1c1ccc(C#N)cn1]

Solid Na$_2$CO$_3$ (50 mg, 0.47 mmol, 1.5 eq) is added to a solution of 6-chloronicotinonitrile (50 mg, 0.36 mmol, 1.2 eq), 1-benzyl-4-((R)-3-methyl-piperazin-1-yl)-phthalazine (100 mg, 0.31 mmol, 1.0 eq) in DMF (1 mL) and dioxane (2 mL) in a microwave vial. The vial is sealed and irradiated in the microwave at 180° C. (high absorption setting) for 30 minutes. The reaction mixture is concentrated, dichloromethane is added and is washed with water then brine. The organic fraction is dried over sodium sulfate, and is evaporated under reduced pressure, then purified by flash chromatography (50%-90% EtOAc/Hexane) to afford the title compound as a white solid (55 mg, 42% yield).

1H NMR (400 MHz, CHLOROFORM-d) δ ppm 8.39 (d, J=2.02 Hz, 1H) 8.09 (d, J=7.45 Hz, 1H) 7.97 (d, J=7.71 Hz, 1H) 7.66-7.76 (m, 2H) 7.59 (dd, J=9.03, 2.34 Hz, 1H) 7.24-7.30 (m, 2H) 7.16-7.22 (m, 2H) 7.08-7.14 (m, 1H) 6.60 (d, J=9.09 Hz, 1H) 4.68-4.76 (m, 1H) 4.54-4.59 (m, 2H) 4.30 (d, J=13.01 Hz, 1H) 3.86-3.94 (m, 1H) 3.71-3.78 (m, 1H) 3.53 (td, J=12.69, 3.41 Hz, 1H) 3.35 (dd, J=12.76, 3.66 Hz, 1H) 3.20 (td, J=12.47, 3.47 Hz, 1H) 1.44 (d, J=6.69 Hz, 3H)

HR-MS (m/z, MH+): meas. 421.2153

Example 143

6-[(S)-4-(4-Benzyl-phthalazin-1-yl)-2-methyl-piperazin-1-yl]-nicotinonitrile

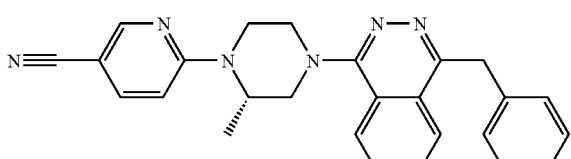

Following the above procedure, 6-chloro-nicotinonitrile (50 mg, 0.36 mmol, 1.2 eq) and 1-benzyl-4-((S)-3-methyl-piperazin-1-yl)-phthalazine (100 mg, 0.31 mmol, 1.0 eq) afford the title compound as a white solid (30 mg, 23% yield).

1H NMR (400 MHz, CHLOROFORM-d) δ ppm 8.39 (d, J=2.27 Hz, 1H) 8.09 (d, J=8.72 Hz, 1H) 7.97 (d, J=7.83 Hz, 1H) 7.71-7.77 (m, 1H) 7.66-7.71 (m, 1H) 7.60 (dd, J=9.03, 2.34 Hz, 1H) 7.25-7.30 (m, 2H) 7.16-7.23 (m, 2H) 7.09-7.14 (m, 1H) 6.60 (d, J=8.97 Hz, 1H) 4.67-4.77 (m, 1H) 4.56 (s, 2H) 4.31 (d, J=13.14 Hz, 1H) 3.90 (d, J=11.87 Hz, 1H) 3.75 (dt, J=12.79, 2.13 Hz, 1H) 3.53 (ddd, J=12.66, 3.47 Hz, 1H) 3.36 (dd, J=12.69, 3.60 Hz, 1H) 3.20 (td, J=12.47, 3.47 Hz, 1H) 1.42 (d, 6.31 Hz, 3H)

HR-MS (m/z, MH+): meas. 421.2151

Example 144

6-[(R)-4-(4-Benzyl-phthalazin-1-yl)-2-methyl-piperazin-1-yl]-nicotinic acid ethyl ester

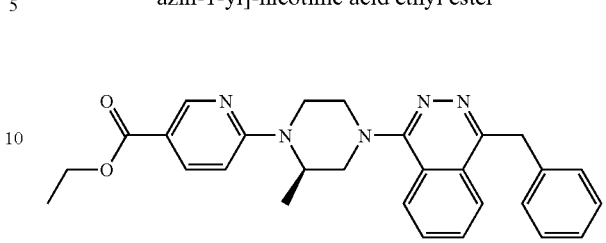

Following the above procedure, 6-chloronicotinic acid ethyl ester (100 mg, 0.54 mmol, 1.7 eq) and 1-benzyl-4-((R)-3-methyl-piperazin-1-yl)-phthalazine (100 mg, 0.31 mmol, 1.0 eq) afford the title compound as a white solid (103 mg, 71% yield).

1H NMR (400 MHz, CHLOROFORM-d) δ ppm 8.85 (d, J=2.01 Hz, 1H) 8.17 (d, J=8.03 Hz, 1H) 8.08 (dd, J=9.03, 2.51 Hz, 1H) 8.02 (d, J=8.03 Hz, 1H) 7.80 (t, J=7.53 Hz, 1H) 7.75 (t, J=7.28 Hz, 1H) 7.31-7.38 (m, 2H) 7.23-7.30 (m, 2H) 7.14-7.21 (m, 1H) 6.66 (d, J=9.03 Hz, 1H) 4.77-4.87 (m, 1H) 4.63 (s, 2H) 4.35-4.42 (m, 1H) 4.34 (q, J=7.36 Hz, 2H) 3.96 (d, J=12.55 Hz, 1H) 3.82 (d, J=12.55 Hz, 1H) 3.58 (td, J=12.55, 3.51 Hz, 1H) 3.42 (dd, J=12.55, 3.51 Hz, 1H) 3.28 (td, J=12.42, 3.26 Hz, 1H) 1.50 (d, J=6.53 Hz, 3H) 1.37 (t, J=7.28 Hz, 3H)

HR-MS (m/z, MH+): meas. 468.2412

Example 145

(R)-4-(4-Benzyl-phthalazin-1-yl)-2-methyl-3,4,5,6-tetrahydro-2H-[1,2']bipyrazinyl-5'-carboxylic acid methyl ester

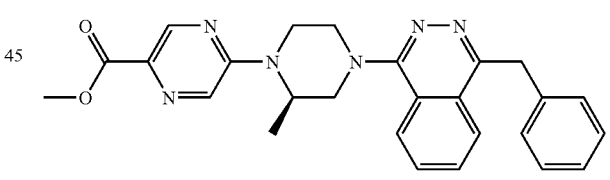

(R)-2-Methyl-3,4,5,6-tetrahydro-2H-[1,2']bipyrazinyl-5'-carboxylic acid methyl ester (150 mg, 0.63 mmol), 1-benzyl-4-chloro-phthalazine (161.75 mg, 0.635 mmol) are added into a microwave vial followed by NMP (3.3 mL) and triethylamine (0.265 mL, 1.91 mmol). The vial is sealed and irradiated in the microwave at 180° C. for 30 min. The crude material is directly purified via flash chromatography on silica gel (40-100% EtOAc in heptane). Desired product is then washed with water and lyophilized to afford the title compound (52 mg, 18% yield).

$^1$H NMR (400 MHz, DMSO-d6) δ 8.74 (s, 1H), 8.45 (s, 1H), 8.22-8.25 (m, 2H), 7.91-8.00 (m, 2H), 7.16-7.34 (m, 5H), 4.93 (s, br, 1H), 4.61 (s, 2H), 4.50 (d, J=13.55 Hz, 1H), 3.92 (d, J=12.05 Hz, 1H), 3.84 (s, 3H), 3.78 (d, J=13.05 Hz, 1H), 3.63-3.69 (m, 1H), 3.27-3.31 (m, 1H), 3.09-3.18 (m, 1H), 1.47 (d, J=6.53 Hz, 3H).

Example 146

6-[(S)-4-(4-Benzyl-phthalazin-1-yl)-3-methyl-piperazin-1-yl]-nicotinic acid methyl ester

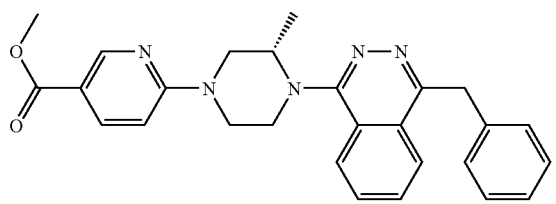 [SMILES: COC(=O)c1ccc(N2CCN(c3nnc(Cc4ccccc4)c4ccccc34)[C@@H](C)C2)nc1]

A solution of 6-[(S)-4-(4-benzyl-phthalazin-1-yl)-3-methyl-piperazin-1-yl]-nicotinonitrile (210 mg, 0.5 mmol) in MeOH (30 mL) and conc. HCl (2 mL) is heated to reflux for 48 h. The solution is concentrated and the residue dissolved in EtOAc (50 mL), then washed with a saturated solution of NaHCO$_3$. The organic layer is dried over sodium sulfate, then concentrated. The desired compound is isolated by silica gel chromatography (15-95% EtOAc/Hex), (150 mg, 0.33 mmol, 66% yield)

1H NMR (400 MHz, CHLOROFORM-d) δ ppm 8.84 (d, J=2.27 Hz, 1H) 8.17 (d, J=8.34 Hz, 1H) 8.06 (dd, J=8.97, 2.40 Hz, 1H) 8.03 (d, J=7.20 Hz, 1H) 7.70-7.83 (m, 2H) 7.32-7.39 (m, 2H) 7.23-7.31 (m, 2H) 7.15-7.22 (m, 1H) 6.68 (d, J=8.97 Hz, 1H) 4.65 (s, 2H) 4.16-4.25 (m, 1H) 4.02-4.12 (m, 1H) 3.89-3.96 (m, 2H) 3.88 (s, 3H) 3.81-3.86 (m, 1H) 3.65-3.76 (m, 1H) 3.52-3.59 (m, 1H) 1.25 (d, J=6.44 Hz, 3H)

MS (m/z, MH+): meas. 454.3

Example 147

2-[(S)-4-(4-Benzyl-phthalazin-1-yl)-2-methoxycarbonyl-piperazin-1-yl]-4-trifluoromethyl-pyrimidine-5-carboxylic acid ethyl ester

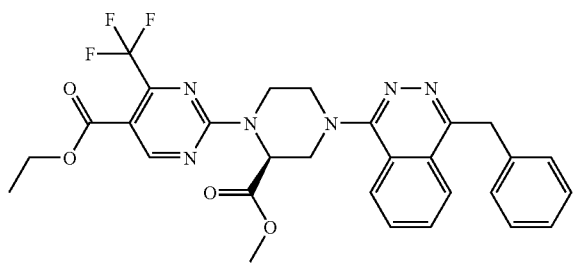 [SMILES: CCOC(=O)c1cnc(N2CCN(c3nnc(Cc4ccccc4)c4ccccc34)C[C@H]2C(=O)OC)nc1C(F)(F)F]

Combine 2-Chloro-4-trifluoromethyl-pyrimidine-5-carboxylic acid methyl ester (240 mg, 1.70 mmol), (S)-piperazine-1,3-dicarboxylic acid 1-tert-butyl ester 3-methyl ester (2.04 mmol) and triethylamine (5.11 mmol) in a 0.85 M solution of dioxane. Microwave reaction mixture for 30 min at 150° C. Filter reaction mixture and rinse with acetonitrile. Purify filtrate by column chromatography in a 0-70% ethyl acetate/heptane gradient to give (S)-4-(5-Methoxycarbonyl-4-trifluoromethyl-pyrimidin-2-yl)-piperazine-1,3-dicarboxylic acid 1-tert-butyl ester 3-methyl-ester contaminated with approximately 15% of the mono hydrolysis product. The mixture is carried on to next step without further purification. (61% yield)

To a methylene chloride (0.02M) solution of (S)-4-(5-Methoxycarbonyl-4-trifluoromethyl-pyrimidin-2-yl)-piperazine-1,3-dicarboxylic acid 1-tert-butyl ester 3-methyl-ester (69 mg, 0.153 mmol), is added 1N HCl (2 mmol), 2M in diethyl ether. Stir reaction mixture at room temperature for 18 h. Concentrate and dilute with dioxane (0.1 M), followed by addition of 1-benzyl-4-chloro-phthalazine (0.153 mmol) and triethylamine (0.459 mmol). Microwave reaction mixture for 30 min at 150° C. MS shows some starting material still present. Microwave for an additional 2.5 h at 150° C. Concentrate reaction mixture and purify by column chromatography 0-75% ethyl acetate/heptane gradient to afford the title compound. (8% yield)

1H NMR (400 MHz, CHLOROFORM-d) δ ppm 8.92 (d, J=31.62 Hz, 1H) 8.11 (t, J=7.53 Hz, 1H) 7.98 (d, J=7.53 Hz, 1H) 7.63-7.83 (m, 2H) 7.03-7.37 (m, 5H) 5.62 (br. s., 1H) 4.83 (d, J=12.05 Hz, 1H) 4.58 (s, 2H) 4.46 (d, J=13.05 Hz, 1H) 3.77-3.94 (m, 4H) 3.61-3.77 (m, 4H) 3.28-3.46 (m, 1H) 3.08-3.27 (m, 1H)

HR-MS (m/z, MH+): meas. 567.1951, calc. 567.1968

Synthesis of Examples 54a, 148-157 Via Grignard Addition

General Protocol for the Addition of Methyl Grignard to Heteroaryl Esters.

To a solution of heteroaryl ester (0.65 mmol) in THF (3 mL) at 23° C. is added dropwise MeMgI (2.6 mmol, 3.0 M solution in Et$_2$O). The reaction is stirred for 2 h, and then quenched by addition of sat. aq. NH$_4$Cl (3 mL). Additional water (10 mL) is added, and the organics were extracted with EtOAc (3×20 mL). The combined organic layers are dried over magnesium sulfate, filtered and concentrated. Crude material is purified by flash chromatography on silica gel (30-100% EtOAc in heptanes).

Example 54a

2-{6-[4-(4-Benzyl-phthalazin-1-yl)-piperazin-1-yl]-pyridin-3-yl}-propan-2-ol

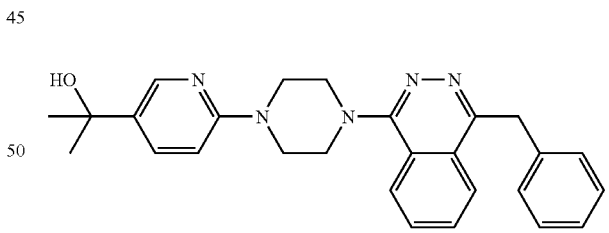

Following the general protocol, 54 (300 mg, 0.65 mmol) affords the title compound as a light yellow powder (202 mg, 71% yield).

$^1$H NMR (400 MHz, CDCl$_3$): δ=8.36 (d, J=4 Hz, 1H); 8.13 (d, J=8 Hz, 1H); 8.03 (d, J=8 Hz, 1H); 7.83-7.74 (m, 3H); 7.37-7.18 (m, 5H); 6.82 (d, J=8 Hz, 1H); 4.66 (s, 2H); 3.87-3.92 (m, 4H); 3.65-3.70 (m, 4H); 1.61 (s, 6H).

HR-MS (m/z, MH+): meas. 440.2452 calc. 440.2450

Examples 148-157

The following table (Table 2a) lists examples of compounds prepared according to the general protocol above.

TABLE 2a

| Example | Structure | MS [m/z; M + 1] |
|---|---|---|
| 148 | 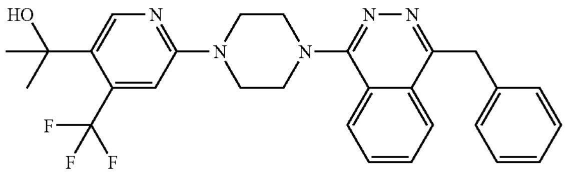 [SMILES: CC(C)(O)c1cnc(N2CCN(c3nnc(Cc4ccccc4)c4ccccc34)CC2)cc1C(F)(F)F] | 509 |
| 149 | 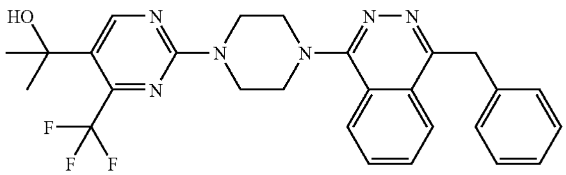 [SMILES: CC(C)(O)c1cnc(N2CCN(c3nnc(Cc4ccccc4)c4ccccc34)CC2)nc1C(F)(F)F] | 510 |
| 150 | 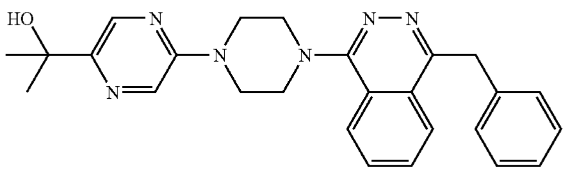 | 442 |
| 151 | 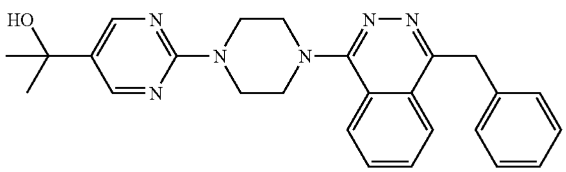 | 442 |
| 152 | 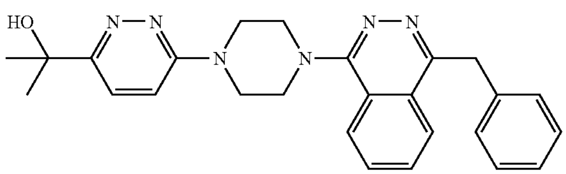 | 442 |
| 153 | 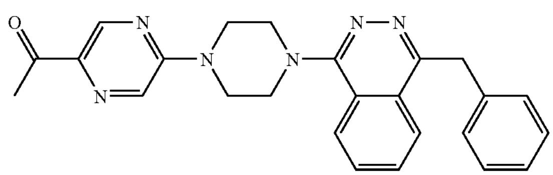 [SMILES: CC(=O)c1cnc(N2CCN(c3nnc(Cc4ccccc4)c4ccccc34)CC2)cn1] | 426 |
| 154 | 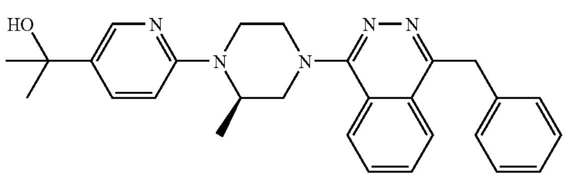 | 454 |
| 155 | 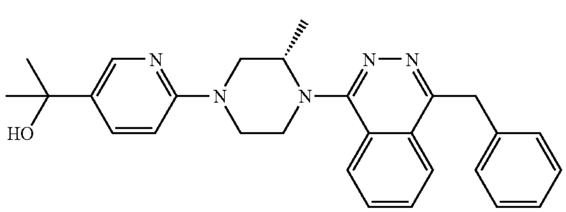 | 454 |

TABLE 2a-continued

| Example | Structure | MS [m/z; M + 1] |
|---|---|---|
| 156 | 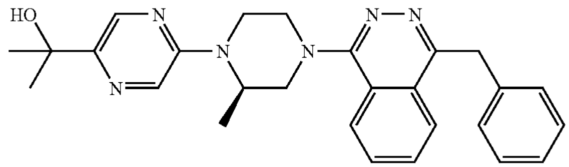 [SMILES: C[C@@H]1CN(c2nnc(Cc3ccccc3)c3ccccc23)CCN1c1ccc(C(C)(C)O)cn1] | 456 |
| 157 | 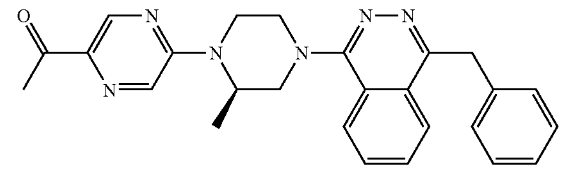 [SMILES: CC(=O)c1cnc(N2CCN(c3nnc(Cc4ccccc4)c4ccccc34)C[C@H]2C)cn1] | 440 |

Interconversion of Example 54 into Examples 158-160 by Reduction and Acylation/Carbamoylation

Example 158

{6-[4-(4-Benzyl-phthalazin-1-yl)-piperazin-1-yl]-pyridin-3-yl}-methanol

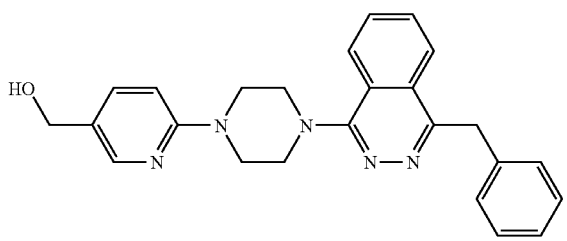

54 (700 mg, 1.543 mmol) is added to a 1 L round bottom flask along with THF (20 mL). Lithium aluminum hydride (1.85 mL, 1M in THF, 1.852 mmol) is added dropwise at room temperature. Reaction is stirred at room temperature for 4-18 h as necessary for complete conversion. Add saturated sodium sulfate (1 mL) and solid lithium salts precipitate. Filter off salts and concentrate filtrate in vacuo. The residue is purified by flash chromatography on silica gel (0-8% MeOH/CH$_2$Cl$_2$) to afford the title compound (355 mg, 56%).

$^1$H NMR (400 MHz, DMSO-d6) δ 8.13-8.22 (m, 2H) 8.08 (d, J=2.02 Hz, 1H) 7.84-7.94 (m, 2H) 7.53 (dd, J=8.72, 2.40 Hz, 1H) 7.31 (dm, J=7.07 Hz, 2H) 7.25 (ddm, J=7.58, 7.58 Hz, 2H) 7.15 (ddm, J=7.26, 7.25 Hz, 1H) 6.89 (d, J=8.72 Hz, 1H) 4.99 (t, J=5.62 Hz, 1H) 4.57 (s, 2H) 4.36 (d, J=5.68 Hz, 2H) 3.70-3.78 (m, 4H) 3.43-3.51 (m, 4H)

HR-MS (m/z, MH$^+$): meas. 412.2134 calc. 412.2137

Example 159

Methoxy-acetic acid 6-[4-(4-benzyl-phthalazin-1-yl)-piperazin-1-yl]-pyridin-3-ylmethyl ester

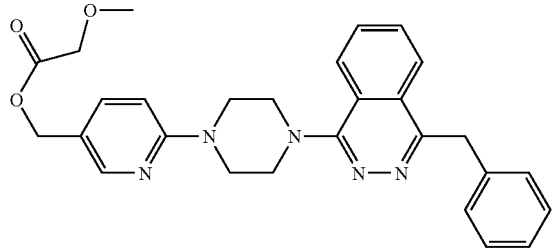 [SMILES: COCC(=O)OCc1ccc(N2CCN(c3nnc(Cc4ccccc4)c4ccccc34)CC2)nc1]

{6-[4-(4-Benzyl-phthalazin-1-yl)-piperazin-1-yl]-pyridin-3-yl}-methanol (80 mg, 0.194 mmol), CH$_2$Cl$_2$ (1 mL), and triethylamine (40 µL, 2.916 mmol) are added to a flask. Add methoxyacetyl chloride (23.2 mg, 0.214 mmol) dropwise at room temperature. Stir 1 h. The crude mixture is purified by flash chromatography on silica gel (MeOH/CH$_2$Cl$_2$) to afford the title compound (38 mg, 40%).

$^1$H NMR (400 MHz, DMSO-d6) δ 8.18 (d, J=2.46 Hz, 1H) 8.22-8.15 (m, 2H) 7.96-7.86 (m, 2H) 7.61 (dd, J=8.78, 2.46 Hz, 1H) 7.32 (dm, J=6.95 Hz, 2H) 7.26 (ddm, J=7.52, 7.52 Hz, 2H) 7.16 (ddd, J=7.20, 7.20, 1.26 Hz, 1H) 6.93 (d, J=8.84 Hz, 1H) 5.05 (s, 2H) 4.58 (s, 2H) 4.05 (s, 2H) 3.84-3.76 (m, 4H) 3.52-3.43 (m, 4H) 3.29 (s, 3H)

HR-MS (m/z, MH$^+$): meas. 484.2353 calc. 484.2349

Example 160

Dimethyl-carbamic acid 6-[4-(4-benzyl-phthalazin-1-yl)-piperazin-1-yl]-pyridin-3-ylmethyl ester

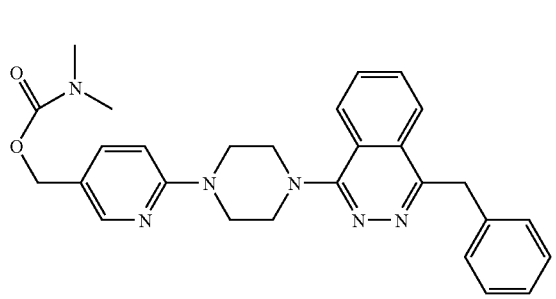 [SMILES: CN(C)C(=O)OCc1ccc(N2CCN(c3nnc(Cc4ccccc4)c4ccccc34)CC2)nc1]

{6-[4-(4-Benzyl-phthalazin-1-yl)-piperazin-1-yl]-pyridin-3-yl}-methanol (75 mg, 0.182 mmol) is dissolved in THF (1 mL) and added to a flask containing NaH (7.5 mg, 0.188 mmol). Stir 1 h at room temperature. Add dimethyl carbamoyl chloride (22 mg, 2.096 mmol) and stir for 16 h at room temperature. Incomplete conversion observed. Reaction is heated to 60° C. and stirred 16 h. Add additional NaH (7.5 mg, 0.188 mmol) is added and reaction quickly reaches 95% conversion. Concentrate reaction mixture in vacuo. The residue is purified by flash chromatography on silica gel (MeOH/CH$_2$Cl$_2$) to afford the title compound (24 mg, 27%).

$^1$H NMR (400 MHz, DMSO-d6) δ 8.24-8.16 (m, 2H) 8.18 (d, J=2.27 Hz, 1H) 7.98-7.88 (m, 2H) 7.62 (dd, J=8.78, 2.34 Hz, 1H) 7.33 (dm, J=6.95 Hz, 2H) 7.27 (ddm, J=7.58, 7.58 Hz, 2H) 7.18 (ddm, J=7.20, 7.20 Hz, 1H) 6.93 (d, J=8.97 Hz, 1H) 4.95 (s, 2H) 4.60 (s, 2H) 3.83-3.77 (m, 4H) 3.53-3.46 (m, 4H) 2.83 (s, 6H)

HR-MS (m/z, MH$^+$): meas. 483.2527 calc. 483.2508

Interconversion of Example 54 into Examples 54b-54cc by Hydrolysis and Amide Formation Example 54b 6-[4-(4-Benzyl-phthalazin-1-yl)-piperazin-1-yl]-nicotinic acid

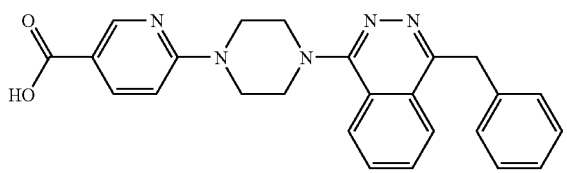 [SMILES: O=C(O)c1ccc(N2CCN(c3nnc(Cc4ccccc4)c4ccccc34)CC2)nc1]

Ethanol (40 mL) is added to a 100 mL round-bottom flask containing example 54 (1.00 g, 2.21 mmol) under N2. Aqueous sodium hydroxide (1 M, 13.22 mL, 13.22 mmol) is added and the reaction is stirred overnight at 5° C. The mixture is then concentrated under reduced pressure, diluted with DCM, and acidified to ~pH 3 using glacial AcOH. The organic layer is washed with brine, dried over Na$_2$SO$_4$, filtered and concentrated under reduced pressure to afford the title compound as a yellowish solid (1.10 g, 100% yield).

$^1$H NMR (400 MHz, DMSO-d$_6$): δ=12.27 (br, s, 1H); 8.62 (s, 1H); 8.21 (m, 2H); 8.01 (d, 1H), 7.93 (m, 2H); 7.25-7.34 (m, 5H); 6.97 (d, 1H); 6.60 (s, 2H); 3.95 (m, 4H); 3.50 (m, 4H). LC/MS (M+H)=426.

Example 54c

6-[4-(4-Benzyl-phthalazin-1-yl)-piperazin-1-yl]-N-(2-hydroxy-ethyl)-N-methyl-nicotinamide

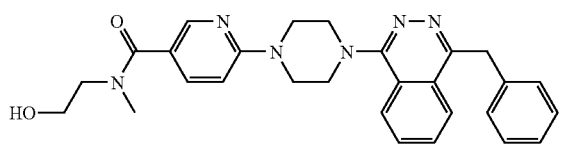 [SMILES: CN(CCO)C(=O)c1ccc(N2CCN(c3nnc(Cc4ccccc4)c4ccccc34)CC2)nc1]

Anhydrous DMF (4.5 mL) is added to a sealed tube containing 2-methylaminoethanol (26.5 mg, 0.353 mmol) under N2. After 15 min, diisopropylamine (0.32 mL, 1.77 mmol) is added, and the reaction is stirred at room temperature for 40 minutes. Example 54b (150 mg, 0.353 mmol) is then added and the reaction is stirred for 1 hr. HBTU (147.15 mg, 0.389 mmol) was then added followed by HOBt (52.88 mg, 0.392 mmol), and the reaction is stirred at room temperature overnight. The reaction mixture is then transferred to a flask, mixed with silica gel and concentrated under reduced pressure. Crude material is purified via flash chromatography on silica gel (DCM: MeOH gradient) to afford a mixture of the desired product and a diisopropylamine salt. The mixture is dissolved in DCM, washed with water, and concentrated to afford the title compound as a light yellow powder (42 mg, 25% yield).

$^1$H NMR (400 MHz, DMSO-d$_6$): δ=8.21 (s, 1H); 8.14 (m, 2H); 7.87 (m, 2H); 7.62 (d, 1H); 7.09-7.28 (m, 5H); 6.87 (d, 1H); 4.78 (br, OH), 4.53 (s, 2H), 3.80 (m, 4H), 3.35-3.50 (m, 8H); 2.93 (s, 3H).

HR-MS (m/z, MH+): meas. 483.2508 calc. 483.2517

Examples 54d-54 cc

The following table (Table 3) lists examples of compounds prepared using a method analogous to that described above.

TABLE 3

| | | |
|---|---|---|
| 54d | 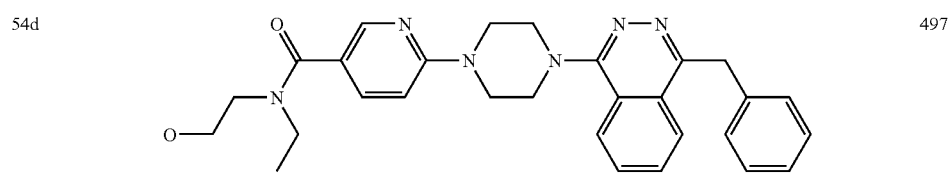 | 497 |
| 54e | 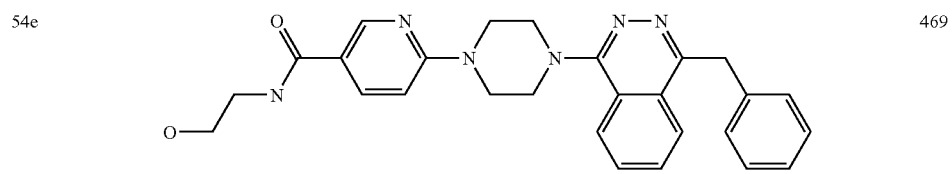 | 469 |

TABLE 3-continued

| | | |
|---|---|---|
| 54f | (structure) | 483 |
| 54g | (structure) | 497 |
| 54h | (structure) | 496 |
| 54i | (structure) | 508 |
| 54j | (structure) | 508 |
| 54k | (structure) | 495 |
| 54l | (structure) | 515 |
| 54lm | (structure) | 521 |

TABLE 3-continued
| | | |
|---|---|---|
| 54n | 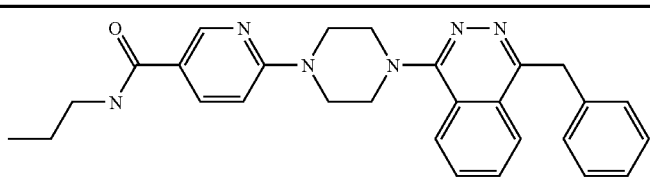 | 467 |
| 54o | 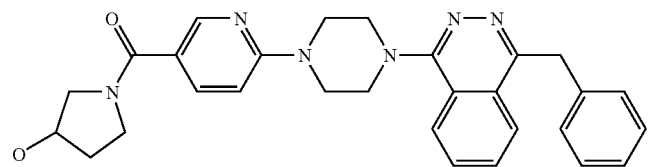 [SMILES: O=C(c1ccc(N2CCN(c3nnc(Cc4ccccc4)c4ccccc34)CC2)nc1)N1CCC(O)C1] | 495 |
| 54p | 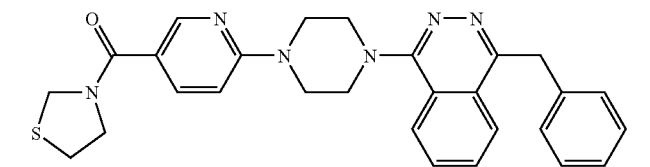 [SMILES: O=C(c1ccc(N2CCN(c3nnc(Cc4ccccc4)c4ccccc34)CC2)nc1)N1CCSC1] | 497 |
| 54q | 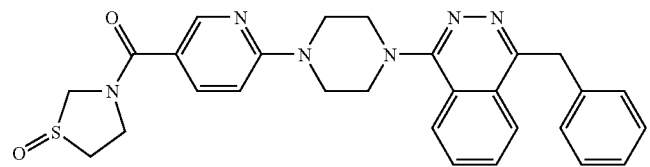 | 513 |
| 54r | 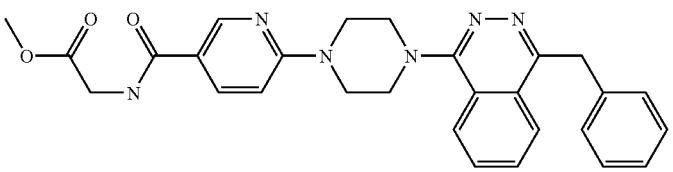 | 497 |
| 54s | 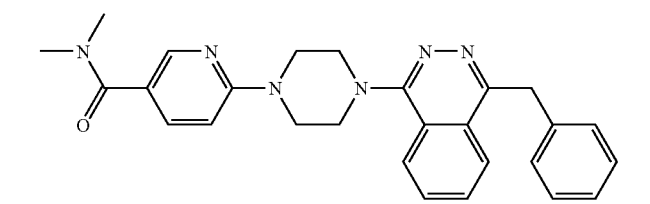 | 454 |
| 54t | 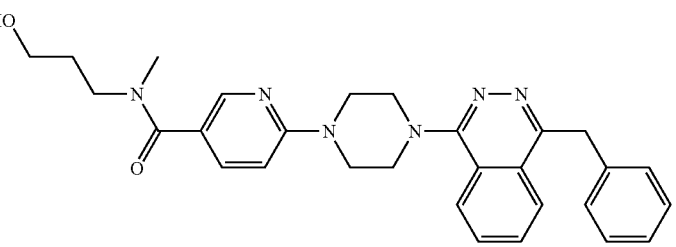 | 498 |
| 54u | 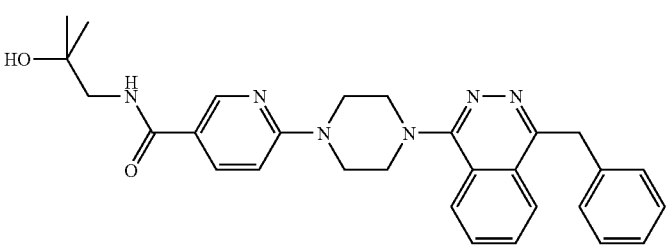 [SMILES: CC(C)(O)CNC(=O)c1ccc(N2CCN(c3nnc(Cc4ccccc4)c4ccccc34)CC2)nc1] | 498 |

TABLE 3-continued
| | | |
|---|---|---|
| 54v | 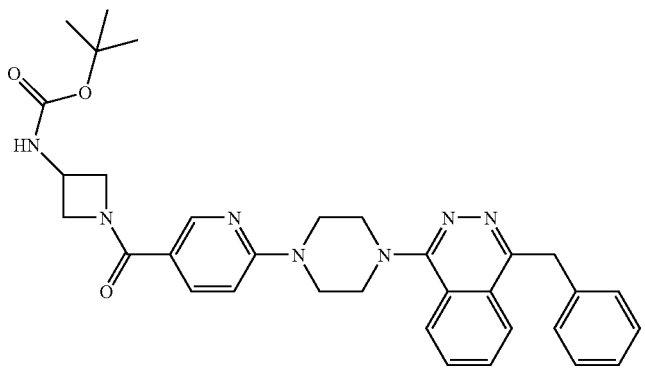 [SMILES: CC(C)(C)OC(=O)NC1CN(C(=O)c2ccc(N3CCN(c4nnc(Cc5ccccc5)c5ccccc45)CC3)nc2)C1] | 581 |
| 54w | 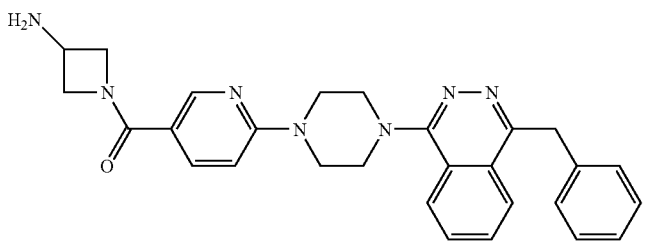 [SMILES: NC1CN(C(=O)c2ccc(N3CCN(c4nnc(Cc5ccccc5)c5ccccc45)CC3)nc2)C1] | 481 |
| 54x | 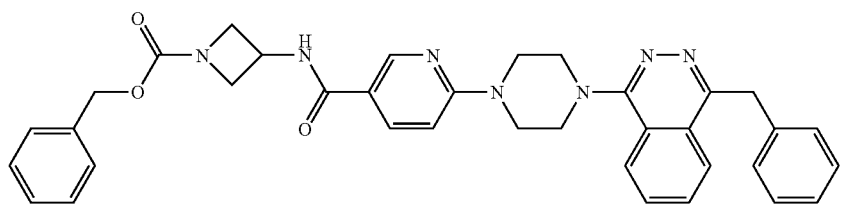 [SMILES: O=C(NC1CN(C(=O)OCc2ccccc2)C1)c1ccc(N2CCN(c3nnc(Cc4ccccc4)c4ccccc34)CC2)nc1] | 615 |
| 54y | 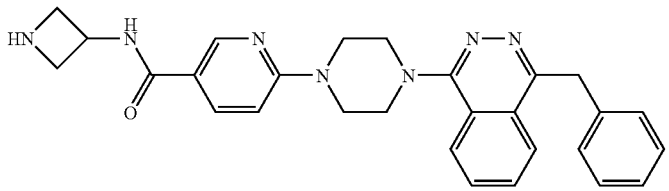 [SMILES: O=C(NC1CNC1)c1ccc(N2CCN(c3nnc(Cc4ccccc4)c4ccccc34)CC2)nc1] | 481 |
| 54z | 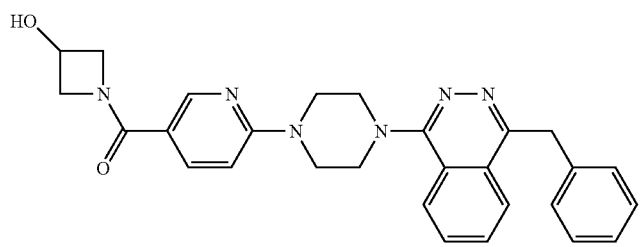 [SMILES: O=C(c1ccc(N2CCN(c3nnc(Cc4ccccc4)c4ccccc34)CC2)nc1)N1CC(O)C1] | 482 |
| 54aa | 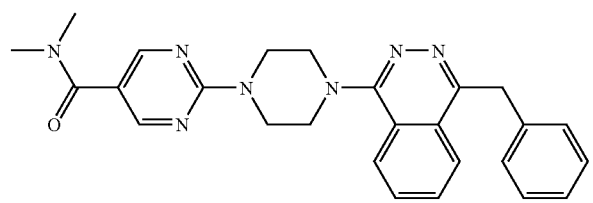 | 455 |

TABLE 3-continued

| | | |
|---|---|---|
| 54bb | (structure) | 497 |
| 54cc | (structure) | 485 |

Interconversion of Example 54a into Example 161 by Alkylation

Example 161

1-Benzyl-4-{-4-[5-(1-methoxy-1-methyl-ethyl)-pyridin-2-yl]-piperazin-1-yl}-phthalazine

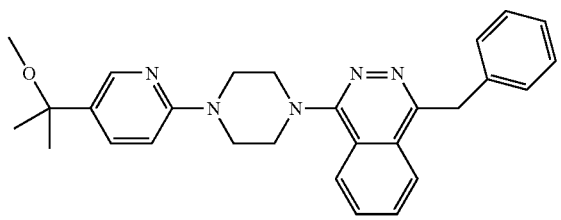 [SMILES: COC(C)(C)c1ccc(N2CCN(c3nnc(Cc4ccccc4)c4ccccc34)CC2)nc1]

54a (135 mg, 0.307 mmol) is dissolved in DMF. HBTU (128.1 mg, 0.338 mmol) and HOBT (46 mg, 0.34 mmol) are added and the reaction is stirred at room temperature for 72 h. The crude material is dry loaded to a column and purified via flash chromatography on silica gel (10-100% EtOAc in heptane) to afford the title compound (12 mg, 9% yield).
$^1$H NMR (400 MHz, DMSO-d6) ∂ 1.37 (s, 6H) 2.88 (s, 3H) 3.40-3.43 (m, 4H) 3.69-3.71 (m, 4H) 4.53 (s, 2H) 6.85 (d, J=8 Hz, 1H) 7.09-7.28 (m, 5H) 7.52 (dd, J=12 Hz, 4 Hz, 1H) 7.82-7.88 (m, 2H) 8.09-8.15 (m, 3H).
HR-MS (m/z, MH+): meas. 454.2607

Interconversion of Example 54a into Example 162 by Ritter Reaction

Example 162

N-(1-{6-[4-(4-Benzyl-phthalazin-1-yl)-piperazin-1-yl]-pyridin-3-yl}-1-methyl-ethyl)-acetamide

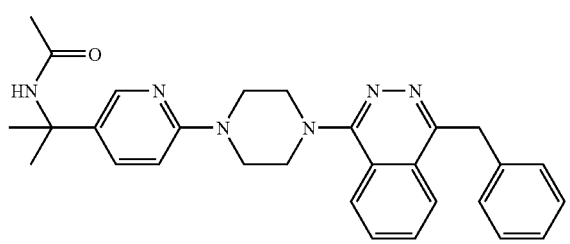 [SMILES: CC(=O)NC(C)(C)c1ccc(N2CCN(c3nnc(Cc4ccccc4)c4ccccc34)CC2)nc1]

To 54a (100 mg, 0.22 mmol) is added acetic acid (0.153 mL, 2.67 mmol) and acetonitrile (0.190 mL, 3.57 mmol). The solution is cooled to 0° C., and then conc. $H_2SO_4$ (0.143 mL, 2.67 mmol) is added dropwise. The reaction is stirred at this temperature for 10 min and then allowed to warm to room temperature. After 3 h, the reaction is poured into ice water and then brought to neutral pH by the dropwise addition of aq. sat. $Na_2CO_3$. The resulting precipitate was isolated by filtration and purified by flash chromatography on silica gel (95:5 to 60:40 gradient of 85:15:5 heptanes/iPrOH/$Et_3$N and 85:15:5 EtOAc/iPrOH/$Et_3$N) to afford the title compound (42 mg, 39% yield).
$^1$H NMR (400 MHz, CDCl$_3$) δ 8.15-8.20 (m, 1H) 7.99-8.08 (m, 1H) 7.91-7.98 (m, 1H) 7.59-7.77 (m, 4H) 7.24-7.31 (m, 2H) 7.16-7.23 (m, 2H) 7.07-7.15 (m, 1H) 5.70 (s, 1H) 4.58 (s, 2H) 3.84 (s, 3H) 3.51-3.66 (m, 5H) 1.89 (s, 3H) 1.61 (s, 6H).
HR-MS (m/z, MH+): meas. 481.2708 calc. 481.2716

Interconversion of Example 134 into Example 163 by Reduction

Example 163

1-{6-[4-(4-Benzyl-phthalazin-1-yl)-piperazin-1-yl]-pyridin-3-yl}-ethanol

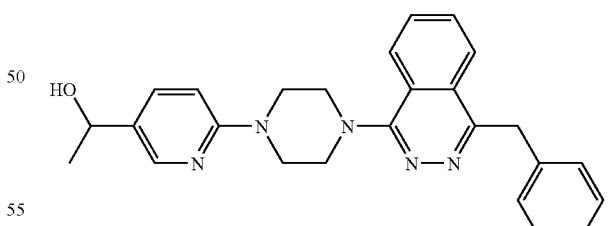

Methanol (4 mL) is added to 134 (60 mg, 0.139 mmol), and the resulting solution cooled to 0° C. Sodium borohydride (11 mg, 0.277 mmol) is added portionwise. The reaction is stirred at 0° C. for 40 min, and then quenched by the addition of aq. sat. NaHCO$_3$. The solution is diluted with H$_2$O (25 mL), and the organics are extracted with EtOAc (3×25 mL), dried over MgSO$_4$, and concentrated. The residue was recrystallized from EtOAc:heptanes to afford the title compound as yellow needles (19 mg, 32% yield).

¹H NMR (400 MHz, CDCl₃) δ 8.08 (d, J=2.3 Hz, 1H) 7.96 (dd, J=18.6, 8.0 Hz, 2H) 7.61-7.77 (m, 3H) 7.19-7.27 (m, 2H) 7.11-7.18 (m, 2H) 7.02-7.10 (m, 1H) 6.86 (d, J=9.1 Hz, 1H) 4.78 (q, J=6.4 Hz, 1H) 4.55 (s, 2H) 3.89 (s, 3H) 3.47-3.69 (m, 5H) 2.08 (d, J=2.9 Hz, 1H) 1.38 (d, J=6.6 Hz, 3H).

HR-MS (m/z, MH+): meas. 426.2304 calc. 426.2294

Interconversion of Example 132 into Example 164 by Ketal Formation

Example 164

1-Benzyl-4-(4-(5-(2-methyl-1,3-dioxolan-2-yl)pyridin-2-yl)piperazin-1-yl)phthalazine

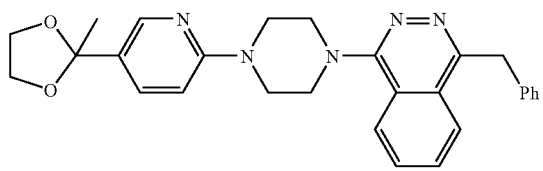 [SMILES: CC1(c2ccc(N3CCN(c4nnc(Cc5ccccc5)c5ccccc45)CC3)nc2)OCCO1]

A solution of 132 (70 mg, 0.165 mmol) in anhydrous toluene (5 mL) is prepared in a flask equipped with a Dean-Stark apparatus. 1,2-Ethanediol (92 μL, 1.65 mmol) and TsOH.H₂O (47.9 mg, 0.29 mmol) are added, and the reaction mixture is refluxed for 48 h. It is then diluted with DCM and washed with sat. aq. NaHCO₃ and brine. The organic layer is dried over Na₂SO₄ and concentrated. The resulting solid was purified by semi-prep HPLC, eluting with 10-100% acetonitrile in water (both mobile phases modified by 3% n-PrOH). Fractions containing the desired product were combined and freeze-dried to afford the title compound as a white solid (50 mg, yield: 77%).

HR-MS (m/z, MH+): meas. 468.2388 calc. 468.2400

Interconversion of Examples 132 and 153 into Examples 165-167 by Olefination and Hydrogenation or Dihydroxylation 4-(4-Benzyl-phthalazin-1-yl)-5'-isopropenyl-3,4,5,6-tetrahydro-2H-[1,2']bipyrazinyl (Compound 20)

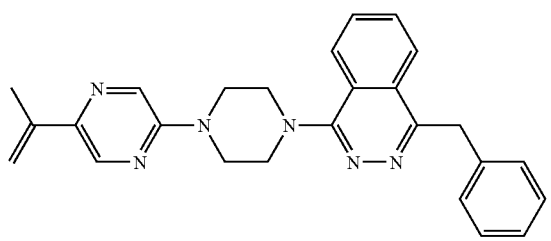 [SMILES: C=C(C)c1cnc(N2CCN(c3nnc(Cc4ccccc4)c4ccccc34)CC2)cn1]

Methyltriphenylphosphonium iodide (115 mg, 0.28 mmol) is dissolved in THF (750 μL) and chilled to 5° C. While stirring add potassium t-butoxide (310 μL, 1M in THF, 0.31 mmol) to the solution. After 30 minutes add the mixture to a solution of 1-[4-(4-Benzyl-phthalazin-1-yl)-3,4,5,6-tetrahydro-2H-[1,2']bipyrazinyl-5'-yl]-ethanone (100 mg, 0.24 mmol) and THF (750 μL). Stir 30 minutes. Analysis shows 60-70% completion. A second portion of methyl triphenyl phosphonium iodide (115 mg, 0.28 mmol) is dissolved in THF (750 μL) and chilled to 5° C. While stirring add potassium t-butoxide (310 μL, 1M in THF, 0.31 mmol) to the solution. Again add this mixture to the current reaction. Reaction quickly proceeds to completion. Quench by adding saturated ammonium chloride. Concentrate in vacuo to remove THF and partition between water and EtOAc. Extract with EtOAc, and wash combined organics with brine. Concentrate EtOAc in vacuo. The residue is purified by flash chromatography on silica gel (EtOAc/Heptane) to afford the title compound (80 mg, 78%).

1-Benzyl-4-[4-(5-isopropenyl-pyridin-2-yl)-piperazin-1-yl]-phthalazine (Compound 21)

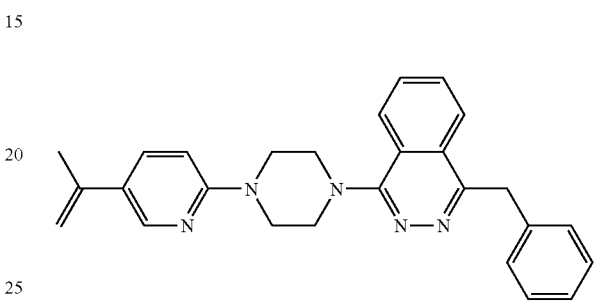

¹H NMR (400 MHz, CDCl₃) δ 8.27 (d, J=2.3 Hz, 1H) 8.05 (d, J=7.5 Hz, 1H) 7.95 (d, J=7.7 Hz, 1H) 7.61-7.76 (m, 3H) 7.25-7.31 (m, 2H) 7.16-7.23 (m, 2H) 7.08-7.15 (m, 1H) 6.70 (d, J=8.7 Hz, 1H) 5.21-5.27 (m, 1H) 4.90-4.99 (m, 1H) 4.57 (s, 2H) 3.82 (s, 4H) 3.53-3.68 (m, 4H) 2.01-2.12 (m, 3H).

Example 165

4-(4-Benzyl-phthalazin-1-yl)-5'-isopropyl-3,4,5,6-tetrahydro-2H-[1,2']bipyrazinyl

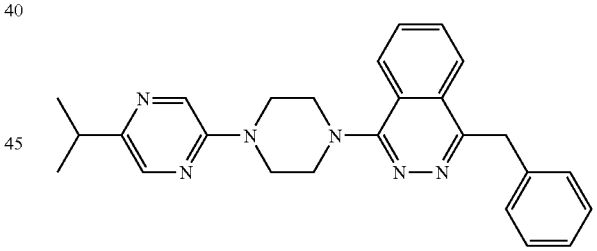

4-(4-Benzyl-phthalazin-1-yl)-5'-isopropenyl-3,4,5,6-tetrahydro-2H-[1,2']bipyrazinyl (50 mg, 0.118 mmol) is dissolved in MeOH (2 mL). Palladium hydroxide (25 mg) is added to the flask capped with a septum and balloon of hydrogen. The reaction is stirred 3 h at room temperature. Filter through a small pad of silica gel and wash behind with EtOAc. Concentrate the filtrate in vacuo. The residue is purified by flash chromatography on silica gel (EtOAc/Heptane) to afford the title compound (17.6 mg, 35%).

¹H NMR (400 MHz, CDCl₃) δ 8.12 (d, J=1.39 Hz, 1H), 8.04 (dd, J=7.71, 1.14 Hz, 1H), 7.96 (d, J=1.34 Hz, 1H), 7.95 (dd, J=7.45, 1.14 Hz, 1H), 7.75-7.64 (m, 2H), 7.28 (dm, J=7.58 Hz, 2H), 7.20 (ddm, J=7.45 Hz, 2H), 7.11 (ddm, J=7.33, 7.33 Hz, 1H), 4.57 (s, 2H), 3.80-3.70 (m, 4H), 3.63-3.55 (m, 4H), 2.94 (sep, J=6.95 Hz, 1H), 1.23 (d, J=6.95 Hz, 6H).

HR-MS (m/z, MH⁺): meas. 425.2447 calc. 425.2454

Example 166

2-[4-(4-Benzyl-phthalazin-1-yl)-3,4,5,6-tetrahydro-2H-[1,2']bipyrazinyl-5'-yl]-propane-1,2-diol

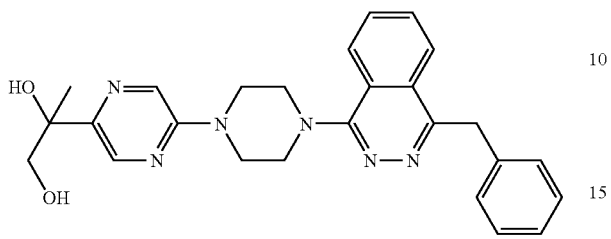

Dissolve 4-(4-Benzyl-phthalazin-1-yl)-5'-isopropenyl-3,4,5,6-tetrahydro-2H-[1,2']bipyrazinyl (100 mg, 0.237 mmol) in acetone (1.5 mL), t-Butanol (0.7 mL) and water (0.7 mL). Add $K_2OsO_4$ (0.79 mg, 0.0024 mmol) then NMO (30.5 mg, 0.26 mmol) and stir reaction for 16 h at room temperature. Quench with saturated sodium sulfite (1 mL) and extract with EtOAc. The residue is purified by flash chromatography on silica gel (MeOH/$CH_2Cl_2$) to afford the title compound (100 mg, 92%).

$^1$H NMR (400 MHz, DMSO-d6) δ 8.35 (d, J=1.39 Hz, 1H) 8.31 (d, J=1.52 Hz, 1H) 8.23-8.17 (m, 2H) 7.97-7.87 (m, 2H) 7.33 (dm, J=6.95 Hz, 2H) 7.27 (ddm, J=7.58, 7.58 Hz, 2H) 7.17 (ddm, J=7.33, 7.33 Hz, 1H) 4.99 (s, 1H) 4.60 (s, 2H) 4.57 (t, J=5.94 Hz, 1H) 3.86-3.78 (m, 4H) 3.50 (d, J=5.94 Hz, 2H) 3.54-3.47 (m, 4H) 1.38 (s, 3H)

MS (m/z, MH+): meas. 457.5 calc. 457.2352

Example 167

2-{6-[4-(4-Benzyl-phthalazin-1-yl)-piperazin-1-yl]-pyridin-3-yl}-propane-1,2-diol

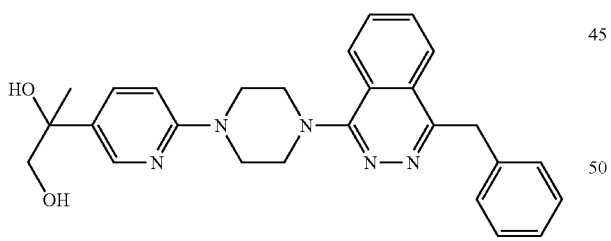

To 1-benzyl-4-[4-(5-isopropenyl-pyridin-2-yl)-piperazin-1-yl]-phthalazine (68 mg, 0.158 mmol) is added acetone (1 mL), t-butanol (0.5 mL), and $H_2O$ (0.5 mL). To this suspension is then added potassium osmate (VI) dihydrate (536 µg, 1.58 µM), and NMO (21 mg, 0.174 mmol), and the reaction is stirred at room temperature for 3 h. Sodium sulfite (350 mg) is added to the resulting clear orange solution and the mixture is stirred for 1 h. Additional $H_2O$ (25 mL) is added, and the organics extracted with EtOAc (3×25 mL), dried over $MgSO_4$, and concentrated. Purification by flash chromatography on silica gel (90:10 $CH_2Cl_2$:MeOH) afforded a clear oil which was then triturated with EtOAc to afford the title compound as a white powder (52 mg, 72% yield).

$^1$H NMR (400 MHz, DMSO-D6) δ 8.13-8.30 (m, 3H) 7.84-7.99 (m, 2H) 7.64 (dd, J=8.8, 2.5 Hz, 1H) 7.23-7.38 (m, 4H) 7.14-7.22 (m, 1H) 6.87 (d, J=8.8 Hz, 1H) 4.81-4.89 (m, 1H) 4.67 (dd, J=5.8, 5.8 Hz, 1H) 4.60 (s, 2H) 3.69-3.81 (m, 4H) 3.45-3.54 (m, 4H) 3.34-3.43 (m, 2H) 1.39 (s, 3H).

HR-MS (m/z, MH+): meas. 456.2426 calc. 456.2400.

Interconversion of Example 166 into Further Examples by Mesylation/Amine Displacement

Example 168

Methanesulfonic acid 2-[4-(4-benzyl-phthalazin-1-yl)-3,4,5,6-tetrahydro-2H-[1,2']bipyrazinyl-5'-yl]-2-hydroxy-propyl ester

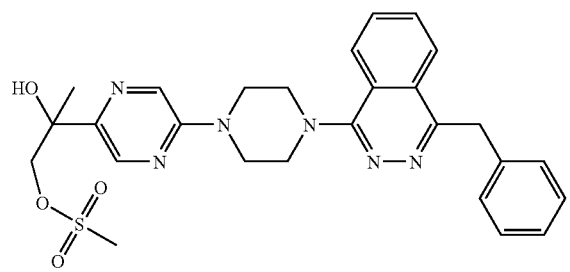 [SMILES: CC(O)(COS(C)(=O)=O)c1cnc(N2CCN(c3nnc(Cc4ccccc4)c4ccccc34)CC2)cn1]

2-[4-(4-Benzyl-phthalazin-1-yl)-3,4,5,6-tetrahydro-2H-[1,2']bipyrazinyl-5'-yl]-propane-1,2-diol (100 mg, 0.219 mmol) is combined with THF (1.5 mL). The reaction is chilled to 0° C. and triethylamine (95 µL, 0.329 mmol) is added followed by mesyl chloride (100 µL, 0.2 M in THF, 0.263 mmol). The reaction is allowed to warm to room temperature and stir for 96 h. Reaction is quenched with saturated ammonium chloride solution (0.5 mL), diluted with additional water and extracted with EtOAc. Wash combined organics with brine. Concentrate organics in vacuo to afford the title compound (117 mg, 99%).

Example 169

2-[4-(4-Benzyl-phthalazin-1-yl)-3,4,5,6-tetrahydro-2H-[1,2']bipyrazinyl-5'-yl]-1-dimethylamino-propan-2-ol

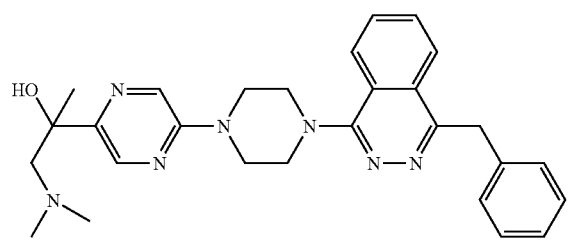 [SMILES: CN(C)CC(C)(O)c1cnc(N2CCN(c3nnc(Cc4ccccc4)c4ccccc34)CC2)cn1]

Methanesulfonic acid 2-[4-(4-benzyl-phthalazin-1-yl)-3,4,5,6-tetrahydro-2H-[1,2']bipyrazinyl-5'-yl]-2-hydroxy-propyl ester (64 mg, 0.120 mmol) is combined with dimethylamine (300 µL, 2M in THF, 0.600 mmol), diisoproylethylamine (63 µL, 0.360 mmol), and acetonitrile (1 mL). The mixture is heated to reflux for 16 h. Concentrate the crude mixture in vacuo. The residue is purified by flash chromatography on silica gel (MeOH/CH₂Cl₂) to afford the title compound (13.4 mg, 23%).

¹H NMR (400 MHz, MeOD) δ 8.38 (d, J=1.39 Hz, 1H), 8.36 (d, J=1.39 Hz, 1H), 8.28 (d, J=7.83 Hz, 1H), 8.18 (d, J=8.21 Hz, 1H), 7.97-7.91 (m, 1H), 7.91-7.84 (m, 1H), 7.32-7.21 (m, 4H), 7.20-7.13 (m, 1H), 4.64 (s, 2H), 4.07-4.02 (m, 1H), 4.02-3.97 (m, 4H), 3.92-3.87 (m, 1H), 3.66-3.57 (m, 4H), 2.77 (br. s, 6H), 1.72 (br. s., 3H).

HR-MS (m/z, MH⁺): meas. 484.2806 calc. 484.2825.

Example 170

1-{2-[4-(4-Benzyl-phthalazin-1-yl)-3,4,5,6-tetrahydro-2H-[1,2']bipyrazinyl-5'-yl]-2-hydroxy-propyl}-piperidin-4-ol

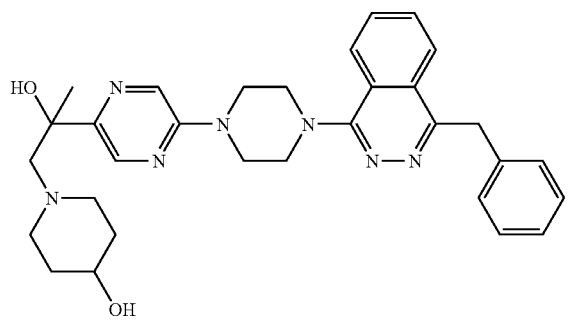 [SMILES: CC(O)(CN1CCC(O)CC1)c1cnc(N2CCN(c3nnc(Cc4ccccc4)c4ccccc34)CC2)cn1]

Methanesulfonic acid 2-[4-(4-benzyl-phthalazin-1-yl)-3,4,5,6-tetrahydro-2H-[1,2']bipyrazinyl-5'-yl]-2-hydroxy-propyl ester (64 mg, 0.120 mmol) is combined with 4-hydroxy piperidine (61 mg, 0.600 mmol), diisoproylethylamine (63 μL, 0.360 mmol), and acetonitrile (1 mL). The mixture is heated to reflux for 16 h. Concentrate the crude mixture in vacuo. The residue is purified by flash chromatography on silica gel (MeOH/CH₂Cl₂) to afford the title compound (15.6 mg, 24%).

HR-MS (m/z, MH⁺): meas. 540.3093 calc. 540.3087

Synthesis of Compounds Via Route C

Example 55

1-Benzyl-4-[4-(4-trifluoromethyl-phenyl)-piperazin-1-yl]-phthalazine

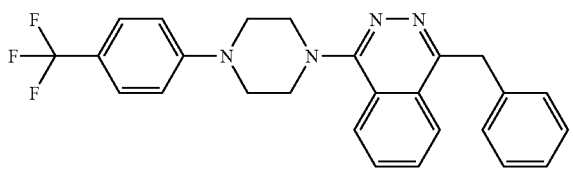

To a solution of 1-benzyl-4-piperazin-1yl-phthalazine (100 mg, 0.329 mmol) in 1 mL THF is added 4-bromobenzotrifluoride (99 mg, 0.443 mmol), potassium tert-butoxide (55.3 mg, 0.493 mmol), XPhos [2-(Dicyclohexylphosphino)-2',4',6'-tri-1-propyl-1'-1'-biphenyl] (15.7 mg, 0.033 mmol), and palladium (II) acetate (11 mg, 0.16 mmol) in a 2 dram screw-top vial. The vial is evacuated and flushed with argon. The reaction mixture was heated to 110° C. for 18 hrs. The mixture is then poured into water (50 mL), and the precipitate is isolated by filtration. The resulting solid is purified by flash chromatography on silica gel (10-70% EtOAc: heptanes) to provide the desired product as yellow crystals (54 mg, 37% yield).

¹H NMR (400 MHz, DMSO-d₆): δ=8.17-8.25 (m, 2H), 7.88-7.97 (m, 2H), 7.570 (d, 2H, J=8.8), 7.32-7.36 (m, 2H), 7.25-7.30 (m, 2H), 7.17-7.20 (m, 1H), 7.21 (d, 2H, J=8.8), 4.61 (s, 2H), 3.53-3.62 (m, 8H).

HR-MS (m/z, MH+): meas. 449.1952 calc. 449.1953

Example 171

2-{6-[4-(4-Benzyl-phthalazin-1-yl)-piperazin-1-yl]-pyridin-3-yl}-1-pyrrolidin-1-yl-ethanone

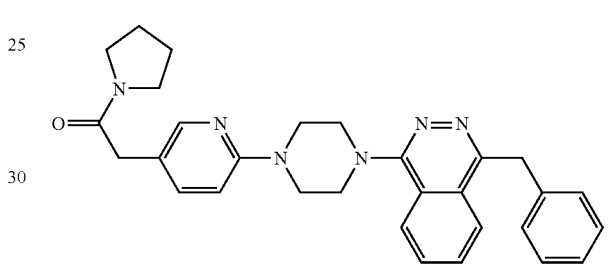

To 3-chloro-pyridyl acetic acid (800 mg, 4.66 mmol) in DMF (15 mL) was added EDC hydrochloride (1.38 g, 7.02 mmol) followed by pyrrolidine (398 mg, 5.6 mmol) and dimethylaminopyridine (114 mg, 0.93 mmol). The mixture was stirred at room temperature for 16 h. Water was added to the mixture and the crude product extracted with ethyl acetate. The combined organic layers were washed with water, sat. NaHCO₃, brine, dried over Na₂SO₄, filtered and concentrated.

The crude product was purified by flash chromatography (EtOAc/heptane 10%-30%) to give 220 mg (21%) of 2-(6-chloro-pyridin-3-yl)-1-pyrrolidin-1-yl-ethanone.

To a solution of this amide (0.22 g, 1 mmol) and 1-benzyl-4-piperazin-1-yl-phthalazine (0.15 g, 0.5 mmol) in toluene (10 mL) were added (2-biphenyl)dicyclohexyl phosphine (35 mg, 0.1 mmol), Pd(OAc)₂ (11 mg, 0.05 mmol) and KOᵗBu (336 mg, 3 mmol). The mixture was degassed and then heated in a microwave reactor at 90° C. The reaction mixture was cooled to room temperature and filtered. Water was added to the filtrate and extracted with EtOAc. The combined organic layers were washed with water, sat. NaHCO₃, brine, dried over Na₂SO₄, filtered and concentrated.

The crude product was purified by flash chromatography (EtOAc/heptane 20%-95%) to give 70 mg (14%) of the title compound.

¹H NMR (400 MHz, CD₂Cl₂): δ=8.06 (m, 1H), 7.95 (m, 2H), 7.70 (m, 2H), 7.40 (m, 1H), 7.24-7.08 (m, 5H), 6.67 (d, J=8.5 Hz, 1H), 4.52 (s, 2H), 3.70 (m, 4H), 3.51 (m, 4H), 3.40 (s, 2H), 3.36 (m, 4H), 1.87 (m, 2H), 1.75 (m, 2H).

HR-MS (m/z, MH+): meas. 493.2716

Example 172

1-{6-[4-(4-Benzyl-phthalazin-1-yl)-piperazin-1-yl]-pyridin-3-yl}-2-methyl-propan-2-ol

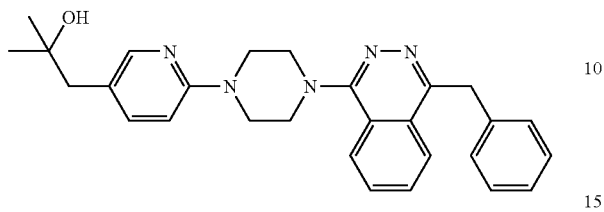

The addition of methyl magnesium iodide (0.29 mL, 3M in ether, 0.87 mmol) to the corresponding ethyl ester (50 mg, 0.107 mmol) in THF (5 mL) yields the title compound (16 mg, 33%).

HRMS (m/z, MH+) meas. 454.2591

Examples 56-69

Alternatively, compounds of Formula Id can be prepared according to the general route outlined in Scheme 2. Addition of 1 equivalent of amine to a 1,4-dichlorophthalazine to prepare compounds of type IV is followed by Negishi coupling with benzyl- or alkylzinc halides. Zinc halide complexes that are not available commercially can be prepared from the corresponding alkyl bromides following the protocol of Fu et al. (*Synlett* 2006, 630-632).

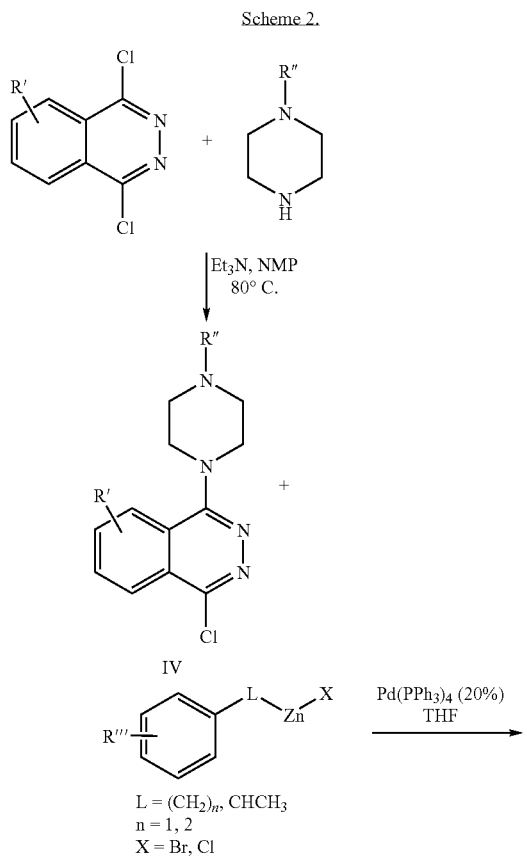

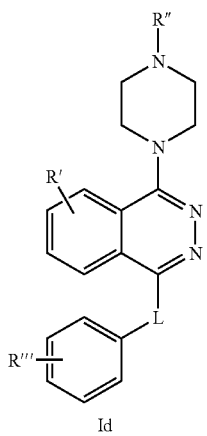

Id

Synthesis of Intermediates

6-[4-(4-Chloro-phthalazin-1-yl)-piperazin-1-yl]-nicotinonitrile (Compound 22)

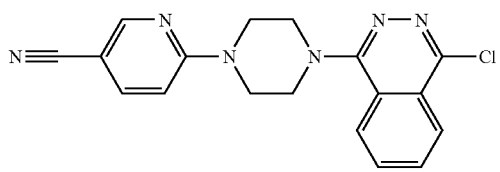 [SMILES: N#Cc1ccc(N2CCN(c3nnc(Cl)c4ccccc34)CC2)nc1]

To a 100-mL round-bottom flask is added 6-piperazin-1-yl-nicotinonitrile (9.60 g, 50 mmol), 1,4-dichlorophthalazine (11.2 g, 55.1 mmol, 1.1 eq), Et$_3$N (3.5 mL, 250 mmol, 5 eq.), and NMP (100 mL). The mixture is heated to 80° C. for 2.5 h. Upon cooling to room temperature, the reaction is poured into H$_2$O (500 mL) and the precipitate isolated by filtration, rinsing with additional H$_2$O. Crude material is purified by recrystallization (CH$_2$Cl$_2$:heptanes) to afford 8.96 g title compound as a beige solid.

$^1$H NMR (400 MHz, CDCl$_3$): δ=8.39 (s, 1H); 8.20-8.24 (m, 1H); 8.03-8.08 (m, 1H); 7.86-7.93 (m, 2H); 7.62 (d, J=8 Hz, 1H); 6.65 (d, J=12 Hz, 1H); 3.88-3.95 (m, 4H); 3.62-3.67 (m, 4H).

6-[4-(4-Chloro-phthalazin-1-yl)-piperazin-1-yl]-nicotinic acid ethyl ester (Compound 23)

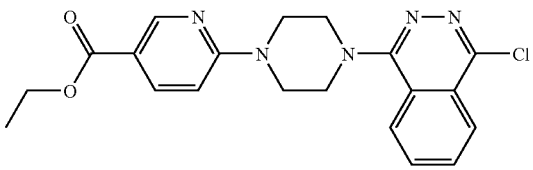 [SMILES: CCOC(=O)c1ccc(N2CCN(c3nnc(Cl)c4ccccc34)CC2)nc1]

Combine 6-piperazin-1-yl-nicotinic acid ethyl ester (1.30 g, 5.40 mmol), 1,4-dichlorophthalazine (932 mg, 4.59 mmol), triethylamine (1.78 mL, 13.50 mmol), and NMP (8 mL) and heat to 85° C. for 6 h. Cool to room temperature, dilute with H$_2$O (50 mL) and extract organics with EtOAc (3×50 mL). Combined organic layers are dried over MgSO$_4$ and concentrated. Resulting solid is triturated with EtOAc to give the title compound as a fine tan powder (895 mg, 49% yield).

¹H NMR (400 MHz, CDCl₃) δ 8.87 (d, J=2.3 Hz, 1H) 8.26-8.32 (m, 1H) 8.08-8.17 (m, 2H) 7.91-8.00 (m, 2H) 6.72 (d, J=9.1 Hz, 1H) 4.37 (q, J=7.1 Hz, 2H) 3.94-4.02 (m, 4H) 3.64-3.72 (m, 4H) 1.40 (t, J=7.1 Hz, 3H).

6-((S)-3-Methyl-piperazin-1-yl)-nicotinic acid ethyl ester (Compound 24)

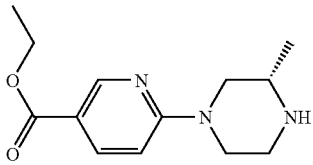 [SMILES: CCOC(=O)c1ccc(N2CCN[C@@H](C)C2)nc1]

Triethylamine (3.7 mL, 27 mmol, 5.0 eq) is added to a solution of 6-chloronicotinic acid ethyl ester (1.0 g, 5.4 mmol, 1 eq), (S)-2-methyl-piperazine (540 mg, 5.4 mmol, 1 eq) in NMP (6 mL) in a microwave vial. The vial is sealed and irradiated in the microwave at 150° C. (high absorption setting) for 30 min. Water (15 mL) and EtOAc (100 mL) are added, the organic layer is separated, dried over sodium sulfate and concentrated under reduced pressure to a white residue. The desired compound is isolated by silica gel chromatography (5-60% EtOAc/Heptane, then 10% MeOH/Heptane), (700 mg, 52% yield).

1H NMR (400 MHz, CHLOROFORM-d) δ ppm 8.81 (d, J=2.27 Hz, 1H) 8.02 (dd, J=9.03, 2.34 Hz, 1H) 6.59 (d, J=8.97 Hz, 1H) 4.34 (q, J=7.24 Hz, 2H) 3.12 (d, J=9.09 Hz, 1H) 2.89-3.00 (m, 2H) 2.81-2.90 (m, 2H) 2.60 (d, J=10.48 Hz, 1H) 2.56 (d, J=10.36 Hz, 1H) 1.37 (t, J=7.07 Hz, 3H) 1.15 (d, J=6.32 Hz, 3H)

MS (m/z, MH+): meas. 250.1

6-[(S)-4-(4-Chloro-phthalazin-1-yl)-3-methyl-piperazin-1-yl]-nicotinic acid ethyl ester (Compound 25)

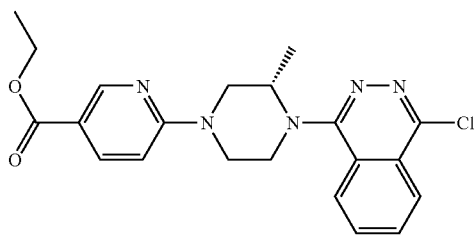 [SMILES: CCOC(=O)c1ccc(N2CCN(c3nnc(Cl)c4ccccc34)[C@@H](C)C2)nc1]

A solution of 6-((S)-3-methyl-piperazin-1-yl)-nicotinic acid ethyl ester (1.0 g, 4.0 mmol, 1 eq), 1,4-dichlorophthalazine (840 mg, 4.2 mmol, 1.05 eq) and triethyl amine (3.9 g, 2.8 mL, 38 mmol, 9.5 eq) in NMP (8 mL) is heated at 100 C for 26 h. Reaction is diluted with water (15 mL) and extracted with EtOAc (3×25 mL). The combined organic fractions are dried over magnesium sulfate, concentrated and purified by silica gel chromatography (5-50% EtOAc/Heptane) to yield the desired compound (500 mg, 30% yield).

1H NMR (400 MHz, CHLOROFORM-d) δ ppm 8.85 (d, J=2.15 Hz, 1H) 8.26-8.31 (m, 1H) 8.15-8.20 (m, 1H) 8.09 (dd, J=9.03, 2.34 Hz, 1H) 7.92-7.98 (m, 2H) 6.69 (d, J=8.97 Hz, 1H) 4.37 (q, J=7.20 Hz, 2H) 4.19-4.28 (m, 1H) 4.08-4.15 (m, 1H) 3.96-4.03 (m, 1H) 3.86-3.92 (m, 1H) 3.77-3.85 (m, 1H) 3.68-3.76 (m, 1H) 3.56-3.63 (m, 1H) 1.40 (t, J=7.14 Hz, 3H) 1.27 (d, J=6.44 Hz, 3H)

MS (m/z, MH+): meas. 412.3

6-Chloro-2,3-dihydro-phthalazine-1,4-dione (Compound 26)

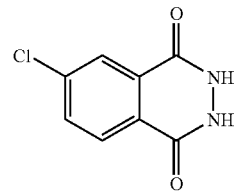 [SMILES: O=c1[nH][nH]c(=O)c2cc(Cl)ccc12]

A mixture of 4-chlorophthalic anhydride (1.81 g, 10 mmol) and acetic acid (15 mL) was added to a solution of hydrazine hydrate (0.62 mL, 10 mmol) in acetic acid (2 mL). The resulting mixture was stirred at reflux for 2 h. The precipitate was collected and dried to give the title compound as a white solid (1.82 g, 95%).

¹H NMR (400 MHz, DMSO-d₆): δ=11.71 (s, 2H), 8.08 (d, J=8.3 Hz, 1H), 8.02 (s, 1H), 7.93 (d, J=8.3 Hz, 1H).

1,4,6-Trichloro-phthalazine (Compound 27)

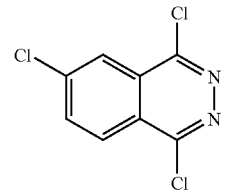 [SMILES: Clc1ccc2c(Cl)nnc(Cl)c2c1]

To a mixture of pyridine (1.75 mL) and POCl₃ (10 mL) was added compound x (see above, 1.81 g, 9.2 mmol). The suspension was heated to 100° C. for 2 h. A clear solution was observed. The solution was concentrated under reduced pressure and the residue was poured on crushed ice. The solid was collected and washed thoroughly with water, dried under vacuum to give the title compound as a solid (1.82 g, 85%).

¹H NMR (400 MHz, CDCl₃): δ=8.23 (d, J=2.0 Hz, 1H), 8.21 (d, J=8.8 Hz, 1H), 7.94 (dd, J=2.0, 8.8 Hz, 1H).

6-[4-(4,7-Dichloro-phthalazin-1-yl)-piperazin-1-yl]-nicotinonitrile and 6-[4-(4,6-dichloro-phthalazin-1-yl)-piperazin-1-yl]-nicotinonitrile (Compounds 28a and 28b)

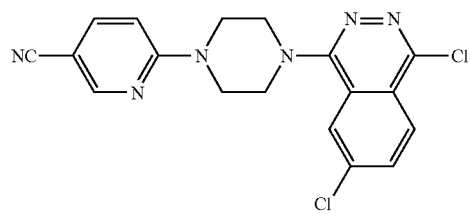

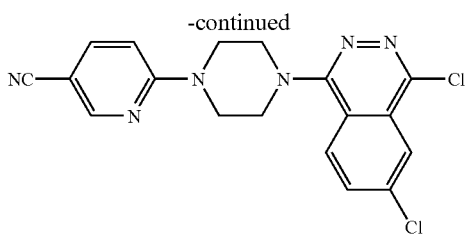

To a solution of compound 30 (see above, 234 mg, 1 mmol) 1-[(cyano)-pyrid-2-yl]-piperazine (188 mg, 1 mmol) in NMP (3 mL) was added triethyl amine (277 μL, 2 mmol). The mixture was heated to 150° C. in a microwave reactor for 30 min. EtOAc (10 mL) and water (10 mL) were added to the dark solution. The precipitate was collected, washed with EtOAc and dried to give the title compounds in a 1:1 ratio as yellow solids (255 mg, 66%).

$^1$H NMR of the 1:1 mixture of compounds 31 and 32 (400 MHz, DMSO-$d_6$): δ=8.54/8.53 (overlapping s, together 1H), 8.24-8.20 (m, 2H), 8.10 (m, 1H), 7.91 (m, 1H), 7.02 (m, 1H), 3.95 (m, 4H), 3.56 (m, 4H).

Synthesis of Examples 56-69, 173-189

General Procedure for Negishi-Type Coupling of 6-[4-(4-chloro-phthalazin-1-yl)-piperazin-1-yl]-nicotinonitrile To a sealable tube under $N_2$ is added 6-[4-(4-Chloro-phthalazin-1-yl)-piperazin-1-yl]-nicotinonitrile (150 mg, 0.43 mmol), Pd(PPh$_3$)$_4$ (100 mg, 0.086 mmol, 0.2 eq), and THF (10 mL). The solution is degassed by bubbling in $N_2$ for several minutes. A 0.5M solution of benzylzinc chloride (3.0 eq.) in THF is then added via syringe. The tube is sealed and the reaction is stirred at room temperature for 3 h. (Note: Some substrates require additional reaction time and/or heating to 75° C. to achieve full conversion.) Upon completion, the reaction is concentrated and purified by flash chromatography on silica gel.

Example 56

6-{4-[4-(3-Trifluoromethyl-benzyl)-phthalazin-1-yl]-piperazin-1-yl}-nicotinonitrile

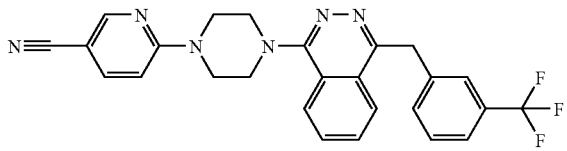 [SMILES: N#Cc1ccc(N2CCN(c3nnc(Cc4cccc(C(F)(F)F)c4)c4ccccc34)CC2)nc1]

The general protocol affords 70 mg of the above compound as a white powder.

$^1$H NMR (400 MHz, DMSO-$d_6$): δ=8.54 (s, 1H); 8.29 (t, J=4 Hz, 1H); 8.22 (t, J=4 Hz, 1H); 7.95-8.00 (m, 2H); 7.92 (d, J=8 Hz, 1H); 7.78 (s, 1H); 7.50-7.65 (m, 3H); 7.04 (d, J=8 Hz, 1H); 4.72 (s, 2H); 3.96 (bs, 4H); 3.50 (bs, 4H).

HR-MS (m/z, MH+): meas. 475.1837 calc. 475.1858

Examples 57-69, 173-188

The following table (Table 4) lists examples of compounds prepared by Negishi coupling as described above:

TABLE 4

| Example | Structure | MS [m/z; M + 1] |
|---|---|---|
| 57 | 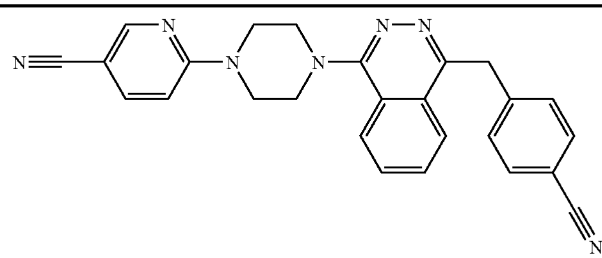 | 432 |
| 58 | 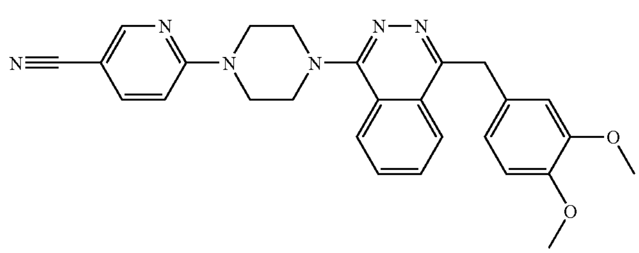 [SMILES: COc1ccc(Cc2nnc(N3CCN(c4ccc(C#N)cn4)CC3)c3ccccc23)cc1OC] | 467 |
| 59 | 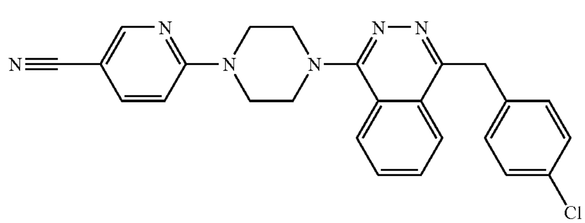 [SMILES: N#Cc1ccc(N2CCN(c3nnc(Cc4ccc(Cl)cc4)c4ccccc34)CC2)nc1] | 441 |

TABLE 4-continued

| Example | Structure | MS [m/z; M + 1] |
|---|---|---|
| 60 | 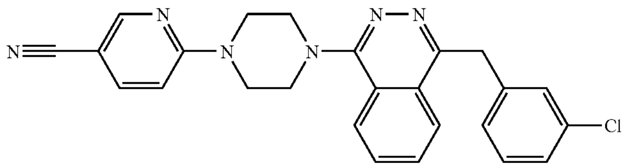 | 441 |
| 61 | 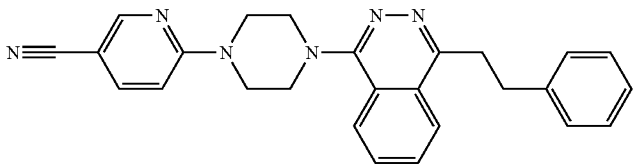 [SMILES: N#Cc1ccc(N2CCN(c3nnc(CCc4ccccc4)c4ccccc34)CC2)nc1] | 421 |
| 62 | 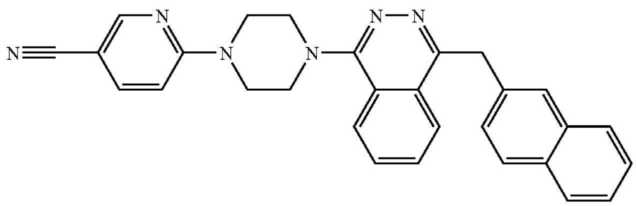 [SMILES: N#Cc1ccc(N2CCN(c3nnc(Cc4ccc5ccccc5c4)c4ccccc34)CC2)nc1] | 457 |
| 63 | 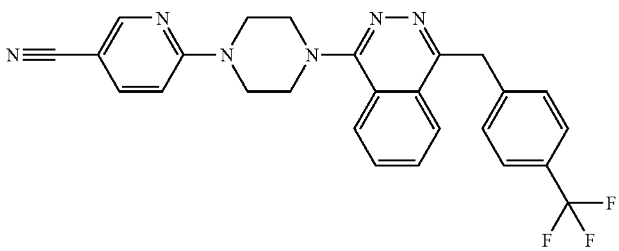 [SMILES: N#Cc1ccc(N2CCN(c3nnc(Cc4ccc(C(F)(F)F)cc4)c4ccccc34)CC2)nc1] | 475 |
| 64 | 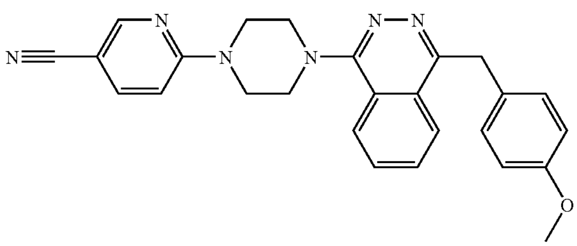 [SMILES: COc1ccc(Cc2nnc(N3CCN(c4ccc(C#N)cn4)CC3)c3ccccc23)cc1] | 437 |
| 65 | 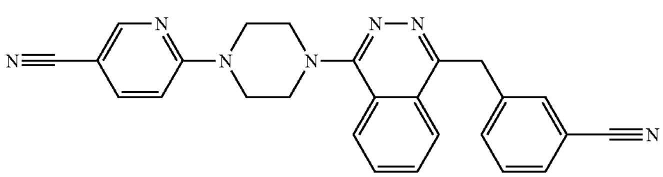 [SMILES: N#Cc1ccc(N2CCN(c3nnc(Cc4cccc(C#N)c4)c4ccccc34)CC2)nc1] | 432 |
| 66 | 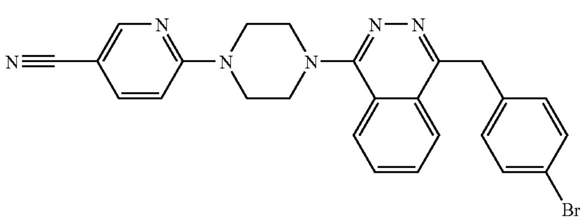 [SMILES: N#Cc1ccc(N2CCN(c3nnc(Cc4ccc(Br)cc4)c4ccccc34)CC2)nc1] | 485 |

TABLE 4-continued

| Example | Structure | MS [m/z; M + 1] |
|---|---|---|
| 67 | 5-cyanopyridin-2-yl-piperazinyl-phthalazine-benzyl-3-Br | 485 |
| 68 | 5-cyanopyridin-2-yl-piperazinyl-phthalazine-1-phenylethyl | 421 |
| 69 | 5-cyanopyridin-2-yl-piperazinyl-phthalazine-benzyl-3-methyl | 421 |
| 173 | 5-cyanopyridin-2-yl-piperazinyl-phthalazine-benzyl-4-methyl | 422 |
| 174 | 5-cyanopyridin-2-yl-piperazinyl-phthalazine-benzyl-2-Cl | 442 |
| 175 | 5-cyanopyridin-2-yl-piperazinyl-phthalazine-benzyl-2-OMe | 438 |
| 176 | 5-cyanopyridin-2-yl-piperazinyl-phthalazine-benzyl-3,4-diCl | 476 |
| 177 | 5-cyanopyridin-2-yl-piperazinyl-phthalazine-benzyl-2,4-diCl | 476 |

TABLE 4-continued

| Example | Structure | MS [m/z; M + 1] |
|---|---|---|
| 178 | 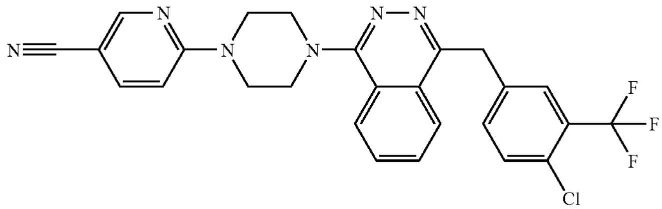 [SMILES: N#Cc1ccc(N2CCN(c3nnc(Cc4ccc(Cl)c(C(F)(F)F)c4)c4ccccc34)CC2)nc1] | 510 |
| 179 | 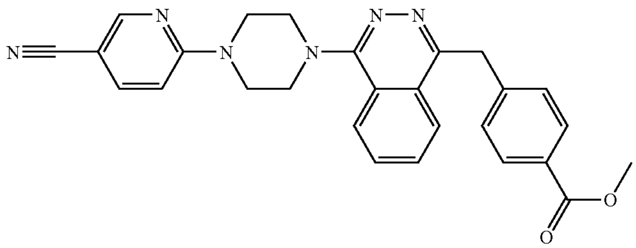 [SMILES: COC(=O)c1ccc(Cc2nnc(N3CCN(c4ccc(C#N)cn4)CC3)c3ccccc23)cc1] | 466 |
| 180 | 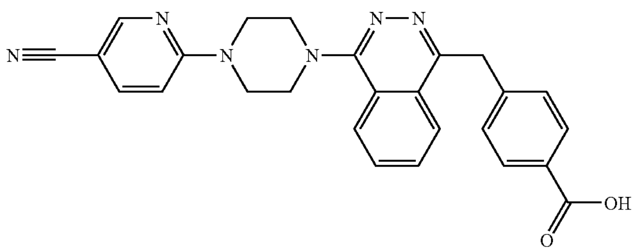 | 452 |
| 181 | 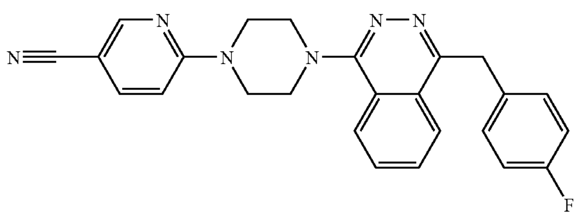 [SMILES: N#Cc1ccc(N2CCN(c3nnc(Cc4ccc(F)cc4)c4ccccc34)CC2)nc1] | 425 |
| 182 | 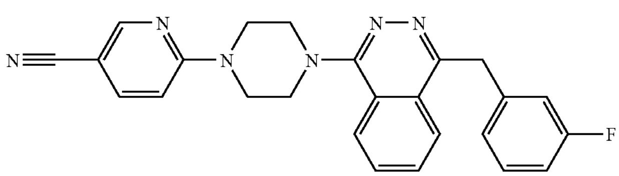 [SMILES: N#Cc1ccc(N2CCN(c3nnc(Cc4cccc(F)c4)c4ccccc34)CC2)nc1] | 425 |
| 183 | 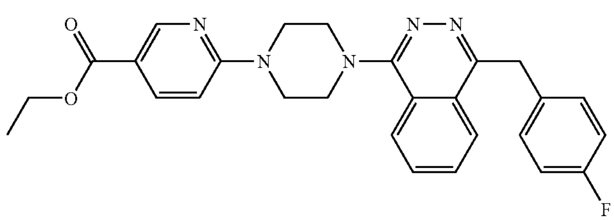 [SMILES: CCOC(=O)c1ccc(N2CCN(c3nnc(Cc4ccc(F)cc4)c4ccccc34)CC2)nc1] | 473 |
| 184 | 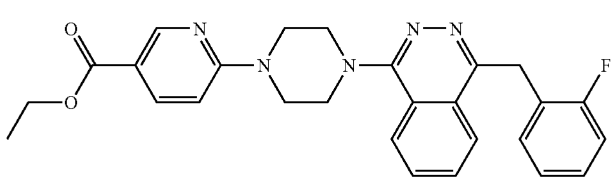 [SMILES: CCOC(=O)c1ccc(N2CCN(c3nnc(Cc4ccccc4F)c4ccccc34)CC2)nc1] | 473 |

TABLE 4-continued

| Example | Structure | MS [m/z; M + 1] |
|---|---|---|
| 185 | 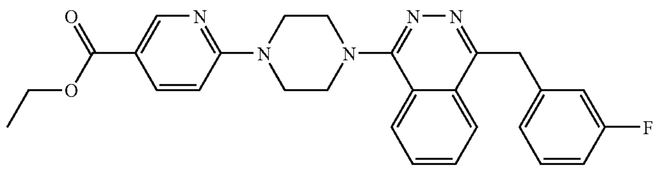 [SMILES: CCOC(=O)c1ccc(N2CCN(c3nnc(Cc4cccc(F)c4)c4ccccc34)CC2)nc1] | 473 |
| 186 | 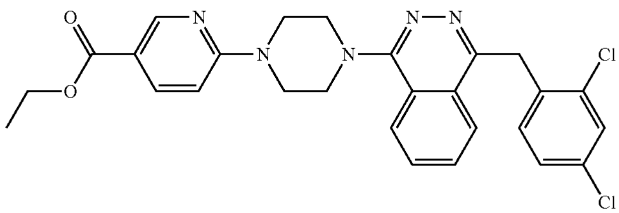 [SMILES: CCOC(=O)c1ccc(N2CCN(c3nnc(Cc4ccc(Cl)cc4Cl)c4ccccc34)CC2)nc1] | 523 |
| 187 | 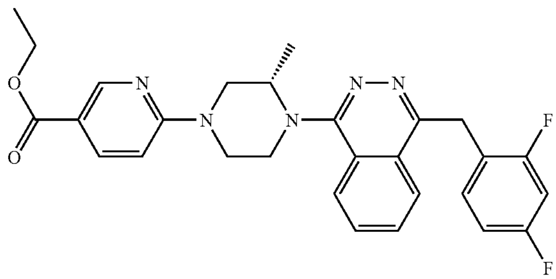 [SMILES: CCOC(=O)c1ccc(N2CCN(c3nnc(Cc4ccc(F)cc4F)c4ccccc34)[C@@H](C)C2)nc1] | 504 |
| 188 | 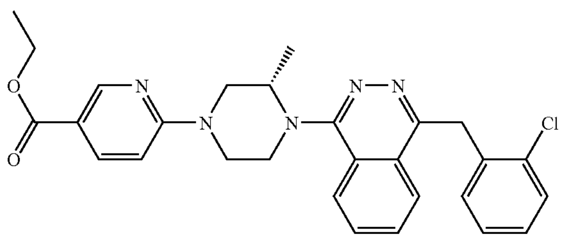 [SMILES: CCOC(=O)c1ccc(N2CCN(c3nnc(Cc4ccccc4Cl)c4ccccc34)[C@@H](C)C2)nc1] | 502 |

Examples 189a and 189b

6-{4-[7-Chloro-4-(4-fluoro-benzyl)-phthalazin-1-yl]-piperazin-1-yl}-nicotinonitrile and 6-{4-[6-Chloro-4-(4-fluoro-benzyl)-phthalazin-1-yl]-piperazin-1-yl}-nicotinonitrile

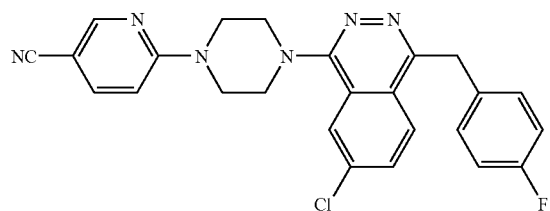

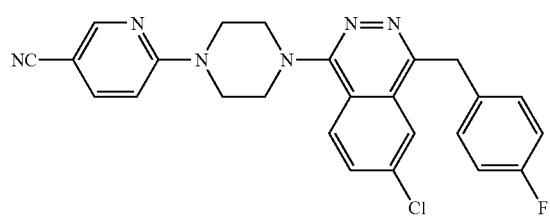

A solution of 6-[4-(4,7-dichloro-phthalazin-1-yl)-piperazin-1-yl]-nicotinonitrile and 6-[4-(4,6-dichloro-phthalazin-1-yl)-piperazin-1-yl]-nicotinonitrile (255 mg, 0.66 mmol) and Pd(PPh$_3$)$_4$ (96 mg, 0.08 mmol) in THF (2.5 mL) was degassed for 15 min. p-Fluorobenzyl zinc bromide (1.32 mL, 0.5N in THF, 0.66 mmol) was added and the resulting mixture was stirred at 60° C. for 30 min to give a yellow solution. The organic layer was separated and the aqueous layer was extracted with dichloromethane. The combined organic layers were dried over Na$_2$SO$_4$ and evaporated to give a yellow residue. Flash chromatography on silica gel (EtOAc/heptane 3:1) afforded the title compounds as a 1:1 mixture (244 mg, 81%).

$^1$H NMR of the 1:1 mixture of examples 189a and 189b (400 MHz, CDCl$_3$): δ=8.38 (m, 1H), 7.98 (m, 1H), 7.88 (m, 1H), 7.69-7.59 (m, 2H), 7.21 (m, 2H), 6.91 (m, 2H), 6.64 (m, 1H), 4.51 (s, 1H), 4.49 (s, 1H), 3.89 (m, 4H), 3.56 (m, 4H).

Interconversion of Examples 189a and 189b into 190a and 190b Via Palladium-Catalyzed Coupling with Zinc Cyanide Examples 190a and 190b 4-[4-(5-Cyano-pyridin-2-yl)-piperazin-1-yl]-1-(4-fluorobenzyl)-phthalazine-6-carbonitrile and 1-[4-(5-Cyano-pyridin-2-yl)-piperazin-1-yl]-4-(4-fluoro-benzyl)-phthalazine-6-carbonitrile

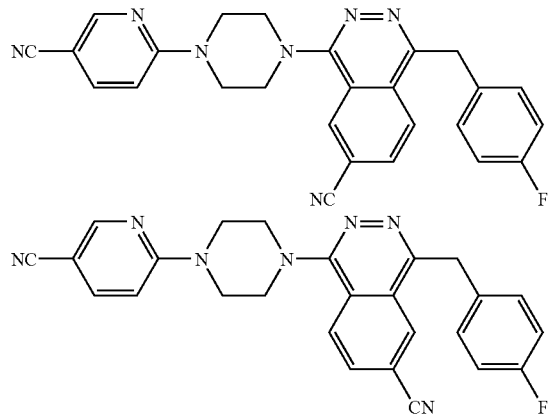

To a solution of 6-{4-[7-chloro-4-(4-fluoro-benzyl)-phthalazin-1-yl]-piperazin-1-yl}-nicotinonitrile and 6-{4-[6-chloro-4-(4-fluoro-benzyl)-phthalazin-1-yl]-piperazin-1-yl}-nicotinonitrile (46 mg, 0.1 mmol) in DMF (2 mL) was added $Zn(CN)_2$ (24 mg, 0.2 mmol) and $Pd_2(dba)_3$ (9.2 mg, 0.1 eq.) and X-phos (6 mg, 0.125 eq.). The mixture was degassed and heated in a microwave reactor at 120° C. for 45 min. EtOAc (4 mL) was added and solids were filtered off through a silica gel plug. The filtrate was washed with water, brine, dried over $Na_2SO_4$ and evaporated to a yellow residue. Flash chromatography on silica gel (heptane/EtOAc 1:3) gave the 1:1 mixture as a yellow powder (41 mg, 91%).

$^1$H NMR of the 1:1 mixture of examples 190a and 190b (400 MHz, $CDCl_3$): δ=8.37 (m, 0.5H), 8.36 (s, 1H), 8.26 (m, 0.5H), 8.14 (d, J=8.6 Hz, 0.5H), 8.02 (d, J=8.6 Hz, 0.5H), 7.91 (m, 0.5H), 7.87 (m, 0.5H), 7.61 (m, 1H), 7.20 (m, 2H), 6.90 (m, 2H), 6.63 (m, 1H), 4.53 (s, 2H), 3.90 (m, 4H), 3.58 (m, 4H).

Interconversion of Example 183 into Example 191 by Grignard Addition

Example 191

2-(6-{4-[4-(4-Fluoro-benzyl)-phthalazin-1-yl]-piperazin-1-yl}-pyridin-3-yl)-propan-2-ol

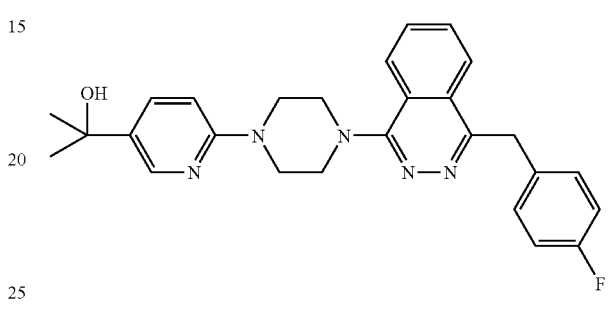

6-{4-[4-(4-Fluoro-benzyl)-phthalazin-1-yl]-piperazin-1-yl}-nicotinic acid ethyl ester (85 mg, 0.180 mmol) is dissolved in THF (1 mL). Methyl magnesium iodide (240 µL, 3M in diethyl ether, 0.72 mmol) is added dropwise. Stir reaction for 2 h at room temperature. Concentrate in vacuo. The residue is purified by flash chromatography on silica gel (MeOH/$CH_2Cl_2$) to afford the title compound (8 mg, 10%).

$^1$H NMR (600 MHz, DMSO-$d_6$) δ ppm 8.25 (d, J=2.27 Hz, 1H) 8.20 (dd, J=13.97, 7.55 Hz, 2H) 7.93 (ddm, J=13.60, 7.18 Hz, 2H) 7.66 (dd, J=8.88, 2.46 Hz, 1H) 7.37 (dd, J=8.31, 5.67 Hz, 2H) 7.10 (t, J=8.88 Hz, 2H) 6.87 (d, J=8.69 Hz, 1H) 4.96 (s, 1H) 4.59 (s, 2H) 3.78-3.69 (m, 4H) 3.53-3.44 (m, 4H) 1.42 (s, 6H)

HR-MS (m/z, $MH^+$): meas. 458.2348 calc. 458.2356

Examples 192-196

The following table (Table 4a) lists examples of compounds prepared by Grignard addition as described above:

TABLE 4a

| Example | Structure | MS [m/z; M + 1] |
|---|---|---|
| 192 | 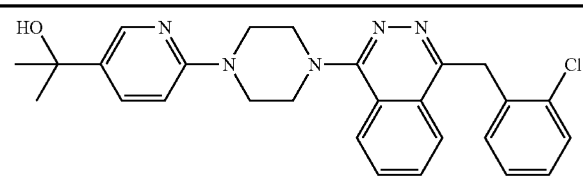 | 475 |
| 193 | 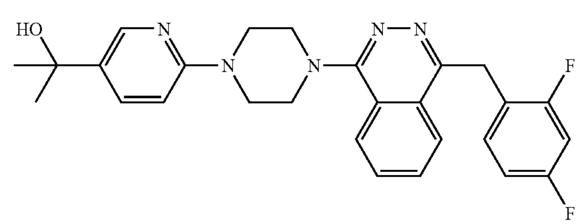 [SMILES: CC(C)(O)c1ccc(N2CCN(c3nnc(Cc4ccc(F)cc4F)c4ccccc34)CC2)nc1] | 477 |

TABLE 4a-continued

| Example | Structure | MS [m/z; M + 1] |
|---|---|---|
| 194 | 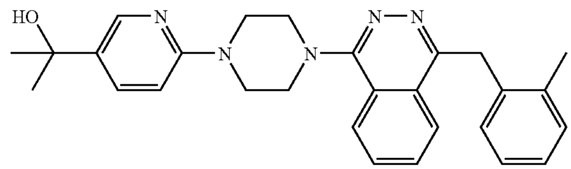 [SMILES: Cc1ccccc1Cc1nnc(N2CCN(c3ccc(C(C)(C)O)cn3)CC2)c2ccccc12] | 455 |
| 195 | 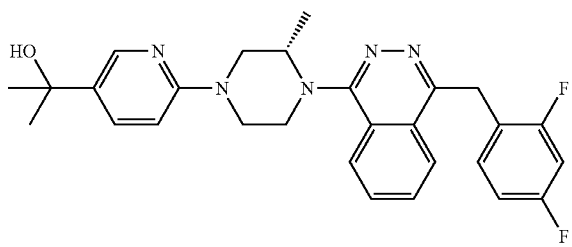 [SMILES: C[C@H]1CN(c2ccc(C(C)(C)O)cn2)CCN1c1nnc(Cc2ccc(F)cc2F)c2ccccc12] | 491 |
| 196 | 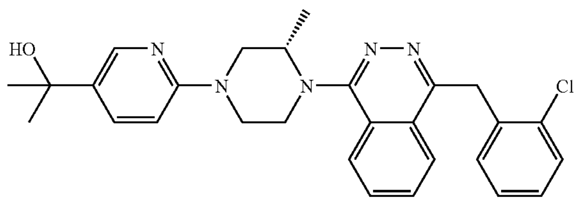 [SMILES: C[C@H]1CN(c2ccc(C(C)(C)O)cn2)CCN1c1nnc(Cc2ccccc2Cl)c2ccccc12] | 488 |

Interconversion of Example 183 into Examples 197-202 by Hydrolysis/Amidation

Example 197

6-{4-[4-(4-Fluoro-benzyl)-phthalazin-1-yl]-piperazin-1-yl}-nicotinic acid

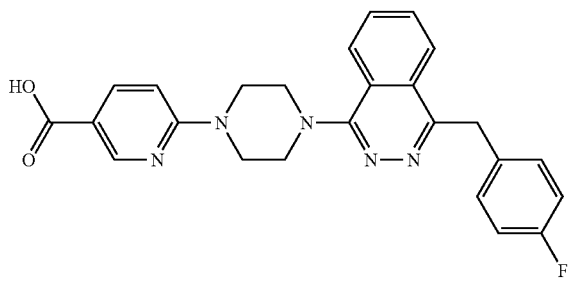 [SMILES: O=C(O)c1ccc(N2CCN(c3nnc(Cc4ccc(F)cc4)c4ccccc34)CC2)nc1]

6-{4-[4-(4-Fluoro-benzyl)-phthalazin-1-yl]-piperazin-1-yl}-nicotinic acid ethyl ester (188 mg, 0.4 mmol), Lithium hydroxide (96 mg, 4.0 mmol), THF (750 μL), MeOH (750 μL), and H$_2$O (400 μL) are combined at room temperature and stirred 16 h. Adjust pH to between three and four with 1N HCl. Extract with CH$_2$Cl$_2$/EtOH 4:1 and combined organics are washed with brine. Concentrate in vacuo to yield the title compound without further purification (165 mg, 93%).

Example 198

6-{4-[4-(4-Fluoro-benzyl)-phthalazin-1-yl]-piperazin-1-yl}-N-(2-hydroxyethyl)-N-methyl-nicotinamide

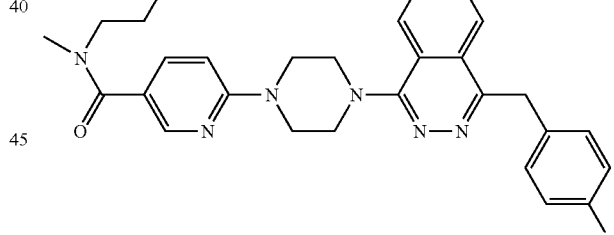

6-{4-[4-(4-Fluoro-benzyl)-phthalazin-1-yl]-piperazin-1-yl}-nicotinic acid (100 mg, 0.225 mmol), DMF (0.5 mL), Diisopropylethylamine (195 μL, 1.125 mmol), HBTU (102 mg, 0.270 mmol), and 2-(methylamino)ethanol (18 μL, 0.225 mmol) are combined in a 10 mL flask and stirred for 4 h at room temperature. Concentrate to remove DMF in vacuo. The residue is purified by flash chromatography on silica gel (0-25% MeOH/CH$_2$Cl$_2$ with 5% TEA) to afford the title compound (68.2 mg, 61%).

$^1$H NMR (400 MHz, DMSO-d6) δ 8.28 (d, J=2.01 Hz, 1H), 8.25-8.18 (m, 2H), 7.98-7.90 (m, 2H), 7.70 (dd, J=8.78, 2.26 Hz, 1H), 7.41-7.34 (m, 2H), 7.16-7.05 (m, 2H), 6.94 (d, J=9.03 Hz, 1H), 4.84 (br.s, 1H), 4.60 (s, 2H), 3.95-3.78 (m, 4H), 3.57 (br.s, 2H), 3.53-3.47 (m, 4H), 3.43 (br.s, 2H), 3.00 (br.s, 3H).

HR-MS (m/z, MH$^+$): meas. 501.2414 calc. 501.2414

Examples 199-202

The following table (Table 4b) lists examples of compounds prepared by hydrolysis/amidation as described above:

TABLE 4b

| Example | Structure | MS [m/z; M + 1] |
|---|---|---|
| 199 | 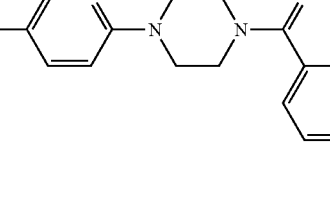 | 520 |
| 200 | 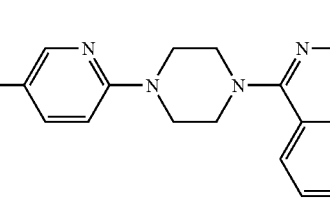 | 518 |
| 201 | 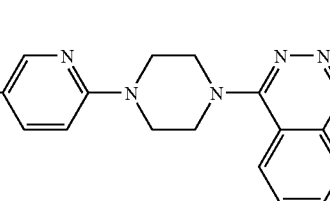 | 552 |
| 202 | 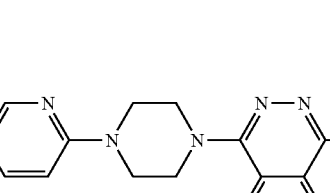 | 490 |

Example 203

6-[4-(4-Morpholin-4-ylmethyl-phthalazin-1-yl)-piperazin-1-yl]-nicotinic acid ethyl ester

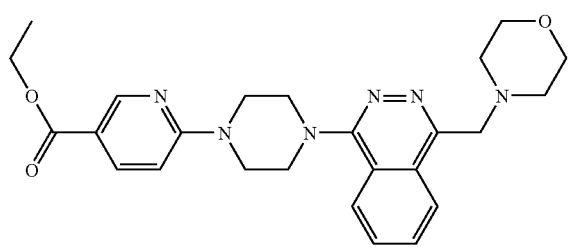 [SMILES: CCOC(=O)c1ccc(N2CCN(c3nnc(CN4CCOCC4)c4ccccc34)CC2)nc1]

Potassium-4-trifluoroborate-methyl-morpholine (50 mg, 0.24 mmol), 6-[4-(4-Chloro-phthalazin-1-yl)-piperazin-1-yl]-nicotinic acid ethyl ester (86.3 mg, 0.217 mmol), cesium carbonate (212.22 mg, 0.651 mmol), palladium (II) acetate (1.5 mg, 0.007 mmol), XPhos (6.3 mg, 0.013 mmol), THF (0.9 mL) and water (0.1 mL) are added to a sealed tube and then heated at 80° C. for 16 h. The organics are extracted with $CH_2Cl_2$ and dried over $Na_2SO_4$, filtered and concentrated under reduced pressure. The aqueous layer is also concentrated since it contains product. Combined crude material is purified via reverse-phase HPLC (trifluoroacetic acid as a modifier) followed by flash chromatography on silica gel (0-2% methanol in $CH_2Cl_2$). The purified material is dried under high vacuum to afford the title compound (7 mg, 7% yield).

$^1$H NMR (400 MHz, DMSO-d6) ∂ 8.70 (s, 1H), 8.24-8.31 (m, 2H), 8.07-8.09 (m, 2H), 8.02 (dd, J=11 Hz, 3 Hz, 1H), 6.98 (d, J=12 Hz, 1H), 5.05 (s, br, 2H), 4.27 (q, 2H), 3.97 (s, br, 4H), 3.87 (s, br, 4H), 3.59 (s, br, 4H), 3.45 (s, br, 4H), 1.31 (t, 3H).

HR-MS (m/z, MH+): meas. 463.2462

Examples 70-78, 204-216

As illustrated in Scheme 3, alternatively compounds of Formula Ie can be prepared by nitrile reduction of compounds V and subsequent functionalization of the resulting amines VI.

SCHEME 3.

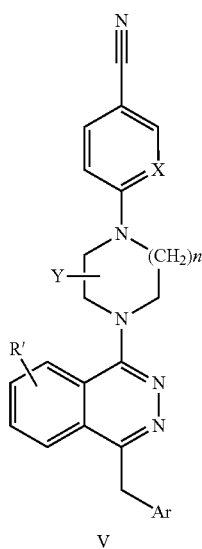

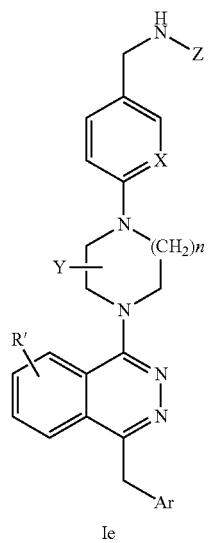

Z = SO$_2$R" or C(O)OR" or C(O)R"

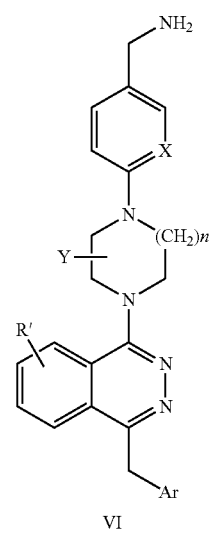

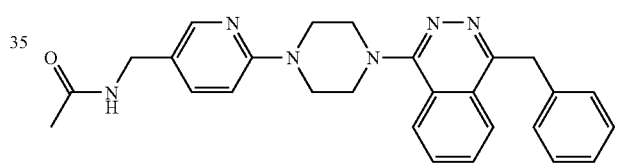

Example 70

N-{6-[4-(4-Benzyl-phthalazin-1-yl)-piperazin-1-yl]-pyridin-3-ylmethyl}-acetamide In a 100 ml, round-bottom flask equipped with a stir bar, 6-[4-(4-Benzyl-phthalazin-1-yl)-piperazin-1-yl]-nicotinonitrile (150 mg, 0.362 mmol) is dissolved in anhydrous EtOH (7 mL) followed by the addition of NiCl$_2$ (0.398 mmol). NaBH$_4$ (0.723 mmol) is added in portions and the reaction is stirred for 2 h under a N2 atmosphere. The septum is removed and Ac$_2$O (1.08 mmol) is added. The reaction is capped again and stirred for one additional hour. LC/MS shows full conversion to the acylated product. The reaction is filtered through a Celite pad and rinsed with 50 ml of MeOH. The final compound is purified by preparative HPLC using a C-18 column and propanol as the modifier (85 mg, 52% yield).

$^1$H NMR (400 MHz, CDCl$_3$): δ=8.13 (m, 2H) 8.03 (d, J=8 Hz, 1H), 7.77 (m, 2H), 7.55 (dd, J=9.1 Hz, 2.5 Hz, 1H), 7.35 (d, J=7.0 Hz, 2H) 7.27 (t, J=7.5 Hz, 2H), 7.18 (t, J=7.5 Hz, 1H) 6.75 (d, J=8.6 Hz, 1H) 5.71 (s, 1H) 4.63 (s, 2H) 4.33 (d, J=6.1 Hz, 2H) 3.82 (t, J=5.5 Hz, 4H), 3.65 (t, J=5.5 Hz, 4H), 2.01 (s, 3H).

HR-MS (m/z, MH+): meas. 453.2393

Examples 71-78, 204-216

The following table (Table 5) lists examples of compounds prepared as described above:

TABLE 5

| Example | Structure | MS [m/z; M + 1] |
|---|---|---|
| 71 | 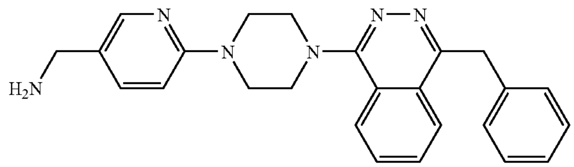 | 411 |
| 72 | 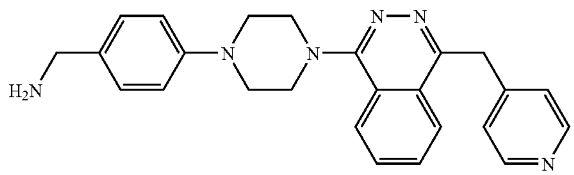 [SMILES: NCc1ccc(N2CCN(c3nnc(Cc4ccncc4)c4ccccc34)CC2)cc1] | 411 |
| 73 | 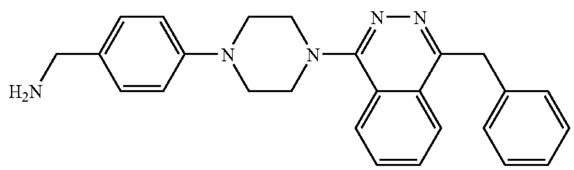 [SMILES: NCc1ccc(N2CCN(c3nnc(Cc4ccccc4)c4ccccc34)CC2)cc1] | 410 |
| 74 | 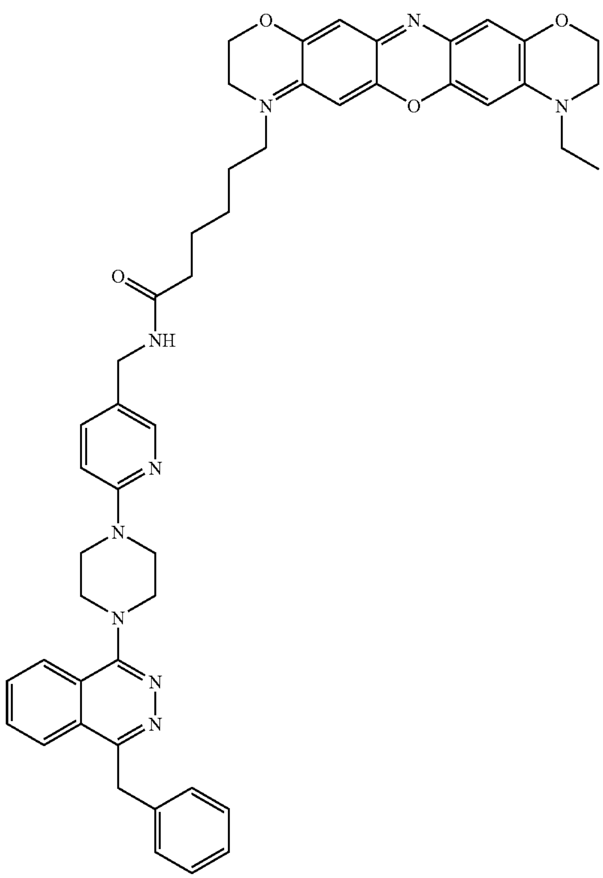 | 831 |
| 75 | 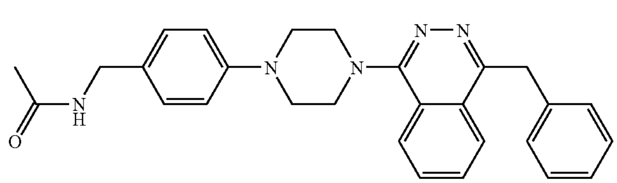 [SMILES: CC(=O)NCc1ccc(N2CCN(c3nnc(Cc4ccccc4)c4ccccc34)CC2)cc1] | 452 |

TABLE 5-continued

| Example | Structure | MS [m/z; M + 1] |
|---|---|---|
| 76 | 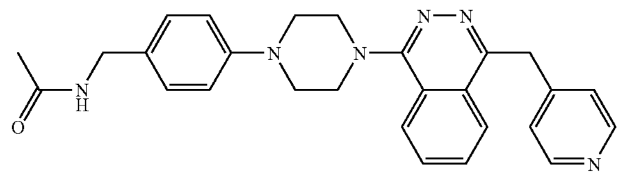 [SMILES: CC(=O)NCc1ccc(N2CCN(c3nnc(Cc4ccncc4)c4ccccc34)CC2)cc1] | 453 |
| 77 | 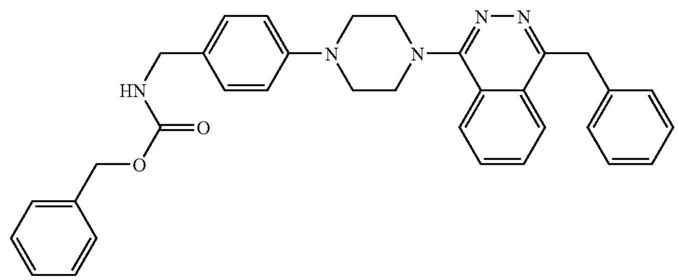 [SMILES: O=C(NCc1ccc(N2CCN(c3nnc(Cc4ccccc4)c4ccccc34)CC2)cc1)OCc1ccccc1] | 544 |
| 78 | 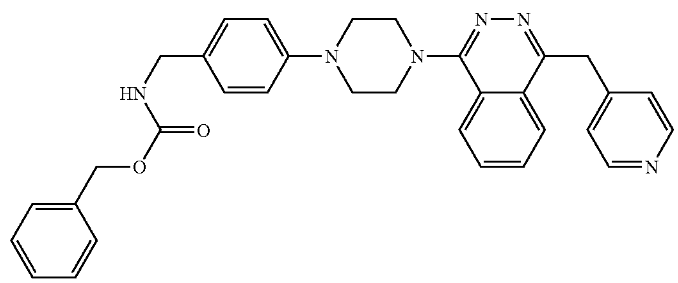 | 545 |
| 78a | 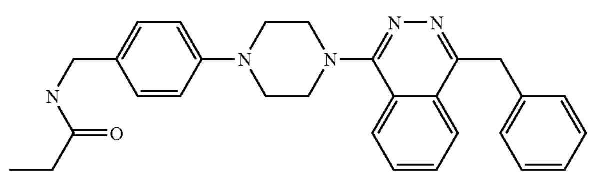 [SMILES: CCC(=O)NCc1ccc(N2CCN(c3nnc(Cc4ccccc4)c4ccccc34)CC2)cc1] | 466 |
| 78b | 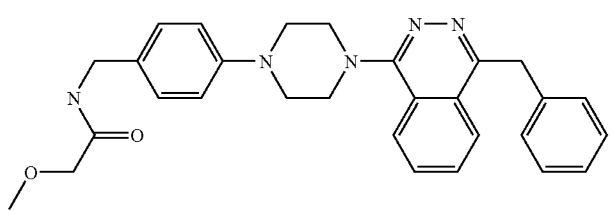 | 482 |
| 78c | 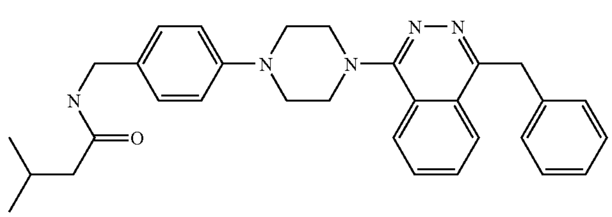 [SMILES: CC(C)CC(=O)NCc1ccc(N2CCN(c3nnc(Cc4ccccc4)c4ccccc34)CC2)cc1] | 494 |
| 204 | 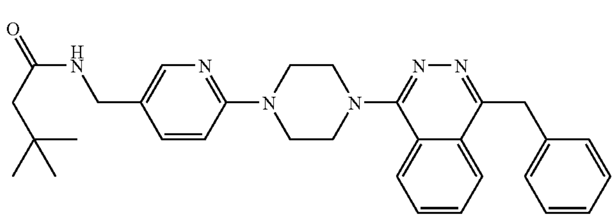 [SMILES: CC(C)(C)CC(=O)NCc1ccc(N2CCN(c3nnc(Cc4ccccc4)c4ccccc34)CC2)nc1] | 512 |

TABLE 5-continued

| Example | Structure | MS [m/z; M + 1] |
|---|---|---|
| 205 | 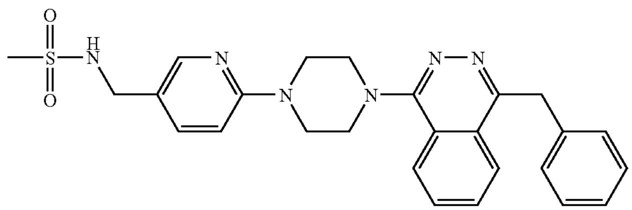 [SMILES: CS(=O)(=O)NCc1ccc(N2CCN(c3nnc(Cc4ccccc4)c4ccccc34)CC2)nc1] | 490 |
| 206 | 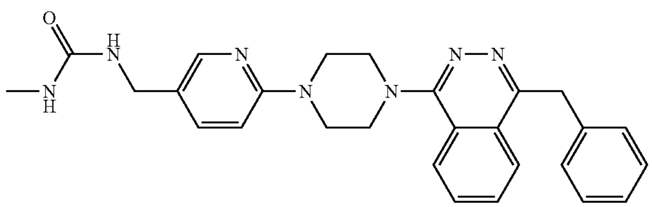 [SMILES: CNC(=O)NCc1ccc(N2CCN(c3nnc(Cc4ccccc4)c4ccccc34)CC2)nc1] | 469 |
| 207 | 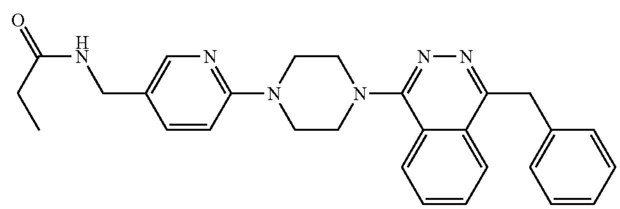 [SMILES: CCC(=O)NCc1ccc(N2CCN(c3nnc(Cc4ccccc4)c4ccccc34)CC2)nc1] | 468 |
| 208 | 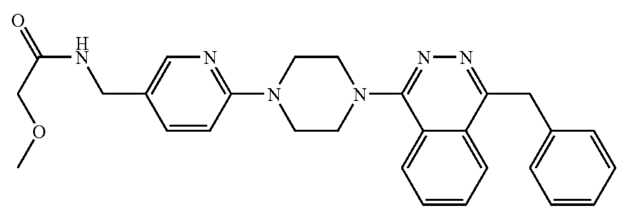 [SMILES: COCC(=O)NCc1ccc(N2CCN(c3nnc(Cc4ccccc4)c4ccccc34)CC2)nc1] | 484 |
| 209 | 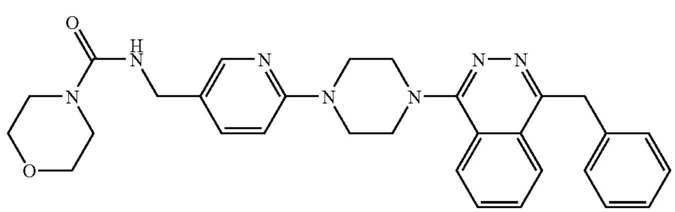 [SMILES: O=C(NCc1ccc(N2CCN(c3nnc(Cc4ccccc4)c4ccccc34)CC2)nc1)N1CCOCC1] | 425 |
| 210 | 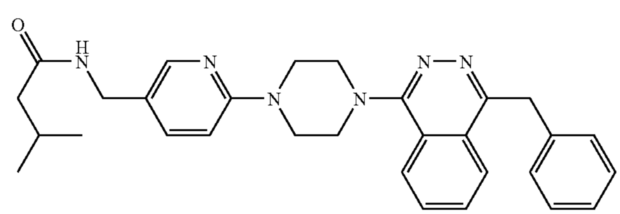 [SMILES: CC(C)CC(=O)NCc1ccc(N2CCN(c3nnc(Cc4ccccc4)c4ccccc34)CC2)nc1] | 496 |
| 211 | 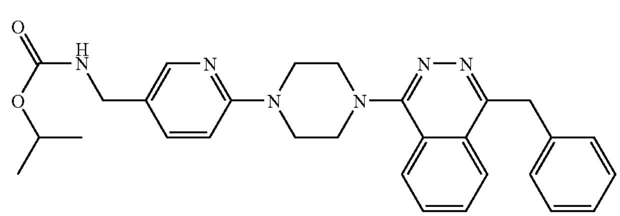 | 498 |

TABLE 5-continued

| Example | Structure | MS [m/z; M + 1] |
| --- | --- | --- |
| 212 | 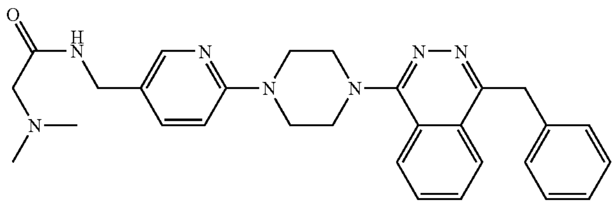 [SMILES: CN(C)CC(=O)NCc1ccc(N2CCN(c3nnc(Cc4ccccc4)c4ccccc34)CC2)nc1] | 497 |
| 213 | 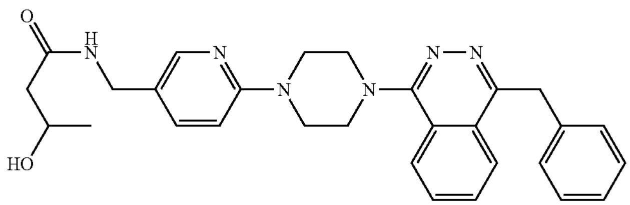 [SMILES: CC(O)CC(=O)NCc1ccc(N2CCN(c3nnc(Cc4ccccc4)c4ccccc34)CC2)nc1] | 498 |
| 214 | 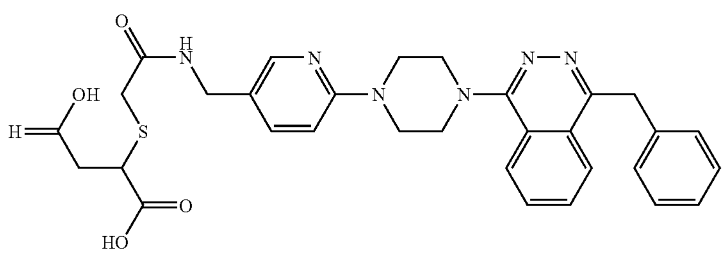 | 602 |
| 215 | 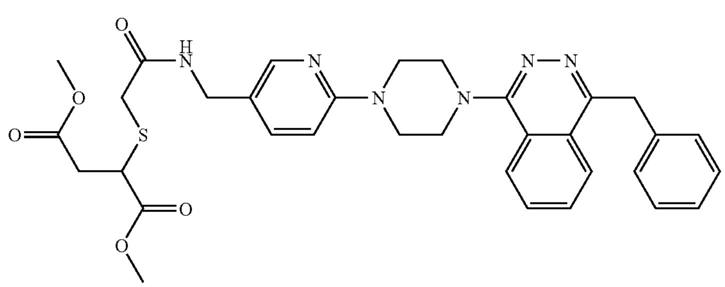 [SMILES: COC(=O)CC(SCC(=O)NCc1ccc(N2CCN(c3nnc(Cc4ccccc4)c4ccccc34)CC2)nc1)C(=O)OC] | 630 |
| 216 | 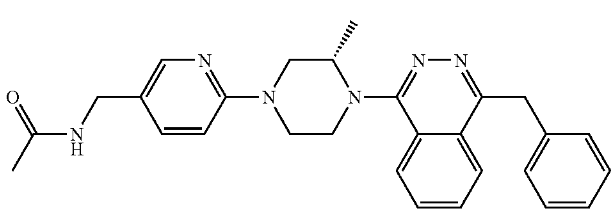 [SMILES: CC(=O)NCc1ccc(N2CCN(c3nnc(Cc4ccccc4)c4ccccc34)[C@@H](C)C2)nc1] | 467 |

Example 217

{6-[4-(4-Benzyl-phthalazin-1-yl)-piperazin-1-yl]-pyridin-3-ylmethyl}-dimethyl-amine

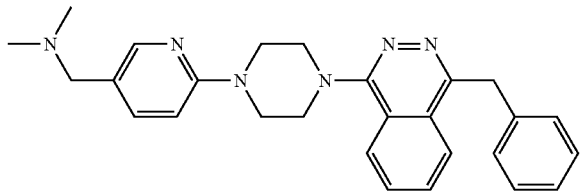 [SMILES: CN(C)Cc1ccc(N2CCN(c3nnc(Cc4ccccc4)c4ccccc34)CC2)nc1]

To a solution of C-{6-[4-(4-benzyl-phthalazin-1-yl)-piperazin-1-yl]-pyridin-3-yl}-methyl amine (35 mg, 0.064 mmol) in DCM (10 mL) was added NaBH(OAc)$_3$ (41 mg, 0.19 mmol) followed by formaldehyde (13 mg, 30% solution, 0.128 mmol), The mixture was stirred at room temperature for 30 min. Sat. NaHCO$_3$ was added and the layers were separated. The aqueous layer was extracted with DCM. The combined organic layers were washed with water, sat. NaHCO$_3$, brine, dried over Na$_2$SO$_4$, filtered and concentrated. The crude product was purified by preparative HPLC (acetonitrile/water 10% to 50%) and isolated as the free base (15 mg, 57%)

$^1$H NMR (400 MHz, CD$_2$Cl$_2$): δ=8.06 (d, J=7.5 Hz, 1H), 7.98 (s, 1H), 7.93 (d, J=8.5 Hz, 1H), 7.70 (m, 2H), 7.43 (m, 1H), 7.24-7.10 (m, 5H), 6.67 (d, J=9 Hz, 1H), 4.53 (s, 2H), 3.71 (m, 4H), 3.51 (m, 4H), 3.22 (s, 2H), 2.11 (s, 6H).

HR-MS (m/z, MH+): meas. 439.2600

Examples 218-231

As illustrated in Scheme 3a, alternatively compounds of Formula If or Ig can be prepared by functionalization of compounds VII via either Grignard addition or reductive amination.

SCHEME 3a.

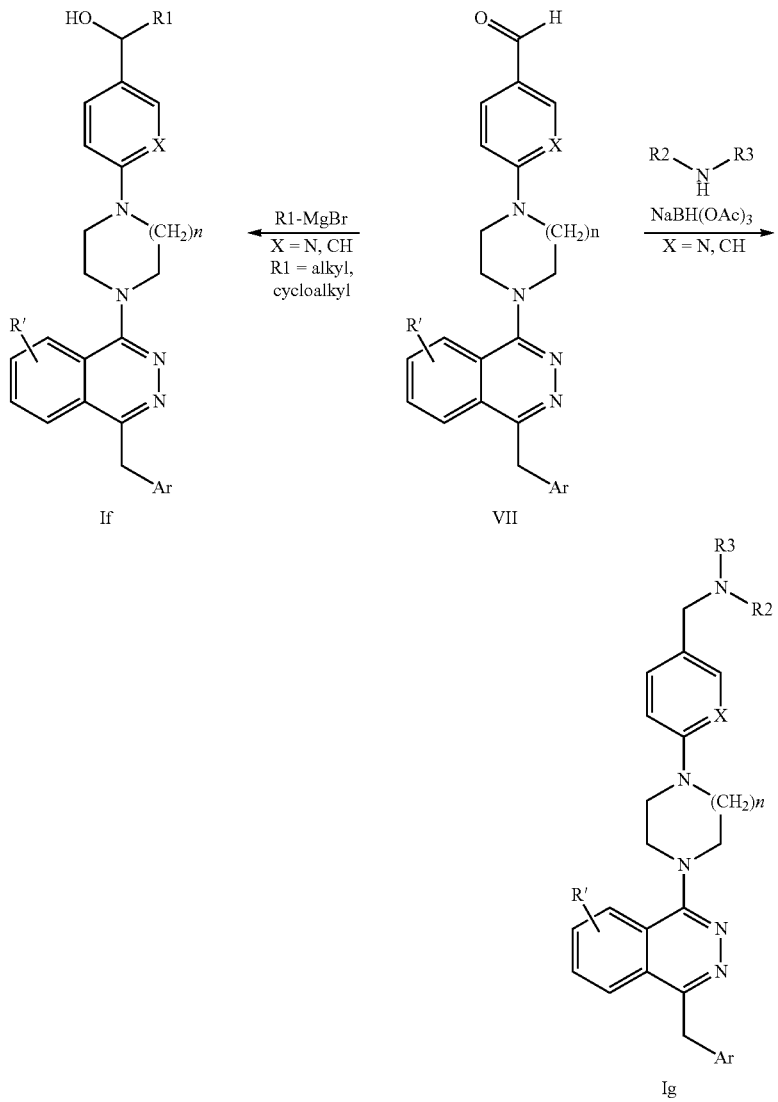

Example 218

6-[4-(4-Benzyl-phthalazin-1-yl)-piperazin-1-yl]-pyridine-3-carbaldehyde

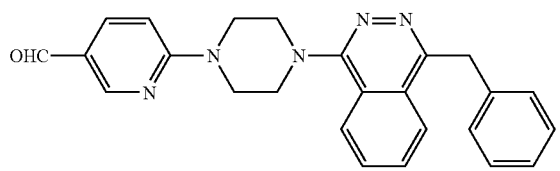 [SMILES: O=Cc1ccc(N2CCN(c3nnc(Cc4ccccc4)c4ccccc34)CC2)nc1]

$^1$H NMR (400 MHz, CD$_2$Cl$_2$): δ=9.83 (s, 1H), 8.62 (d, J=2.5 Hz, 1H), 8.18 (d, J=8.1 Hz, 1H), 8.07 (d, J=8.0 Hz, 1H), 7.99 (dd, J=2.5 and 9.1 Hz, 1H), 7.84 (m, 2H), 7.37-7.21 (m, 5H), 6.83 (d, J=9.1 Hz, 1H), 4.66 (s, 2H), 4.09 (m, 4H), 3.65 (m, 4H).

HR-MS (m/z, MH+): meas. 410.1978

Example 219

(6-(4-(4-benzylphthalazin-4-yl)piperazin-1-yl)pyridin-3-yl)(cyclopropyl)methanol

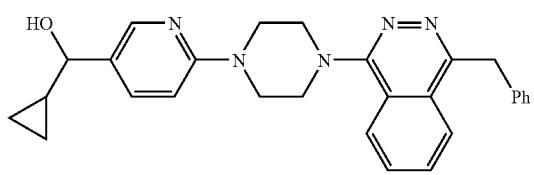 [SMILES: OC(c1ccc(N2CCN(c3nnc(Cc4ccccc4)c4ccccc34)CC2)nc1)C1CC1]

To a solution of 6-(4-(4-benzylphthalazin-1-yl)piperazin-1-yl)nicotinaldehyde (100 mg, 0.244 mmol) in 2 mL anhydrous THF was added with 0.5 M cyclopropyl magnesium bromide (980 μL, 0.49 mmol) at −78° C. under nitrogen atmosphere. The reaction mixture was stirred at −78° C. for 1 h, before warmed to room temperature and stirred for 2 h. The reaction mixture was quenched with sat. aq. NH$_4$Cl at −78° C. and diluted with DCM. The organic solution was washed with brine, dried over Na$_2$SO$_4$ and concentrated to afford the crude material. The resulting solid was purified by running through semi-prep HPLC, eluting with 10-100% acetonitrile in water (both mobile phases modified by 3% n-PrOH). Fractions containing the desired product were combined and freeze-dried to afford a white solid (60 mg, yield: 54%).

HR-MS (m/z, MH+): meas. 452.2430 calc. 452.2450

Examples 220-221

The following table (Table 5a) lists examples of compounds prepared via Grignard addition as described above:

TABLE 5a

| Example | Structure | MS [m/z; M + 1] |
| --- | --- | --- |
| 220 | 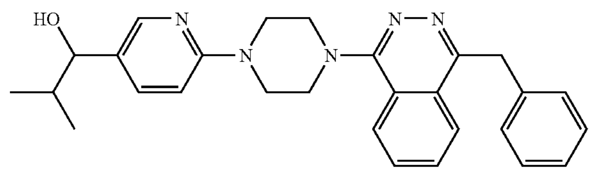 [SMILES: CC(C)C(O)c1ccc(N2CCN(c3nnc(Cc4ccccc4)c4ccccc34)CC2)nc1] | 455 |
| 221 | 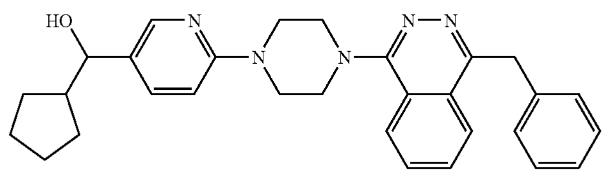 [SMILES: OC(c1ccc(N2CCN(c3nnc(Cc4ccccc4)c4ccccc34)CC2)nc1)C1CCCC1] | 481 |

Example 222

1-Benzyl-4-[4-(5-morpholin-4-ylmethyl-pyridin-2-yl)-piperazin-1-yl]-phthalazine

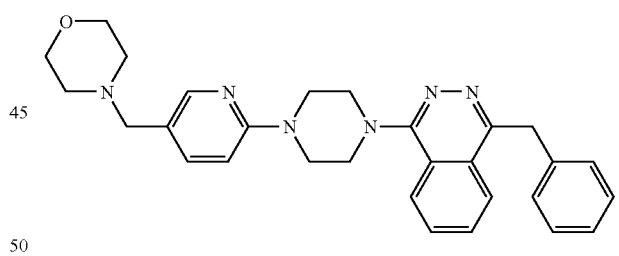

To a solution of 6-[4-(4-benzyl-phthalazin-1-yl)-piperazin-1-yl]-pyridine-3-carbaldehyde (40 mg, 0.1 mmol) in 5 mL DCM is added a drop of acetic acid, NaBH(OAc)$_3$ (41.4 mg, 0.2 mmol) and morpholine (7.5 mL, 0.12 mmol). The reaction mixture is stirred for 30 min at rt. Aqueous NaHCO$_3$ solution is added and the reaction mixture is stirred for an additional 30 min. The layers are separated and the aqueous layer is extracted with DCM. The combined organic layers are washed with water, brine, dried over Na$_2$SO$_4$, filtered and concentrated. The crude product is purified by flash chromatography on silica gel (EtOAc/heptane 10%-70%) to yield the title compound (37.8 mg, 80%).

HR MS (m/z, MH+) meas. 481.2716.

Examples 223-231

The following table (Table 5b) lists examples of compounds prepared via reductive amination as described above:

TABLE 5b
| Example | Structure | MS [m/z; M + 1] |
|---|---|---|
| 223 | 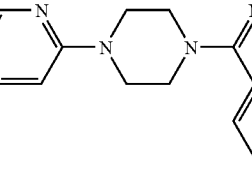 | 482 |
| 224 | 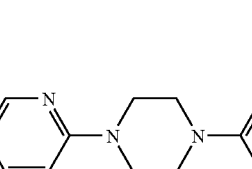 | 468 |
| 225 | 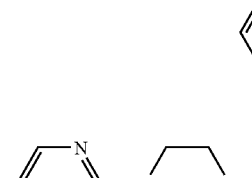 | 496 |
| 226 | 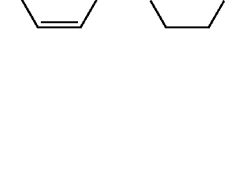 | 510 |
| 227 | 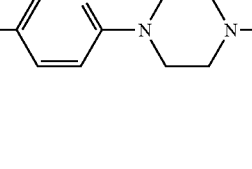 | 498 |
| 228 | 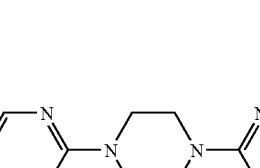 | 516 |

TABLE 5b-continued
| Example | Structure | MS [m/z; M + 1] |
|---|---|---|
| 229 | 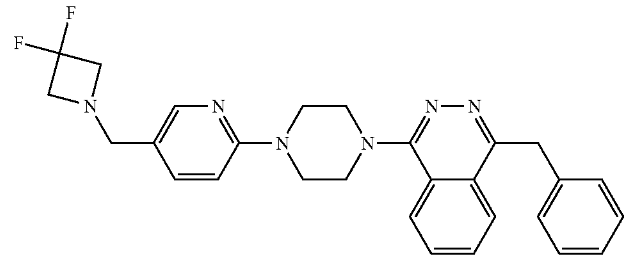 [SMILES: FC1(F)CN(Cc2ccc(N3CCN(c4nnc(Cc5ccccc5)c5ccccc45)CC3)nc2)C1] | 488 |
| 230 | 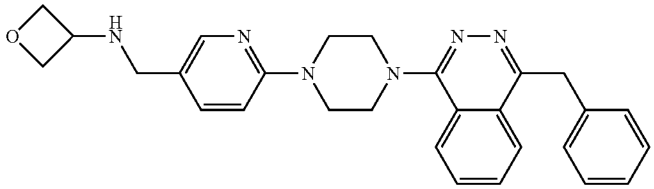 [SMILES: c1ccc(Cc2nnc(N3CCN(c4ccc(CNC5COC5)cn4)CC3)c3ccccc23)cc1] | 468 |
| 231 | 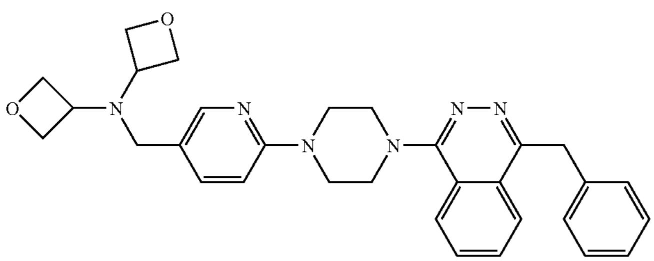 [SMILES: c1ccc(Cc2nnc(N3CCN(c4ccc(CN(C5COC5)C5COC5)cn4)CC3)c3ccccc23)cc1] | 524 |
Examples 232-239
As illustrated in Scheme 3b, alternatively compounds of Formula Ih can be prepared by nitro reduction of compounds VIII and subsequent functionalization of the resulting anilines IX.
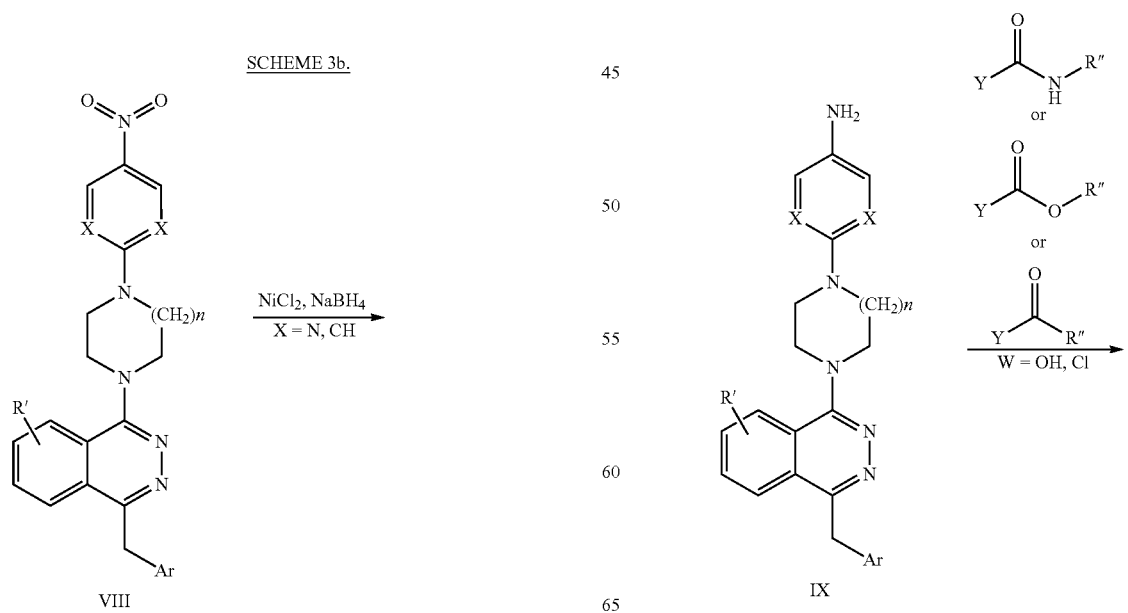
SCHEME 3b.

-continued

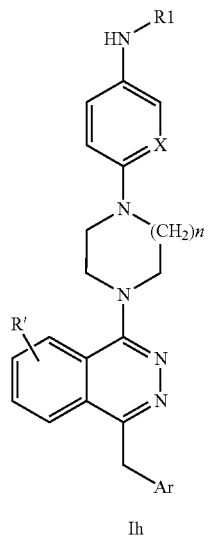

R1 = C(O)NHR″ or C(O)OR″ or C(O)R″

Example 232

1-Benzyl-4-[4-(5-nitro-pyridin-2-yl)-piperazin-1-yl]-phthalazine

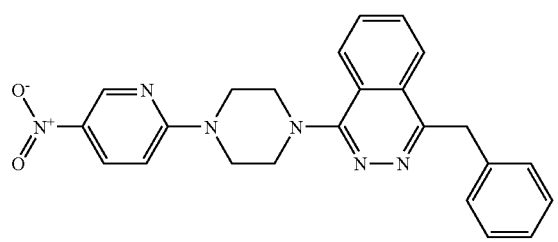 [SMILES: O=[N+]([O-])c1ccc(N2CCN(c3nnc(Cc4ccccc4)c4ccccc34)CC2)nc1]

1-Benzyl-4-piperazin-1-yl-phthalazine (500 mg, 1.64 mmol) and 2-chloro-5-nitropyridine are combined in a 10 mL microwave vial. Triethylamine (2.96 mL, 2.14 mmol) and NMP (4.8 mL) are added. The vial is sealed and heated to 180° C. for 15 min. The crude reaction mixture is poured into water and the resulting precipitate is isolated by filtration to afford the title compound (500 mg, 70% yield).

Example 233

1-Benzyl-4-[4-(5-nitro-pyrimidin-2-yl)-piperazin-1-yl]-phthalazine

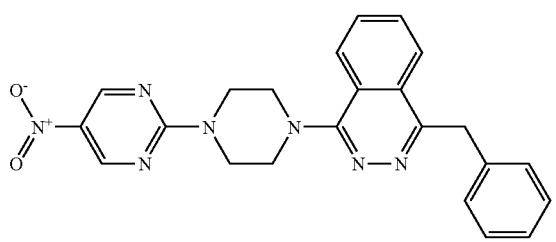 [SMILES: O=[N+]([O-])c1cnc(N2CCN(c3nnc(Cc4ccccc4)c4ccccc34)CC2)nc1]

Following the above procedure, 1-benzyl-4-piperazin-1-yl-phthalazine (500 mg, 1.64 mmol) and 2-chloro-5-nitropyridine afford the title compound (200 mg, 57% yield).

Example 234

6-[4-(4-Benzyl-phthalazin-1-yl)-piperazin-1-yl]-pyridin-3-ylamine

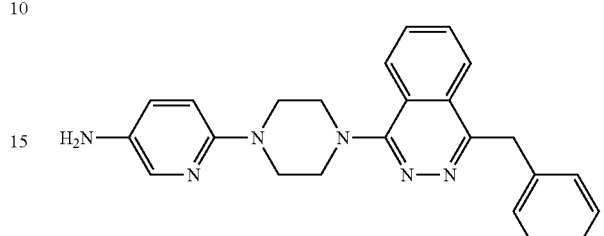

1-Benzyl-4-[4-(5-nitro-pyridin-2-yl)-piperazin-1-yl]-phthalazine (500 mg, 1.17 mmol), iron powder (523 mg, 9.38 mmol), ammonium chloride (125 mg, 0.234 mmol), ethanol (6 mL) and water (1.5 mL) are all combined in 50 mL round bottom flask with stir bar. The mixture is stirred and heated to 70° C. for 4 h. Material is filtered through a pad of Celite and washed with $CH_2Cl_2$. Concentrate to remove all ethanol and residual water. The residue is purified by flash chromatography on silica gel (0-18% $MeOH/CH_2Cl_2$) to afford the title compound (323 mg, 70%).

Example 235

2-[4-(4-Benzyl-phthalazin-1-yl)-piperazin-1-yl]-pyrimidin-5-ylamine

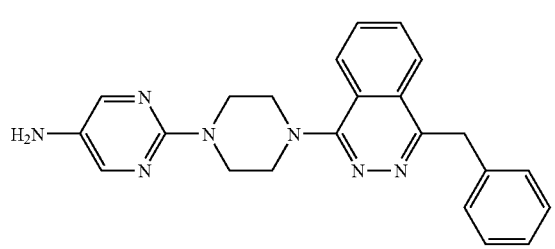 [SMILES: Nc1cnc(N2CCN(c3nnc(Cc4ccccc4)c4ccccc34)CC2)nc1]

Following the above procedure, 1-Benzyl-4-[4-(5-nitro-pyrimidin-2-yl)-piperazin-1-yl]-phthalazine (200 mg, 1.17 mmol) affords the title compound (110 mg, 59%).

Example 236

N-{2-[4-(4-Benzyl-phthalazin-1-yl)-piperazin-1-yl]-pyrimidin-5-yl}-acetamide

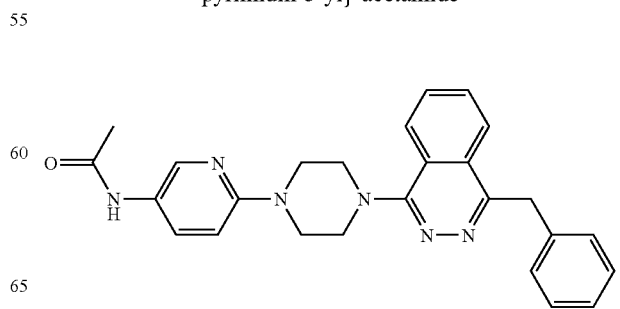

6-[4-(4-Benzyl-phthalazin-1-yl)-piperazin-1-yl]-pyridin-3-ylamine (60 mg, 0.151 mmol) is added to a 2 dram screw-top vial. Acetic acid (1 mL) and acetic anhydride (22.2 µL, 0.235 mmol) is added. The reaction is heated to 40° C. for 16 h. Concentrate in vacuo to remove acetic acid. The residue is purified by flash chromatography on silica gel (0-18% MeOH/CH$_2$Cl$_2$) to afford the title compound (42 mg, 63%).

$^1$HNMR (400 MHz, DMSO-d6) δ 9.830 (s, 1H), 8.350 (d, J=2.653 Hz, 1H), 8.192-8.260 (m, 2H), 7.905-7.994 (m, 2H), 7.846 (dd, J=8.968, 2.652 Hz, 1H), 7.361 (d, J=7.200 Hz, 2H), 7.302 (m, 2H), 7.205 (dd, J=7.263, 7.260 Hz, 1H), 6.940 (d, J=9.095 Hz, 1H), 4.630 (s, 2H), 3.712-3.774 (m, 4H), 3.492-3.553 (m, 4H), 2.053 (s, 3H).

HR-MS (m/z, MH$^+$): meas. 439.2232 calc. 439.2246

Example 237

N-{2-[4-(4-Benzyl-phthalazin-1-yl)-piperazin-1-yl]-pyrimidin-5-yl}-acetamide

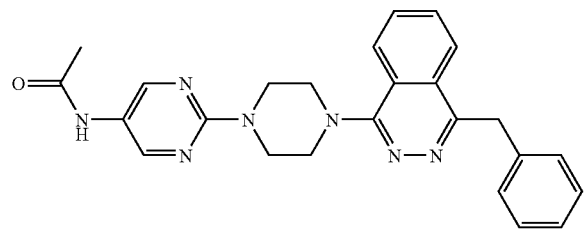 [SMILES: CC(=O)Nc1cnc(N2CCN(c3nnc(Cc4ccccc4)c4ccccc34)CC2)nc1]

Following the above procedure, 2-[4-(4-Benzyl-phthalazin-1-yl)-piperazin-1-yl]-pyrimidin-5-ylamine (60 mg, 0.15 mmol) and acetic anhydride (22.2 µL, 0.235 mmol) afford the title compound (21 mg, 31%).

$^1$HNMR (400 MHz, DMSO-d6) δ 9.901 (s, 1H), 8.594 (s, 2H), 8.282-8.188 (m, 2H), 8.003-7.907 (m, 2H), 7.360 (m, 2H), 7.302 (m, 2H), 7.214 (m, 1H), 4.629 (s, 2H), 4.046-3.975 (m, 4H), 3.534-3.452 (m, 4H), 2.065 (s, 3H).

HR-MS (m/z, MH$^+$): meas. 440.2204 calc. 440.2199

Example 238

3-{6-[4-(4-Benzyl-phthalazin-1-yl)-piperazin-1-yl]-pyridin-3-yl}-1,1-dimethyl-urea

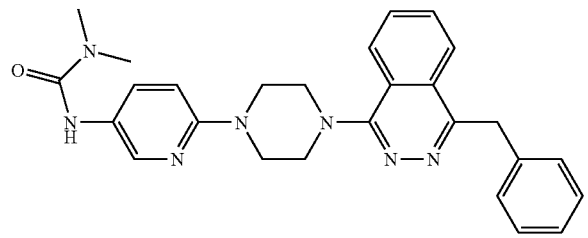 [SMILES: CN(C)C(=O)Nc1ccc(N2CCN(c3nnc(Cc4ccccc4)c4ccccc34)CC2)nc1]

6-[4-(4-Benzyl-phthalazin-1-yl)-piperazin-1-yl]-pyridin-3-ylamine (80 mg, 0.202 mmol), CH$_2$Cl$_2$ (0.5 mL), triethylamine (37 µL, 0.227 mmol), and dimethylcarbamoyl chloride (20 µL, 0.222 mmol) are combined and stirred at room temperature for 16 h. Concentrate the crude reaction mixture in vacuo. The residue is purified by flash chromatography on silica gel (MeOH/CH$_2$Cl$_2$) to afford the title compound (64 mg, 68%).

$^1$H NMR (400 MHz, DMSO-d6) δ 8.20 (d, J=2.78 Hz, 1H), 8.24-8.17 (m, 2H), 8.15 (s, 1H), 7.97-7.87 (m, 2H), 7.67 (dd, J=9.03, 2.72 Hz, 1H), 7.33 (m, 2H), 7.27 (m, 2H), 7.18 (m, 1H), 6.87 (d, J=8.97 Hz, 1H), 4.60 (s, 2H), 3.73-3.66 (m, 4H), 3.54-3.46 (m, 4H), 2.92 (s, 6H).

HR-MS (m/z, MH$^+$): meas. 468.2505 calc. 468.2512

Example 239

{6-[4-(4-Benzyl-phthalazin-1-yl)-piperazin-1-yl]-pyridin-3-yl}-carbamic acid methyl ester

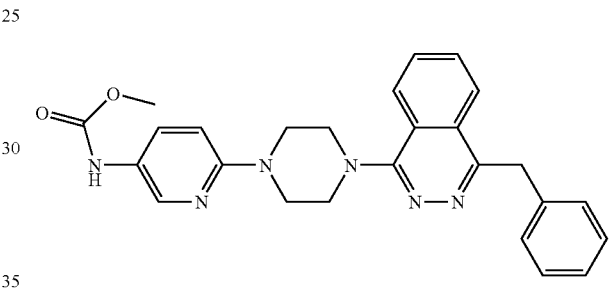

6-[4-(4-Benzyl-phthalazin-1-yl)-piperazin-1-yl]-pyridin-3-ylamine (80 mg, 0.202 mmol), CH$_2$Cl$_2$ (0.5 mL), triethylamine (37 µL, 0.227 mmol), and methyl chloroformate (17 µL, 0.222 mmol) are combined and stirred at room temperature. Reaction complete in less than 15 minutes. Concentrate reaction mixture in vacuo. The residue is purified by flash chromatography on silica gel (MeOH/CH$_2$Cl$_2$) to afford the title compound (39 mg, 42%).

$^1$H NMR (400 MHz, DMSO-d6) δ 9.41 (br.s, 1H), 8.23 (br.s, 1H), 8.16-8.22 (m, 2H), 7.97-7.87 (m, 2H), 7.74-7.64 (m, 1H), 7.33 (m, 2H), 7.27 (m, 2H), 7.18 (m, 1H), 6.92 (d, J=9.09 Hz, 1H), 4.60 (s, 2H), 3.75-3.68 (m, 4H), 3.66 (s, 3H), 3.53-3.45 (m, 4H).

HR-MS (m/z, MH$^+$): meas. 455.2205 calc. 455.2195

Isochinolines

As illustrated in Scheme 4, isochinolines of Formula Ii can be prepared via Route A, i.e., chloride displacement from an intermediate of Type X with an arylmethyl zinc bromide under palladium catalysis and subsequent displacement of the bromide in intermediate XI with a substituted amine under palladium catalysis. Regioisomeric isochinolines of Formula Ij can be prepared from the same intermediates X by Negishi coupling of the in situ formed Zn species with arylmethyl bromides under palladium catalysis (Route B). Intermediates XII can be transformed by treatment with a substituted amine in N-methylmorpholine at elevated temperatures into compounds of Formula Ij.

SCHEME 4.

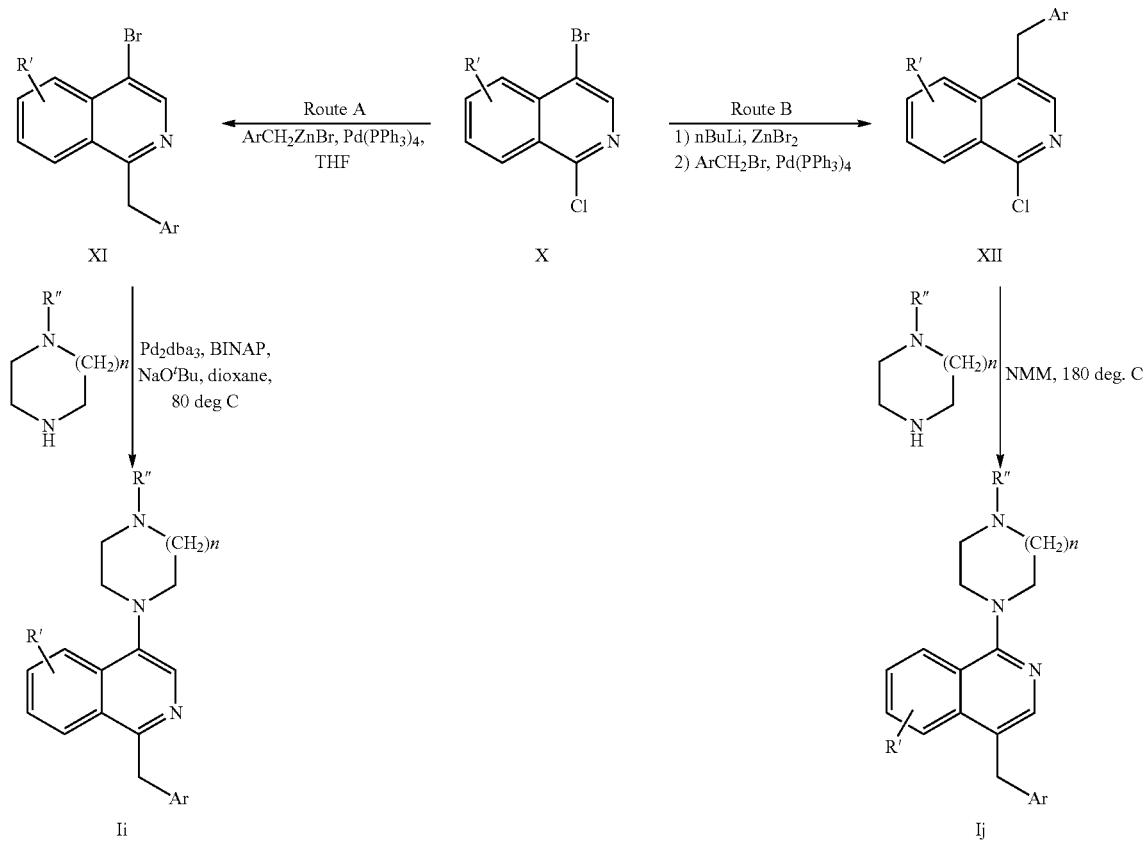

Synthesis of Intermediates

1-Benzyl-4-bromo-isoquinoline (Compound 29)

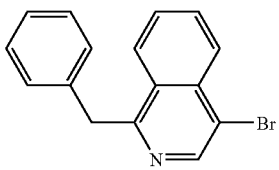 [SMILES: Brc1cnc(Cc2ccccc2)c2ccccc12]

In a 40 mL vial 490 mg (2.00 mmol) 1-chloro-4-bromo-isoquinoline and 40 mg (0.034 mmol) tetrakis(triphenylphosphine)palladium(0) is added to 4 mL THF. After all solids are dissolved, 8 mL of 0.5 M (4.0 mmol) benzyl zinc bromide in THF is slowly added by syringe and the resulting reaction mixture is stirred at 25° C. After 12 hrs, the mixture is poured into cold solution of saturated $NH_4Cl$ and extracted with EtOAc. The organic extracts are concentrated in vacuo and the resulting residue is purified by silica chromatography using a heptane/EtOAc gradient. Pure fractions are pooled and evaporated to give 150 mg (0.50 mmol) of the title compound.

3-(4-Bromo-isoquinolin-1-ylmethyl)-benzonitrile (Compound 30)

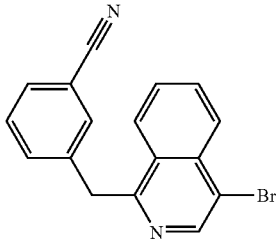 [SMILES: N#Cc1cccc(Cc2ncc(Br)c3ccccc23)c1]

The same procedure as described above is used except that benzylzinc bromide in THF is replaced by 3-cyanobenzylzinc bromide in THF.

4-Bromo-1-(3-chloro-benzyl)-isoquinoline (Compound 31)

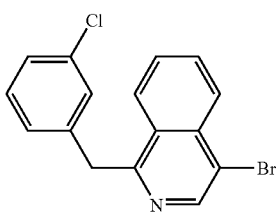 [SMILES: Clc1cccc(Cc2ncc(Br)c3ccccc23)c1]

The same procedure as described above is used except that benzylzinc bromide in THF is replaced by 3-chlorobenzylzinc bromide in THF.

4-Bromo-1-(3-trifluoromethyl-benzyl)-isoquinoline (Compound 32)

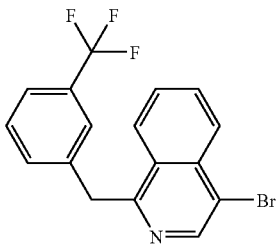 [SMILES: FC(F)(F)c1cccc(Cc2ncc(Br)c3ccccc23)c1]

The same procedure as described as above is used except that benzylzinc bromide in THF is replaced by 3-(trifluoromethyl)benzylzinc bromide in THF.

Synthesis of Examples 79-83

Example 79

6-[4-(1-Benzyl-isoquinolin-4-yl)-piperazin-1-yl]-nicotinonitrile

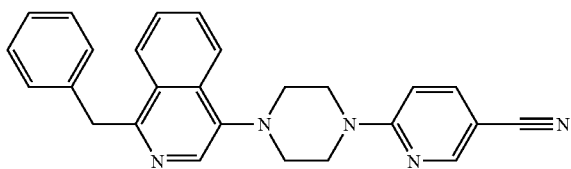 [SMILES: N#Cc1ccc(N2CCN(c3cnc(Cc4ccccc4)c4ccccc34)CC2)nc1]

In a 40 mL vial 120 mg (0.40 mmol) 1-benzyl-4-bromo-isoquinoline (see above), 160 mg (0.84 mmol) 6-piperazin-1-yl-nicotinonitrile, 40 mg (0.04 mmol) tris(dibenzylideneaceton)dipalladium(0), and 60 mg (±)-(1,1'-binaphthalene-2-2'diyl)bis(diphenylphosphine) are added to 5 mL dioxane. After flushing the vial with nitrogen for 5 min, the reaction mixture is stirred for 2 min followed by the addition of 150 mg (1.55 mmol) sodium tert-butoxide. After flushing with nitrogen for 5 min, the vial is sealed and heated at 80° C. for 12 h. After cooling, the mixture is loaded onto a silica column directly and purified. The eluent containing the correct mass is concentrated in vacuo and the resulting residue is purified by reversed phase HPLC using a Varian Prostar system equipped with a Waters xTerra column (50×100 mm) and a solvent gradient of 0.1% $NH_3$ in water/0.1% $NH_3$ in acetonitrile (0→100%). Pure fractions are pooled and evaporated to give 40 mg (0.10 mmol, 25% yield) of the title compound.

m/z=406 [M+1].

Examples 80-82

The following table (Table 6) lists examples of compounds prepared by amination of intermediates VIII as described above for example 79:

TABLE 6

| Example | Structure | MS [m/z; M + 1] |
|---|---|---|
| 80 | 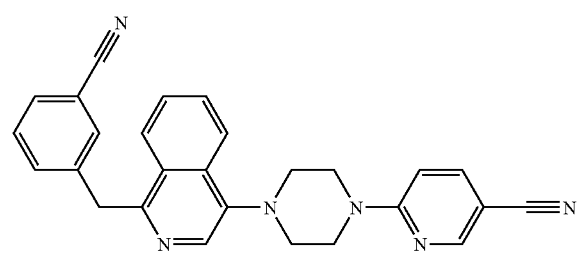 [SMILES: N#Cc1ccc(N2CCN(c3cnc(Cc4cccc(C#N)c4)c4ccccc34)CC2)nc1] | 431 |
| 81 | 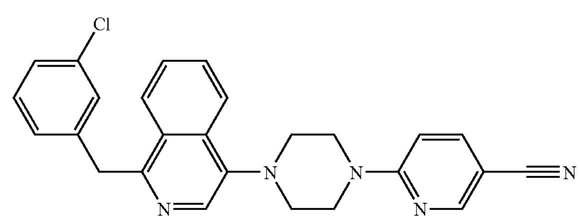 [SMILES: N#Cc1ccc(N2CCN(c3cnc(Cc4cccc(Cl)c4)c4ccccc34)CC2)nc1] | 440 |
| 82 | 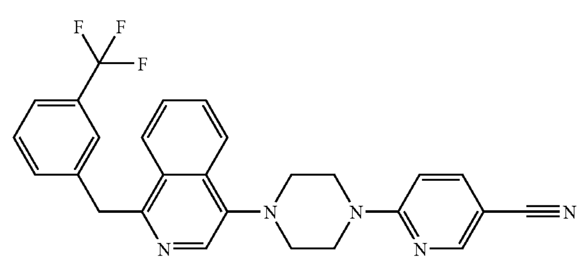 [SMILES: N#Cc1ccc(N2CCN(c3cnc(Cc4cccc(C(F)(F)F)c4)c4ccccc34)CC2)nc1] | 474 |

Example 83

6-[4-(4-Benzyl-isoquinolin-1-yl)-piperazin-1-yl]-nicotinonitrile

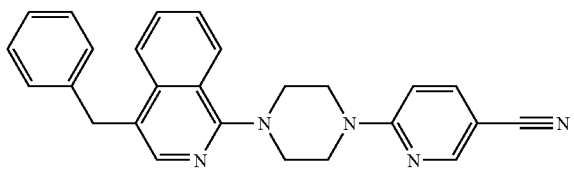

m/z=406 [M+1].

Pyridazines

Scheme 5 shows a general synthetic scheme for the preparation of compounds of Formula Ik and Il. Substituted 1,4-dichloropyridazines XIII can be reacted with organo-zinc reagents under palladium catalysis to form intermediates XIVa and XIVb (for R not equal to R'). Displacement of the remaining chlorine with an amine in the presence of base yields compounds Ik, l which can be separated by chromatography into their regioisomers (for compounds with R not equal to R').

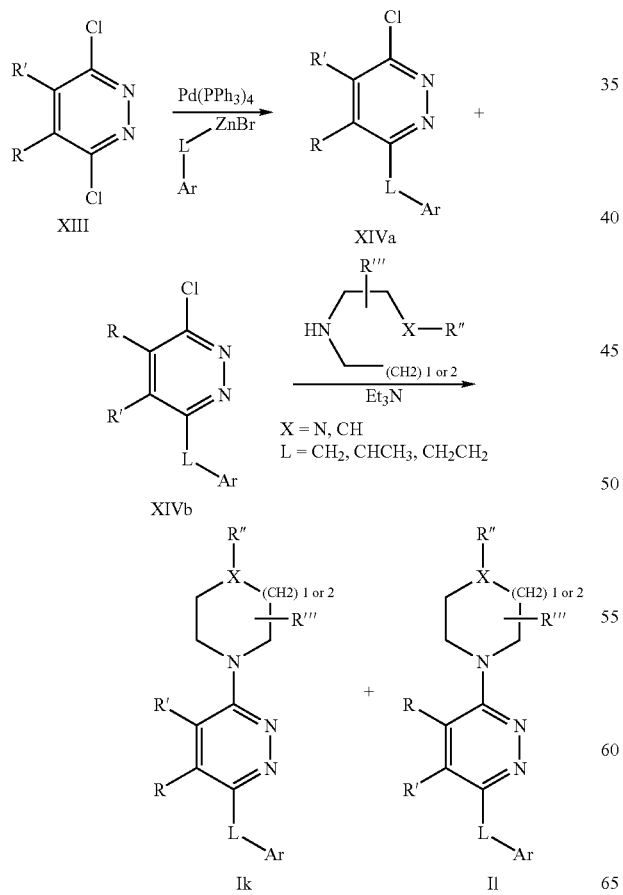

Synthesis of Intermediates

3-Chloro-6-(4-fluoro-benzyl)-4-methyl-pyridazine (Compound 33a) and 6-chloro-3-(4-fluoro-benzyl)-4-methyl-pyridazine (Compound 33b)

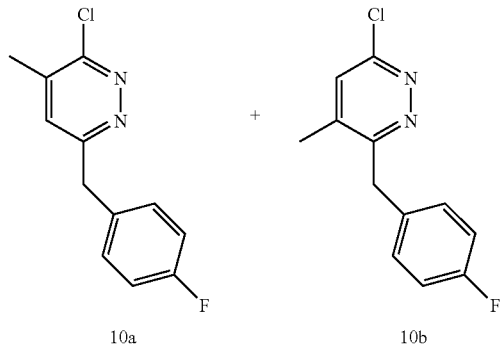 [SMILES: Cc1cc(Cc2ccc(F)cc2)nnc1Cl ; Cc1cc(Cl)nnc1Cc1ccc(F)cc1]

To a solution of 4-methyl-3,6-dichloropyridazine (0.30 g, 1.84 mmol) in THF (5 mL) is added 4-fluoro benzyl zinc bromide (0.5M in THF) (7.36 mL, 3.68 mmol) and palladium tetrakis triphenylphosphine (0.27 g, 0.23 mmol). The mixture is degassed and stirred at 50° C. overnight. Then the reaction mixture is cooled down to room temperature, sat. NaHCO$_3$ and water are added and the mixture is extracted with EtOAc. The combined organic layers are washed with brine, dried over Na$_2$SO$_4$, filtered and concentrated down. The crude product is purified by chromatography on silica gel (EtOAc/Hexane: 10%~40%) to give a mixture of 3-chloro-6-(4-fluoro-benzyl)-4-methyl-pyridazine (10a) and 6-chloro-3-(4-fluoro-benzyl)-4-methyl-pyridazine (10b) (0.28 g, 64%) at a ratio of 1.78:1.

m/z=237.03 [M+1].

3-Chloro-6-(4-fluoro-benzyl)-4,5-dimethyl-pyridazine (Compound 34)

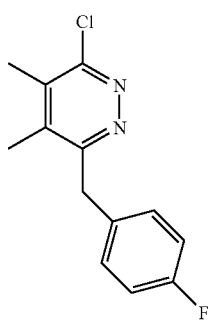

Compound 34 is prepared following a similar protocol as described above for compounds 33a and 33b.

2,3,5,6,7,8-Hexahydro-phthalazin-1,4-dione (Compound 35)

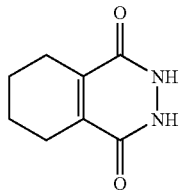 [SMILES: O=c1[nH][nH]c(=O)c2c1CCCC2]

To a solution of hydrazine (392 μL, 13.1 mmol) in water (6 mL) and HOAc (2 mL) is added 4,5,6,7-tetrahydro-isobenzofuran-1,3-dione (2 g, 13.1 mmol). The reaction mixture is refluxed for 3 h, then cooled down to room temperature and the precipitate is collected by filtration, washed with water and dried under vacuum oven to give 2,3,5,6,7,8-hexahydro-phthalazin-1,4-dione (compound 10d) (2.09 g, 95.7%). m/z=167.05 [M+1]

1,4-Dichloro-5,6,7,8-tetrahydro-phthalazine (Compound 36)

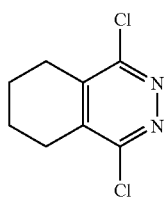 [SMILES: Clc1nnc(Cl)c2c1CCCC2]

The suspension of 2,3,5,6,7,8-Hexahydro-phthalazin-1,4-dione (2.09 g, 12.6 mmol) in POCl$_3$ (10 mL) is refluxed for 1 h, cooled down, and poured into ice. The precipitate is collected by filtration and dried in a vacuum oven to give 1,4-dichloro-5,6,7,8-tetrahydro-phthalazine (2) (2.23 g, 87.3%). HRMS: m/z=203.0139 [M+1]

1-Chloro-4-(4-fluoro-benzyl)-5,6,7,8-tetrahydrophthalazine (Compound 37)

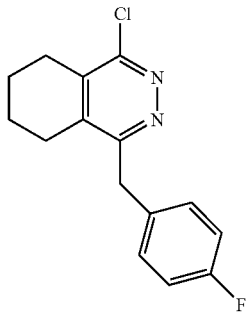 [SMILES: Fc1ccc(Cc2nnc(Cl)c3c2CCCC3)cc1]

To a solution of 1,4-dichloro-5,6,7,8-tetrahydro-phthalazine (0.50 g, 2.46 mmol) in THF (5 mL) are added 4-fluorobenzyl zinc chloride (0.5M in THF) (6.40 mL, 3.20 mmol) and palladium tetrakis triphenylphosphine (0.36 g, 0.31 mmol). The mixture is degassed and stirred at 50° C. overnight. Then the reaction mixture is cooled down to room temperature, sat. NaHCO$_3$ and water are added and the mixture is extracted with EtOAc. The combined organic layers are washed with brine, dried over Na$_2$SO$_4$, filtered and concentrated down. The crude product is purified by chromatography (EtOAc/Hexane: 10%~40%) to give 1-chloro-4-(4-fluoro-benzyl)-5,6,7,8-tetrahydro-phthalazine (compound 10f) (0.51 g, 30%). m/z=277.11 [M+1]

2,3-Dihydrophthalazine-1,4(5H,8H)-dione (Compound 38)

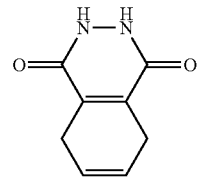

A suspension of isobenzofuran-1,3(4H,7H)-dione (4.2 g, 28 mmol) in 45 mL toluene was heated at reflux and charged with hydrazine hydrate (1.63 mL, 33.6 mmol) dropwisely in a round bottom flask equipped with a condenser. The reaction mixture was heated at reflux for 2 h. The mixture was filtered to afford the titled compound a white solid (4.2 g, yield: 91%).

$^1$H NMR (400 MHz, DMSO-d6): d=5.63 (br, 2H), 2.81 (br, 4H)

MS (m/z, MH+): meas. 165.1 calc. 165.06

1,4-Dichloro-5,6-dihydrophthalazine (Compound 39)

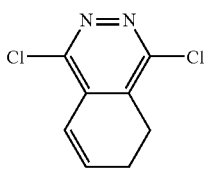 [SMILES: Clc1nnc(Cl)c2c1C=CCC2]

A suspension of 2,3-dihydrophthalazine-1,4(5H,8H)-dione (1 g, 6.1 mmol) in phosphoroxidchloride (30 mL, 15 mmol) was heated at reflux for 2 h under a consistent nitrogen flow. The reaction mixture was poured onto ice, adjusted to pH 6 by adding with ammonia hydroxide and the precipitate was isolated by filtration. The crude material was purified by flash chromatography on silica gel, eluting with 10-30% EtOAc:heptane to afford a white solid (600 mg, yield: 49%).

$^1$H NMR (400 MHz, CDCl$_3$): d=6.73-6.67 (m, 1H), 6.59-6.54 (m, 1H), 2.93-2.91 (m, 2H), 2.56-2.51 (m, 2H)

MS (m/z, MH+): meas. 201.1 calc. 200.99

N-benzyl-1-(3,6-dichloro-5-methylpyridazin-4-yl)methanamine (Compound 40)

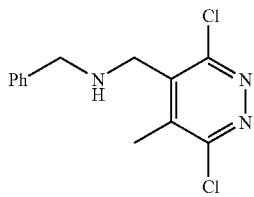 [SMILES: Cc1c(Cl)nnc(Cl)c1CNCc1ccccc1]

To a stirred solution of 3,6-dichloro-4,5-dimethylpyridazine (500 mg, 2.82 mmol) in carbon tetrachloride (10 mL) was added N-bromosuccinimide (503 mg, 2.82 mmol), and AIBN (2.3 mg, 0.014 mmol) in a round bottom flask equipped with condenser. The reaction was continuously irradiated with a 300 W light and refluxed for 5 h. The formed succimide was filtered and the filtrate was concentrated to afford 4-(bromomethyl)-3,6-dichloro-5-methylpyridazine as a brown solid. To a solution of 4-(bromomethyl)-3,6-dichloro-5-methylpyridazine (400 mg, 1.56 mmol) in DMF was added with benzyl amine (188 µL, 1.72 mmol) and TEA (326 µL, 2.34 mmol). The reaction mixture was heated at 90° C. for 2 h, diluted with DCM and washed with water and brine. The organic layer was dried over $Na_2SO_4$ and concentrated to afford a brown oil. The crude material was purified by flash chromatography on silica gel, eluting with 30-80% EtOAc:heptane. Fractions containing the desired product were combined and concentrated to afford a the title compound as a greasy solid (430 mg, yield: 54% (two steps)).

MS (m/z, MH+): meas. 282.2 calc. 282.05

4,5-bis(bromomethyl)-3,6-dichloropyridazine (Compound 41)

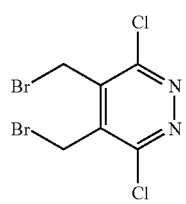 [SMILES: Clc1nnc(Cl)c(CBr)c1CBr]

To a stirred solution of 3,6-dichloro-4,5-dimethylpyridazine (3 g, 16.9 mmol) in 56 mL carbon tetrachloride was added with N-bromosuccinimide (9.1 g, 50.8 mmol), and AIBN (27.8 mg, 0.17 mmol) in a round bottom flask equipped with a condenser. The reaction was continuously irradiated with a 300 W light and refluxed for 16 h. The formed succimide was filtered and the filtrate was concentrated to afford the crude material. The mixture was purified by flash chromatography on silica gel, eluting with 10-30% EtOAc:heptane to afford a light yellow solid (3 g, yield: 53%).

$^1$H NMR (400 MHz, $CDCl_3$): 4.61 (s, 4H)

MS (m/z, MH+): meas. 335.0 calc. 334.8

1,4-dichloro-6-(4-methoxybenzyl)-6,7-dihydro-5H-pyrrolo[3,4-d]pyridazine (Compound 42)

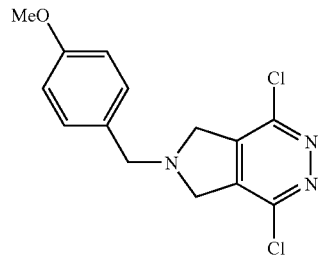 [SMILES: COc1ccc(CN2Cc3c(Cl)nnc(Cl)c3C2)cc1]

To a suspension of 4,5-bis(bromomethyl)-3,6-dichloropyridazine (800 mg, 2.39 mmol) in 40 mL anhydrous THF was added with sodium carbonate (507 mg, 4.78 mmol) and tetrabutylammonium iodide (88.3 mg, 0.24 mmol). The reaction mixture was added with 4-methylbenzylamine (0.31 mL, 2.39 mmol) in 20 mL THF dropwisely for 2 h. The reaction mixture was heated at 70° C. for 8 h and concentrated. The crude material was dissolved in DCM and washed with water and brine. The organic solution was dried over $Na_2SO_4$ and concentrated to afford a crude oil. The mixture was purified by flash chromatography on silica gel, eluting with 10-80% EtOAc:heptane to afford a off-white solid (300 mg, yield: 41%).

$^1$H NMR (400 MHz, $CDCl_3$): 7.28-7.25 (m, 2H), 6.90 (d, 2H, J=8.6 Hz), 4.12-4.07 (m, 2H), 3.89 (s, 2H), 3.83 (s, 3H)

MS (m/z, MH+): meas. 310.4 calc. 310.04

1,4-dichloro-6-isopropyl-6H-pyrrolo[3,4-d]pyridazine (Compound 43)

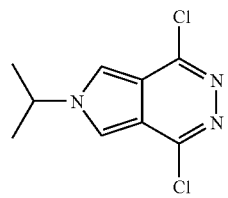

To a suspension of 4,5-bis(bromomethyl)-3,6-dichloropyridazine (700 mg, 2.09 mmol) in 66 mL anhydrous THF was added with sodium carbonate (443 mg, 4.18 mmol) and tetrabutylammonium iodide (77.2 mg, 0.21 mmol). The reaction mixture was added with isopropyl amine (0.18 mL, 2.09 mmol) in 10 mL THF dropwisely for 2 h. The reaction mixture was heated at 70° C. for 3 h. The reaction mixture was concentrated, dissolved in DCM and washed with water and brine. The organics solution was dried over $Na_2SO_4$ and concentrated to afford a crude oil. The mixture was purified by flash chromatography on silica gel, eluting with 10-80% EtOAc:heptane to afford a off-white solid (280 mg, yield: 47%).

MS (m/z, MH+): meas. 230.2 calc. 230.02

Synthesis of Examples 84-93

Example 84

4-{4-[6-(4-fluoro-benzyl)-4-methyl-pyridazin-3-yl]-piperazin-1-yl}-nicotinonitrile and

Example 85

4-{4-[6-(4-fluoro-benzyl)-5-methyl-pyridazin-3-yl]-piperazin-1-yl}-nicotinonitrile

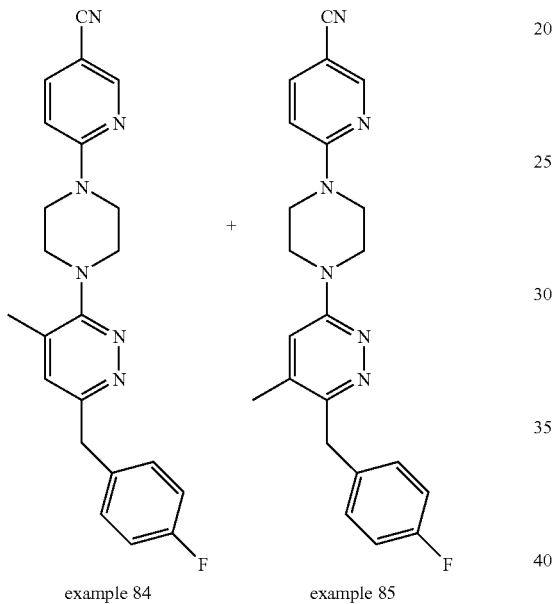

example 84        example 85

To a solution of the mixture of compounds 33a and 33b (80 mg, 0.34 mmol) in NMP (3 mL) is added 1-[5-cyano]-pyrid-2-yl]-piperazine (91 mg, 0.49 mmol) and TEA (0.15 mL, 1.08 mmol). The mixture is heated in microwave at 210° C. for 60 min. Water is added and the resulting mixture is extracted with EtOAc. The combined organic layers are washed with water, brine, dried over Na$_2$SO$_4$, filtered and concentrated down. The crude product is purified by chromatography on silica gel (EtOAc/Hexane: 10%~70%) to give 4-{4-[6-fluoro-benzyl)-4-methyl-pyridazin-3-yl]-piperazin-1-yl}-benzonitrile (example 84) (35 mg, 27%) and 4-{4-[6-(4-fluoro-benzyl)-5-methyl-pyridazin-3-yl]-piperazin-1-yl}-benzonitrile (example 85) (11 mg, 8%).

example 84: HR mass: m/z=389.1871 [M+1]. $^1$H-NMR (400 MHz, DMSO-d$_6$): δ=2.25 (3H, s), 3.25 (4H, m), 3.80 (3H, m), 4.12 (2H, s), 7.01 (1H, d), 7.13 (2H, m), 7.32 (3H, m), 7.90 (1H, d), 8.52 (1H, s).

example 85: HR mass: m/z=389.1877 [M+1]. $^1$H-NMR (400 MHz, DMSO-d$_6$): δ=2.15 (3H, s), 3.67 (4H, m), 3.82 (3H, m), 4.15 (2H, s), 6.98 (1H, d), 7.09 (3H, m), 7.19 (2H, m), 7.90 (1H, d), 8.52 (1H, s).

General Protocol for the Amination of Chlorides with Amines to Yield Examples 86 to 93a To a solution of the mixture of XIa and XIb (0.34 mmol) in NMP (3 mL) is added the substituted piperazine (0.49 mmol) and TEA (0.15 mL, 1.08 mmol). The mixture is heated in a microwave synthesizer at 210° C. for 60 min. Water is added and the resulting mixture is extracted with EtOAc. The combined organic layers are washed with water, brine, dried over Na$_2$SO$_4$, filtered and concentrated down. The crude product is purified by chromatography on silica gel (EtOAc/Hexane: 10%~70%) to give the regioisomeric compounds Ih and Ij.

Examples 86-93a

The following table (Table 7) lists examples of compounds prepared by amination as described above:

TABLE 7

| Example | Structure | MS [m/z; M + 1] |
|---------|-----------|-----------------|
| 86 | 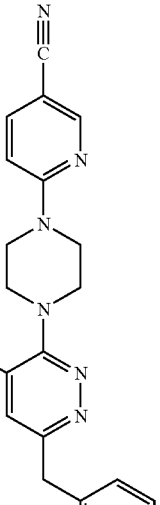 | 371 |
| 87 | 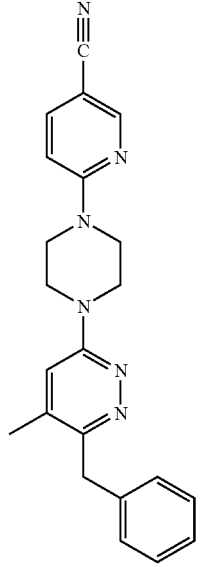 [SMILES: Cc1cc(N2CCN(c3ccc(C#N)cn3)CC2)nnc1Cc1ccccc1] | 371 |

TABLE 7-continued
| Example | Structure | MS [m/z; M + 1] |
|---|---|---|
| 88 | 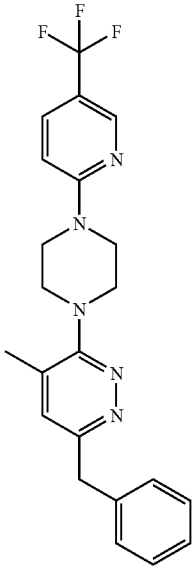 [SMILES: Cc1cc(Cc2ccccc2)nnc1N1CCN(c2ccc(C(F)(F)F)cn2)CC1] | 414 |
| 89 | 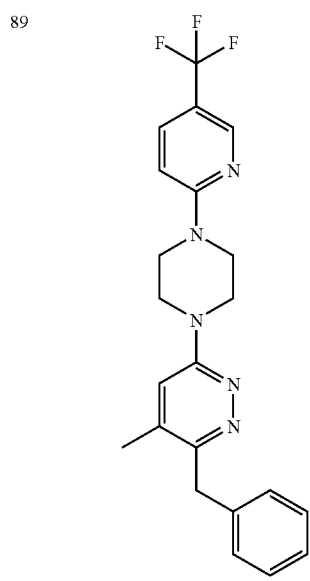 | 414 |
| 90 | 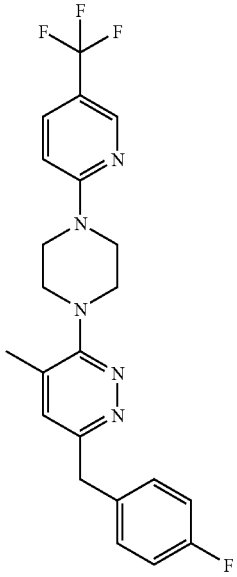 [SMILES: Cc1cc(Cc2ccc(F)cc2)nnc1N1CCN(c2ccc(C(F)(F)F)cn2)CC1] | 432 |
| 91 | 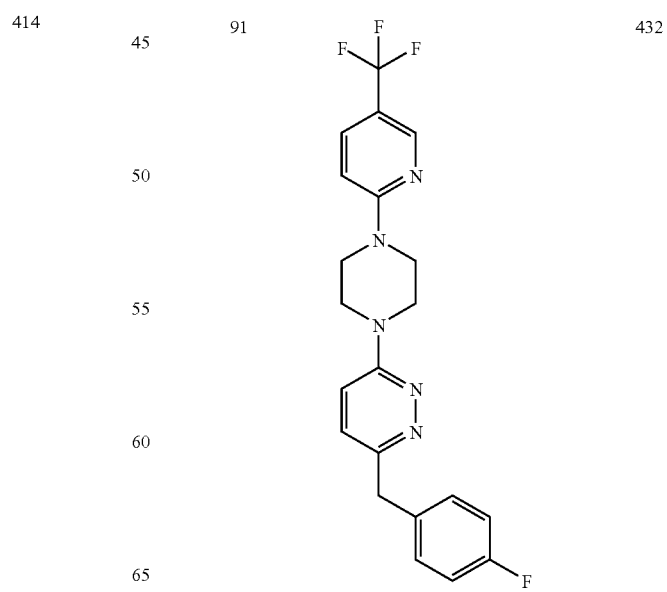 | 432 |

TABLE 7-continued

| Example | Structure | MS [m/z; M + 1] |
|---|---|---|
| 92 | (structure) | 405 |
| 93 | (structure) | 405 |
| 93a | (structure) | 402 |

Example 93b

4-{4-[4-(4-fluoro-benzyl)-5,6,7,8-tetrahydro-phthalzin-1-yl]-piperazin-1-yl}-nicotinonitrile To a solution of 1-chloro-4-(4-fluoro-benzyl)-5,6,7,8-tetrahydro-phthalazine (compound 10f) (100 mg, 0.15 mmol) in NMP (3 mL) is added 1-[5-cyano]-pyrid-2-yl]-piperazine (54 mg, 0.29 mmol) and TEA (0.15 mL, 1.08 mmol). The mixture is heated in microwave at 210° C. for 60 min. Water is added to the mixture and extracted with EtOAc. The combined organic layers are washed with water, brine, dried over $Na_2SO_4$, filtered and concentrated down. The crude product is purified by chromatography (EtOAc/Hexane: 10%~70%) to give 4-{4-[4-(4-fluoro-benzyl)-5,6,7,8-tetrahydro-phthalzin-1-yl]-piperazin-1-yl}-nicotinonitrile (example 93b) (55 mg, 89%).

HR mass: m/z=429.2206 [M+1].

$^1$H-NMR (400 MHz, DMSO-d$_6$): δ=2.61 (2H, m), 1.75 (2H, m), 2.51 (2H, m), 2.62 (2H, m), 3.22 (4H, m), 3.81 (4H, m), 4.13 (2H, s), 7.01 (1H, d), 7.13 (2H, m), 7.22 (2H, m), 7.88 (1H, d), 8.52 (1H, s)

Example 93c

6-{4-[4-(4-Fluoro-benzyl)-6,7-dihydro-5H-cyclopenta[d]pyridazin-1-yl]-piperazin-1-yl}-nicotinonitrile

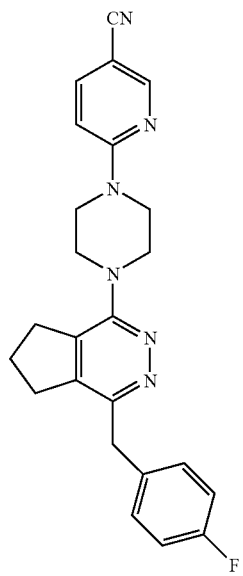 [SMILES: N#Cc1ccc(N2CCN(c3nnc(Cc4ccc(F)cc4)c4c3CCC4)CC2)nc1]

Following the synthetic procedures of example 93b, example 93c was prepared starting from 5,6-dihydro-4H-cyclopenta[c]furan-1,3-dione instead of 4,5,6,7-tetrahydro-isobenzofuran-1,3-dione.

HR mass: m/z=415.2040 [M+1].

$^1$H-NMR (400 MHz, CD$_2$Cl$_2$): δ=1.95 (2H, m), 2.61 (2H, m), 2.82 (2H, m), 3.48 (4H, m), 3.82 (4H, m), 4.15 (2H, s), 6.61 (1H, d), 6.87 (2H, m), 7.12 (2H, m), 7.68 (1H, d), 8.29 (1H, s).

Example 240

4-Benzyl-1-(4-(5-(trifluoromethyl)pyridin-2-yl)piperazin-1-yl)-5,6-dihydrophthalazine

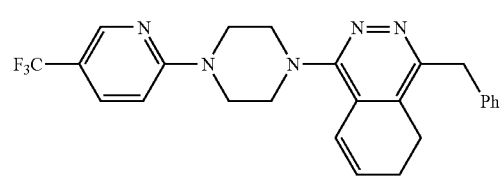 [SMILES: FC(F)(F)c1ccc(N2CCN(c3nnc(Cc4ccccc4)c4c3C=CCC4)CC2)nc1]

$^1$H NMR (400 MHz, CDCl$_3$): 8.40 (s, 1H), 7.78 (dd, 1H, J=2.0 Hz, 9.1 Hz), 7.29-7.24 (m, 2H), 7.19-7.17 (m, 3H), 7.02 (d, 1H, J=9.1 Hz), 6.53-6.51 (m, 1H), 6.45-6.40 (m, 1H), 4.25-4.21 (m, 2H), 3.82-3.80 (m, 4H), 3.27-3.25 (m, 4H), 2.54-2.47 (m, 2H), 2.35-2.25 (m, 2H)

MS (m/z, MH+): meas. 452.2062 calc. 452.2062

Example 241

N-benzyl-1-(6-benzyl-5-methyl-3-(4-(5-(trifluoromethyl)pyridin-2-yl)piperazin-1-yl)pyridazin-4-yl)methanamine

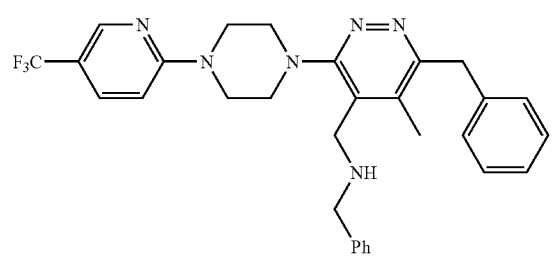 [SMILES: Cc1c(Cc2ccccc2)nnc(N2CCN(c3ccc(C(F)(F)F)cn3)CC2)c1CNCc1ccccc1]

$^1$H NMR (400 MHz, DMSO-d$_6$): d=8.87 (b, 1H), 8.44 (s, 1H), 7.84 (dd, 1H, J=2.1 Hz, 9.1 Hz), 7.52-7.50 (m, 2H), 7.39-7.35 (m, 2H), 7.32-7.28 (m, 3H), 7.23-7.19 (m, 3H), 6.97 (d, 1H, J=9.1 Hz), 4.31 (br, 4H), 4.17 (br, 2H), 3.55-3.48 (m, 4H), 3.12-3.04 (m, 4H), 2.27 (s, 3H).

HR-MS (m/z, MH+): meas. 533.2645 calc. 533.2641

Example 242

N-benzyl-1-(3-benzyl-5-methyl-6-(4-(5-(trifluoromethyl)pyridin-2-yl)piperazin-1-yl)pyridazin-4-yl)methanamine

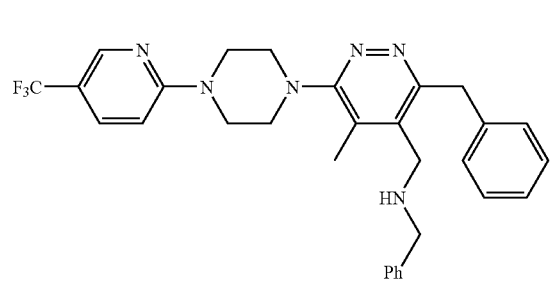 [SMILES: Cc1c(N2CCN(c3ccc(C(F)(F)F)cn3)CC2)nnc(Cc2ccccc2)c1CNCc1ccccc1]

MS (m/z, MH+): meas. 533.7 calc. 533.26

Example 243

1-benzyl-6-(4-methoxybenzyl)-4-(4-(5-(trifluoromethyl)pyridin-2-yl)piperazin-1-yl)-6,7-dihydro-5H-pyrrolo[3,4-d]pyridazine

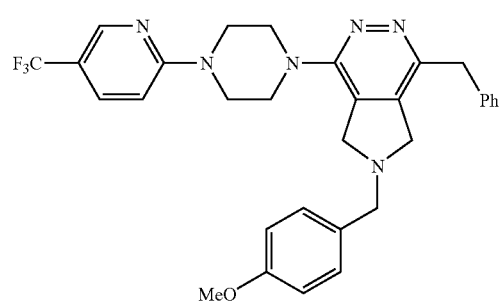 [SMILES: COc1ccc(CN2Cc3c(Cc4ccccc4)nnc(N4CCN(c5ccc(C(F)(F)F)cn5)CC4)c3C2)cc1]

¹H NMR (400 MHz, DMSO-d6): 8.43 (s, 1H), 7.82 (dd, 1H, J=2.5 Hz, 9.1 Hz), 7.63-7.52 (m, 5H), 7.28-7.14 (m, 3H), 6.98 (d, 1H, J=9.1 Hz), 6.90-6.87 (m, 1H), 4.11 (s, 2H), 3.98 (s, 2H), 3.76-3.71 (m, 11H), 3.51-3.49 (m, 4H)

HR-MS (m/z, MH+): meas. 561.2572 calc. 561.2590

Example 244

1-benzyl-6-isopropyl-4-(4-(5-(trifluoromethyl)pyridin-2-yl)piperazin-1-yl)-6H-pyrrolo[3,4-d]pyridazine

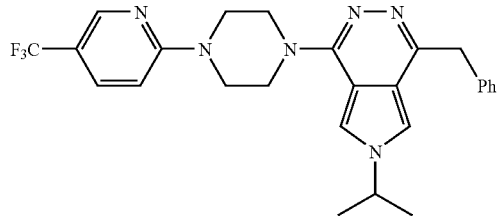 [SMILES: CC(C)n1cc2c(Cc3ccccc3)nnc(N3CCN(c4ccc(C(F)(F)F)cn4)CC3)c2c1]

¹H NMR (400 MHz, DMSO-d6): 8.46 (s, 1H), 8.38 (s, 1H), 8.19 (s, 1H), 7.85 (dt, 1H, J=2.5 Hz, 9.1 Hz), 7.42-7.40 (m, 1H), 7.30 (t, 1H, J=7.6 Hz), 7.24-7.21 (m, 1H), 6.92 (d, 1H, J=9.1 Hz), 4.74 (p, 1H, J=6.5 Hz), 4.25 (s, 2H), 4.03-4.02 (m, 4H), 3.94-3.93 (m, 4H), 1.54 (d, 6H, J=6.6 Hz)

HRMS (m/z, MH+): meas. 481.2320 calc. 481.2328

Furo[2,3-d]- and imidazo[4,5-d]-pyridazines

Scheme 5a shows a general synthetic scheme for the preparation of compounds of Formula Im and In. Substituted furo [2,3-d]- and imidazo[4,5-d]-pyridazines XV can be reacted with an amine in the presence of base to form intermediates XVIa and XVIb. Cross-coupling with organo-zinc reagents under palladium catalysis yields compounds Im, n which can be separated by chromatography into their regioisomers.

SCHEME 5a

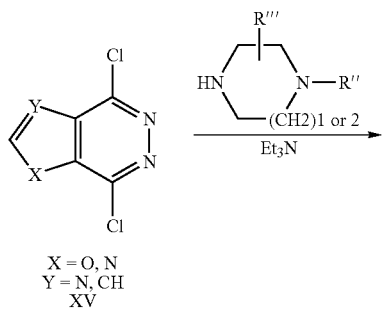

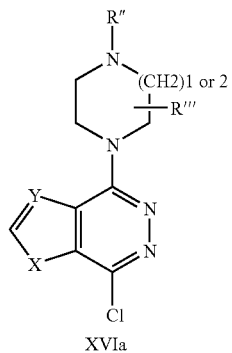

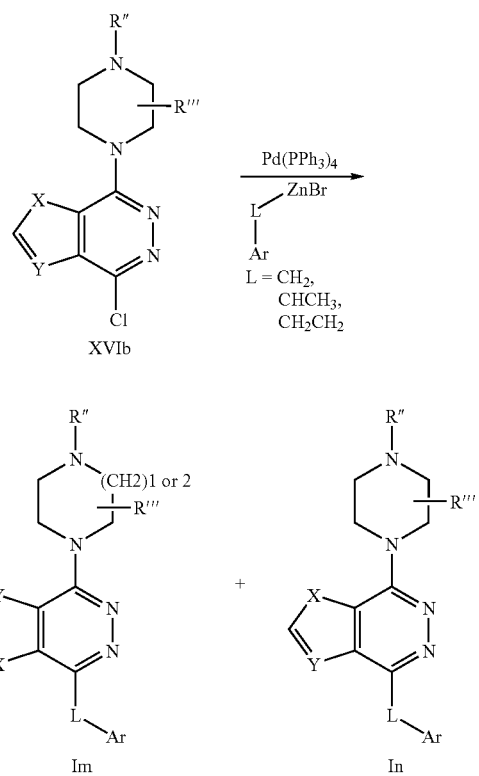

Synthesis of Intermediates

Furan-2,3-dicarboxylic acid dimethyl ester
(Compound 44)

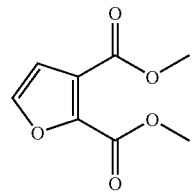

Furan-2,3-dicarboxylic acid (1 g, 6.41 mmol) is dissolved in MeOH (10 mL). To this solution is added thionyl chloride (1.4 mL, 19.22 mmol). The reaction is allowed to continue stirring at room temperature for 16 h. Add H₂O (1 mL) to quench the reaction and remove the MeOH in vacuo. Add additional H₂O and extract with EtOAc. Combined organic layers are washed with brine and concentrated in vacuo to yield the title compound without further purification (650 mg, 55%).

¹H NMR (400 MHz, DMSO-d₆) δ 8.02 (d, J=1.77 Hz, 1H), 6.94 (d, J=1.89 Hz, 1H), 3.84 (s, 3H), 3.81 (s, 3H).

5,6-Dihydro-furo[2,3-d]pyridazine-4,7-dione (Compound 45)

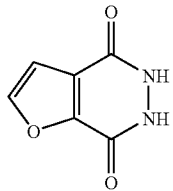 [SMILES: O=c1[nH][nH]c(=O)c2occc12]

Furan-2,3-dicarboxylic acid dimethyl ester (1.6 g, 8.69 mmol) is added to EtOH (10 mL) and hydrazine hydrate (1.46 mL, 55% in water). Heat the reaction to reflux for 5-6 h. Cool and concentrate in vacuo to form a slurry. Dilute the material with additional $H_2O$ and filter the precipitate. Wash with additional $H_2O$. Transfer material from filter to a round bottom flask and add HCl (7.2 mL, 2N in $H_2O$). Heat reaction mixture to reflux for 4 h. Cool and filter the precipitate washing with $H_2O$, to yield the title compound without further purification (930 mg, 70%)

$^1$H NMR (400 MHz, DMSO-$d_6$) δ 11.77 (br. s., 1.7H), 8.21 (d, J=1.89 Hz, 1H), 7.03 (d, J=1.52 Hz, 1H), 3.42 (br. s., 1.65H).

4,7-Dichloro-furo[2,3-d]pyridazine (Compound 46)

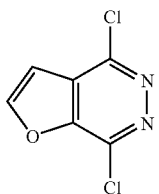 [SMILES: Clc1nnc(Cl)c2occc12]

5,6-Dihydro-furo[2,3-d]pyridazine-4,7-dione (930 mg, 6.11 mmol) is combined with pyridine (1.8 mL) and $POCl_3$ (18 mL). The reaction mixture is heated to reflux for 4 h. Concentrate in vacuo. Pour viscous solution over ice. Extract product with $CH_2Cl_2$. Wash the combined organics layers with brine and dry over sodium sulfate. Concentrate in vacuo. The residue is purified by flash chromatography on silica gel (0-8% MeOH/$CH_2Cl_2$) to afford the title compound (577 mg, 50%).

$^1$H NMR (400 MHz, DMSO-$d_6$) δ 8.66 (d, J=2.15 Hz, 1H), 7.43 (d, J=2.15 Hz, 1H).

5,6-Dihydro-1H-imidazo[4,5-d]pyridazine-4,7-dione (Compound 47)

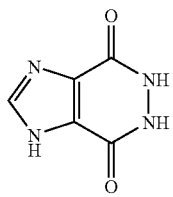 [SMILES: O=c1[nH][nH]c(=O)c2[nH]cnc12]

1H-Imidazole-4,5-dicarboxylic acid dimethyl ester (592 mg, 3.21 mmol) is combined with hydrazine (600 mg, 18.8 mmol) and MeOH (10 mL). The reaction mixture is heated to 115° C. for 30 min. Cool and filter off the resulting precipitate. Wash with additional water. Combine the precipitate with hydrazine (1.38 mL) and reflux for 4 h. Pour the reaction mixture into ice water and adjust the to pH 2 with HCl (12 N). The new precipitate is isolated by filtration to afford the title product (293 mg, 60%)

$^1$H NMR (400 MHz, DMSO-$d_6$) δ 11.41 (br. s., 1.47H), 8.27 (s, 1H), 3.37 (br. s., 6.2 2H).

4,7-Dichloro-1H-imidazo[4,5-d]pyridazine (Compound 48)

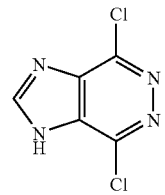

5,6-Dihydro-1H-imidazo[4,5-d]pyridazine-4,7-dione (1 g, 6.57 mmol) is combined with $POCl_3$ (28 mL) and dimethylamine (1 mL). The reaction mixture is heated to reflux for 16 h. Remove excess $POCl_3$ in vacuo and pour syrupy mixture into $H_2O$ (45 mL) with an ice bath maintaining an internal temperature less than 5° C. Stir for 1 h at room temperature and isolate precipitate by filtration. Wash with $H_2O$ to afford the title compound (830 mg, 67%)

$^1$H NMR (400 MHz, DMSO-$d_6$) δ 14.43 (br. s., 0.75H), 8.87 (s, 1H).

7-Chloro-4-[4-(5-trifluoromethyl-pyridin-2-yl)-piperazin-1-yl]-furo[2,3-d]pyridazine & 4-Chloro-7-[4-(5-trifluoromethyl-pyridin-2-yl)-piperazin-1-yl]-furo[2,3-d]pyridazine (Compounds 49a and 49b)

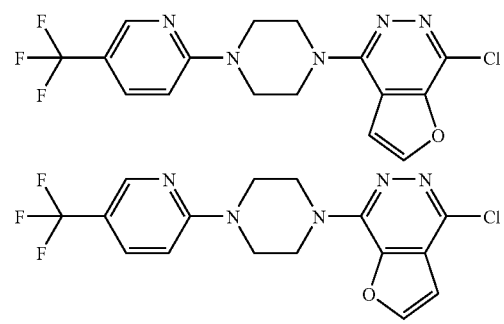

4,7-Dichloro-furo[2,3-d]pyridazine (250 mg, 1.32 mmol) is combined with 145-Trifluoromethyl-pyridin-2-yl)-piperazine (290 mg, 1.26 mmol), triethylamine (270 μL, 1.98 mmol), and dioxane (2 mL). The reaction mixture is heated to 80° C. for 70 h. Concentrate dioxane in vacuo. The residue is purified by flash chromatography on silica gel (EtOAc/Heptane) to afford a regioisomeric mix (60:40) of both title compounds (210 mg, 41%).

7-Chloro-4-[4-(5-trifluoromethyl-pyridin-2-yl)-piperazin-1-yl]-1H-imidazo[4,5-d]pyridazine (Compound 50)

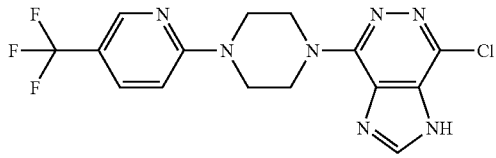 [SMILES: FC(F)(F)c1ccc(N2CCN(c3nnc(Cl)c4[nH]cnc34)CC2)nc1]

4,7-Dichloro-1H-imidazo[4,5-d]pyridazine (250 mg, 1.32 mmol) is combined with triethylamine (270 µL), dioxane (2 mL), and 1-(5-Trifluoromethyl-pyridin-2-yl)-piperazine (290 mg, 1.26 mmol). The reaction mixture is heated to 80° C. for 70 h. Concentrate in vacuo to remove dioxane. The residue is purified by flash chromatography on silica gel (MeOH/$CH_2Cl_2$) to afford the title compound (176 mg, 57%).

Synthesis of Examples 245-247

Example 245

7-Benzyl-4-[4-(5-trifluoromethyl-pyridin-2-yl)-piperazin-1-yl]-furo[2,3-d]pyridazine

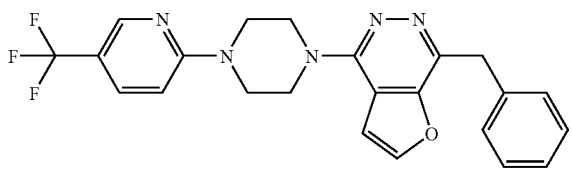 [SMILES: FC(F)(F)c1ccc(N2CCN(c3nnc(Cc4ccccc4)c4occc34)CC2)nc1]

The mixture of 7-chloro-4-[4-(5-trifluoromethyl-pyridin-2-yl)-piperazin-1-yl]-furo[2,3-d]pyridazine and 4-chloro-7-[4-(5-trifluoromethyl-pyridin-2-yl)-piperazin-1-yl]-furo[2,3-d]pyridazine (210 mg, 0.547 mmol) are combined with benzyl zinc bromide (6.75 mL, 0.5M in THF, 3.28 mmol) and tetrakis (triphenylphosphine) palladium⁰ (31.5 mg, 0.027 mmol). The reaction is heated to 80° C. for 40 h. Add $H_2O$ and extract with EtOAc. Concentrate in vacuo. The residue is purified by flash chromatography on silica gel (EtOAc/Heptane) to afford a mix of title compounds. This mixture is separated by HPLC using a 30% isocratic gradient of $CH_3CN/H_2O$ with a formic acid modifier (0.1%) to yield both title compounds (16.9 mg, 7%).

¹H NMR (600 MHz, DMSO-$d_6$) δ 8.45 (s, 1H), 8.26 (s, 1H), 7.84 (d, J=9.06 Hz, 1H), 7.39-7.33 (m, 1H), 7.32-7.24 (m, 4H), 7.19 (dd, J=6.80 Hz, 1H), 7.00 (d, J=9.06 Hz, 1H), 4.38 (s, 2H), 3.89-3.81 (m, 8H).

HR-MS (m/z, MH⁺): meas. 440.1683 calc. 440.1698

Example 246

4-Benzyl-7-[4-(5-trifluoromethyl-pyridin-2-yl)-piperazin-1-yl]-furo[2,3-d]pyridazine

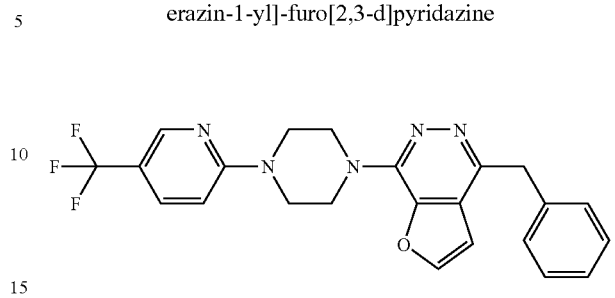

The above procedure and method of separation also produced the title compound (17.9 mg, 7.4%).

¹H NMR (600 MHz, DMSO-$d_6$) δ 8.45 (s, 1H), 8.25 (s, 1H), 7.85 (d, J=9.06 Hz, 1H), 7.36-7.30 (m, 2H), 7.27 (q, J=7.55, 7.55 Hz, 2H), 7.18 (dd, J=7.18, 7.18 Hz, 1H), 7.11 (s, 1H), 7.04 (d, J=9.06 Hz, 1H), 4.37 (s, 2H), 3.94-3.88 (m, 4H), 3.88-3.81 (m, 4H).

HR-MS (m/z, MH⁺): meas. 440.1683 calc. 440.1698

Example 247

7-Benzyl-4-[4-(5-trifluoromethyl-pyridin-2-yl)-piperazin-1-yl]-1H-imidazo[4,5-d]pyridazine

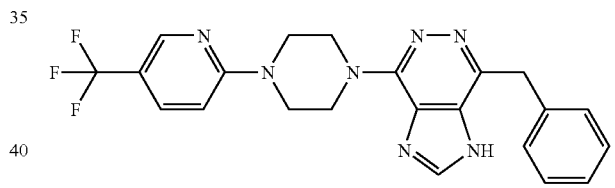

7-Chloro-4-[4-(5-trifluoromethyl-pyridin-2-yl)-piperazin-1-yl]-1H-imidazo[4,5-d]pyridazine (149 mg, 0.389 mmol), benzyl zinc bromide (9.34 mL, 0.5M in THF, 4.67 mmol), and tetrakis (triphenylphosphine) palladium⁰ (23 mg, 0.020). The reaction mixture is heated to 80° C. for 32 h. Add $H_2O$ and extract product with EtOAc. Wash combined organics with brine and concentrate in vacuo. The residue is purified by flash chromatography on silica gel (60-100% EtOAc/Heptane flushed with 10% MeOH/EtOAc) to afford the title compound (12.1 mg, 7%).

¹H NMR (400 MHz, MeOD) δ 8.40-8.35 (m, 1H), 8.30-8.27 (m, 1H). 7.74 (dd, J=9.09, 2.53 Hz, 1H), 7.34-7.29 (m, 2H), 7.28-7.22 (m, 2H), 7.21-7.14 (m, 1H), 6.94 (d, J=9.09 Hz, 1H), 4.46 (s, 2H), 4.21-4.15 (m, 4H), 3.90-3.84 (m, 4H).

HR-MS (m/z, MH⁺): meas. 440.1799 calc. 440.1811

Indoles

Scheme 6 shows a general synthetic scheme for the preparation of compounds of Formula Io. Substituted indoles XVII can be reacted with e.g., acylation reagents, arylation or alkylation reagents to form intermediates XVIII. Reaction of the indole-nitrogen with alkylation reagents under basic conditions yields examples Io.

SCHEME 6

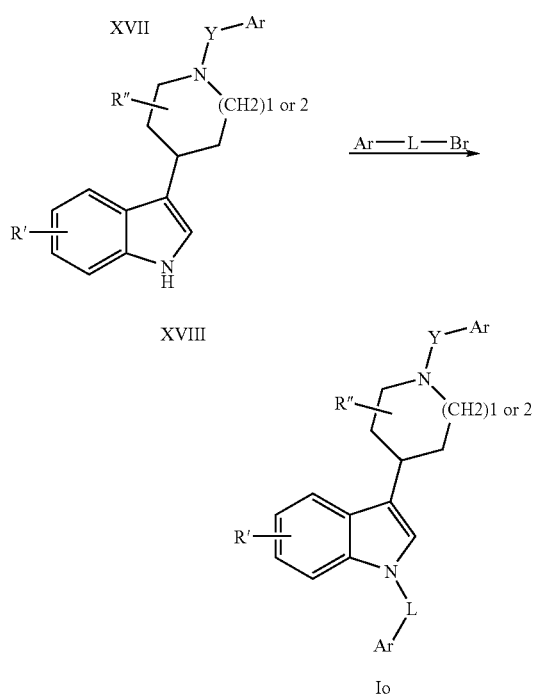

for Y—Z = CO—OH: HBTU, HOBt, DIPEA, DMF
for L = CH₂: 50% NaOH, THF, phase transfer catalyst
for Y—Z = Cl: K₂CO₃, DMF, heat

Synthesis of Intermediates

3-[4-(1H-Indol-3-yl)-piperidine-1-carbonyl]-benzonitrile (Compound 63)

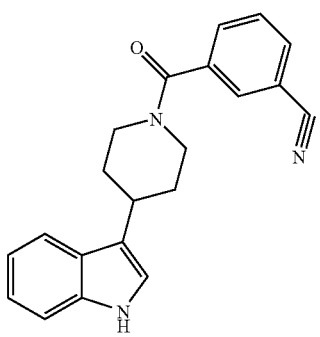 [SMILES: N#Cc1cccc(C(=O)N2CCC(c3c[nH]c4ccccc34)CC2)c1]

3-Cyano-benzoic acid (0.09 g, 0.6 mmol) is dissolved in 3 ml of DMF, then HBTU (0.28 g, 0.75 mmol), HOBt (0.10 g, 0.75 mmol) and DIPEA (0.26 g, 2.0 mmol) are added. The mixture is stirred at RT for 20 min before adding the 3-piperidin-4-yl-1H-indole (0.09 g, 0.6 mmol). The reaction was stirred at RT for 3 hours, monitored with LC/MS. The organic solvent is removed under the reduced pressure and the residue is purified by a silica gel flash column using heptane and ethyl acetate as the elutes.

LC/MS: Method 1, retention time=1.21 min, M+1=330.1 ($C_{21}H_{19}N_3O$).
¹H-NMR (400 MHz, CDCl₃): δ=7.9-7.5 (m, 9H), 3.2 (m, 1H), 1.4-1.2 (m, 8H).

4-(1H-Indol-3-yl)-5'-trifluoromethyl-3,4,5,6-tetrahydro-2H-[1,2]-bipyridinyl (Compound 64)

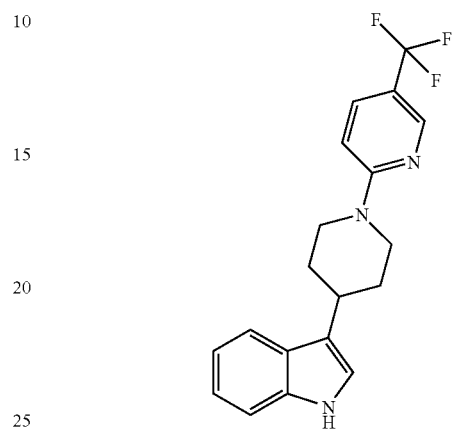

3-piperidin-4-yl-1H-indole (0.5 g, 2.5 mmol) is suspended in 10 ml of DMF and is heated to 60° C. K₂CO₃ and 5-trifluoromethyl-2-chloropyridine (0.54 g, 3.0 mmol) are added and the reaction mixture is stirred at 95° C. for 1 hour. K₂CO₃ is removed by filtration and the filtrate is concentrated and purified with a silica gel flash column using heptane and ethyl acetate as the elutes.

LC/MS: Method 8, retention time=1.13 min, M+1=346.2 ($C_{19}H_{18}N_3F_3$).
¹H-NMR (400 MHz, CDCl₃): δ=8.35 (s, 1H), 7.72 (t, 1H), 7.59 (t, 1H), 7.33 (t, 3H), 7.09 (q, 1H), 7.00 (t, 1H), 6.93 (d, 1H), 4.60 (b, 2H), 3.20-3.00 (m, 3H), 2.18 (d, 2H), 1.82-1.71 (m, 2H).

Synthesis of Examples 94-105

Example 94

3-{4-[1-(4-Fluoro-benzyl)-1H-indol-3-yl]-piperidine-1-carbonyl}-benzonitrile

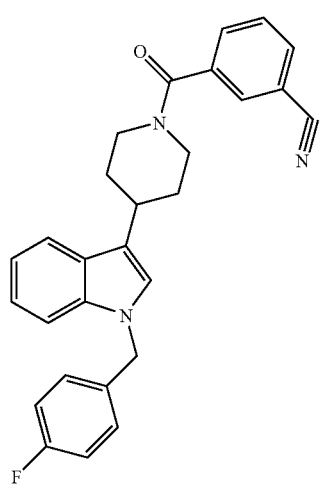 [SMILES: N#Cc1cccc(C(=O)N2CCC(c3cn(Cc4ccc(F)cc4)c4ccccc34)CC2)c1]

3-[4-(1H-Indol-3-yl)-piperidine-1-carbonyl]-benzonitrile (0.08 g, 0.24 mmol) is dissolved in 2 ml THF, then 2 ml of 50% NaOH, 0.2 ml tetrabutyl ammonium hydroxide (1.0M in MeOH), 4-fluoro-benzyl bromide (0.055 g, 0.29 mmol) are added and the reaction mixture is stirred at RT for 1.5 hours. The layers are separated and the organic solvent is removed under the reduced pressure, purified by a silica gel flash column using heptane and ethyl acetate as the elutes.

LC/MS: Method 8, retention time=1.24 min, M+1=438.2 ($C_{28}H_{24}N_3O$).

$^1$H-NMR (400 MHz, CDCl$_3$): δ=7.90-7.60 (m, 5H), 7.20-6.90 (m, 8H), 5.30 (s, 2H), 3.40-3.00 (m, 4H), 2.20 (m, 1H), 1.4-1.2 (m, 4H).

Example 95

4-[1-(4-Fluoro-benzyl)-1H-indol-3-yl)-5'-trifluoromethyl-3,4,5,6-tetrahydro-2H-[1,2]-bipyridinyl

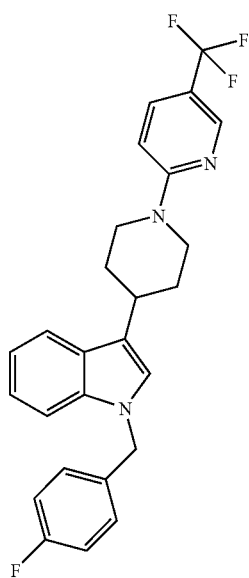 [SMILES: Fc1ccc(Cn2cc(C3CCN(c4ccc(C(F)(F)F)cn4)CC3)c3ccccc32)cc1]

4-(1H-Indol-3-yl)-5'-trifluoromethyl-3,4,5,6-tetrahydro-2H-[1,2]-bipyridinyl (0.15 g, 0.44 mmol) is dissolved in 3 ml THF, then 3 ml of 50% NaOH, 0.3 ml tetrabutyl ammonium hydroxide (1.0M in MeOH) and 4-fluoro-benzyl bromide (0.10 g, 0.52 mmol) are added, the reaction mixture is stirred at RT for 1.5 hours. The layers are separated and the organic solvent is removed by the reduced pressure. The residue is purified with a silica gel flash column using heptane and ethyl acetate as the elutes.

LC/MS: Method 8, retention time=1.77 min, M+1=454.2 ($C_{26}H_{23}N_3F_4$).

$^1$H-NMR (400 MHz, CDCl$_3$): δ=7.90-7.60 (m, 5H), 7.20-6.90 (m, 8H), 5.30 (s, 2H), 3.40-3.00 (m, 4H), 2.20 (m, 1H), 1.4-1.2 (m, 4H).

General Protocol for the Alkylation of Indoles to Yield Examples 96 to 105

The indole XIII (0.44 mmol) is dissolved in 3 ml THF, then 3 ml of 50% NaOH, 0.3 ml tetrabutyl ammonium hydroxide (1.0M in MeOH) and benzyl bromide (0.52 mmol) are added, the reaction mixture is stirred at RT for 1.5 hours. The layers are separated and the organic solvent is removed by the reduced pressure. The residue is purified with a silica gel flash column using heptane and ethyl acetate as the elutes.

Examples 96-105

The following table (Table 8) lists examples of compounds prepared by alkylation as described above:

TABLE 8

| Example | Structure | MS [m/z; M + 1] |
|---------|-----------|-----------------|
| 96 | 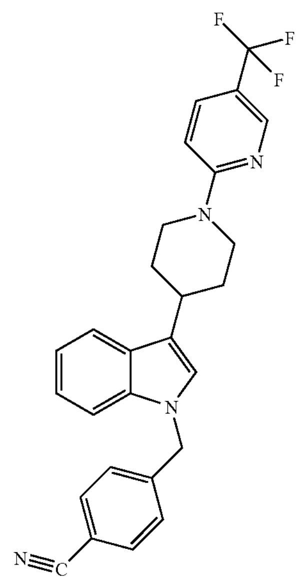 [SMILES: N#Cc1ccc(Cn2cc(C3CCN(c4ccc(C(F)(F)F)cn4)CC3)c3ccccc32)cc1] | 461 |
| 97 | 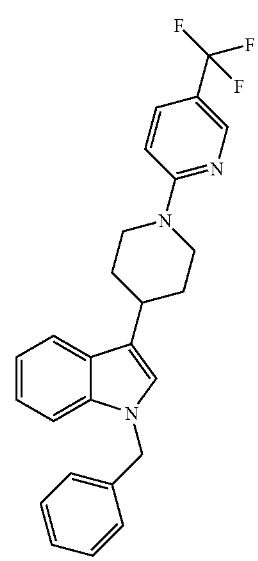 [SMILES: FC(F)(F)c1ccc(N2CCC(c3cn(Cc4ccccc4)c4ccccc34)CC2)nc1] | 435 |

TABLE 8-continued
| Example | Structure | MS [m/z; M + 1] |
|---|---|---|
| 98 | 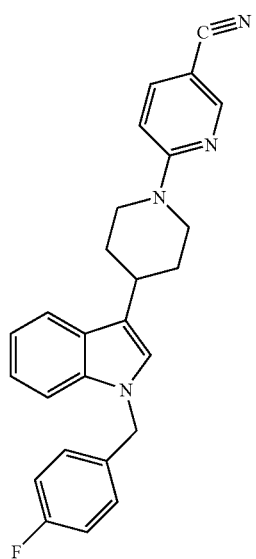 [SMILES: N#Cc1ccc(N2CCC(c3cn(Cc4ccc(F)cc4)c4ccccc34)CC2)nc1] | 411 |
| 99 | 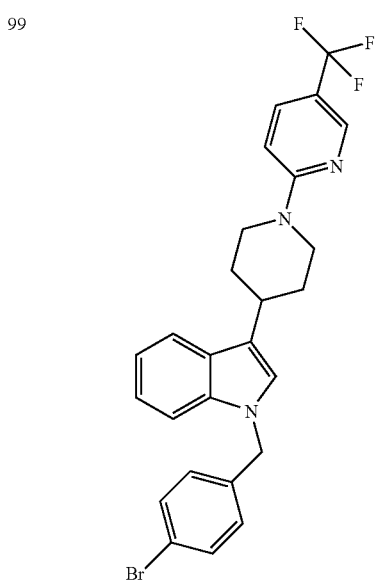 | 514/516 |
TABLE 8-continued
| Example | Structure | MS [m/z; M + 1] |
|---|---|---|
| 100 | 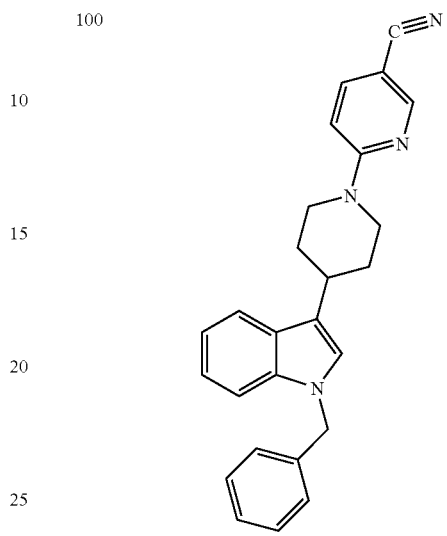 | 393 |
| 101 | 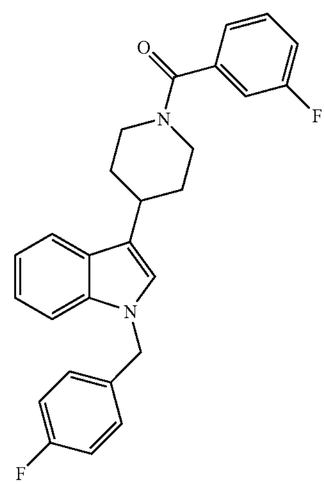 [SMILES: O=C(c1cccc(F)c1)N1CCC(c2cn(Cc3ccc(F)cc3)c3ccccc23)CC1] | 431 |
| 102 | 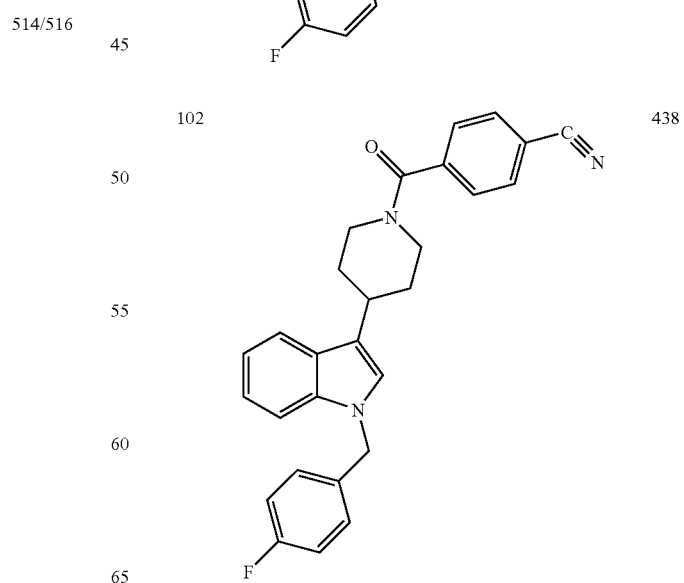 | 438 |

TABLE 8-continued

| Example | Structure | MS [m/z; M + 1] |
|---|---|---|
| 103 | 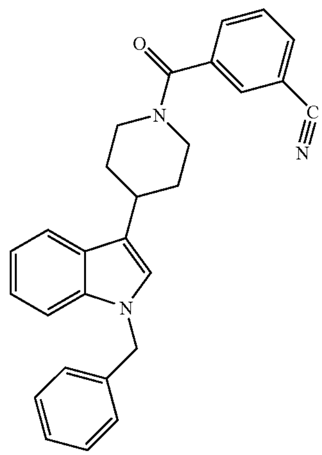 [SMILES: N#Cc1cccc(C(=O)N2CCC(c3cn(Cc4ccccc4)c4ccccc34)CC2)c1] | 420 |
| 104 | 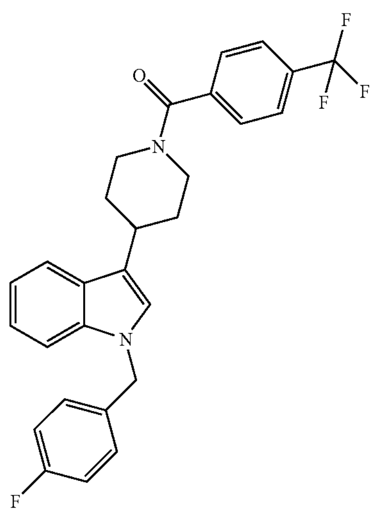 [SMILES: O=C(c1ccc(C(F)(F)F)cc1)N1CCC(c2cn(Cc3ccc(F)cc3)c3ccccc23)CC1] | 481 |
| 105 | | 463 |

Biological Activity

Activity of the compounds was evaluated using a reporter gene assay (RGA) in TMHh12 cells. IC50 for antagonism of Gli-luciferase activity was tested in the presence of increasing concentrations of a small molecule agonist which binds to Smo with 1 nM affinity and activates the Hh pathway (Frank-Kamenetsky et al 2002, Journal of Biology 1, 10.1-10.19). Antagonist compounds from screening which show increased IC50s for Gli-luc as the agonist dose is increased may be directly interacting with Smo (either through competition for the same binding site on Smo, or via competition between an active conformational state of Smo that is induced by agonist and an inactive state that is induced by the test antagonist). In validation experiments, a variety of small molecule antagonists of Smo demonstrate "IC50 shift" behavior.

Table 9 lists the IC50 of antagonists determined in the presence of different (1 nM and 25 nM) concentrations of a small agonist of Smoothened (Frank-Kamenetsky et al 2002, Journal of Biology 1, 10.1-10.19).

A Smo binding assay was developed using radio-labeled smoothened agonist for compound competition. Table 9 lists the IC50 for displacement of a small molecule agonist of Smoothened determined in a filter binding format for the mouse and human Smoothened receptor.

TABLE 9

| Example no. | RGA (1 nM Smo agonist) $IC_{50}$ [μM] | RGA (25 nM Smo agonist) $IC_{50}$ [μM] | Mouse Smo bdg., $IC_{50}$ [μM] | Human Smo bdg., $IC_{50}$ [μM] |
|---|---|---|---|---|
| 1 | <0.1 | 1-10 | <0.1 | 0.1-1 |
| 2 | <0.1 | 0.1-1 | <0.1 | <0.1 |
| 3 | 0.1-1 | 0.1-1 | <0.1 | |
| 4 | 0.1-1 | 1-10 | 1-10 | |
| 5 | <0.1 | 0.1-1 | <0.1 | <0.1 |
| 6 | 1-10 | 10-40 | | |
| 7 | <0.1 | 0.1-1 | <0.1 | 0.1-1 |
| 8 | 0.1-1 | 1-10 | <0.1 | |
| 9 | <0.1 | 0.1-1 | <0.1 | |
| 10 | <0.1 | 1-10 | <0.1 | |
| 11 | 1-10 | 10-40 | | |
| 12 | 1-10 | 1-10 | 10-40 | |
| 13 | 1-10 | 1-10 | 1-10 | |
| 14 | 1-10 | 1-10 | | |
| 15 | | | | |
| 16 | 1-10 | 1-10 | 1-10 | 1-10 |

TABLE 9-continued

| Example no. | RGA (1 nM Smo agonist) IC$_{50}$ [μM] | RGA (25 nM Smo agonist) IC$_{50}$ [μM] | Mouse Smo bdg., IC$_{50}$ [μM] | Human Smo bdg., IC$_{50}$ [μM] |
|---|---|---|---|---|
| 17 | <0.1 | 1-10 | 0.1-1 | |
| 18 | <0.1 | 0.1-1 | <0.1 | |
| 19 | <0.1 | 0.1-1 | <0.1 | |
| 20 | 1-10 | | 1-10 | |
| 21 | 0.1-1 | 1-10 | 0.1-1 | |
| 22 | 1-10 | 10-40 | | |
| 23 | 1-10 | 10-40 | 10-40 | |
| 24 | 0.1-1 | 1-10 | 0.1-1 | |
| 25 | <0.1 | 1-10 | 0.1-1 | |
| 26 | 1-10 | | 1-10 | |
| 27 | 0.1-1 | 1-10 | 1-10 | |
| 28 | 1-10 | 1-10 | 1-10 | |
| 29 | 1-10 | 10-40 | 10-40 | |
| 30 | 0.1-1 | 1-10 | 1-10 | |
| 31 | 0.1-1 | 1-10 | 0.1-1 | |
| 32 | 0.1-1 | 1-10 | 0.1-1 | |
| 33 | 1-10 | 1-10 | 0.1-1 | |
| 34 | 0.1-1 | 1-10 | 1-10 | |
| 35 | 1-10 | 1-10 | | |
| 36 | 0.1-1 | 1-10 | 1-10 | |
| 37 | 0.1-1 | 1-10 | 1-10 | |
| 38 | 1-10 | 1-10 | 10-40 | |
| 39 | <0.1 | 0.1-1 | 0.1-1 | 0.1-1 |
| 40 | <0.1 | 0.1-1 | 0.1-1 | |
| 41 | <0.1 | 0.1-1 | 0.1-1 | |
| 42 | <0.1 | 0.1-1 | <0.1 | |
| 43 | <0.1 | <0.1 | <0.1 | |
| 44 | <0.1 | 0.1-1 | <0.1 | |
| 45 | <0.1 | 0.1-1 | <0.1 | |
| 46 | 1-10 | 10-40 | 0.1-1 | 0.1-1 |
| 47 | <0.1 | <0.1 | <0.1 | |
| 48 | <0.1 | 1-10 | <0.1 | 0.1-1 |
| 49 | <0.1 | 0.1-1 | 0.1-1 | 0.1-1 |
| 50 | <0.1 | 0.1-1 | 0.1-1 | 0.1-1 |
| 51 | 0.1-1 | 1-10 | 1-10 | 1-10 |
| 52 | 0.1-1 | 1-10 | 0.1-1 | 0.1-1 |
| 53 | <0.1 | 0.1-1 | 0.1-1 | 0.1-1 |
| 54 | <0.1 | 0.1-1 | <0.1 | <0.1 |
| 54a | <0.1 | <0.1 | <0.1 | <0.1 |
| 54b | | | | |
| 54c | <0.1 | 0.1-1 | 0.1-1 | |
| 54d | <0.1 | <0.1 | <0.1 | <0.1 |
| 54e | <0.1 | 0.1-1 | 0.1-1 | |
| 54f | 0.1-1 | 0.1-1 | 0.1-1 | |
| 54g | <0.1 | 0.1-1 | 0.1-1 | |
| 54h | 0.1-1 | 0.1-1 | | |
| 54i | 0.1-1 | 1-10 | 0.1-1 | 1-10 |
| 54j | 0.1-1 | 1-10 | 1-10 | |
| 54k | <0.1 | 0.1-1 | <0.1 | 0.1-1 |
| 54l | <0.1 | 0.1-1 | <0.1 | |
| 54m | <0.1 | 0.1-1 | <0.1 | |
| 54n | <0.1 | 0.1-1 | <0.1 | |
| 54o | <0.1 | 0.1-1 | 0.1-1 | |
| 54p | <0.1 | 0.1-1 | <0.1 | |
| 54q | <0.1 | 0.1-1 | 0.1-1 | 0.1-1 |
| 54r | 0.1-1 | 0.1-1 | <0.1 | 0.1-1 |
| 54s | <0.1 | 0.1-1 | <0.1 | 0.1-1 |
| 54t | <0.1 | 0.1-1 | <0.1 | 0.1-1 |
| 54u | <0.1 | 0.1-1 | <0.1 | 0.1-1 |
| 54v | 0.1-1 | 1-10 | 0.1-1 | 0.1-1 |
| 54w | 0.1-1 | 1-10 | 1-10 | 10-40 |
| 54x | 0.1-1 | 0.1-1 | 0.1-1 | <0.1 |
| 54y | 1-10 | 1-10 | 1-10 | 1-10 |
| 54z | <0.1 | 0.1-1 | 0.1-1 | 0.1-1 |
| 54aa | <0.1 | 0.1-1 | 0.1-1 | 0.1-1 |
| 54bb | <0.1 | 0.1-1 | <0.1 | 0.1-1 |
| 54cc | <0.1 | 0.1-1 | 0.1-1 | 0.1-1 |
| 55 | 0.1-1 | 1-10 | 0.1-1 | 0.1-1 |
| 56 | <0.1 | 1-10 | <0.1 | 0.1-1 |
| 57 | <0.1 | 0.1-1 | <0.1 | <0.1 |
| 58 | 1-10 | | 1-10 | 1-10 |
| 59 | <0.1 | 0.1-1 | <0.1 | <0.1 |
| 60 | <0.1 | 0.1-1 | <0.1 | 0.1-1 |
| 61 | 0.1-1 | 1-10 | <0.1 | 0.1-1 |
| 62 | <0.1 | 1-10 | <0.1 | <0.1 |
| 63 | 0.1-1 | 1-10 | 0.1-1 | 0.1-1 |

TABLE 9-continued

| Example no. | RGA (1 nM Smo agonist) IC$_{50}$ [μM] | RGA (25 nM Smo agonist) IC$_{50}$ [μM] | Mouse Smo bdg., IC$_{50}$ [μM] | Human Smo bdg., IC$_{50}$ [μM] |
|---|---|---|---|---|
| 64 | <0.1 | 1-10 | 0.1-1 | 0.1-1 |
| 65 | 0.1-1 | 1-10 | 0.1-1 | 0.1-1 |
| 66 | <0.1 | 0.1-1 | <0.1 | <0.1 |
| 67 | 0.1-1 | 0.1-1 | <0.1 | 0.1-1 |
| 68 | 0.1-1 | 1-10 | 1-10 | 1-10 |
| 69 | <0.1 | 1-10 | 0.1-1 | 0.1-1 |
| 70 | <0.1 | 0.1-1 | 0.1-1 | 0.1-1 |
| 71 | <0.1 | 0.1-1 | | |
| 72 | 1-10 | 10-40 | | |
| 73 | 0.1-1 | 1-10 | 0.1-1 | |
| 74 | <0.1 | 0.1-1 | | |
| 75 | 0.1-1 | 1-10 | 0.1-1 | |
| 76 | 1-10 | 10-40 | 10-40 | |
| 77 | 0.1-1 | 1-10 | 0.1-1 | |
| 78 | 1-10 | 10-40 | 1-10 | |
| 78a | <0.1 | 0.1-1 | 0.1-1 | 0.1-1 |
| 78b | <0.1 | 0.1-1 | 0.1-1 | 0.1-1 |
| 78c | <0.1 | <0.1 | <0.1 | <0.1 |
| 79 | 0.1-1 | 0.1-1 | 0.1-1 | 1-10 |
| 80 | 1-10 | 10-40 | | |
| 81 | 1-10 | 10-40 | 1-10 | 10-40 |
| 82 | 1-10 | 10-40 | 1-10 | 1-10 |
| 83 | 0.1-1 | 0.1-1 | 1-10 | 1-10 |
| 84 | <0.1 | 1-10 | 0.1-1 | 0.1-1 |
| 85 | 0.1-1 | | 0.1-1 | 0.1-1 |
| 86 | 0.1-1 | 1-10 | 1-10 | 1-10 |
| 87 | 0.1-1 | | 0.1-1 | 0.1-1 |
| 88 | <0.1 | 1-10 | 0.1-1 | 0.1-1 |
| 89 | 0.1-1 | | <0.1 | <0.1 |
| 90 | <0.1 | 1-10 | <0.1 | <0.1 |
| 91 | <0.1 | | <0.1 | <0.1 |
| 92 | 0.1-1 | 1-10 | 0.1-1 | 0.1-1 |
| 93 | 0.1-1 | | <0.1 | |
| 93a | 0.1-1 | 0.1-1 | <0.1 | |
| 93b | 0.1-1 | 0.1-1 | 0.1-1 | 0.1-1 |
| 93c | <0.1 | 0.1-1 | <0.1 | <0.1 |
| 94 | 0.1-1 | 1-10 | 0.1-1 | 0.1-1 |
| 95 | <0.1 | 1-10 | 0.1-1 | 0.1-1 |
| 96 | <0.1 | 0.1-1 | 0.1-1 | 0.1-1 |
| 97 | <0.1 | 1-10 | 0.1-1 | 0.1-1 |
| 98 | 0.1-1 | 1-10 | 1-10 | 1-10 |
| 99 | 0.1-1 | 1-10 | 0.1-1 | 0.1-1 |
| 100 | 0.1-1 | 1-10 | 0.1-1 | 0.1-1 |
| 101 | 0.1-1 | 10-40 | 0.1-1 | 0.1-1 |
| 102 | 0.1-1 | | 0.1-1 | 0.1-1 |
| 103 | 1-10 | 1-10 | 1-10 | 1-10 |
| 104 | 1-10 | 10-40 | 1-10 | 1-10 |
| 105 | 1-10 | 10-40 | 1-10 | 1-10 |
| 106 | 0.1-1 | 1-10 | 1-10 | 1-10 |
| 107 | <0.1 | 0.1-1 | 0.1-1 | 0.1-1 |
| 108 | 0.1-1 | 1-10 | 0.1-1 | 0.1-1 |
| 109 | <0.1 | 0.1-1 | <0.1 | <0.1 |
| 110 | <0.1 | <0.1 | <0.1 | <0.1 |
| 111 | <0.1 | 0.1-1 | <0.1 | 0.1-1 |
| 112 | <0.1 | 0.1-1 | <0.1 | 0.1-1 |
| 113 | 0.1-1 | 1-10 | 0.1-1 | 0.1-1 |
| 114 | <0.1 | 0.1-1 | <0.1 | <0.1 |
| 115 | 1-10 | 1-10 | 1-10 | 1-10 |
| 116 | 1-10 | 1-10 | 1-10 | 1-10 |
| 117 | <0.1 | 0.1-1 | <0.1 | <0.1 |
| 118 | 0.1-1 | 1-10 | 0.1-1 | 0.1-1 |
| 119 | 0.1-1 | 1-10 | 0.1-1 | 0.1-1 |
| 120 | <0.1 | <0.1 | <0.1 | <0.1 |
| 121 | <0.1 | <0.1 | <0.1 | <0.1 |
| 122 | <0.1 | 0.1-1 | <0.1 | 0.1-1 |
| 123 | <0.1 | 0.1-1 | <0.1 | <0.1 |
| 124 | <0.1 | 1-10 | 0.1-1 | 0.1-1 |
| 125 | 0.1-1 | 1-10 | 0.1-1 | 1-10 |
| 126 | | | | |
| 127 | | | | |
| 128 | | | | |
| 129 | 0.1-1 | 1-10 | 0.1-1 | 1-10 |
| 130 | 0.1-1 | 1-10 | 1-10 | 1-10 |
| 131 | 0.1-1 | 0.1-1 | <0.1 | <0.1 |
| 132 | <0.1 | 0.1-1 | <0.1 | <0.1 |
| 133 | <0.1 | 0.1-1 | 0.1-1 | 0.1-1 |

TABLE 9-continued

| Example no. | RGA (1 nM Smo agonist) IC$_{50}$ [μM] | RGA (25 nM Smo agonist) IC$_{50}$ [μM] | Mouse Smo bdg., IC$_{50}$ [μM] | Human Smo bdg., IC$_{50}$ [μM] |
|---|---|---|---|---|
| 134 | <0.1 | <0.1 | <0.1 | <0.1 |
| 135 | <0.1 | 0.1-1 | <0.1 | <0.1 |
| 136 | <0.1 | 0.1-1 | <0.1 | <0.1 |
| 137 | <0.1 | <0.1 | <0.1 | <0.1 |
| 138 | <0.1 | 0.1-1 | <0.1 | <0.1 |
| 139 | 0.1-1 | 1-10 | <0.1 | <0.1 |
| 140 | 1-10 | 1-10 | 0.1-1 | |
| 141 | 0.1-1 | 1-10 | 1-10 | 1-10 |
| 142 | <0.1 | 0.1-1 | <0.1 | <0.1 |
| 143 | <0.1 | 0.1-1 | <0.1 | <0.1 |
| 144 | <0.1 | 0.1-1 | <0.1 | <0.1 |
| 145 | <0.1 | 0.1-1 | | <0.1 |
| 146 | | | | |
| 147 | 0.1-1 | 1-10 | 0.1-1 | <0.1 |
| 148 | <0.1 | <0.1 | <0.1 | <0.1 |
| 149 | <0.1 | <0.1 | <0.1 | <0.1 |
| 150 | <0.1 | <0.1 | <0.1 | <0.1 |
| 151 | <0.1 | 0.1-1 | <0.1 | <0.1 |
| 152 | <0.1 | 0.1-1 | <0.1 | 0.1-1 |
| 153 | <0.1 | 0.1-1 | <0.1 | |
| 154 | <0.1 | <0.1 | <0.1 | <0.1 |
| 155 | <0.1 | <0.1 | <0.1 | <0.1 |
| 156 | <0.1 | <0.1 | <0.1 | <0.1 |
| 157 | <0.1 | <0.1 | <0.1 | <0.1 |
| 158 | 0.1-1 | 1-10 | 0.1-1 | |
| 159 | 0.1-1 | 1-10 | 0.1-1 | 0.1-1 |
| 160 | <0.1 | 0.1-1 | 0.1-1 | 0.1-1 |
| 161 | <0.1 | <0.1 | <0.1 | <0.1 |
| 162 | <0.1 | <0.1 | <0.1 | <0.1 |
| 163 | <0.1 | 0.1-1 | <0.1 | <0.1 |
| 164 | <0.1 | <0.1 | <0.1 | <0.1 |
| 165 | <0.1 | <0.1 | <0.1 | <0.1 |
| 166 | <0.1 | 0.1-1 | <0.1 | <0.1 |
| 167 | <0.1 | 0.1-1 | <0.1 | <0.1 |
| 168 | | | | |
| 169 | <0.1 | 0.1-1 | <0.1 | <0.1 |
| 170 | <0.1 | 0.1-1 | 0.1-1 | 0.1-1 |
| 171 | <0.1 | 0.1-1 | <0.1 | <0.1 |
| 172 | <0.1 | <0.1 | <0.1 | <0.1 |
| 173 | <0.1 | 0.1-1 | <0.1 | <0.1 |
| 174 | <0.1 | 1-10 | 0.1-1 | 0.1-1 |
| 175 | 0.1-1 | 1-10 | 0.1-1 | 1-10 |
| 176 | 0.1-1 | 1-10 | 0.1-1 | 0.1-1 |
| 177 | 0.1-1 | 0.1-1 | <0.1 | <0.1 |
| 178 | 0.1-1 | 0.1-1 | 0.1-1 | 0.1-1 |
| 179 | 0.1-1 | 10-40 | 0.1-1 | 0.1-1 |
| 180 | 1-10 | 10-40 | 10-40 | 10-40 |
| 181 | <0.1 | 0.1-1 | <0.1 | 0.1-1 |
| 182 | 0.1-1 | 0.1-1 | 0.1-1 | 0.1-1 |
| 183 | 0.1-1 | 1-10 | <0.1 | <0.1 |
| 184 | 0.1-1 | 0.1-1 | <0.1 | <0.1 |
| 185 | 0.1-1 | 1-10 | <0.1 | <0.1 |
| 186 | 0.1-1 | 0.1-1 | <0.1 | <0.1 |
| 187 | <0.1 | 0.1-1 | <0.1 | <0.1 |
| 188 | <0.1 | 0.1-1 | <0.1 | <0.1 |
| 189 | <0.1 | 0.1-1 | <0.1 | <0.1 |
| 190 | 0.1-1 | 0.1-1 | 0.1-1 | 0.1-1 |
| 191 | <0.1 | <0.1 | <0.1 | <0.1 |
| 192 | <0.1 | 0.1-1 | <0.1 | <0.1 |
| 193 | <0.1 | <0.1 | <0.1 | <0.1 |
| 194 | <0.1 | 0.1-1 | <0.1 | <0.1 |
| 195 | <0.1 | <0.1 | <0.1 | <0.1 |
| 196 | <0.1 | <0.1 | <0.1 | <0.1 |
| 197 | | | | |
| 198 | <0.1 | 0.1-1 | <0.1 | <0.1 |
| 199 | <0.1 | 0.1-1 | 0.1-1 | 0.1-1 |
| 200 | <0.1 | 0.1-1 | <0.1 | <0.1 |
| 201 | <0.1 | 0.1-1 | <0.1 | <0.1 |
| 202 | <0.1 | 0.1-1 | <0.1 | |
| 203 | 0.1-1 | 1-10 | 0.1-1 | 0.1-1 |
| 204 | <0.1 | 0.1-1 | <0.1 | |
| 205 | 0.1-1 | 0.1-1 | <0.1 | |
| 206 | <0.1 | 0.1-1 | 0.1-1 | |
| 207 | <0.1 | 0.1-1 | 0.1-1 | 0.1-1 |
| 208 | <0.1 | <0.1 | 0.1-1 | 0.1-1 |
| 209 | 0.1-1 | 0.1-1 | 1-10 | 1-10 |

TABLE 9-continued

| Example no. | RGA (1 nM Smo agonist) IC$_{50}$ [μM] | RGA (25 nM Smo agonist) IC$_{50}$ [μM] | Mouse Smo bdg., IC$_{50}$ [μM] | Human Smo bdg., IC$_{50}$ [μM] |
|---|---|---|---|---|
| 210 | <0.1 | <0.1 | <0.1 | <0.1 |
| 211 | <0.1 | 0.1-1 | <0.1 | <0.1 |
| 212 | <0.1 | 0.1-1 | <0.1 | <0.1 |
| 213 | <0.1 | 0.1-1 | 0.1-1 | 0.1-1 |
| 214 | 0.1-1 | 1-10 | | |
| 215 | 0.1-1 | 1-10 | | |
| 216 | <0.1 | <0.1 | <0.1 | <0.1 |
| 217 | <0.1 | 1-10 | 1-10 | 1-10 |
| 218 | | | | |
| 219 | 0.1-1 | 0.1-1 | <0.1 | <0.1 |
| 220 | <0.1 | <0.1 | <0.1 | <0.1 |
| 221 | <0.1 | 0.1-1 | <0.1 | <0.1 |
| 222 | <0.1 | <0.1 | <0.1 | <0.1 |
| 223 | <0.1 | 0.1-1 | <0.1 | 0.1-1 |
| 224 | <0.1 | 0.1-1 | 0.1-1 | 0.1-1 |
| 225 | <0.1 | 0.1-1 | 0.1-1 | 0.1-1 |
| 226 | <0.1 | 0.1-1 | <0.1 | 0.1-1 |
| 227 | <0.1 | 0.1-1 | <0.1 | 0.1-1 |
| 228 | 0.1-1 | 0.1-1 | <0.1 | <0.1 |
| 229 | 0.1-1 | 0.1-1 | <0.1 | <0.1 |
| 230 | <0.1 | 0.1-1 | 0.1-1 | 0.1-1 |
| 231 | <0.1 | <0.1 | <0.1 | <0.1 |
| 232 | | | | |
| 233 | | | | |
| 234 | | | | |
| 235 | | | | |
| 236 | 0.1-1 | 0.1-1 | 0.1-1 | |
| 237 | 0.1-1 | 0.1-1 | 0.1-1 | |
| 238 | <0.1 | 0.1-1 | 0.1-1 | 0.1-1 |
| 239 | <0.1 | 0.1-1 | <0.1 | 0.1-1 |
| 240 | 0.1-1 | 0.1-1 | <0.1 | <0.1 |
| 241 | 1-10 | 10-40 | 1-10 | 1-10 |
| 242 | 1-10 | 1-10 | 1-10 | 1-10 |
| 243 | 1-10 | 1-10 | 0.1-1 | 1-10 |
| 244 | 1-10 | 1-10 | 0.1-1 | 0.1-1 |
| 245 | <0.1 | 1-10 | 0.1-1 | 0.1-1 |
| 246 | <0.1 | 1-10 | 10-40 | 1-10 |
| 247 | 1-10 | 1-10 | 0.1-1 | 0.1-1 |

The above preferred embodiments are given to illustrate the scope and spirit of the present invention. The descriptions provided herein will make apparent to those skilled in the art other embodiments and examples. These other embodiments and examples are within the contemplation of the present invention. Therefore, the present invention should be limited only by the appended claims.

What is claimed is:

1. A compound of Formula I:

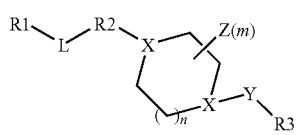

and pharmaceutically acceptable salts thereof, wherein

R$_1$ is selected from phenyl, pyridinyl, naphthyl and morpholino; wherein said phenyl or pyridinyl is unsubstituted or substituted with 1 to 2 groups independently selected from halo, methyl, methoxy, trifluoromethyl, cyano, methoxy-carbonyl and carboxyl;

R$_2$ is selected from:

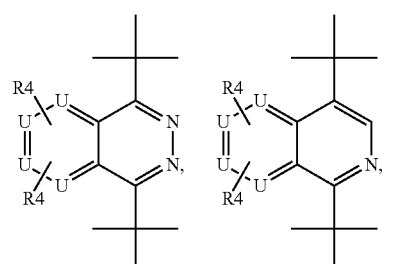

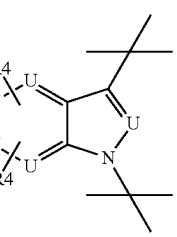

where N is connected to L, where U is C(H)$_{0-1}$ or N, and not more than two U are N; R$_4$ is independently H, —N(R$_6$)$_2$, —OH, halo, —CN, —C(O)OR$_6$, —C(O)N(R$_6$)$_2$, lower alkyl, or lower alkoxy, in which lower alkyl and lower alkoxy may be unsubstituted or substituted with one or more halo, —OH, —CN, —NH$_2$, —NO$_2$, —C(O)NH$_2$, —C(O)NH(C$_1$-C$_6$-alkyl), —C(O)N(C$_1$-C$_6$-alkyl)$_2$-C(O)(C$_1$-C$_6$-alkyl), —NHC(O)(C$_1$-C$_6$-alkyl), NH(C$_1$-C$_6$-alkyl), —N(C$_1$-C$_6$-alkyl)$_2$-SO$_2$(C$_1$-C$_6$-alkyl), —SO$_2$NH$_2$, —SO$_2$NH(C$_1$-C$_6$-alkyl); R$_5$ is H, aryl, het, lower alkyl, lower alkoxy, or cycloalkyl, which can be unsubstituted or substituted with one or more halo, cycloalkyl, aryl, het, and wherein at least one R$_5$ is not H;

L is lower alkyl, (CH$_2$)$_{1-2}$-A, A-(CH$_2$)$_{1-2}$, or CH$_2$-A-CH$_2$, and A is O, S, NH, or N-alkyl, wherein lower alkyl may be unsubstituted or substituted with lower alkyl, or one or more fluorines;

X is N or CH, and at least one X is N;

Y is a single bond, CH$_2$, C(O), or SO$_2$;

R$_3$ is aryl or het, which is substituted;

Z is H, lower alkyl, lower alkoxy, oxo, C(O)OR$_6$, or —CN; in which lower alkyl and lower alkoxy may be unsubstituted or substituted with one or more halo, —OH, —CN, —NH$_2$, or oxo, and two Z connected to the same atom can form a cycloalkyl ring, and m is 0 to 3;

substitutions of phenyl, aryl or het of R$_1$, R$_2$, or R$_3$ may be one or more of alkyl, cycloalkyl, alkoxy, cycloalkoxy, halo, —CN, oxo, aryl, carbalkoxy, OCF$_3$, CF$_3$, OH, —C(O)N(R$_6$)$_2$, C(O)R$_6$, —C(O)OR$_6$, —N(R$_6$)$_2$, —NHC(O)R$_6$, —SO$_2$(R$_6$), —SO$_2$N(R$_6$)$_2$; CH$_2$OC(O)N(R$_6$)$_2$, —CH$_2$N(R$_6$)$_2$, —NHC(O)OR$_6$, NHC(O)N(R$_6$)$_2$, —CH$_2$NHC(O)R$_6$, CH$_2$NHC(O)N(R$_6$)$_2$, CH$_2$NHSO$_2$(R$_6$), CH$_2$NHC(O)OR$_6$—OC(O)R$_6$, NHC(O)R$_6$, O-aryl, het, or O-het, in which alkyl, het, cycloalkyl, cycloalkoxy, N(R$_6$)$_2$, aryl, carbalkoxy, and alkoxy can be unsubstituted or substituted with one or more halo, —OCH$_3$, —OCF$_3$, —OH, —NH$_2$, alkyl, OR$_6$, oxo, —N(H)$_{0-2}$—R$_6$, —CN, —C(O)N(R$_6$)$_2$, C(O)R$_6$, C(O)OR$_6$, —N(R$_6$)$_2$, NHC(O)R$_6$, —SO$_2$(R$_6$), —SO$_2$N(R$_6$)$_2$, OSO$_2$R$_6$, —CH$_2$N(R$_6$)$_2$, —CH$_2$NHC(O)R$_6$, —OC(O)R$_6$, aryl, NHC(O)(R$_6$), O-aryl, O-het, or cycloalkyl;

R$_6$ is H, alkyl, alkenyl, aryl, het, or two R$_6$ on one atom may form het; and alkyl, alkenyl, aryl, het, cycloalkyl, or het may be unsubstituted or substituted by OH, oxo, alkoxy, NR$_6$, Nalkyl, aryl or het group;

het is a 5-7 membered monocyclic heterocyclic ring which may be aromatic or non-aromatic, containing 1-4 heteroring atoms selected from N, O, and S; or an 8-12 membered fused ring system that includes at least one 5-7 membered heterocyclic ring which may be aromatic or non-aromatic, containing 1, 2, or 3 heteroring atoms selected from N, O and S, which het is unsubstituted or substituted;

aryl is an aromatic radical having 6 to 14 ring carbon atoms in which said aryl group may be monocyclic or fused bicyclic or tricyclic, which may be unsubstituted or substituted by one or more substituents; and n is 0, 1, 2, or 3.

2. The compound according to claim 1 wherein:

R$_3$ is aryl or het; and when R$_3$ is het, at least one heteroring atom is N;

U is C(H)$_{0-1}$;

R$_4$ is H, CH$_3$, halo or —CN;

L is CH$_2$;

X is N;

Y is a single bond; and

Z is H or CH$_3$.

3. The compound according to claim 2 wherein:

R$_2$ is

R$_4$ is H, and U is C(H)$_{0-1}$,

R$_3$ is phenyl, pyridinyl, pyrazinyl, pyridazinyl or pyrimidinyl

Z is H or CH$_3$ and n is 1.

4. A pharmaceutical composition comprising a therapeutically effective amount of a compound according to claim 1.

5. A compound selected from: 6-[4-(4-Benzyl-phthalazin-1-yl)-piperazin-1-yl]-nicotinonitrile; 1-Benzyl-4-[4-(5-trifluoromethyl-pyridin-2-yl)-piperazin-1-yl]-phthalazine; 1-Benzyl-4-[4-(5-trifluoromethyl-pyridin-2-yl)-[1,4]diazepan-1-yl]-phthalazine; 6-[4-(4-Pyridin-4-ylmethyl-phthalazin-1-yl)-piperazin-1-yl]-nicotinonitrile; 4-[4-(4-Benzyl-phthalazin-1-yl)-piperazin-1-yl]-benzoic acid ethyl ester; 1-(4-Phenyl-piperazin-1-yl)-4-pyridin-4-ylmethyl-phthalazine; 1-Benzyl-4-[4-(4-tert-butyl-phenyl)-piperazin-1-yl]-phthalazine; 1-[4-(4-tert-Butyl-phenyl)-piperazin-1-yl]-4-pyridin-4-ylmethyl-phthalazine; 1-[4-(4-tert-Butyl-phenyl)-piperazin-1-yl]-4-(3,5-dichloro-benzyl)-phthalazine; 4-[4-(4-tert-Butyl-phenyl)-piperazin-1-yl]-6-methyl-1-pyridin-4-ylmethyl-phthalazine; 1-(2-Methyl-pyridin-4-ylmethyl)-4-(4-phenyl-piperazin-1-yl)-phthalazine; 1-Benzyl-4-(4-phenyl-piperidin-1-yl)-phthalazine; 1-(4-Phenyl-piperidin-1-yl)-4-pyridin-4-ylmethyl-phthalazine; 1-(2-Methyl-pyridin-4-ylmethyl)-4-(4-phenyl-piperidin-1-yl)-phthalazine; 1-Pyridin-4-ylmethyl-4-[4-(3-trifluoromethyl-phenyl)-piperazin-1-yl]-phthalazine; 4-[4-(4-Benzyl-phthalazin-1-yl)-piperazin-1-yl]-benzoic acid; 1-Benzyl-4-[4-(3-chloro-5-trifluoromethyl-pyridin-2-yl)-[1,4]diazepan-1-yl]-phthalazine; 1-Benzyl-4-(4-quinolin-2-yl-piperazin-1-yl)-phthalazine; 6-[4-(4-Benzyl-phthalazin-1-yl)-[1,4]diazepan-1-yl]-nicotinonitrile; 4-(4-Pyridin-4-ylmethyl-phthalazin-1-yl)-3,4,5,6-tetrahydro-2H-[1,2']bipyrazinyl; 4-(4-Benzyl-phthalazin-1-yl)-3,4,5,6-tetrahydro-2H-[1,2']bipyrazinyl; 1-(2-Methyl-pyridin-4-ylmethyl)-4-(4-pyridin-2-yl-piperazin-1-yl)-phthalazine; 1-Pyridin-4-ylmethyl-4-(4-pyridin-2-yl-piperazin-1-yl)-phthalazine; 1-Benzyl-4-(4-pyridin-2-yl-piperazin-1-yl)-phthalazine; 1-Benzyl-4-(4-pyrimidin-2-yl-piperazin-1-yl)-phthalazine; 1-Pyridin-4-ylmethyl-4-(4-pyridin-4-yl-piperazin-1-yl)-phthalazine; 1-Benzyl-4-(3-methyl-4-p-tolyl-piperazin-1-yl)-phthalazine; 1-(3-Methyl-4-p-tolyl-piperazin-1-yl)-4-pyridin-4-ylmethyl-phthalazine; 1-(2-Methyl-pyridin-4-ylmethyl)-4-(3-methyl-4-p-tolyl-piperazin-1-yl)-Phthalazine; 1-Benzyl-4-[4-(3,4-dichloro-phenyl)-piperazin-1-yl]-phthalazine; 1-Benzyl-4-(4-naphthalen-2-yl-piperazin-1-yl)-phthalazine; 1-(4-Naphthalen-2-yl-piperazin-1-yl)-4-pyridin-4-ylmethyl-phthalazine; 1-(2-Methyl-pyridin-4-ylmethyl)-4-(4-naphthalen-2-yl-piperazin-1-yl)-phthalazine; 1-Benzyl-4-(4-naphthalen-1-yl-piperazin-1-yl)-phthalazine; 1-(2-Methyl-pyridin-4-ylmethyl)-4-(4-naphthalen-1-yl-piperazin-1-yl)-phthalazine; 1-(4-Naphthalen-1-yl-piperazin-1-yl)-4-pyridin-4-ylmethyl-phthalazine; 1-Benzyl-4-(4-pyridin-4-yl-piperazin-1-yl)-phthalazine; 1-Benzyl-4-(4-o-tolyl-piperazin-1-yl)-phthalazine; 2-[4-(4-Benzyl-phthalazin-1- yl)-piperazin-1-yl]-pyrimidine-5-carbonitrile; 1-Benzyl-4-(4-pyrimidin-2-yl-[1,4]diazepan-1-yl)-phthalazine; 1-Benzyl-4-[4-(4-methyl-pyrimidin-2-yl)-[1,4]diazepan-1-yl]-phthalazine; 1-Benzyl-4-[4-(5-propyl-pyrimidin-2-yl)-piperazin-1-yl]-phthalazine; 1-Benzyl-4-[4-(5-ethyl-pyrimidin-2-yl)-piperazin-1-yl]-phthalazine; 1-Benzyl-4-[4-(5-propyl-pyrimidin-2-yl)-[1,4]diazepan-1-yl]-phthalazine; 1-Benzyl-4-[4-(5-ethyl-pyrimidin-2-yl)-[1,4]diazepan-1-yl]-phthalazine; 2-[4-(4-Benzyl-phthalazin-1-yl)-piperazin-1-yl]-6-methoxy-3H-pyrimidin-4-one; 1-Benzyl-4-[4-(4-methyl-pyrimidin-2-yl)-piperazin-1-yl]-phthalazine; 1-Benzyl-4-[4-(4,6-dimethyl-pyrimidin-2-yl)-piperazin-1-yl]-phthalazine; 1-Benzyl-4-[4-(5-chloro-3-fluoro-pyridin-2-yl)-piperazin-1-yl]-phthalazine; 1-Benzyl-4-[4-(4-trifluoromethyl-pyrimidin-2-yl)-piperazin-1-yl]-phthalazine; 1-Benzyl-4-[4-(2,5-difluoro-pyridin-3-yl)-piperazin-1-yl]-phthalazine; 1-Benzyl-4-[4-(3,5-difluoro-pyridin-2-yl)-piperazin-1-yl]-phthalazine; 6-[4-(4-Benzyl-phthalazin-1-yl)-piperazin-1-yl]-nicotinamide; 6-[4-(4-Benzyl-phthalazin-1-yl)-piperazin-1-yl]-nicotinic acid ethyl ester; 2-{6-[4-(4-Benzyl-phthalazin-1-yl)-piperazin-1-yl]-pyridin-3-yl}-propan-2-ol; 6-[4-(4-Benzyl-phthalazin-1-yl)-piperazin-1-yl]-nicotinic acid; 6-[4-(4-Benzyl-phthalazin-1-yl)-piperazin-1-yl]-N-(2-hydroxy-ethyl)-N-methyl-nicotinamide; 6-[4-(4-Benzyl-phthalazin-1-yl)-piperazin-1-yl]-N-ethyl-N-(2-hydroxy-ethyl)-nicotinamide; 6-[4-(4-Benzyl-phthalazin-1-yl)-piperazin-1-yl]-N-(2-hydroxy-ethyl)-nicotinamide; 6-[4-(4-Benzyl-phthalazin-1-yl)-piperazin-1-yl]-N-(2-methoxy-ethyl)-nicotinamide; 6-[4-(4-Benzyl-phthalazin-1-yl)-piperazin-1-yl]-N-(2-methoxy-ethyl)-N-methyl-nicotinamide; 6-[4-(4-Benzyl-phthalazin-1-yl)-piperazin-1-yl]-N-(2-dimethylamino-ethyl)-nicotinamide; {6-[4-(4-Benzyl-phthalazin-1-yl)-piperazin-1-yl]-pyridin-3-yl}-(4-methyl-piperazin-1-yl)-methanone; {6-[4-(4-Benzyl-phthalazin-1-yl)-piperazin-1-yl]-pyridin-3-yl}-piperazin-1-yl-methanone; {6-[4-(4-Benzyl-phthalazin-1-yl)-piperazin-1-yl]-pyridin-3-yl}-morpholin-4-yl-methanone; N-Benzyl-6-[4-(4-benzyl-phthalazin-1-yl)-piperazin-1-yl]-nicotinamide; 6-[4-(4-Benzyl-phthalazin-1-yl)-piperazin-1-yl]-N-cyclohexylmethyl-nicotinamide; 6-[4-(4-Benzyl-phthalazin-1-yl)-piperazin-1-yl]-N-propyl-nicotinamide; {6-[4-(4-Benzyl-phthalazin-1-yl)-piperazin-1-yl]-pyridin-3-yl}-(3-hydroxy-pyrrolidin-1-yl)-methanone; {6-[4-(4-Benzyl-phthalazin-1-yl)-piperazin-1-yl]-pyridin-3-yl}-thiazolidin-3-yl-methanone; {6-[4-(4-Benzyl-phthalazin-1-yl)-piperazin-1-yl]-pyridin-3-yl}-(1-oxo-1lambda*4*-thiazolidin-3-yl)-methanone; ({6-[4-(4-Benzyl-phthalazin-1-yl)-piperazin-1-yl]-pyridine-3-carbonyl}-amino)-acetic acid methyl ester; 1-Benzyl-4-[4-(4-trifluoromethyl-phenyl)-piperazin-1-yl]-phthalazine; 6-{4-[4-(3-Trifluoromethyl-benzyl)-phthalazin-1-yl]-piperazin-1-yl}-nicotinonitrile; 6-{4-[4-(4-Cyano-benzyl)-phthalazin-1-yl]-piperazin-1-yl}-nicotinonitrile; 6-{4-[4-(3,4-Dimethoxy-benzyl)-phthalazin-1-yl]-piperazin-1-yl}-nicotino-nitrile; 6-{4-[4-(4-Chloro-benzyl)-phthalazin-1-yl]-piperazin-1-yl}-nicotinonitrile; 6-{4-[4-(3-Chloro-benzyl)-phthalazin-1-yl]-piperazin-1-yl}-nicotinonitrile; 6-[4-(4-Phenethyl-phthalazin-1-yl)-piperazin-1-yl]-nicotinonitrile; 6-[4-(4-Naphthalen-2-ylmethyl-phthalazin-1-yl)-piperazin-1-yl]-nicotino-nitrile; 6-{4-[4-(4-Trifluoromethyl-benzyl)-phthalazin-1-yl]-piperazin-1-yl}-nicotinonitrile; 6-{4-[4-(4-Methoxy-benzyl)-phthalazin-1-yl]-piperazin-1-yl}-nicotinonitrile; 6-{4-[4-(3-Cyano-benzyl)-phthalazin-1-yl]-piperazin-1-yl}-nicotinonitrile; 6-{4-[4-(4-Bromo-benzyl)-phthalazin-1-yl]-piperazin-1-yl}-nicotinonitrile; 6-{4-[4-(3-Bromo-benzyl)-phthalazin-1-yl]-piperazin-1-yl}-nicotinonitrile; 6-{4-[4-(1-Phenyl-ethyl)-phthalazin-1-yl]-piperazin-1-yl}-nicotinonitrile; 6-{4-[4-(4-Methyl-benzyl)-phthalazin-1-yl]-piperazin-1-yl}-nicotinonitrile; N-{6-[4-(4-Benzyl-phthalazin-1-yl)-piperazin-1-yl]-pyridin-3-ylmethyl}-acetamide; C-{6-[4-(4-Benzyl-phthalazin-1-yl)-piperazin-1-yl]-pyridin-3-yl}-methyl-amine; 4-[4-(4-Pyridin-4-ylmethyl-phthalazin-1-yl)-piperazin-1-yl]-benzylamine; 4-[4-(4-Benzyl-phthalazin-1-yl)-piperazin-1-yl]-benzylamine; 4-[5-({6-[4-(4-Benzyl-phthalazin-1-yl)-piperazin-1-yl]-pyridin-3-ylmethyl}-carbamoyl)-pentyl]-8-ethyl-3,8,9,10-tetrahydro-2H-1,6,11-trioxa-8,13-diaza-4-azonia-pentacene; N-{4-[4-(4-Benzyl-phthalazin-1-yl)-piperazin-1-yl]-benzyl}-acetamide; N-{4-[4-(4-Pyridin-4-ylmethyl-phthalazin-1-yl)-piperazin-1-yl]-benzyl}-acetamide; {4-[4-(4-Benzyl-phthalazin-1-yl)-piperazin-1-yl]-benzyl}-carbamic acid benzyl ester; {4-[4-(4-Pyridin-4-ylmethyl-phthalazin-1-yl)-piperazin-1-yl]-benzyl}-carbamic acid benzyl ester; N-{4-[4-(4-Benzyl-phthalazin-1-yl)-piperazin-1-yl]-benzyl}-propionamide; N-{4-[4-(4-Benzyl-phthalazin-1-yl)-piperazin-1-yl]-benzyl}-2-methoxy-acetamide; N-{4-[4-(4-Benzyl-phthalazin-1-yl)-piperazin-1-yl]-benzyl}-3-methyl-butyramide; 6-[4-(1-Benzyl-isoquinolin-4-yl)-piperazin-1-yl]-nicotinonitrile; 6-{4-[1-(3-Cyano-benzyl)-isoquinolin-4-yl]-piperazin-1-yl}-nicotinonitrile; 6-{4-[1-(3-Chloro-benzyl)-isoquinolin-4-yl]-piperazin-1-yl}-nicotinonitrile; 6-{4-[1-(3-Trifluormethyl-benzyl)-isoquinolin-4-yl]-piperazin-1-yl}-nicotinonitrile; 6-[4-(4-Benzyl-isoquinolin-1-yl)-piperazin-1-yl]-nicotinonitrile; 4-{4-[6-(4-Fluoro-benzyl)-4-methyl-pyridazin-3-yl]-piperazin-1-yl}-benzo-nitrile; 4-{4-[6-(4-Fluoro-benzyl)-5-methyl-pyridazin-3-yl]-piperazin-1-yl}-benzo-nitrile; 4-{4-[6-(4-Benzyl)-4-methyl-pyridazin-3-yl]-piperazin-1-yl}-nicotinonitrile; 4-{4-[6-(4-Benzyl)-5-methyl-pyridazin-3-yl]-piperazin-1-yl}-nicotinonitrile; 6-Benzyl-4-methyl-3-[4-(5-trifluoromethyl-pyridin-2-yl)-piperazin-1-yl]-pyridazine; 6-Benzyl-5-methyl-3-[4-(5-trifluoromethyl-pyridin-2-yl)-piperazin-1-yl]-pyridazine; 6-(4-Fluoro-benzyl)-4-methyl-3-[4-(5-trifluoromethyl-pyridin-2-yl)-piperazin-1-yl]-pyridazine; 6-(4-Fluoro-benzyl)-5-methyl-3-[4-(5-trifluoromethyl-pyridin-2-yl)-piperazin-1-yl]-pyridazine; 4-{4-[6-(4-chloro-benzyl)-4-methyl-pyridazin-3-yl]-piperazin-1-yl}-nicotinonitrile; 4-{4-[6-(4-chloro-benzyl)-5-methyl-pyridazin-3-yl]-piperazin-1-yl}-nicotinonitrile; 4-{4-[6-(4-Fluoro-benzyl)-4,5-dimethyl-pyridazin-3-yl]-piperazin-1-yl}-nicotinonitrile; 4-{4-[4-(4-fluoro-benzyl)-5,6,7,8-tetrahydro-phthalzin-1-yl]-piperazin-1-yl}-nicotinonitrile; 6-{4-[4-(4-Fluoro-benzyl)-6,7-dihydro-5H-cyclopenta[d]pyridazin-1-yl]-piperazin-1-yl}-nicotinonitrile; 3-{4-[1-(4-Fluoro-benzyl)-1H-indol-3-yl]-piperidine-1-carbonyl}-benzo-nitrile; 4-[1-(4-Fluoro-benzyl)-1H-indol-3-yl)-5'-trifluoromethyl-3,4,5,6-tetra-hydro-2H-[1,2]-bipyridinyl; 4-[3-(5'-Trifluoromethyl-3,4,5,6-tetrahydro-2H-[1,2]bipyridinyl-4-yl)-indol-1-ylmethyl]-benzonitrile; 4-[1-Benzyl-1H-indol-3-yl)-5'-trifluoromethyl-3,4,5,6-tetra-hydro-2H-[1,2]-bipyridinyl; 4-[1-(4-Fluoro-benzyl)-1H-indol-3-yl]-3,4,5,6-tetrahydro-2H-[1,2]bipyridinyl-5'-carbonitrile; 4-[1-(4-Bromo-benzyl)-1H-indol-3-yl)-5'-trifluoromethyl-3,4,5,6-tetra-hydro-2H-[1,2]-bipyridinyl; 4-(1-Benzyl-1H-indol-3-yl)-3,4,5,6-tetrahydro-2H-[1,2]bipyridinyl-5'-carbonitrile; {4-[1-(4-Fluoro-benzyl)-1H-indol-3-yl]-piperidin-1-yl}-(3-fluoro-phenyl)-methanone; 4-{4-[1-(4-Fluoro-benzyl)-1H-indol-3-yl]-piperidine-1-carbonyl}-benzonitrile; 3-{4-[1-(4-Fluoro-benzyl)-1H-indol-3-yl]-piperidine-1-carbonyl}-benzonitrile; {4-[1-(4-Fluoro-benzyl)-1H-indol-3-yl]-piperidin-1-yl}-(4-trifluoromethyl-phenyl)-methanone; or {4-[1-Benzyl-1H-indol-3-yl]-piperidin-1-yl}-(4-trifluoromethyl-phenyl)-methanone.

\* \* \* \* \*